(12) United States Patent
Pliushchev et al.

(10) Patent No.: US 8,372,841 B2
(45) Date of Patent: Feb. 12, 2013

(54) INHIBITORS OF THE 11-BETA-HYDROXYSTEROID DEHYDROGENASE TYPE 1 ENZYME

(75) Inventors: Marina A. Pliushchev, Vernon Hills, IL (US); Dariusz Wodka, Monmouth Junction, NJ (US); Bryan K. Sorensen, Antioch, IL (US); James T. Link, Stanford, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/217,831

(22) Filed: Aug. 25, 2011

(65) Prior Publication Data

US 2012/0004206 A1 Jan. 5, 2012

Related U.S. Application Data

(63) Continuation of application No. 12/725,560, filed on Mar. 17, 2010, now abandoned, which is a continuation of application No. 11/119,022, filed on Apr. 29, 2005, now Pat. No. 7,880,001.

(60) Provisional application No. 60/618,857, filed on Oct. 13, 2004, provisional application No. 60/566,265, filed on Apr. 29, 2004.

(51) Int. Cl.
| | |
|---|---|
| A61K 31/496 | (2006.01) |
| A61K 31/55 | (2006.01) |
| A61K 31/445 | (2006.01) |
| C07D 233/04 | (2006.01) |
| C07D 401/04 | (2006.01) |
| C07D 211/46 | (2006.01) |

(52) U.S. Cl. ............ 514/253.01; 514/217.12; 514/331; 540/610; 544/360; 546/233

(58) Field of Classification Search ............... 544/360, 544/380; 546/233; 548/528; 564/191; 514/252.12, 514/253.01, 317, 428, 613
See application file for complete search history.

(56) References Cited

U.S. PATENT DOCUMENTS

| | | | |
|---|---|---|---|
| 4,273,704 A | 6/1981 | Mazur | |
| 4,324,791 A | 4/1982 | Welstead, Jr. | |
| 4,514,332 A | 4/1985 | Hansen, Jr. et al. | |
| 4,751,292 A | 6/1988 | Fox | |
| 4,921,958 A | 5/1990 | Abou-Gharbia et al. | |
| 5,397,788 A | 3/1995 | Horwell et al. | |
| 5,622,983 A | 4/1997 | Horwell et al. | |
| 5,723,494 A * | 3/1998 | Makovec et al. ............... 514/563 |
| 6,368,816 B2 | 4/2002 | Walker et al. | |
| 6,784,167 B2 | 8/2004 | Wood et al. | |
| 7,087,400 B2 | 8/2006 | Walker et al. | |
| 7,122,531 B2 | 10/2006 | Walker et al. | |
| 7,217,838 B2 | 5/2007 | Rohde et al. | |
| 7,435,833 B2 | 10/2008 | Yeh et al. | |
| 7,511,175 B2 | 3/2009 | Patel et al. | |
| 7,528,282 B2 | 5/2009 | Rohde et al. | |
| 7,855,308 B2 | 12/2010 | Brune et al. | |
| 7,880,001 B2 | 2/2011 | Link et al. | |
| 2003/0229094 A1* | 12/2003 | Bhatia et al. ............. 514/252.02 |
| 2004/0122033 A1 | 6/2004 | Nargund et al. | |
| 2004/0133011 A1 | 7/2004 | Waddell et al. | |
| 2005/0245534 A1 | 11/2005 | Link et al. | |
| 2005/0261302 A1 | 11/2005 | Hoff et al. | |
| 2005/0277647 A1 | 12/2005 | Link et al. | |
| 2005/0288338 A1 | 12/2005 | Yao et al. | |
| 2006/0004049 A1 | 1/2006 | Yao et al. | |
| 2006/0009471 A1 | 1/2006 | Yao et al. | |
| 2006/0009491 A1 | 1/2006 | Yao et al. | |
| 2006/0079506 A1 | 4/2006 | Linders et al. | |
| 2006/0089349 A1 | 4/2006 | Gundertofte et al. | |
| 2006/0094699 A1 | 5/2006 | Kampen et al. | |
| 2006/0100235 A1 | 5/2006 | Andersen et al. | |
| 2006/0106008 A1 | 5/2006 | Andersen et al. | |
| 2006/0106071 A1 | 5/2006 | Lin et al. | |
| 2006/0111348 A1 | 5/2006 | Kampen et al. | |
| 2006/0111366 A1 | 5/2006 | Andersen et al. | |
| 2006/0281773 A1 | 12/2006 | Patel et al. | |
| 2007/0161641 A1 | 7/2007 | Hendrix et al. | |
| 2008/0064693 A1 | 3/2008 | Jaroskova et al. | |
| 2009/0131434 A1 | 5/2009 | Brune et al. | |
| 2009/0192141 A1 | 7/2009 | Bitner et al. | |
| 2010/0152179 A9 | 6/2010 | Bitner et al. | |

FOREIGN PATENT DOCUMENTS

| | | |
|---|---|---|
| EP | 215297 A2 | 3/1987 |
| EP | 336356 A2 | 10/1989 |
| EP | 405537 A1 | 1/1991 |
| EP | 564924 A2 | 10/1993 |
| EP | 697403 A1 | 2/1996 |
| EP | 1180513 A1 | 2/2002 |
| SU | 740752 | 6/1980 |
| SU | 803348 | 9/1981 |
| WO | 9113081 A1 | 9/1991 |
| WO | 9214697 A1 | 9/1992 |
| WO | 9428885 A1 | 12/1994 |
| WO | 9500146 A1 | 1/1995 |
| WO | 9902145 A1 | 1/1999 |
| WO | 0129007 A1 | 4/2001 |
| WO | 03059905 A1 | 7/2003 |

(Continued)

OTHER PUBLICATIONS

Bundgaard, Design of Prodrugs, 1985, Elseview, Chapter 1, p. 1-4.*
Glozman, CA Plus Abstract 95:24693, 1980.*
Han, Targeted Prodrug Design to Optimize Drug Delivery, 2000, AAPS Pharmsci, vol. 2(1), p. 1-11.*
Patani, Bioisosterism: A Rational Approach in Drug Design, 1996, Chem. Rev, vol. 96, p. 3147-3176.*

(Continued)

*Primary Examiner* — Golam M M Shameem
*Assistant Examiner* — Karen Cheng
(74) *Attorney, Agent, or Firm* — Lisa V. Mueller; Michael Best & Friedrich LLP

(57) ABSTRACT

The present invention relates to compounds which are inhibitors of the 11-beta-hydroxysteroid dehydrogenase Type 1 enzyme. The present invention further relates to the use of inhibitors of 11-beta-hydroxysteroid dehydrogenase Type 1 enzyme for the treatment of non-insulin dependent type 2 diabetes, insulin resistance, obesity, lipid disorders, metabolic syndrome, and other diseases and conditions that are mediated by excessive glucocorticoid action.

13 Claims, No Drawings

FOREIGN PATENT DOCUMENTS

| | | |
|---|---|---|
| WO | 03065983 A2 | 8/2003 |
| WO | 03075660 A1 | 9/2003 |
| WO | 2004011310 A1 | 2/2004 |
| WO | 2004033427 A1 | 4/2004 |
| WO | 2004037251 A1 | 5/2004 |
| WO | 2004056744 A1 | 7/2004 |
| WO | 2004056745 A2 | 7/2004 |
| WO | 2004065351 A1 | 8/2004 |
| WO | 2004089367 A1 | 10/2004 |
| WO | 2004089380 A2 | 10/2004 |
| WO | 2004089416 A2 | 10/2004 |
| WO | 2004089470 A2 | 10/2004 |
| WO | 2004089471 A2 | 10/2004 |
| WO | 2004089896 A1 | 10/2004 |
| WO | 2004113310 A1 | 12/2004 |
| WO | 2005016877 A2 | 2/2005 |
| WO | 2005042513 A1 | 5/2005 |
| WO | 2005046685 A1 | 5/2005 |
| WO | 2005047250 A1 | 5/2005 |
| WO | 2005060963 A1 | 7/2005 |
| WO | 2005097764 A1 | 10/2005 |
| WO | 2005103023 A1 | 11/2005 |
| WO | 2005108359 A1 | 11/2005 |
| WO | 2005108361 A1 | 11/2005 |
| WO | 2005116002 A2 | 12/2005 |
| WO | 2006002349 A1 | 1/2006 |
| WO | 2006002350 A1 | 1/2006 |
| WO | 2006002361 A2 | 1/2006 |
| WO | 2006012173 A1 | 2/2006 |
| WO | 2006012226 A2 | 2/2006 |
| WO | 2006012227 A2 | 2/2006 |
| WO | 2006012642 A2 | 2/2006 |
| WO | 2006017542 A1 | 2/2006 |
| WO | 2006020598 A2 | 2/2006 |
| WO | 2006024627 A2 | 3/2006 |
| WO | 2006024628 A1 | 3/2006 |
| WO | 2006040329 A1 | 4/2006 |
| WO | 2006048330 A1 | 5/2006 |
| WO | 2006048331 A1 | 5/2006 |
| WO | 2006048750 A2 | 5/2006 |
| WO | 2006049952 A1 | 5/2006 |
| WO | 2006050908 A1 | 5/2006 |
| WO | 2006053024 A2 | 5/2006 |
| WO | 2006104280 A1 | 5/2006 |
| WO | 2006066109 A2 | 6/2006 |

OTHER PUBLICATIONS

Moisan et al., "11-beta-Hydroxysteroid Dehydrogenase Bioactivity and Messenger RNA Expression in Rat Forebrain: Localization in Hypothalamus, Hippocampus, and Cortex," Endocrinology, 1990, 127 (3), 1450-1455.
Monder et al., Vitamins and Hormones, 1983, pp. 187-271, vol. 47.
Montague C.T. et al., "The Perils of Portliness: Causes and Consequences of Fisceral Adiposity," Diabetes, 2000, pp. 883-888, vol. 49 (6).
Morton N.M. et al., "Improved Lipid and Lipoprotein Profile, Hepatic Insulin Sensitivity, and Glucose Tolerance in 11.beta.-Hydroxysteroid Dehydrogenase Type 1 Null Mice," J. of Biol. Chem, 2001, pp. 41293-41300, vol. 276 (44).
Nagasawa et al., Journal of Medicinal Chemistry, 1975, pp. 826-830, vol. 18 (8).
Norman et al., "Emerging treatments for major depression," Expert Rev. Neurotherapeutics, 2007, vol. 7, pp. 203-213.
Orth D., "Normal Hypothalamic-Pituitary-Adrenal Physiology," The New England Journal of Medicine, 1995, pp. 791-803, vol. 332 (12).
Ortsater H. et al., "Regulation of 11 Is-hydroxytercid dehydrogenase type 1 and glucose-stimulated insulin secretion in pancreatic islets of Langerhans," Diabetes Metab. Res. Rev, 2005, pp. 359-366.
Parks W. G., "Gordon Research Conferences: Program for 1966," Science, 1966, pp. 1249-1251, vol. 272.
Paterson J.M. et al., "Metabolic syndrome without obesity: Hepatic overexpression of 11.beta.-hydroxysteroiddehydrogenase type 1 in transgenic mice," Proc. Natl. Acad. Sci, 2004, pp. 7088-7093, vol. 101 (18).
Pirkle et al., "Use of intercalative effects to enhance enantioselectivity chiral stationary phase desiqn," Journal of Chromatoqraphy, 1993, pp. 11-19, vol. 641.

Pirpiris M., "Hypertension Pressor Responsiveness in Corticosteroid-Induced Hypertension in Humans," 1992, pp. 567-574, vol. 19.
Rajan et al., "11 beta-Hydroxysteroid dehydrogenase in cultured hippocampal cells reactivates inert 11-dehydrocorticosterone, potentiating neurotoxicity," Journal of Neuroscience, 1996, pp. 65-70, vol. 16.
Rauz S. et al., "Expression and Putative Role of 11.beta.-Hydroxysteroid Dehydrogenase Isozymes within the Human Eye," Invest. Ophthal. & Vis. Sci, 2001, pp. 2037-2042, vol. 42 (9).
Rauz S. et al., "Inhibition of 11.beta.-hydroxysteroid dehydrogenase type 1 lowers intraocular pressure in patients with ocular hypertension," Q. J. Med, 2003, pp. 481-490, vol. 96.
Ringman J., "What the Study of Persons at Risk for Familial Alzheimer's Disease Can Tell Us about the Earliest Stages of the disorder," J Geriatr Psychiatry Neurology, 2005, pp. 228-233.
Roche E., "Bioreversible Carriers in Drug Design, American Pharmaceutical Association and Perqamon Press Table of Contents," 1987.
Rook, G.A.W. et al., "Clinical Endocrinology and Metabolism Glucocorticoids and Immune Function," 1999, pp. 567-581, vol. 13 (4).
Sakai R. R. et al., "Immunocytochemical Localization of 11 Beta-Hydroxysteroid Dehydrogenase in Hippocampus and Other Brain Regions of the Rat," J Neuroendocrinol, 1992, 101-106, vol. 4.
Schteingart D.E., "Crushing Syndrome," in: Princ. & Prac. of Endoc. & Metab, 3rd ed., Becker KL, ed., 2001, pp. 723-728, Chap. 75.
Seckl et al., "The 11-beta hydroxysteroid dehydrogenase inhibitor glycyrrhetinic acid affects corticosteroid feedback regulation of hypothalamic corticotrophin-releasing peptides in rats," Journal of Endocrinoloqy, 1993, pp. 471-477, vol. 136.
Seckl J.R et al., "11 beta-Hydroxysteroid Dehydrogenase Type 1-A Tissue Specific Amplifier of Glucocorticoid Action," Endocrinology Minireview, 2001, pp. 1371-1376, vol. 142.
Small G.R. et al., "Preventing local regeneration of glucocorticoids by 11β-hydroxysteroid dehydrogenase type 1 enhances angiogenesis," Proc. Natl. Acad. Sci, 2005, pp. 12165-12170.
Stokes J. et al., "Altered Peripheral Sensitivity to Glucocorticoids in Primary Open-Angle Glaucoma," Invest Ophthalmol Vis Sci, 2003, pp. 5163-5167, vol. 44 (12).
Strohle et al.,"Stress Responsive Neurohormones in Depression and Anxiety," Pharrnacopsychiatry, 2003, vol. 36, pp. S207-S214.
Tadayyon M., "Insulin sensitization in the treatment of Type 2 diabetes," Expert Opin Investig Drugs, 2003, pp. 307-324, vol. 12 (3).
Thekkepat C., et al., "11β-Hydroxysteroid dehydrogenase inhibition improves cognitive function in healthy elderly men and type 2 diabetics," Proc Natl Acad Sci USA., 2004, pp. 6743-6749, vol. 101.
Tronche F., "Disruption of the glucocorticoid receptor gene in the nervous system results in reduced anxiety," Nature Genetics, 1999, pp. 99-103, vol. 23.
Turner R.T., "Calcif. Tissue Int. Prednisone Inhibits Formation of Cortical Bone in Sham-Operated and Ovariectomized Female Rats," 1995, pp. 311-315, vol. 56.
Vaidyanathan ., "Decarboxylation of 1-Aminocyclopropanecarboxylic Acid and Its Derivatives," J Oro Chem, 1989, pp. 1810-1815, vol. 54.
Walker B.R et al., "Carbenoxolone increases Hepatic insulin Sensitivity in Man: A Novel Role for 11-0xosteroid Reductase in Enhancing Glucocorticoid Receptor Activation," Journal of Clin. Endocrinology and Met, 1995, pp. 3155-3159, vol. 80 (11).
Walker B.R, "Corticosteroids and Vascular Tone: Mapping the Messenger Maze," Clinical Science, 1992, pp. 597-605, vol. 82 (6).
Wolkowitz O.M., "The Steroid Dementia Syndrome: An Unrecognized Complication of Glucocorticoid Treatment," Annals New York Academy of Sciences, 2004, pp. 191-194, vol. 1032.
Woolley C.S. et al., "Exposure to excess glucocorticoids alters dendritic morphology of adult hippocampal pyramidal neurons," Brain Res, 1990, pp. 225-331, vol. 531.
Yau J.L. et al., "Lack of tissue glucocorticoid reactivation in 11.beta.-hydroxysteroid dehydrogenase type 1 knockout mice ameliorates age-related learning impairments," Proc. Natl. Acad. Sci, 2001, pp. 4716-4721, vol. 98 (8).

Yau J.L., "Glucocorticoids, Hippocampal Corticosteroid Receptor Gene Expression and Antidepressant Treatment: Relationship with Spatial learning in Young and Aged Rats," Neuroscience, 1995, pp. 571-581, vol. 66 (3).

Yeh et al., "Discovery of orally active butyrolactam 11beta-HSD1 inhibitors," Bioorganic & Medicinal Chemistry Letters, Oxford, GB, 2006, pp. 5555-5560, vol. 16 (21).

Yeh Vince S.C. et al., "A highly efficient synthesis of potent and selective butyrolactam inhibitors of 11beta-HSD1," Organic Letters, 2006, pp. 3963-3966, vol. 8 (18).

Ziegler, F. E.; Fowler, K. W. Substitution reactions of specifically ortho-metalated piperonal cyclohexylimine. J. Org. Chem. 1976, 1564-1566.vol. 41 (9).

International Search Report for application No. PCT/US2005/015304, Mailed Aug. 10, 2005., 5 pages.

Jenneskens, et al., Rec. des Travaux Chimiques des Pays Bas.,1995, vol. 114 (3), pp. 97-102.

Albrecht S. et al., "Nonpituitary Tumors of the Sellar Region," Cushing's Disease in:Melmed S. Ed. The Pituitary, 2002, pp. 592-612, 2nd Ed.

Anstead G. M., "Steroids, Retinoids, and Wound Healing," Adv Wound Care, 1998, pp. 277-285, vol. 11.

Armaly M. F., "Dexamethasone Ocular Hypertension and Eosinopenia, and Glucose Tolderance Test," Arch Ophthalmol, 1967, pp. 193-197, vol. 78.

Baxter J. D., "Glucocorticoid Hormone Action," Pharmac Ther, 1976, pp. 605-659, vol. 2.

Beer H. D. et al., "Glucocorticoid-Regulated Gene Expression during Cutaneous Wound Repair," Vitam Horm, 2000, pp. 217-239, vol. 59.

Belanoff J. K. et al., "Corticosteroids and cognition," J. of Psych. Res, 2001, pp. 127-145, vol. 35.

Bellows C.G. et al., "Osteoprogenitor Cells in Cell Populations Derived From Mouse and Rat Calvaria Differ in Their Response to Corticosterone, Cortisol, and Cortisone," Bone, 1998, pp. 119-125, vol. 23 (2).

Bertagna X, "Pituitary Tumors Cushing's Disease," 2002, pp. 592-612, Chap. 13 Sec. 3.

Billaudel B. et al., "Direct Effect of Corticostrone upon Insuline Secretion Studied by Three Different Techniques," Horm. Metabl. Res, 1979, pp. 555-560, vol. 11.

Billaudel B., "Immediate in-vivo effect of corticosterone on glucose-induced insulin secretion in the rat," Journ of Endocrin, 1982, pp. 315-320, vol. 95.

Bland R. et al., "Characterization of 11.beta.-hydroxysteroid dehydrongenase activity and corticosteroid receptor expression in human osteosarcoma cell lines," J. of Endocrin, 1999, pp. 455-464, vol. 161.

Boscaro M. et al., "Cushing's syndrome," The Lancet, 2001, pp. 783-791, vol. 357.

Budziszewska., "Effect of antidepressant drugs on the hypothalamic-pituitary-adrenal axis activity and glucocorticoid receptor function," Polish Journal of Pharm, 2002, pp. 343-349, vol. 54.

Cooper M.S. et al., "Expression and Functional Consequences of 11.beta.—Hydroxysteroid Dehydrogenase Activity in Human Bone," Bone, 2000, pp. 375-381, vol. 27 (3).

Cooper M.S. et al., "Modulation of 110-Hydroxysteroid Dehydrogenase Enzymes by Proinflammatory Cytokines in Osteoblasts: An Autocrine Switch from Glucocorticoid Inactivation to Activation," J Bone Miner Res, 2001, pp. 1037-1044, vol. 16.

Cooper M.S. et al., "Osteoblastic 11.beta.-Hydroxysteroid Dehydrogenase Type 1 Activity Increases With Age and Glucocorticoid Exposure," J. of Bone & Mineral Res, 2002, pp, 979-986, vol. 17 (6).

Davani et al., "Type 1 11.beta.-Hydroxysteroid Dehydrogenase Mediates Glucocorticoid Activation and Insulin Release in Pancreatic Islets," Journal of Biol. Chem, 2000, pp. 34841-34844, vol. 275.

De Battista et al., "The use of mifepristone in the treatment of neuropsychiatric disorders," Trends in Endoc. Metab, 2006, pp. 117-120, vol. 17.

De Quervain, "Glucocorticoid-related genetic susceptibility for Alzheimer's Disease," Hum. Molec. Genetics, 2004, pp. 47-52, vol. 13 (1).

Gomez Sanchez et al., "Central hypertensinogenic effects of glycyrrhizic acid and carbenoxolone," AJP Endocrinology and Metabolism, 2006, pp. E1125-E1130, vol. 263 (6).

Goodman ,Gilman's., "The Pharmacological Basis of Therapeutics, seventh Edition MacMillan Publishing Company New York, NY," 1985.

Greene T.W. et al., "Protective Groups in Organic Synthesis," 1999, pp. 494-653, 3rd Ed, John Wiley & Sons.

Hammami M.M., "Regulation of 11.beta.-Hydroxysteroid Dehydrogenase Activity in Human SkinFibroblasts: enzymatic Modulation of Glucocorticoid Action," Journal of Clin endocrinology Metab, 1991, pp. 326-334, vol. 73.

Han et al., "Properly Designed Modular Asymmetric Synthesis for Enantiopure Sulfinamise Auxiliaries from N-Sulfonyl1 ,2,3-oxathiazolidine-2-oxide Agents," J. Am. Chem. Soc., 2002, pp. 7880-7881, 124.

Harris, H.J. et al., "Intracellular regeneration of glucocorticoids by 11 beta- hydroxysteroid dehydrogenase (11 beta-HSD)-1 plays a key role in regulation of the hypothalamic-pituitary-adrenal axis: analysis of 11 beta-HSD-1-deficient mice," Endocrinology, 2001, pp. 114-120, 142 (1).

Hermanowski Vosatka A. et al., "11.beta.-HSD1 inhibition ameliorates metabolic syndrome and prevents progression of atherosclerosis in mice," J. of Exp. Med, 2005, pp. 517-527, vol. 202 (4).

Higuchi T., "Pro-drugs as Novel Delivery Systems," Bioreversible Carriers in Drug Design, 1975, vol. 14, American Pharmaceutical Association and Pergamon Press.

Hodge G. et al., "Salt-sensitive hypertension resulting from nitric oxide synthase inhibition is associated with loss of regulation of angiotensin II in the rat," Exp. Physiol, 2002, pp. 1-8, vol. 87 (1).

Hong et al., "Synthesis and biological studies of novel neurotensin (8-13) mimetics," Bioorganic & Medicinal Chemistry, 2002, pp. 3849-3858, vol. 10 (12).

International Search Report for application No. PCT/US2006/000210, Mailed on Aug. 11, 2006, 5 pages.

International Search Report for application No. PCT/US2006/000402, Mailed on Sep. 11, 2006, 6 pages.

International Search Report for application No. PCT/US2007/066125, Mailed on Sep. 21, 2007,5 pages.

International Search Report for application No. PCT/US2008/073830, Mailed on Mar. 12, 2009,5 pages.

Issa A.M. et al., "Hypothalamic-Pituitary-Adrenal Activity in Aged, Cognitively Impaired and Cognitively Unimpaired Rats," J. of Neurosci, 1990, pp. 3247-3254, vol. 10 (10).

Jones CD et al., "Effects of Substituent Modification on Face Selection in Reduction," Journal OrQ. Chem, 1998, pp. 2758-2760, vol. 63.

Kerr D.S., "Modulation of hippocampal long-term potentiation and long-term depression by corticosteroid receptor activation," Psychobiology, 1994, pp. 123-133, vol. 22.

Kershaw E.E., "Adipocyte-Specific Glucocorticoid Inactivation Protects Against Diet—Induced Obesity," Diabetes, 2005, pp. 1023-1031, vol. 54.

Kim C. H. et al., "Effects of dexamethasone on proliferation, activity, and cytkine secretion of normal human bone marrow stromal cells: possible mechanisms of glucocorticoidinduced bone loss," Journ of Endocrin, 1999, pp. 371-379, vol. 162.

Kolocouris N. et al., "Synthesis and antiviral activity evaluation of some new aminoadamantane derivatives," Journal of Medicinal Chemistry, 1996, pp. 3307-3318, vol. 39 (17).

Kornel L., "Steroids Mechanism of the Effects of Glucocorticoids and mineralocorticoids on Vascular Smooth Muscle Contractility," 1993, pp. 580-587, vol. 58.

Kozlowski J.A. et al., "Substituted 2-R-Methyl Piperazines as Muscarinic M2 Selective Ligands," Bioorg & Medicin Chem Ltrs, 2002, pp. 791-794, vol. 12.

Lakshmi et al., "Regional Distribution of 11-beta-Hydroxysteroid Dehydrogenase in Rat Brain," Endocrinology, 1991, 128 (4),1741-1748.

Landfield.,"Hippocampal Cell Death," Science, 1996, vol. 272, pp. 1249-1251.

Rehman, et al., "Effect of Glucocotrticoids on Bone Density", Medical and Pediatric Oncology, 2003, vol. 41 (3), pp. 212-216.

Le Noble W.J. et al., "5-tert-Butyladamantan-2-one," J Org Chem, 1983, pp. 1099-1101, vol. 48.

Lupien S., "Cortisol Levels during Human aging Predict Hippocampal Atrophy and memory deficits," Nat Neurosci, 1998, pp. 69-73, vol. 1 (1).

Mason D., "Genetic variation in the stress response: susceptibility to experimental allergic encephalomyelitis and implications for human inflammatory disease," Immun, 1991, pp. 57-60, vol. 12 (2).

Masuzaki et al., "Transgenic Amplification of Glucocorticoid Action in Adipose Tissue Causes High Blood Pressure in Mice," Journal of Clin Invest, 2003, pp. 83-90, vol. 112 (1).

Masuzaki H. et al., "A Transgenic Model of Fisceral Obesity and the Metabolic Syndrome," Science, 2001, pp. 2166-2170, vol. 294.

McEwen., "Glucocorticoids, depression, and mood disorders: structural remodeling in the brain," Metab. Clin. and Exp, 2005, vol. 54, pp. 20-23.

* cited by examiner

INHIBITORS OF THE 11-BETA-HYDROXYSTEROID DEHYDROGENASE TYPE 1 ENZYME

CROSS-REFERENCE TO RELATED APPLICATIONS

This is a continuation of U.S. patent application Ser. No. 12/725,560, filed on Mar. 17, 2010, which is a continuation of U.S. patent application Ser. No. 11/119,022, filed on Apr. 29, 2005, now U.S. Pat. No. 7,880,001, which issued on Feb. 1, 2011, which claims priority to U.S. Provisional Patent Application No. 60/618,857, filed on Oct. 13, 2004 and U.S. Provisional Patent Application No. 60/566,265, filed on Apr. 29, 2004, the contents of all of which are hereby incorporated by reference.

FIELD OF INVENTION

The present invention relates to compounds which are inhibitors of the 11-beta-hydroxysteroid dehydrogenase Type 1 enzyme. The present invention further relates to the use of inhibitors of 11-beta-hydroxysteroid dehydrogenase Type 1 enzyme for the treatment of non-insulin dependent type 2 diabetes, insulin resistance, obesity, lipid disorders, metabolic syndrome, and other diseases and conditions that are mediated by excessive glucocorticoid action.

BACKGROUND OF THE INVENTION

Insulin is a hormone which modulates glucose and lipid metabolism. Impaired action of insulin (i.e., insulin resistance) results in reduced insulin-induced glucose uptake, oxidation and storage, reduced insulin-dependent suppression of fatty acid release from adipose tissue (i.e., lipolysis), and reduced insulin-mediated suppression of hepatic glucose production and secretion. Insulin resistance frequently occurs in diseases that lead to increased and premature morbidity and mortality.

Diabetes mellitus is characterized by an elevation of plasma glucose levels (hyperglycemia) in the fasting state or after administration of glucose during a glucose tolerance test. While this disease may be caused by several underlying factors, it is generally grouped into two categories, Type 1 and Type 2 diabetes. Type 1 diabetes, also referred to as Insulin Dependent Diabetes Mellitus ("IDDM"), is caused by a reduction of production and secretion of insulin. In type 2 diabetes, also referred to as non-insulin dependent diabetes mellitus, or NIDDM, insulin resistance is a significant pathogenic factor in the development of hyperglycemia. Typically, the insulin levels in type 2 diabetes patients are elevated (i.e., hyperinsulinemia), but this compensatory increase is not sufficient to overcome the insulin resistance. Persistent or uncontrolled hyperglycemia in both type 1 and type 2 diabetes mellitus is associated with increased incidence of macrovascular and/or microvascular complications including atherosclerosis, coronary heart disease, peripheral vascular disease, stroke, nephropathy, neuropathy, and retinopathy.

Insulin resistance, even in the absence of profound hyperglycemia, is a component of the metabolic syndrome. Recently, diagnostic criteria for metabolic syndrome have been established. To qualify a patient as having metabolic syndrome, three out of the five following criteria must be met: elevated blood pressure above 130/85 mmHg, fasting blood glucose above 110 mg/dl, abdominal obesity above 40" (men) or 35" (women) waist circumference, and blood lipid changes as defined by an increase in triglycerides above 150 mg/dl or decreased HDL cholesterol below 40 mg/dl (men) or 50 mg/dl (women). It is currently estimated that 50 million adults, in the US alone, fulfill these criteria. That population, whether or not they develop overt diabetes mellitus, are at increased risk of developing the macrovascular and microvascular complications of type 2 diabetes listed above.

Available treatments for type 2 diabetes have recognized limitations. Diet and physical exercise can have profound beneficial effects in type 2 diabetes patients, but compliance is poor. Even in patients having good compliance, other forms of therapy may be required to further improve glucose and lipid metabolism.

One therapeutic strategy is to increase insulin levels to overcome insulin resistance. This may be achieved through direct injection of insulin or through stimulation of the endogenous insulin secretion in pancreatic beta cells. Sulfonylureas (e.g., tolbutamide and glipizide) or meglitinide are examples of drugs that stimulate insulin secretion (i.e., insulin secretagogues) thereby increasing circulating insulin concentrations high enough to stimulate insulin-resistant tissue. However, insulin and insulin secretagogues may lead to dangerously low glucose concentrations (i.e., hypoglycemia). In addition, insulin secretagogues frequently lose therapeutic potency over time.

Two biguanides, metformin and phenformin, may improve insulin sensitivity and glucose metabolism in diabetic patients. However, the mechanism of action is not well understood. Both compounds may lead to lactic acidosis and gastrointestinal side effects (e.g., nausea or diarrhea).

Alpha-glucosidase inhibitors (e.g., acarbose) may delay carbohydrate absorption from the gut after meals, which may in turn lower blood glucose levels, particularly in the postprandial period. Like biguanides, these compounds may also cause gastrointestinal side effects.

Glitazones (i.e., 5-benzylthiazolidine-2,4-diones) are a newer class of compounds used in the treatment of type 2 diabetes. These agents may reduce insulin resistance in multiple tissues, thus lowering blood glucose. The risk of hypoglycemia may also be avoided. Glitazones modify the activity of the Peroxisome Proliferator Activated Receptor ("PPAR") gamma subtype. PPAR is currently believed to be the primary therapeutic target for the main mechanism of action for the beneficial effects of these compounds. Other modulators of the PPAR family of proteins are currently in development for the treatment of type 2 diabetes and/or dyslipidemia. Marketed glitazones suffer from side effects including bodyweight gain and peripheral edema.

Additional treatments to normalize blood glucose levels in patients with diabetes mellitus are needed. Other therapeutic strategies are being explored. For example, research is being conducted concerning Glucagon-Like Peptide 1 ("GLP-1") analogues and inhibitors of Dipeptidyl Peptidase IV ("DPP-IV") that increase insulin secretion. Other examples include: Inhibitors of key enzymes involved in the hepatic glucose production and secretion (e.g., fructose-1,6-bisphosphatase inhibitors), and direct modulation of enzymes involved in insulin signaling (e.g., Protein Tyrosine Phosphatase-1B, or "PTP-1B").

Another method of treating or prophylactically treating diabetes mellitus includes using inhibitors of 11-β-hydroxysteroid dehydrogenase Type 1 (11β-HSD1). Such methods are discussed in J. R. Seckl et al., Endocrinology, 142: 1371-1376, 2001, and references cited therein. Glucocorticoids are steroid hormones that are potent regulators of glucose and lipid metabolism. Excessive glucocorticoid action may lead to insulin resistance, type 2 diabetes, dyslipidemia, increased abdominal obesity, and hypertension. Glucocorticoids circulate in the blood in an active form (i.e., cortisol in humans) and an inactive form (i.e., cortisone in humans). 11β-HSD1, which is highly expressed in liver and adipose tissue, converts cortisone to cortisol leading to higher local concentration of cortisol. Inhibition of 11β-HSD1 prevents or decreases the tissue specific amplification of glucocorticoid action thus imparting beneficial effects on blood pressure and glucose- and lipid-metabolism.

Thus, inhibiting 11β-HSD1 benefits patients suffering from non-insulin dependent type 2 diabetes, insulin resistance, obesity, lipid disorders, metabolic syndrome, and other diseases and conditions mediated by excessive glucocorticoid action.

SUMMARY OF THE INVENTION

One aspect of the present invention is directed toward a compound of formula (I)

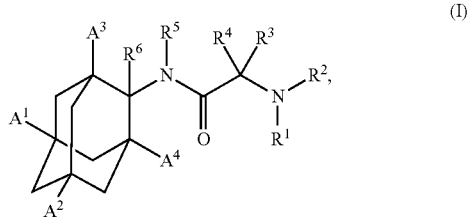

wherein
or therapeutically acceptable salt or prodrug thereof, wherein $A^1$, $A^2$, $A^3$, and $A^4$ are each independently selected from the group consisting of hydrogen, alkyl, alkyl-NH-alkyl, alkylcarbonyl, alkylsulfonyl, cycloalkyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heterocycle, heterocyclealkyl, heterocycleoxyalkyl, —NR$^7$—[C(R$^8$R$^9$)]$_n$—C(O)—R$^{19}$, —O—[C(R$^{11}$R$^{12}$)]$_p$—C(O)—R$^{13}$, —OR$^{14}$, —N(R$^{15}$R$^{16}$), —CO$_2$R$^{17}$, —C(O)—N(R$^{18}$R$^{19}$), —C(R$^{20}$R$^{21}$)—OR$^{22}$, and —C(R$^{23}$R$^{24}$)—N(R$^{25}$R$^{26}$);

n is 0 or 1;
p is 0 or 1;

$R^1$ and $R^2$ are each independently selected from the group consisting of hydrogen, alkyl, alkoxyalkyl, alkyl-NH-alkyl, aryloxyalkyl, aryl-NH-alkyl, carboxyalkyl, carboxycycloalkyl, heterocycleoxyalkyl, heterocycle-NH-alkyl, cycloalkyl, aryl, arylalkyl, haloalkyl, heterocycle, heterocyclealkyl, heterocycle-heterocycle, and aryl-heterocycle, or $R^1$ and $R^2$ together with the atom to which they are attached form a heterocycle;

$R^3$ and $R^4$ are each independently selected from the group consisting of hydrogen, alkyl, carboxyalkyl, carboxycycloalkyl, cycloalkyl, haloalkyl, aryl, and heterocycle, or $R^3$ and $R^4$ together with the atom to which they are attached form a ring selected from the group consisting of cycloalkyl and non-aromatic heterocycle;

or $R^2$ and $R^3$ together with the atoms to which they are attached form a non-aromatic heterocycle;

$R^5$ is selected from the group consisting of hydrogen, alkyl, carboxyalkyl, carboxycycloalkyl, cycloalkyl, aryl, arylalkyl, aryloxyalkyl, heterocycle, heterocyclealkyl, and heterocycleoxyalkyl;

$R^6$ is selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl;

$R^7$ is selected from the group consisting of hydrogen, alkyl, carboxyalkyl, cycloalkyl, carboxycycloalkyl, aryl, arylalkyl, aryloxyalkyl, aryloxy, hydroxy, alkoxy, cycloalkyloxy, heterocycleoxy, heterocycle, heterocyclealkyl, and heterocycleoxyalkyl;

$R^8$ and $R^9$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or $R^8$ and $R^9$ together with the atom to which they are attached form a ring selected from the group consisting of cycloalkyl and non-aromatic heterocycle;

$R^{10}$ is selected from the group consisting of hydrogen, alkyl, carboxy, carboxyalkyl, cycloalkyl, carboxycycloalkyl, aryl, aryloxy, arylalkyl, aryloxyalkyl, hydroxy, alkoxy, cycloalkyloxy, heterocycleoxy, heterocycle, heterocyclealkyl, heterocycleoxyalkyl, and —N(R$^{27}$R$^{28}$);

$R^{11}$ and $R^{12}$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or $R^{11}$ and $R^{12}$ together with the atom to which they are attached form a ring selected from the group consisting of cycloalkyl and non-aromatic heterocycle;

$R^{13}$ is selected from the group consisting of hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heterocycleoxy, heterocycle, heterocyclealkyl, heterocycleoxyalkyl, and —N(R$^{29}$R$^{30}$);

$R^{14}$ is selected from the group consisting of hydrogen, alkyl, carboxyalkyl, cycloalkyl, carboxycycloalkyl, aryl, arylalkyl, aryloxyalkyl, haloalkyl, heterocycle, heterocyclealkyl, and heterocycleoxyalkyl;

$R^{15}$ and $R^{16}$ are each independently selected from the group consisting of hydrogen, alkyl, carboxyalkyl, cycloalkyl, carboxycycloalkyl, aryl, arylalkyl, aryloxyalkyl, heterocycle, heterocyclealkyl, heterocycleoxyalkyl, alkyl sulfonyl, cycloalkylsulfonyl, arylsulfonyl, and heterocyclesulfonyl, or $R^{15}$ and $R^{16}$ together with the atom to which they are attached form a heterocycle;

$R^{17}$ is selected from the group consisting of hydrogen, alkyl, carboxyalkyl, cycloalkyl, carboxycycloalkyl, aryl, arylalkyl, aryloxyalkyl, heterocycle, heterocyclealkyl, and heterocycleoxyalkyl;

$R^{18}$ and $R^{19}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{18}$ and $R^{19}$ together with the atom to which they are attached form a non-aromatic heterocycle;

$R^{20}$, $R^{21}$ and $R^{22}$ are each independently selected from the group consisting of hydrogen, alkyl, carboxyalkyl, carboxycycloalkyl, cycloalkyl, haloalkyl, aryl, and heterocycle;

$R^{23}$ and $R^{24}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, cycloalkyl, aryl, and heterocycle;

$R^{25}$ and $R^{26}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, hydroxy, alkoxy, cycloalkyloxy, aryloxy, heterocycleoxy, cycloalkyl, aryl, and heterocycle, or $R^{25}$ and $R^{26}$ together with the atom to which they are attached form a heterocycle;

$R^{27}$ and $R^{28}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{27}$ and $R^{28}$ together with the atom to which they are attached form a non-aromatic heterocycle; and $R^{29}$ and $R^{30}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{29}$ and $R^{30}$ together with the atom to which they are attached form a non-aromatic heterocycle;

provided that if $R^6$ is hydrogen, then at least one of $A^1$, $A^2$, $A^3$ and $A^4$ is not hydrogen.

A further aspect of the present invention encompasses the use of the compounds of formula (I) for the treatment of disorders that are mediated by 11-beta-hydroxysteroid dehydrogenase Type 1 enzyme, such as non-insulin dependent type 2 diabetes, insulin resistance, obesity, lipid disorders, metabolic syndrome, and other diseases and conditions that are mediated by excessive glucocorticoid action.

According to still another aspect, the present invention is directed to a pharmaceutical composition comprising a therapeutically effective amount of a compound of formula (I) in combination with a pharmaceutically suitable carrier.

DETAILED DESCRIPTION OF THE INVENTION

All patents, patent applications, and literature references cited in the specification are herein incorporated by reference in their entirety.

One aspect of the present invention is directed toward a compound of formula (I)

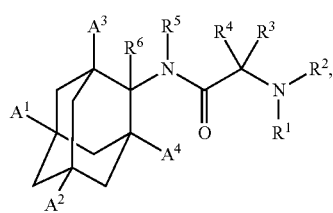

(I)

wherein
or therapeutically acceptable salt or prodrug thereof, wherein $A^1$, $A^2$, $A^3$, and $A^4$ are each independently selected from the group consisting of hydrogen, alkyl, alkyl-NH-alkyl, alkylcarbonyl, alkylsulfonyl, cycloalkyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heterocycle, heterocyclealkyl, heterocycleoxyalkyl, —$NR^7$—[$C(R^8R^9)$]$_n$—$C(O)$—$R^{16}$, —O—[$C(R^{11}R^{12})$]$_p$—C(O)—$R^{13}$, —$OR^{14}$, —$N(R^{15}R^{16})$, —$CO_2R^{17}$, —$C(O)$—N($R^{18}R^{19}$), —$C(R^{20}R^{21})$—$OR^{22}$, and —$C(R^{23}R^{24})$—N($R^{25}R^{26}$);

n is 0 or 1;
p is 0 or 1;

$R^1$ and $R^2$ are each independently selected from the group consisting of hydrogen, alkyl, alkoxyalkyl, alkyl-NH-alkyl, aryloxyalkyl, aryl-NH-alkyl, carboxyalkyl, carboxycycloalkyl, heterocycleoxyalkyl, heterocycle-NH-alkyl, cycloalkyl, aryl, arylalkyl, haloalkyl, heterocycle, heterocyclealkyl, heterocycle-heterocycle, and aryl-heterocycle, or $R^1$ and $R^2$ together with the atom to which they are attached form a heterocycle;

$R^3$ and $R^4$ are each independently selected from the group consisting of hydrogen, alkyl, carboxyalkyl, carboxycycloalkyl, cycloalkyl, haloalkyl, aryl, and heterocycle, or $R^3$ and $R^4$ together with the atom to which they are attached form a ring selected from the group consisting of cycloalkyl and non-aromatic heterocycle;

or $R^2$ and $R^3$ together with the atoms to which they are attached form a non-aromatic heterocycle;

$R^5$ is selected from the group consisting of hydrogen, alkyl, carboxyalkyl, carboxycycloalkyl, cycloalkyl, aryl, arylalkyl, aryloxyalkyl, heterocycle, heterocyclealkyl, and heterocycleoxyalkyl;

$R^6$ is selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl;

$R^7$ is selected from the group consisting of hydrogen, alkyl, carboxyalkyl, cycloalkyl, carboxycycloalkyl, aryl, arylalkyl, aryloxyalkyl, aryloxy, hydroxy, alkoxy, cycloalkyloxy, heterocycleoxy, heterocycle, heterocyclealkyl, and heterocycleoxyalkyl;

$R^8$ and $R^9$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or $R^8$ and $R^9$ together with the atom to which they are attached form a ring selected from the group consisting of cycloalkyl and non-aromatic heterocycle;

$R^{10}$ is selected from the group consisting of hydrogen, alkyl, carboxy, carboxyalkyl, cycloalkyl, carboxycycloalkyl, aryl, aryloxy, arylalkyl, aryloxyalkyl, hydroxy, alkoxy, cycloalkyloxy, heterocycleoxy, heterocycle, heterocyclealkyl, heterocycleoxyalkyl, and —N($R^{27}R^{28}$);

$R^{11}$ and $R^{12}$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or $R^{11}$ and $R^{12}$ together with the atom to which they are attached form a ring selected from the group consisting of cycloalkyl and non-aromatic heterocycle;

$R^{13}$ is selected from the group consisting of hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heterocycleoxy, heterocycle, heterocyclealkyl, heterocycleoxyalkyl, and —N($R^{29}R^{30}$);

$R^{14}$ is selected from the group consisting of hydrogen, alkyl, carboxyalkyl, cycloalkyl, carboxycycloalkyl, aryl, arylalkyl, aryloxyalkyl, haloalkyl, heterocycle, heterocyclealkyl, and heterocycleoxyalkyl;

$R^{15}$ and $R^{16}$ are each independently selected from the group consisting of hydrogen, alkyl, carboxyalkyl, cycloalkyl, carboxycycloalkyl, aryl, arylalkyl, aryloxyalkyl, heterocycle, heterocyclealkyl, heterocycleoxyalkyl, alkylsulfonyl, cycloalkylsulfonyl, arylsulfonyl, and heterocyclesulfonyl, or $R^{15}$ and $R^{16}$ together with the atom to which they are attached form a heterocycle;

$R^{17}$ is selected from the group consisting of hydrogen, alkyl, carboxyalkyl, cycloalkyl, carboxycycloalkyl, aryl, arylalkyl, aryloxyalkyl, heterocycle, heterocyclealkyl, and heterocycleoxyalkyl;

$R^{18}$ and $R^{19}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{18}$ and $R^{19}$ together with the atom to which they are attached form a non-aromatic heterocycle;

$R^{20}$, $R^{21}$ and $R^{22}$ are each independently selected from the group consisting of hydrogen, alkyl, carboxyalkyl, carboxycycloalkyl, cycloalkyl, haloalkyl, aryl, and heterocycle;

$R^{23}$ and $R^{24}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, cycloalkyl, aryl, and heterocycle;

$R^{25}$ and $R^{26}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, hydroxy, alkoxy, cycloalkyloxy, aryloxy, heterocycleoxy, cycloalkyl, aryl, and heterocycle, or $R^{25}$ and $R^{26}$ together with the atom to which they are attached form a heterocycle;

$R^{27}$ and $R^{28}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{27}$ and $R^{28}$ together with the atom to which they are attached form a non-aromatic heterocycle; and $R^{29}$ and $R^{30}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{29}$ and $R^{30}$ together with the atom to which they are attached form a non-aromatic heterocycle;

provided that if $R^6$ is hydrogen, then at least one of $A^1$, $A^2$, $A^3$ and $A^4$ is not hydrogen.

Another aspect of the present invention is directed toward a therapeutically suitable metabolite of a compound of formula (I).

Another aspect of the present invention is directed to a compound of formula (II)

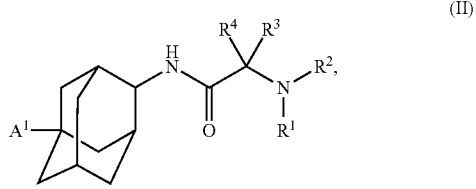

(II)

or a therapeutically suitable salt or prodrug thereof, wherein $A^1$ is selected from the group consisting of alkyl, alkyl-NH-alkyl, alkylcarbonyl, alkylsulfonyl, cycloalkyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heterocycle, heterocyclealkyl, heterocycleoxyalkyl, $-NR^7-[C(R^8R^9)]_n-C(O)-R^{10}$, $-O-[C(R^{11}R^{12})]_p-C(O)-R^{13}$, $-OR^{14}$, $-N(R^{15}R^{16})$, $-CO_2R^{17}$, $-C(O)-N(R^{18}R^{19})$, $-C(R^{20}R^{21})-OR^{22}$, and $-C(R^{23}R^{24})-N(R^{25}R^{26})$;

$R^1$ and $R^2$ are each independently selected from the group consisting of hydrogen, alkyl, alkoxyalkyl, alkyl-NH-alkyl, aryloxyalkyl, aryl-NH-alkyl, carboxyalkyl, carboxycycloalkyl, heterocycleoxyalkyl, heterocycle-NH-alkyl, cycloalkyl, aryl, arylalkyl, haloalkyl, heterocycle, heterocyclealkyl, heterocycle-heterocycle, and aryl-heterocycle, or $R^1$ and $R^2$ together with the atom to which they are attached form a heterocycle;

$R^3$ and $R^4$ are each independently selected from the group consisting of hydrogen, alkyl, carboxyalkyl, carboxycycloalkyl, cycloalkyl, haloalkyl, aryl, and heterocycle, or $R^3$ and $R^4$ together with the atom to which they are attached form a ring selected from the group consisting of cycloalkyl and non-aromatic heterocycle;

or $R^2$ and $R^3$ together with the atoms to which they are attached form a non-aromatic heterocycle;

$R^7$ is selected from the group consisting of hydrogen, alkyl, carboxyalkyl, cycloalkyl, carboxycycloalkyl, aryl, arylalkyl, aryloxyalkyl, aryloxy, hydroxy, alkoxy, cycloalkyloxy, heterocycleoxy, heterocycle, heterocyclealkyl, and heterocycleoxyalkyl;

$R^8$ and $R^9$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or $R^8$ and $R^9$ together with the atom to which they are attached form a ring selected from the group consisting of cycloalkyl and non-aromatic heterocycle;

$R^{10}$ is selected from the group consisting of hydrogen, alkyl, carboxy, carboxyalkyl, cycloalkyl, carboxycycloalkyl, aryl, aryloxy, arylalkyl, aryloxyalkyl, hydroxy, alkoxy, cycloalkyloxy, heterocycleoxy, heterocycle, heterocyclealkyl, heterocycleoxyalkyl, and $-N(R^{27}R^{28})$;

$R^{11}$ and $R^{12}$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or $R^{11}$ and $R^{12}$ together with the atom to which they are attached form a ring selected from the group consisting of cycloalkyl and non-aromatic heterocycle;

$R^{13}$ is selected from the group consisting of hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heterocycleoxy, heterocycle, heterocyclealkyl, heterocycleoxyalkyl, and $-N(R^{29}R^{30})$;

$R^{14}$ is selected from the group consisting of hydrogen, alkyl, carboxyalkyl, cycloalkyl, carboxycycloalkyl, aryl, arylalkyl, aryloxyalkyl, haloalkyl, heterocycle, heterocyclealkyl, and heterocycleoxyalkyl;

$R^{15}$ and $R^{16}$ are each independently selected from the group consisting of hydrogen, alkyl, carboxyalkyl, cycloalkyl, carboxycycloalkyl, aryl, arylalkyl, aryloxyalkyl, heterocycle, heterocyclealkyl, heterocycleoxyalkyl, alkylsulfonyl, cycloalkylsulfonyl, arylsulfonyl, and heterocyclesulfonyl, or $R^{15}$ and $R^{16}$ together with the atom to which they are attached form a heterocycle;

R[17] is selected from the group consisting of hydrogen, alkyl, carboxyalkyl, cycloalkyl, carboxycycloalkyl, aryl, arylalkyl, aryloxyalkyl, heterocycle, heterocyclealkyl, and heterocycleoxyalkyl;

R[18] and R[19] are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or R[18] and R[19] together with the atom to which they are attached form a non-aromatic heterocycle;

R[20], R[21] and R[22] are each independently selected from the group consisting of hydrogen, alkyl, carboxyalkyl, carboxycycloalkyl, cycloalkyl, haloalkyl, aryl, and heterocycle;

R[23] and R[24] are each independently selected from the group consisting of hydrogen, alkyl, alkyl carbonyl, alkylsulfonyl, carboxyalkyl, carboxycycloalkyl, cycloalkyl carbonyl, cycloalkylsulfonyl, arylcarbonyl, arylsulfonyl, heterocyclecarbonyl, heterocyclesulfonyl, cycloalkyl, aryl, and heterocycle;

R[25] and R[26] are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, hydroxy, alkoxy, cycloalkyloxy, aryloxy, heterocycleoxy, cycloalkyl, aryl, and heterocycle, or R[25] and R[26] together with the atom to which they are attached form a heterocycle;

R[27] and R[28] are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or R[27] and R[28] together with the atom to which they are attached form a non-aromatic heterocycle; and R[29] and R[30] are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or R[29] and R[30] together with the atom to which they are attached form a non-aromatic heterocycle.

Another aspect of the present invention is directed to a compound of formula (III),

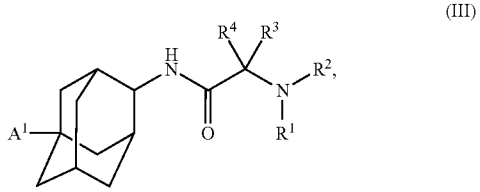

(III)

or a therapeutically suitable salt or prodrug thereof, wherein $A^1$ is selected from the group consisting of alkyl, alkyl-NH-alkyl, alkylcarbonyl, alkylsulfonyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heterocycle, heterocyclealkyl, heterocycleoxyalkyl, —NR[7]—[C(R[8]R[9])]$_n$—C(O)—R[10], —O—[C(R[11]R[12])]$_p$— C(O)—R[13], —OR[14], —N(R[15]R[16]), —CO$_2$R[17], —C(O)—N(R[18]R[19]), —C(R[20]R[21])—OR[22], and —C(R[23]R[24])—N(R[25]R[26]);

$R^1$ and $R^2$ are each independently selected from the group consisting of hydrogen, alkyl, alkoxyalkyl, alkyl-NH-alkyl, aryloxyalkyl, aryl-NH-alkyl, carboxyalkyl, carboxycycloalkyl, heterocycleoxyalkyl, heterocycle-NH-alkyl, cycloalkyl, aryl, arylalkyl, haloalkyl, heterocycle, heterocyclealkyl, heterocycle-heterocycle, and aryl-heterocycle;

$R^3$ and $R^4$ are each independently selected from the group consisting of hydrogen, alkyl, carboxyalkyl, carboxycycloalkyl, cycloalkyl, aryl, and heterocycle;

$R^7$ is selected from the group consisting of hydrogen, alkyl, carboxyalkyl, cycloalkyl, carboxycycloalkyl, aryl, arylalkyl, aryloxyalkyl, aryloxy, hydroxy, alkoxy, cycloalkyloxy, heterocycleoxy, heterocycle, heterocyclealkyl, and heterocycleoxyalkyl;

$R^8$ and $R^9$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or $R^8$ and $R^9$ together with the atom to which they are attached form a ring selected from the group consisting of cycloalkyl and non-aromatic heterocycle;

R[10] is selected from the group consisting of hydrogen, alkyl, carboxy, carboxyalkyl, cycloalkyl, carboxycycloalkyl, aryl, aryloxy, arylalkyl, aryloxyalkyl, hydroxy, alkoxy, cycloalkyloxy, heterocycleoxy, heterocycle, heterocyclealkyl, heterocycleoxyalkyl, and —N(R[27]R[28]);

R[11] and R[12] are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or R[11] and R[12] together with the atom to which they are attached form a group consisting of cycloalkyl and non-aromatic heterocycle;

R[13] is selected from the group consisting of hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heterocycleoxy, heterocycle, heterocyclealkyl, heterocycleoxyalkyl, and —N(R[29]R[30]);

R[14] is selected from the group consisting of hydrogen, alkyl, carboxyalkyl, cycloalkyl, carboxycycloalkyl, aryl, arylalkyl, aryloxyalkyl, haloalkyl, heterocycle, heterocyclealkyl, and heterocycleoxyalkyl;

R[15] and R[16] are each independently selected from the group consisting of hydrogen, alkyl, carboxyalkyl, cycloalkyl, carboxycycloalkyl, aryl, arylalkyl, aryl oxyalkyl, heterocycle, heterocyclealkyl, heterocycleoxyalkyl, alkylsulfonyl, cycloalkylsulfonyl, arylsulfonyl, and heterocyclesulfonyl, or R[15] and R[16] together with the atom to which they are attached form a heterocycle;

R[17] is selected from the group consisting of hydrogen, alkyl, carboxyalkyl, cycloalkyl, carboxycycloalkyl, aryl, arylalkyl, aryloxyalkyl, heterocycle, heterocyclealkyl, and heterocycleoxyalkyl;

R[18] and R[19] are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or R[18] and R[19] together with the atom to which they are attached form a non-aromatic heterocycle;

R[20], R[21] and R[22] are each independently selected from the group consisting of hydrogen, alkyl, carboxyalkyl, carboxycycloalkyl, cycloalkyl, haloalkyl, aryl, and heterocycle;

$R^{23}$ and $R^{24}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, aryl carbonyl, arylsulfonyl, heterocyclecarbonyl, heterocyclesulfonyl, cycloalkyl, aryl, and heterocycle;

$R^{25}$ and $R^{26}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, hydroxy, alkoxy, cycloalkyloxy, aryloxy, heterocycleoxy, cycloalkyl, aryl, and heterocycle, or $R^{25}$ and $R^{26}$ together with the atom to which they are attached form a heterocycle;

$R^{27}$ and $R^{28}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{27}$ and $R^{28}$ together with the atom to which they are attached form a non-aromatic heterocycle; and $R^{29}$ and $R^{30}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{29}$ and $R^{30}$ together with the atom to which they are attached form a non-aromatic heterocycle.

Another aspect of the present invention is directed to a compound of formula (IV),

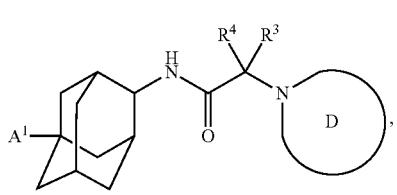

(IV)

or a therapeutically suitable salt or prodrug thereof, wherein $A^1$ is selected from the group consisting of alkyl, alkyl-NH-alkyl, alkylcarbonyl, alkylsulfonyl, cycloalkyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heterocycle, heterocyclealkyl, heterocycleoxyalkyl, $-NR^7-[C(R^8R^9)]_n-C(O)-R^{16}$, $-O-[C(R^{11}R^{12})]_p-C(O)-R^{13}$, $-OR^{14}$, $-N(R^{15}R^{16})$, $-CO_2R^{17}$, $-C(O)-N(R^{18}R^{19})$, $-C(R^{20}R^{21})-OR^{22}$, and $-C(R^{23}R^{24})-N(R^{25}R^{26})$;

D is a non-aromatic heterocycle;

$R^3$ and $R^4$ are each independently selected from the group consisting of hydrogen, alkyl, carboxyalkyl, carboxycycloalkyl, cycloalkyl, haloalkyl, aryl and heterocycle, or $R^3$ and $R^4$ together with the atom to which they are attached form a ring selected from the group consisting of cycloalkyl and non-aromatic heterocycle;

$R^7$ is selected from the group consisting of hydrogen, alkyl, carboxyalkyl, cycloalkyl, cycloalkyl, arylalkyl, aryloxyalkyl, aryloxy, hydroxy, alkoxy, cycloalkyloxy, heterocycleoxy, heterocycle, heterocyclealkyl, and heterocycleoxyalkyl;

$R^8$ and $R^9$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or $R^8$ and $R^9$ together with the atom to which they are attached form a ring selected from the group consisting of cycloalkyl and non-aromatic heterocycle;

$R^{10}$ is selected from the group consisting of hydrogen, alkyl, carboxy, carboxyalkyl, cycloalkyl, carboxycycloalkyl, aryl, aryloxy, arylalkyl, aryloxyalkyl, hydroxy, alkoxy, cycloalkyloxy, heterocycleoxy, heterocycle, heterocyclealkyl, heterocycleoxyalkyl, and $-N(R^{27}R^{28})$;

$R^{11}$ and $R^{12}$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or $R^{11}$ and $R^{12}$ together with the atom to which they are attached form a ring selected from the group consisting of cycloalkyl and non-aromatic heterocycle;

$R^{13}$ is selected from the group consisting of hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heterocycleoxy, heterocycle, heterocyclealkyl, heterocycleoxyalkyl, and $-N(R^{29}R^{30})$;

$R^{14}$ is selected from the group consisting of hydrogen, alkyl, carboxyalkyl, cycloalkyl, carboxycycloalkyl, aryl, arylalkyl, aryloxyalkyl, haloalkyl, heterocycle, heterocyclealkyl, and heterocycleoxyalkyl;

$R^{15}$ and $R^{16}$ are each independently selected from the group consisting of hydrogen, alkyl, carboxyalkyl, cycloalkyl, carboxycycloalkyl, aryl, arylalkyl, aryloxyalkyl, heterocycle, heterocyclealkyl, heterocycleoxyalkyl, alkylsulfonyl, cycloalkylsulfonyl, arylsulfonyl, and heterocyclesulfonyl, or $R^{15}$ and $R^{16}$ together with the atom to which they are attached form a heterocycle;

$R^{17}$ is selected from the group consisting of hydrogen, alkyl, carboxyalkyl, cycloalkyl, carboxycycloalkyl, aryl, arylalkyl, aryloxyalkyl, heterocycle, heterocyclealkyl, and heterocycleoxyalkyl;

$R^{18}$ and $R^{19}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{18}$ and $R^{19}$ together with the atom to which they are attached form a non-aromatic heterocycle;

$R^{20}$, $R^{21}$ and $R^{22}$ are each independently selected from the group consisting of hydrogen, alkyl, carboxyalkyl, carboxycycloalkyl, cycloalkyl, haloalkyl, aryl, and heterocycle;

$R^{23}$ and $R^{24}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, cycloalkyl, awl, and heterocycle;

$R^{25}$ and $R^{26}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, hydroxy, alkoxy, cycloalkyloxy, aryloxy, heterocycleoxy, cycloalkyl, awl, and heterocycle, or $R^{25}$ and $R^{26}$ together with the atom to which they are attached form a heterocycle;

$R^{27}$ and $R^{28}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{27}$ and $R^{28}$ together with the atom to which they are attached form a non-aromatic heterocycle; and $R^{29}$ and $R^{30}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{29}$ and $R^{30}$ together with the atom to which they are attached form a non-aromatic heterocycle.

Another aspect of the present invention is directed to a compound of formula (V),

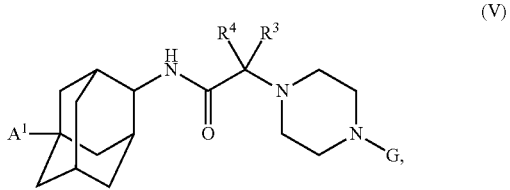

(V)

or a therapeutically suitable salt or prodrug thereof, wherein $A^1$ is selected from the group consisting of alkyl, alkyl-NH-alkyl, alkylcarbonyl, alkylsulfonyl, cycloalkyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heterocycle, heterocyclealkyl, heterocycleoxyalkyl, $-NR^7-[C(R^8R^9)]_n-C(O)-R^{10}$, $-O-[C(R^{11}R^{12})]_p-C(O)-R^{13}$, $-OR^{14}$, $-N(R^{15}R^{16})$, $-CO_2R^{17}$, $-C(O)-N(R^{18}R^{19})$, $-C(R^{20}R^{21})-OR^{22}$; and $-C(R^{23}R^{24})-N(R^{25}R^{26})$;

G is selected from the group consisting of aryl and heterocycle;

$R^3$ and $R^4$ are each independently selected from the group consisting of hydrogen, alkyl, carboxyalkyl, carboxycycloalkyl, cycloalkyl, haloalkyl, aryl, and heterocycle, or $R^3$ and $R^4$ together with the atom to which they are attached form a ring selected from the group consisting of cycloalkyl and non-aromatic heterocycle;

$R^7$ is selected from the group consisting of hydrogen, alkyl, carboxyalkyl, cycloalkyl, carboxycycloalkyl, aryl, arylalkyl, aryloxyalkyl, aryloxy, hydroxy, alkoxy, cycloalkyloxy, heterocycleoxy, heterocycle, heterocyclealkyl, and heterocycleoxyalkyl;

$R^8$ and $R^9$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or $R^8$ and $R^9$ together with the atom to which they are attached form a ring selected from the group consisting of cycloalkyl and non-aromatic heterocycle;

$R^{10}$ is selected from the group consisting of hydrogen, alkyl, carboxy, carboxyalkyl, cycloalkyl, carboxycycloalkyl, aryl, aryloxy, arylalkyl, aryloxyalkyl, hydroxy, alkoxy, cycloalkyloxy, heterocycleoxy, heterocycle, heterocyclealkyl, heterocycleoxyalkyl, and $-N(R^{27}R^{28})$;

$R^{11}$ and $R^{12}$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or $R^{11}$ and $R^{12}$ together with the atom to which they are attached form a non-aromatic heterocycle;

$R^{13}$ is selected from the group consisting of hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heterocycleoxy, heterocycle, heterocyclealkyl, heterocycleoxyalkyl, and $-N(R^{29}R^{30})$;

$R^{14}$ is selected from the group consisting of hydrogen, alkyl, carboxyalkyl, cycloalkyl, carboxycycloalkyl, aryl, aryl alkyl, aryloxyalkyl, haloalkyl, heterocycle, heterocyclealkyl, and heterocycleoxyalkyl;

$R^{15}$ and $R^{16}$ are each independently selected from the group consisting of hydrogen, alkyl, carboxyalkyl, cycloalkyl, carboxycycloalkyl, aryl, arylalkyl, aryloxyalkyl, heterocycle, heterocyclealkyl, heterocycleoxyalkyl, alkylsulfonyl, cycloalkylsulfonyl, arylsulfonyl, and heterocyclesulfonyl, or $R^{15}$ and $R^{16}$ together with the atom to which they are attached form a heterocycle;

$R^{17}$ is selected from the group consisting of hydrogen, alkyl, carboxyalkyl, cycloalkyl, carboxycycloalkyl, aryl, arylalkyl, aryloxyalkyl, heterocycle, heterocyclealkyl, and heterocycleoxyalkyl;

$R^{18}$ and $R^{19}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{18}$ and $R^{19}$ together with the atom to which they are attached form a non-aromatic heterocycle;

$R^{20}$, $R^{21}$ and $R^{22}$ are each independently selected from the group consisting of hydrogen, alkyl, carboxyalkyl, carboxycycloalkyl, cycloalkyl, haloalkyl, aryl, and heterocycle;

$R^{23}$ and $R^{24}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, cycloalkyl, aryl, and heterocycle;

$R^{25}$ and $R^{26}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, hydroxy, alkoxy, cycloalkyloxy, aryloxy, heterocycleoxy, cycloalkyl, aryl, and heterocycle, or $R^{25}$ and $R^{26}$ together with the atom to which they are attached form a heterocycle;

$R^{27}$ and $R^{28}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{27}$ and $R^{28}$ together with the atom to which they are attached form a non-aromatic heterocycle; and $R^{29}$ and $R^{30}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{29}$ and $R^{30}$ together with the atom to which they are attached form a non-aromatic heterocycle.

Another aspect of the present invention is directed to a compound of formula (VI),

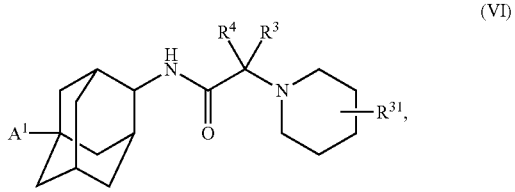

or a therapeutically suitable salt or prodrug thereof, wherein

A¹ is selected from the group consisting of alkyl, alkyl-NH-alkyl, alkylcarbonyl, alkylsulfonyl, cycloalkyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heterocycle, heterocyclealkyl, heterocycleoxyalkyl, —NR⁷—[C(R⁸R⁹)]ₙ—C(O)—R¹⁰, —O—[C(R¹¹R¹²)]ₚ—C(O)—R¹³, —OR¹⁴, —N(R¹⁵R¹⁶), —CO₂R¹⁷, —C(O)—N(R¹⁸R¹⁹), —C(R²⁰R²¹)—OR²², and —C(R²³R²⁴)—N(R²⁵R²⁶);

R³ and R⁴ are each independently selected from the group consisting of hydrogen, alkyl, carboxyalkyl, carboxycycloalkyl, cycloalkyl, haloalkyl, aryl, and heterocycle, or R³ and R⁴ together with the atom to which they are attached form a ring selected from the group consisting of cycloalkyl and non-aromatic heterocycle;

R⁷ is selected from the group consisting of hydrogen, alkyl, carboxyalkyl, cycloalkyl, carboxycycloalkyl, aryl, arylalkyl, aryloxyalkyl, aryloxy, hydroxy, alkoxy, cycloalkyloxy, heterocycleoxy, heterocycle, heterocyclealkyl, and heterocycleoxyalkyl;

R⁸ and R⁹ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or R⁸ and R⁹ together with the atom to which they are attached form a ring selected from the group consisting of cycloalkyl and non-aromatic heterocycle;

R¹⁰ is selected from the group consisting of hydrogen, alkyl, carboxy, carboxyalkyl, cycloalkyl, carboxycycloalkyl, aryl, aryloxy, arylalkyl, aryloxyalkyl, hydroxy, alkoxy, cycloalkyloxy, heterocycleoxy, heterocycle, heterocyclealkyl, heterocycleoxyalkyl, and —N(R²⁷R²⁸);

R¹¹ and R¹² are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or R¹¹ and R¹² together with the atom to which they are attached form a non-aromatic heterocycle;

R¹³ is selected from the group consisting of hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heterocycleoxy, heterocycle, heterocyclealkyl, heterocycleoxyalkyl, and —N(R²⁹R³⁰);

R¹⁴ is selected from the group consisting of hydrogen, alkyl, carboxyalkyl, cycloalkyl, carboxycycloalkyl, aryl, arylalkyl, aryloxyalkyl, haloalkyl, heterocycle, heterocyclealkyl, and heterocycleoxyalkyl;

R¹⁵ and R¹⁶ are each independently selected from the group consisting of hydrogen, alkyl, carboxyalkyl, cycloalkyl, carboxycycloalkyl, aryl, arylalkyl, aryloxyalkyl, heterocycle, heterocyclealkyl, heterocycleoxyalkyl, alkylsulfonyl, cycloalkylsulfonyl, arylsulfonyl, and heterocyclesulfonyl, or R¹⁵ and R¹⁶ together with the atom to which they are attached form a heterocycle;

R¹⁷ is selected from the group consisting of hydrogen, alkyl, carboxyalkyl, cycloalkyl, carboxycycloalkyl, aryl, arylalkyl, aryloxyalkyl, heterocycle, heterocyclealkyl, and heterocycleoxyalkyl;

R¹⁸ and R¹⁹ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or R¹⁸ and R¹⁹ together with the atom to which they are attached form a non-aromatic heterocycle;

R²⁰, R²¹ and R²² are each independently selected from the group consisting of hydrogen, alkyl, carboxyalkyl, carboxycycloalkyl, cycloalkyl, haloalkyl, aryl, and heterocycle;

R²³ and R²⁴ are each independently selected from the group consisting of hydrogen, alkyl, alkylcarbonyl, alkylsulfonyl, carboxyalkyl, carboxycycloalkyl, cycloalkylcarbonyl, cycloalkyl aryl carbonyl, arylsulfonyl, heterocyclecarbonyl, heterocyclesulfonyl, cycloalkyl, awl, and heterocycle;

R²⁵ and R²⁶ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, hydroxy, alkoxy, cycloalkyloxy, aryloxy, heterocycleoxy, cycloalkyl, aryl, and heterocycle, or R²⁵ and R²⁶ together with the atom to which they are attached form a heterocycle;

R²⁷ and R²⁸ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or R²⁷ and R²⁸ together with the atom to which they are attached form a non-aromatic heterocycle;

R²⁹ and R³⁰ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or R²⁹ and R³⁰ together with the atom to which they are attached form a non-aromatic heterocycle; and R³¹ is selected from the group consisting of alkyl, alkoxy, aryl, arylalkyl, aryloxy, aryloxyalkyl, cycloalkoxy, halogen, haloalkyl, heterocycle, heterocyclealkyl, heterocycleoxy, heterocycleoxyalkyl and hydroxy.

Another aspect of the present invention is directed to a compound of formula (VII),

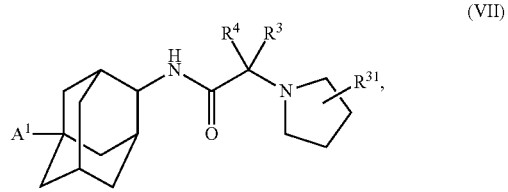

or a therapeutically suitable salt or prodrug thereof, wherein

A¹ is selected from the group consisting of alkyl, alkyl-NH-alkyl, alkylcarbonyl, alkylsulfonyl, cycloalkyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heterocycle, heterocyclealkyl, heterocycleoxyalkyl, —NR$^7$—[C(R$^8$R$^9$)]$_n$—C(O)—R$^{10}$, —O—[C(R$^{11}$R$^{12}$)]$_p$—C(O)—R$^{13}$, —OR$^{14}$, —N(R$^{15}$R$^{16}$), —CO$_2$R$^{17}$, —C(O)—N(R$^{18}$R$^{19}$), —C(R$^{20}$R$^{21}$)—OR$^{22}$, and —C(R$^{23}$R$^{24}$)—N(R$^{25}$R$^{26}$);

R$^3$ and R$^4$ are each independently selected from the group consisting of hydrogen, alkyl, carboxyalkyl, carboxycycloalkyl, cycloalkyl, haloalkyl, aryl, and heterocycle, or R$^3$ and R$^4$ together with the atom to which they are attached form a ring selected from the group consisting of cycloalkyl and non-aromatic heterocycle;

R$^7$ is selected from the group consisting of hydrogen, alkyl, carboxyalkyl, cycloalkyl, carboxycycloalkyl, aryl, arylalkyl, aryloxyalkyl, aryloxy, hydroxy, alkoxy, cycloalkyloxy, heterocycleoxy, heterocycle, heterocyclealkyl, and heterocycleoxyalkyl;

R$^8$ and R$^9$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or R$^8$ and R$^9$ together with the atom to which they are attached form a ring selected from the group consisting of cycloalkyl and non-aromatic heterocycle;

R$^{10}$ is selected from the group consisting of hydrogen, alkyl, carboxy, carboxyalkyl, cycloalkyl, carboxycycloalkyl, aryl, aryloxy, arylalkyl, aryloxyalkyl, hydroxy, alkoxy, cycloalkyloxy, heterocycleoxy, heterocycle, heterocyclealkyl, heterocycleoxyalkyl, and —N(R$^{27}$R$^{28}$);

R$^{11}$ and R$^{12}$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or R$^{11}$ and R$^{12}$ together with the atom to which they are attached form a non-aromatic heterocycle;

R$^{13}$ is selected from the group consisting of hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heterocycleoxy, heterocycle, heterocyclealkyl, heterocycleoxyalkyl, and —N(R$^{29}$R$^{30}$);

R$^{14}$ is selected from the group consisting of hydrogen, alkyl, carboxyalkyl, cycloalkyl, carboxycycloalkyl, aryl, arylalkyl, aryloxyalkyl, haloalkyl, heterocycle, heterocyclealkyl, and heterocycleoxyalkyl;

R$^{15}$ and R$^{16}$ are each independently selected from the group consisting of hydrogen, alkyl, carboxyalkyl, cycloalkyl, carboxycycloalkyl, aryl, arylalkyl, aryloxyalkyl, heterocycle, heterocyclealkyl, heterocycleoxyalkyl, alkylsulfonyl, cycloalkylsulfonyl, arylsulfonyl, and heterocyclesulfonyl, or R$^{15}$ and R$^{16}$ together with the atom to which they are attached form a heterocycle;

R$^{17}$ is selected from the group consisting of hydrogen, alkyl, carboxyalkyl, cycloalkyl, carboxycycloalkyl, aryl, arylalkyl, aryloxyalkyl, heterocycle, heterocyclealkyl, and heterocycleoxyalkyl;

R$^{18}$ and R$^{19}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or R$^{18}$ and R$^{19}$ together with the atom to which they are attached form a non-aromatic heterocycle;

R$^{20}$, R$^{21}$ and R$^{22}$ are each independently selected from the group consisting of hydrogen, alkyl, carboxyalkyl, carboxycycloalkyl, cycloalkyl, haloalkyl, aryl, and heterocycle;

R$^{23}$ and R$^{24}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, cycloalkyl, aryl, and heterocycle;

R$^{25}$ and R$^{26}$ are each independently selected from the group consisting of hydrogen, alkyl, alkyl carbonyl, alkylsulfonyl, carboxyalkyl, carboxycycloalkyl, cycloalkyl carbonyl, cycloalkylsulfonyl, arylcarbonyl, arylsulfonyl, heterocyclecarbonyl, heterocyclesulfonyl, hydroxy, alkoxy, cycloalkyloxy, aryloxy, heterocycleoxy, cycloalkyl, aryl, and heterocycle, or R$^{25}$ and R$^{26}$ together with the atom to which they are attached form a heterocycle;

R$^{27}$ and R$^{28}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or R$^{27}$ and R$^{28}$ together with the atom to which they are attached form a non-aromatic heterocycle;

R$^{29}$ and R$^{30}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or R$^{29}$ and R$^{30}$ together with the atom to which they are attached form a non-aromatic heterocycle; and R$^{31}$ is selected from the group consisting of alkyl, alkoxy, aryl, arylalkyl, aryloxy, aryloxyalkyl, cycloalkoxy, halogen, haloalkyl, heterocycle, heterocyclealkyl, heterocycleoxy, heterocycleoxyalkyl and hydroxy.

Another aspect of the present invention is directed to a compound of formula (VIII)

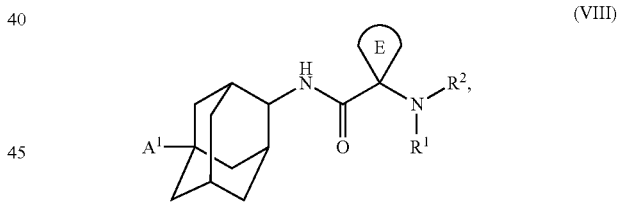

(VIII)

or a therapeutically suitable salt or prodrug thereof, wherein

A$^1$ is selected from the group consisting of —OH, —CO$_2$H, carboxyalkyl, carboxycycloalkyl, and —C(O)—N(R$^{18}$R$^{19}$);

E is selected from the group consisting of cycloalkyl and non-aromatic heterocycle;

R$^1$ and R$^2$ are each independently selected from the group consisting of hydrogen, alkyl, alkoxyalkyl, alkyl-NH-alkyl, aryloxyalkyl, aryl-NH-alkyl, carboxyalkyl, carboxycycloalkyl, heterocycleoxyalkyl, heterocycle-NH-alkyl, cycloalkyl, aryl, arylalkyl, haloalkyl, heterocycle, heterocyclealkyl, heterocycle-heterocycle, and aryl-heterocycle; and R$^{18}$ and R$^{19}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or R$^{18}$ and R$^{19}$ together with the atom to which they are attached form a non-aromatic heterocycle.

Another aspect of the present invention is directed to a compound of formula (IX),

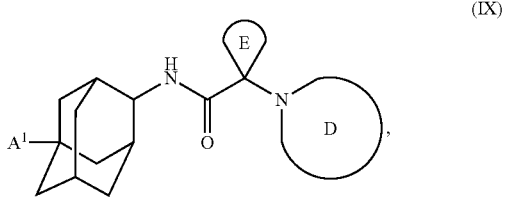

(IX)

or a therapeutically suitable salt or prodrug thereof, wherein

A$^1$ is selected from the group consisting of —OH, —CO$_2$H, carboxyalkyl, carboxycycloalkyl, and —C(O)—N(R$^{18}$R$^{19}$);

D is a non-aromatic heterocycle;

E is selected from the group consisting of cycloalkyl and non-aromatic heterocycle; and R$^{18}$ and R$^{19}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or R$^{18}$ and R$^{19}$ together with the atom to which they are attached form a non-aromatic heterocycle.

Another aspect of the present invention is directed to a method of inhibiting 11-beta-hydroxysteroid dehydrogenase Type I enzyme, comprising administering to a mammal, a therapeutically effective amount of a compound of formula (I, II, III, IV, V, VI, VII, VIII or IX).

Another aspect of the present invention is directed to a method of treating or prophylactically treating disorders in a mammal by inhibiting 11-beta-hydroxysteroid dehydrogenase Type I enzyme, comprising administering to a mammal, a therapeutically effective amount of a compound of formula (I, II, III, IV, V, VI, VII, VIII or IX).

Another aspect of the present invention is directed to a method of treating or prophylactically treating non-insulin dependent type 2 diabetes, insulin resistance, obesity, lipid disorders, metabolic syndrome or diseases and conditions that are mediated by excessive glucocorticoid action, in a mammal by inhibiting 11-beta-hydroxysteroid dehydrogenase Type I enzyme, comprising administering to a mammal, a therapeutically effective amount of a compound of formula (I, II, III, IV, V, VI, VII, VIII or IX).

Another aspect of the present invention is directed to a pharmaceutical composition comprising a therapeutically effective amount of a compound of formula (I, II, III, IV, V, VI, VII, VIII or IX) in combination with a pharmaceutically suitable carrier.

As set forth herein, the invention includes administering a therapeutically effective amount of any of the compounds of formula I-IX and the salts and prodrugs thereof to a mammal. Preferably, the invention also includes administering a therapeutically effective amount of any of the compounds of formula I-IX to a human, and more preferably to a human in need of being treated for or prophylactically treated for any of the respective disorders set forth herein.

Definition Of Terms

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl," as used herein, refers to an alkoxy group, as defined herein, appended to the parent molecular moiety through a carbonyl group, as defined herein.

Representative examples of alkoxycarbonyl include, but are not limited to, methoxycarbonyl, ethoxycarbonyl, and tert-butoxycarbonyl.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkyl carbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkyl-NH," as used herein, refers to an alkyl group, as defined herein, appended to the parent molecular moiety through a nitrogen atom.

The term "alkyl-NH-alkyl," as used herein, refers to an alkyl-NH group, as defined herein, appended to the parent molecular moiety through an alkyl group, as defined herein.

The term "aryl," as used herein, refers to a monocyclic-ring system or a polycyclic-ring system wherein one or more of the fused rings are aromatic. Representative examples of aryl include, but are not limited to, anthracenyl, azulenyl, fluorenyl, indanyl, indenyl, naphthyl, phenyl, and tetrahydronaphthyl.

The aryl groups of this invention may be optionally substituted with 0, 1, 2, 3, 4 or 5 substituents independently selected from alkenyl, alkenylthio, alkenyloxy, alkoxy, alkoxyalkoxy, alkoxyalkoxyalkoxy, alkoxyalkoxyalkyl, alkoxyalkyl, alkoxycarbonyl, alkoxycarbonylalkoxy, alkoxycarbonylalkyl, alkoxysulfonyl, alkyl, alkylcarbonyl, alkylcarbonylalkoxy, alkylcarbonylalkyl, alkylcarbonylalkylthio, alkylcarbonyloxy, alkylcarbonylthio, alkylsulfinyl, alkylsulfinylalkyl, alkyl sulfonyl, alkylsulfonylalkyl, alkylthio, alkylthioalkyl, alkylthioalkoxy, alkynyl, alkynyloxy, alkynylthio, aryl, arylcarbonyl, aryloxy, arylsulfonyl, carboxy, carboxyalkoxy, carboxyalkyl, cyano, cyanoalkoxy, cyanoalkyl, cyanoalkylthio, ethyl en edioxy, formyl, formyl alkoxy, formyl alkyl, haloalkenyl, haloalkenyloxy, haloalkoxy, haloalkyl, haloalkynyl, haloalkynyloxy, halogen, heterocycle, heterocyclecarbonyl, heterocycleoxy, heterocyclsulfonyl, hydroxy, hydroxyalkoxy, hydroxyalkyl, mercapto, mercaptoalkoxy, mercaptoalkyl, methylenedioxy, nitro, $R_fR_gN—$, $R_fR_gNalkyl$, $R_fR_gNcarbonyl$ and $R_fR_gNsulfonyl$, wherein $R_f$ and $R_g$ are members independently selected from the group consisting of hydrogen, alkyl, alkoxyalkyl, alkylcarbonyl, alkylsulfonyl, alkoxycarbonyl, cycloalkyl, cycloalkylalkyl, cycloalkylcarbonyl and cycloalkylsulfonyl, and wherein substituent aryl, the aryl of arylcarbonyl, the aryl of aryloxy, the aryl of arylsulfonyl, the substituent heterocycle, the heterocycle of heterocyclecarbonyl, the heterocycle of heterocycleoxy, the heterocycle of heterocyclesulfonyl may be optionally substituted with 0, 1, 2 or 3 substituents independently selected from the group consisting of alkenyl, alkenylthio, alkenyloxy, alkoxy, alkoxyalkoxy, alkoxyalkoxyalkoxy, alkoxyalkoxyalkyl, alkoxyalkyl, alkoxycarbonyl, alkoxycarbonylalkoxy, alkoxycarbonylalkyl, alkoxysulfonyl, alkyl, alkylcarbonyl, alkylcarbonylalkoxy, alkylcarbonylalkyl, alkylcarbonylalkylthio, alkylcarbonyloxy, alkylcarbonylthio, alkylsulfinyl, alkylsulfinylalkyl, alkyl sulfonyl, alkylsulfonylalkyl, alkylthio, alkylthioalkyl, alkylthioalkoxy, alkynyl, alkynyloxy, alkynylthio, carboxy, carboxyalkoxy, carboxyalkyl, cyano, cyanoalkoxy, cyanoalkyl, cyanoalkylthio, ethylenedioxy, formyl, formyl alkoxy, formyl alkyl, haloalkenyl, haloalkenyloxy, haloalkoxy, haloalkyl, haloalkynyl, haloalkynyloxy, halogen, hydroxy, hydroxyalkoxy, hydroxyalkyl, mercapto, mercaptoalkoxy, mercaptoalkyl, methylenedioxy, oxo, nitro, $R_fR_gN—$, $R_fR_gNalkyl$, $R_fR_gNcarbonyl$ and $R_fR_gNsulfonyl$.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-yl-ethyl.

The term "aryl-heterocycle," as used herein, refers to an aryl group, as defined herein, appended to the parent molecular moiety through a heterocycle group, as defined herein.

The term "aryl-NH—," as used herein, refers to an aryl group, as defined herein, appended to the parent molecular moiety through a nitrogen atom.

The term "aryl-NH-alkyl," as used herein, refers to an aryl-NH— group, as defined herein, appended to the parent molecular moiety through an alkyl group, as defined herein.

The term "aryloxy," as used herein, refers to an aryl group, as defined herein, appended to the parent molecular moiety through an oxy moiety, as defined herein. Representative examples of aryloxy include, but are not limited to phenoxy, naphthyloxy, 3-bromophenoxy, 4-chlorophenoxy, 4-methylphenoxy, and 3,5-dimethoxyphenoxy.

The term "aryloxyalkyl," as used herein, refers to an aryloxy group, as defined herein, appended to the parent molecular moiety through an alkyl group, as defined herein.

The term "arylsulfonyl," as used herein, refers to an aryl group, as defined herein, appended to the parent molecular moiety through a sulfonyl group, as defined herein. Representative examples of arylsulfonyl include, but are not limited to, phenylsulfonyl, 4-bromophenylsulfonyl and naphthylsulfonyl.

The term "carbonyl," as used herein refers to a —C(O)— group.

The term "carboxy," as used herein refers to a —C(O)—OH group.

The term "carboxyalkyl," as used herein refers to a carboxy group as defined herein, appended to the parent molecular moiety through an alkyl group as defined herein.

The term "carboxycycloalkyl," as used herein refers to a carboxy group as defined herein, appended to the parent molecular moiety through an cycloalkyl group as defined herein.

The term "cycloalkyl," as used herein, refers to a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The cycloalkyl groups of this invention may be substituted with 1, 2, 3, 4 or 5 substituents independently selected from alkenyl, alkenylthio, alkenyloxy, alkoxy, alkoxyalkoxy, alkoxyalkoxyalkoxy, alkoxyalkoxyalkyl, alkoxyalkyl, alkoxycarbonyl, alkoxycarbonylalkoxy, alkoxycarbonylalkyl, alkoxysulfonyl, alkyl, alkylcarbonyl, alkylcarbonylalkoxy, alkylcarbonylalkyl, alkylcarbonylalkylthio, alkylcarbonyloxy, alkylcarbonylthio, alkylsulfinyl, alkylsulfinylalkyl, alkyl sulfonyl, alkylsulfonyl alkyl, alkylthio, alkylthioalkyl, alkylthioalkoxy, alkynyl, alkynyloxy, alkynylthio, carboxy, carboxyalkoxy, carboxyalkyl, cyano, cyanoalkoxy, cyanoalkyl, cyanoalkylthio, formyl, formylalkoxy, formylalkyl, haloalkenyl, haloalkenyloxy, haloalkoxy, haloalkyl, haloalkynyl, haloalkynyloxy, halogen, hydroxy, hydroxyalkoxy, hydroxyalkyl, mercapto, mercaptoalkoxy, mercaptoalkyl, nitro, $R_fR_gN—$, $R_fR_gNalkyl$, $R_fR_gNcarbonyl$ and $R_fR_gNsulfonyl$, wherein $R_f$ and $R_g$ are members independently selected from the group consisting of hydrogen, alkyl, alkoxyalkyl, alkylcarbonyl, alkylsulfonyl, alkoxycarbonyl, cycloalkyl, cycloalkylalkyl, cycloalkylcarbonyl and cycloalkylsulfonyl.

The term "cycloalkylsulfonyl," as used herein, refers to cycloalkyl group, as defined herein, appended to the parent molecular moiety through a sulfonyl group, as defined herein. Representative examples of cycloalkylsulfonyl include, but are not limited to, cyclohexylsulfonyl and cyclobutylsulfonyl.

The term "halo" or "halogen," as used herein, refers to —Cl, —Br, —I or —F.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic," as used herein, refers to a monocyclic or bicyclic ring system. Monocyclic ring systems are exemplified by any 3- or 4-membered ring containing a heteroatom independently selected from oxygen, nitrogen and sulfur; or a 5-, 6-, 7- or 8-membered ring containing one, two or three heteroatoms wherein the heteroatoms are independently members selected from nitrogen, oxygen and sulfur. The 5-membered ring has from 0-2 double bonds and the 6-, 7-, and 8-membered rings have from 0-3 double bonds. Representative examples of monocyclic ring systems include, but are not limited to, azetidinyl, azepinyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another heterocyclic monocyclic ring system. Bicyclic ring systems can also be bridged and are exemplified by any of the above monocyclic ring systems joined with a cycloalkyl group as defined herein, or another non-aromatic heterocyclic monocyclic ring system. Representative examples of bicyclic ring systems include but are not limited to, for example, benzimidazolyl, benzoazepine, benzothiazolyl, benzothienyl, benzoxazolyl, benzofuranyl, benzopyranyl, benzothiopyranyl, benzodioxinyl, 1,3-benzodioxolyl, cinnolinyl, 1,5-diazocanyl, 3,9-diaza-bicyclo[4.2.1]non-9-yl, 3,7-diazabicyclo[3.3.1]nonane, octahydro-pyrrolo[3,4-c]pyrrole, indazolyl, indolyl, indolinyl, indolizinyl, naphthyridinyl, isobenzofuranyl, isobenzothienyl, isoindolyl, isoindolinyl, isoquinolinyl, phthalazinyl, pyranopyridyl, quinolinyl, quinolizinyl, quinoxalinyl, quinazolinyl, 2,3,4,5-tetrahydro-1H-benzo[c]azepine, 2,3,4,5-tetrahydro-1H-benzo[b]azepine, 2,3,4,5-tetrahydro-1H-benzo[d]azepine, tetrahydroisoquinolinyl, tetrahydroquinolinyl, and thiopyranopyridyl.

The heterocycles of this invention may be optionally substituted with 0, 1, 2 or 3 substituents independently selected from alkenyl, alkenylthio, alkenyloxy, alkoxy, alkoxyalkoxy, alkoxyalkoxyalkoxy, alkoxyalkoxyalkyl, alkoxyalkyl, alkoxycarbonyl, alkoxycarbonylalkoxy, alkoxycarbonylalkyl, alkoxysulfonyl, alkyl, alkylcarbonyl, alkylcarbonylalkoxy, alkyl carbonyl alkyl, alkyl carbonylalkylthio, alkylcarbonyloxy, alkylcarbonylthio, alkylsulfinyl, alkylsulfinylalkyl, alkyl sulfonyl, alkylsulfonylalkyl, alkylthio, alkylthioalkyl, alkylthioalkoxy, alkynyl, alkynyloxy, alkynylthio, aryl, arylcarbonyl, aryloxy, arylsulfonyl, carboxy, carboxyalkoxy, carboxyalkyl, cyano, cyanoalkoxy, cyanoalkyl, cyanoalkylthio, ethylenedioxy, formyl, formylalkoxy, formylalkyl, haloalkenyl, haloalkenyloxy, haloalkoxy, haloalkyl, haloalkynyl, haloalkynyloxy, halogen, heterocycle, heterocyclecarbonyl, heterocycleoxy, heterocyclesulfonyl, hydroxy, hydroxyalkoxy, hydroxyalkyl, mercapto, mercaptoalkoxy, mercaptoalkyl, methylenedioxy, oxo, nitro, $R_fR_gN-$, $R_fR_gNalkyl$, $R_fR_gNcarbonyl$ and $R_fR_gNsulfonyl$, wherein $R_f$ and $R_g$ are members independently selected from the group consisting of hydrogen, alkyl, alkoxyalkyl, alkylcarbonyl, alkylsulfonyl, alkoxycarbonyl, cycloalkyl, cycloalkylalkyl, cycloalkylcarbonyl and cycloalkylsulfonyl, and wherein substituent aryl, the aryl of arylcarbonyl, the aryl of aryloxy, the aryl of arylsulfonyl, the substituent heterocycle, the heterocycle of heterocyclecarbonyl, the heterocycle of heterocycleoxy, the heterocycle of heterocyclesulfonyl may be optionally substituted with 0, 1, 2 or 3 substituents independently selected from the group consisting of alkenyl, alkenylthio, alkenyloxy, alkoxy, alkoxyalkoxy, alkoxyalkoxyalkoxy, alkoxyalkoxyalkyl, alkoxyalkyl, alkoxycarbonyl, alkoxycarbonylalkoxy, alkoxycarbonylalkyl, alkoxysulfonyl, alkyl, alkylcarbonyl, alkylcarbonylalkoxy, alkylcarbonylalkyl, alkylcarbonylalkylthio, alkylcarbonyloxy, alkylcarbonylthio, alkylsulfinyl, alkylsulfinylalkyl, alkyl sulfonyl, alkylsulfonylalkyl, alkylthio, alkylthioalkyl, alkylthioalkoxy, alkynyl, alkynyloxy, alkynylthio, carboxy, carboxyalkoxy, carboxyalkyl, cyano, cyanoalkoxy, cyanoalkyl, cyanoalkylthio, ethylenedioxy, formyl, formylalkoxy, formylalkyl, haloalkenyl, haloalkenyloxy, haloalkoxy, haloalkyl, haloalkynyl, haloalkynyloxy, halogen, hydroxy, hydroxyalkoxy, hydroxyalkyl, mercapto, mercaptoalkoxy, mercaptoalkyl, methyl enedioxy, oxo, nitro, $R_fR_gN-$, $R_fR_g-Nalkyl$, $R_fR_gNcarbonyl$ and $R_fR_gNsulfonyl$.

The term "heterocyclealkyl," as used herein, refers to a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl.

The term "heterocyclealkoxy," as used herein, refers to a heterocycle, as defined herein, appended to the parent molecular moiety through an alkoxy group, as defined herein.

The term "heterocycleoxy," as used herein, refers to a heterocycle, as defined herein, appended to the parent molecular moiety through an oxy group, as defined herein.

The term "heterocycleoxyalkyl," as used herein, refers to a heterocycleoxy, as defined herein, appended to the parent molecular moiety through an alkyl group, as defined herein.

The term "heterocycle-NH—," as used herein, refers to a heterocycle, as defined herein, appended to the parent molecular moiety through a nitrogen atom.

The term "heterocycle-NH-alkyl," as used herein, refers to a heterocycle-NH—, as defined herein, appended to the parent molecular moiety through an alkyl group, as defined herein.

The term "heterocycle-heterocycle," as used herein, refers to a heterocycle, as defined herein, appended to the parent molecular moiety through a heterocycle group, as defined herein.

The term "heterocyclearbonyl," as used herein, refers to a heterocycle, as defined herein, appended to the parent molecular moiety through a carbonyl group, as defined herein.

Representative examples of heterocyclecarbonyl include, but are not limited to, 1-piperidinylcarbonyl, 4-morpholinylcarbonyl, pyridin-3-ylcarbonyl and quinolin-3-ylcarbonyl.

The term "heterocyclesulfonyl," as used herein, refers to a heterocycle, as defined herein, appended to the parent molecular moiety through a sulfonyl group, as defined herein. Representative examples of heterocyclesulfonyl include, but are not limited to, 1-piperidinylsulfonyl, 4-morpholinylsulfonyl, pyridin-3-ylsulfonyl and quinolin-3-ylsulfonyl.

The term "non-aromatic," as used herein, refers to a monocyclic or bicyclic ring system that does not contain the appropriate number of double bonds to satisfy the rule for aromaticity. Representative examples of a "non-aromatic" heterocycles include, but are not limited to, piperidinyl, piperazinyl, homopiperazinyl, and pyrrolidinyl. Representative bicyclic ring systems are exemplified by any of the above monocyclic ring systems fused to an aryl group as defined herein, a cycloalkyl group as defined herein, or another heterocyclic monocyclic ring system.

The term "oxo," as used herein, refers to a =O group appended to the parent molecule through an available carbon atom.

The term "oxy," as used herein, refers to a —O— group.

The term "sulfonyl," as used herein, refers to a —S(O)$_2$— group.

Salts

The present compounds may exist as therapeutically suitable salts. The term "therapeutically suitable salt," refers to salts or zwitterions of the compounds which are water or oil-soluble or dispersible, suitable for treatment of disorders without undue toxicity, irritation, and allergic response, commensurate with a reasonable benefit/risk ratio, and effective for their intended use. The salts may be prepared during the final isolation and purification of the compounds or separately by reacting an amino group of the compounds with a suitable acid. For example, a compound may be dissolved in a suitable solvent, such as but not limited to methanol and water, and treated with at least one equivalent of an acid, like hydrochloric acid. The resulting salt may precipitate out and be isolated by filtration and dried under reduced pressure. Alternatively, the solvent and excess acid may be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of the compounds may also be quaternized with alkyl chlorides, bromides, and iodides such as methyl, ethyl, propyl, isopropyl, butyl, lauryl, myristyl, stearyl, and the like.

Basic addition salts may be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

Prodrugs

The present compounds may also exist as therapeutically suitable prodrugs. The term "therapeutically suitable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds that are rapidly transformed in vivo to the parent compounds of formula (I-IXc) for example, by hydrolysis in blood. The term "prodrug," refers to compounds that contain, but are not limited to, substituents known as "therapeutically suitable esters." The term "therapeutically suitable ester," refers to alkoxycarbonyl groups appended to the parent molecule on an available carbon atom. More specifically, a "therapeutically suitable ester," refers to alkoxycarbonyl groups appended to the parent molecule on one or more available aryl, cycloalkyl and/or heterocycle groups as defined herein. Compounds containing therapeutically suitable esters are an example, but are not intended to limit the scope of compounds considered to be prodrugs. Examples of prodrug ester groups include pivaloyloxymethyl, acetoxymethyl, phthalidyl, indanyl and methoxymethyl, as well as other such groups known in the art. Other examples of prodrug ester groups are found in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

Optical Isomers-Diastereomers-Geometric Isomers

Asymmetric centers may exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described hereinbelow and resolved by techniques well known in the art.

Geometric isomers may exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, sec C. D. Jones, M. Kaselj, R. N. Salvatore, W. J. le Noble J. Org. Chem. 63: 2758-2760, 1998.

The compounds and processes of the present invention will be better understood in connection with the following synthetic schemes and Experimentals that illustrate a means by which the compounds of the invention may be prepared.

The compounds of this invention may be prepared by a variety of procedures and synthetic routes. Representative procedures and synthetic routes are shown in, but are not limited to, Schemes 1-5.

Abbreviations which have been used in the descriptions of the Schemes and the Examples that follow are: DCM for dichloromethane; DMAP for dimethylaminopyridine; DMF for N,N-dimethylformamide; DMSO for dimethylsulfoxide; DAST for (diethylamino)sulfur trifluoride; DIPEA or Hünig's base for diisopropylethylamine; EDCI for (3-dimethylaminopropyl)-3-ethylcarbodiimide HCl; EtOAc for ethyl acetate; EtOH for ethanol; HATU for O-(7-azabenzotriazol-1-yl)-N,N,N',N'-tetramethyluronium hexafluorophosphate; HOBt for hydroxybenzotriazole hydrate; MeOH for methanol; THF for tetrahydrofuran; tosyl for para-toluene sulfonyl, mesyl for methane sulfonyl, triflate for trifluoromethane sulfonyl.

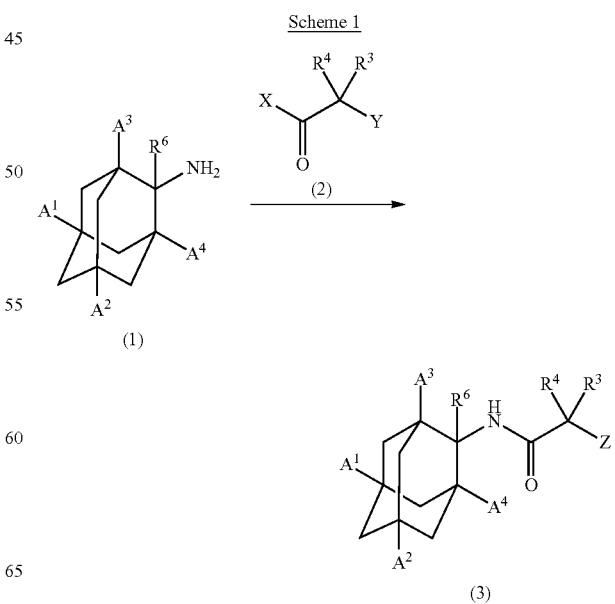

Scheme 1

-continued

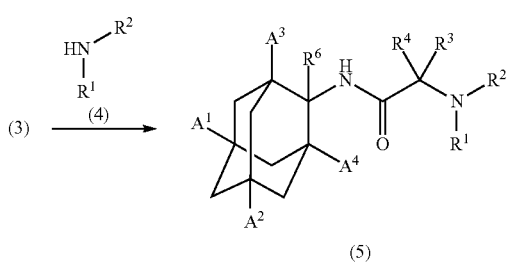

(5)

Substituted adamantanes of general formula (5), wherein $A^1$, $A^2$, $A^3$, $A^4$, $R^1$, $R^2$, $R^3$, $R^4$, and $R^6$ are as defined in formula I, may be prepared as in Scheme 1. Substituted adamantamines of general formula (1), purchased or prepared using methodology known to those in the art, may be treated with acylating agents such as chloroacetyl chloride or 2-bromopropionyl bromide of general formula (2), wherein X is chloro, bromo, or fluoro, Y is a leaving group such as Cl (or a protected or masked leaving group), and $R^3$ and $R^4$ are defined as in formula I, and a base such as diisopropylethylamine to provide amides of general formula (3). Alternatively, acids of general formula (2) wherein X=OH may be coupled to substituted adamantamines of general formula (1) with reagents such as EDCI and HOBt to provide amides of general formula (3) (after conversion of Y into a leaving group Z wherein Z is chloro, bromo, iodo, —O-tosyl, —O-mesyl, or —O-triflate). Amides of general formula (3) may be treated with amines of general formula (4) wherein $R^1$ and $R^2$ are as defined in formula I to provide aminoamides of general formula (5). In some examples, $A^1$, $A^2$, $A^3$, and/or $A^4$ in amines of formula (1) may exist as a group further substituted with a protecting group such as hydroxy protected with acetyl or methoxymethyl. Examples containing a protected functional group may be required due to the synthetic schemes and the reactivity of said groups and could be later removed to provide the desired compound. Such protecting groups may be removed using methodology known to those skilled in the art or as described in T. W. Greene, P. G. M. Wuts "Protective Groups in Organic Synthesis" $3^{1d}$ ed. 1999, Wiley & Sons, Inc.

-continued

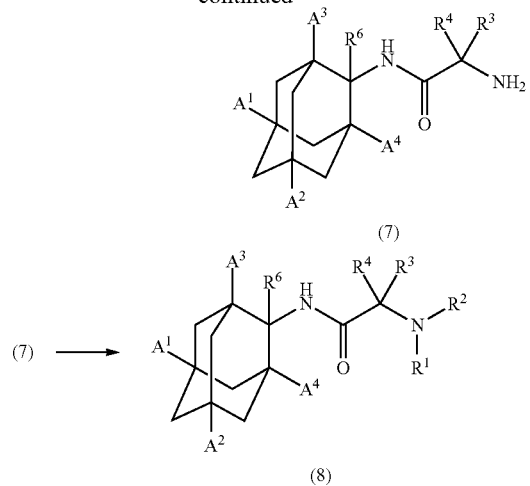

Substituted adamantanes of general formula (8), wherein $A^1$, $A^2$, $A^3$, $A^4$, $R^1$, $R^2$, $R^3$, $R^4$, and $R^6$ are as defined in formula I, may be prepared as in Scheme 2. Substituted adamantamines of general formula (1) may be purchased or prepared using methodology known to those in the art. The amines of general formula (1) may be coupled with protected amino acids of general formula (6) (wherein X is OH, $R^3$ and $R^4$ are defined as in formula I, and Y is a protected or masked amino group) such as N-(tert-butoxycarbonyl)glycine with reagents such as EDCI and HOBt to provide amides of general formula (7) after deprotection. Alternatively, amines of general formula (1) may be treated with activated protected amino acids of general formula (2), wherein Y is a protected or masked amino group, and a base such as diisopropylethylamine to provide amides of general formula (7) after deprotection. Amides of general formula (7) may be treated with alkylating agents such as 1,5-dibromopentane and a base like potassium carbonate to yield amides of general formula (8). Among other methods known to those in the art, amines of general formula (7) may be treated with aldehydes such as benzaldehyde and a reducing agent like sodium cyanoborohydride to yield amides of general formula (8). In some examples, $A^1$, $A^2$, $A^3$, and/or $A^4$ in amines of formula (1) may be a functional group covered with a protecting group such as hydroxy protected with acetyl or methoxymethyl. These protecting groups may be removed using methodology known to those in the art in amides of general formula (7) or (8). Alternatively a group such as chloro may be used and subsequently converted to hydroxyl by irradiating with microwaves in the presence of aqueous hydroxide.

Scheme 2

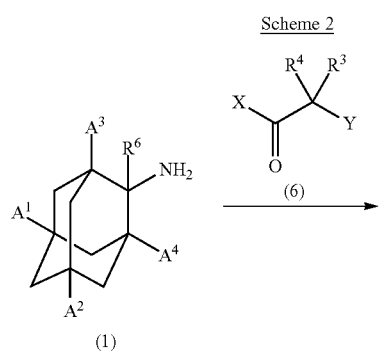

Scheme 3

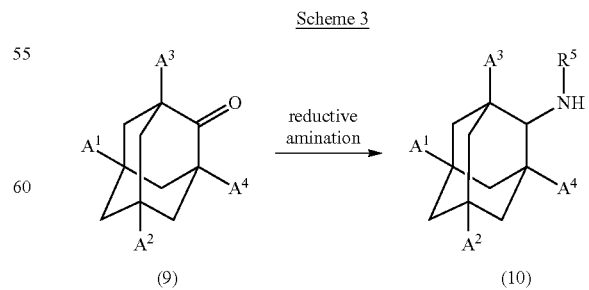

Substituted adamantane amines of general formula (10), wherein $A^1$, $A^2$, $A^3$, $A^4$, and $R^5$ are as defined in formula I, may be prepared as in Scheme 3. Substituted adamantane ketones of general formula (9) may be purchased or prepared using methodology known to those in the art. Ketones of general formula (9) may be treated with ammonia or primary amines ($R^5NH_2$) followed by reduction with sodium borohydride to provide amines of general formula (10). In some examples, $A^1, A^2, A^3$, and/or $A^4$ in ketones of formula (9) may be a functional group covered with a protecting group such as hydroxy protected with acetyl or methoxymethyl. These protecting groups may be removed using methodology known to those in the art in amines of general formula (10) or in compounds subsequently prepared from ketones of general formula (9) or amines of general formula (10). Alternatively a group such as chloro may be used and subsequently converted to hydroxyl by irradiating with microwaves in the presence of aqueous hydroxide.

adamantamines of general formula (15) may be purchased or prepared using methodology known to those in the art. Coupling of acids of general formula (14) and amines of general formula (15) with reagents such as EDCI and HOBt may provide amides of general formula (16). In some examples $A^1, A^2, A^3$ and/or $A^4$ in amines of general formula (15) may contain a functional group such as carboxy protected with a methyl group. In amides of general formula (16), these protecting groups may be removed using methodology known to those skilled in the art.

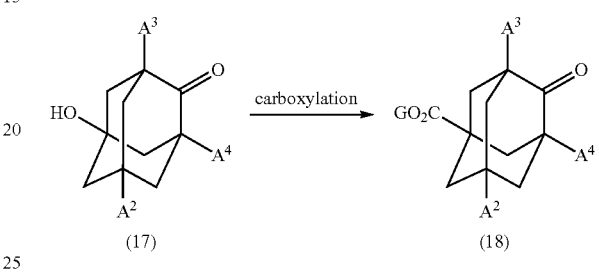

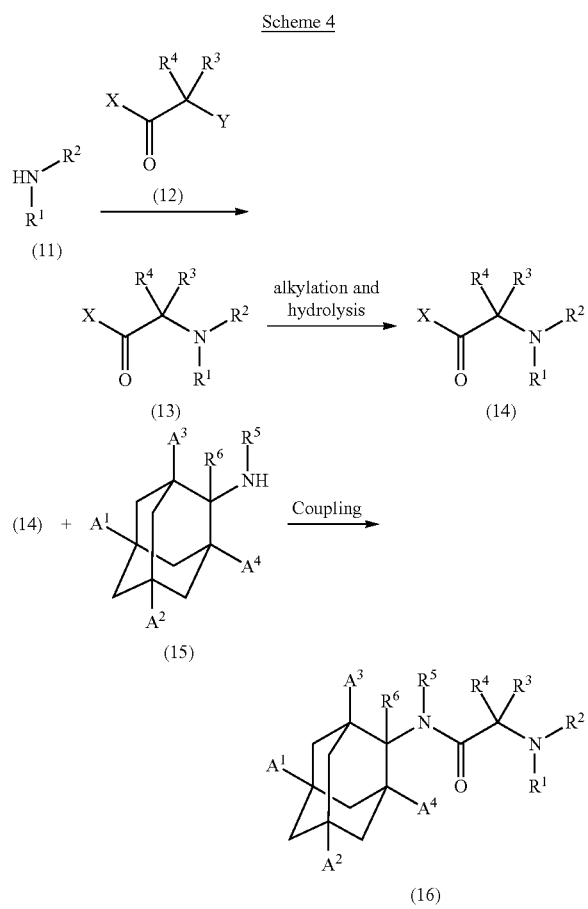

Substituted adamantanes of general formula (18), wherein $A^2, A^3$, and $A^4$ are as defined in formula I, may be prepared as in Scheme 5. Substituted adamantanes of general formula (17) may be purchased or prepared using methodology known to those in the art. Polycycles of general formula (17) may be treated with oleum and formic acid followed by an alcohol GOH, where G is an alkyl, cycloalkyl, aryl, or acid protecting group, to provide polycycles of general formula (18). In some examples, G in formula (9) may be a protecting group such as methyl. These protecting groups may be removed using methodology known to those in the art from polycycles of general formula (18) or in compounds subsequently prepared from (18).

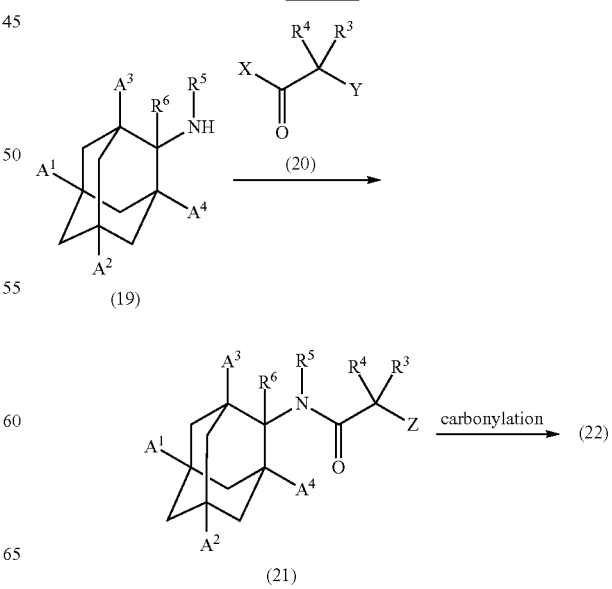

Substituted adamantanes of general formula (16), wherein $A^1, A^2, A^3, A^4, R^1, R^2, R^3, R^4, R^5$, and $R^6$ are as defined in formula I, may be prepared as in Scheme 4. Amines of general formula (11) may be purchased or prepared using methodology known to those in the art. The amines of general formula (11) may be reacted with reagents of general formula (12), wherein $R^3$ and $R^4$ are defined as in formula I and X is an alkoxy group, such as 2-bromopropionic acid methyl ester in the presence of a base like diisopropylethylamine to provide esters of general formula (13). Esters of general formula (13) may be alkylated using a base like lithium diisopropylamide and an alkylating agent such as methyl iodide to yield acids of general formula (14), X=OH, after hydrolysis. Substituted -continued

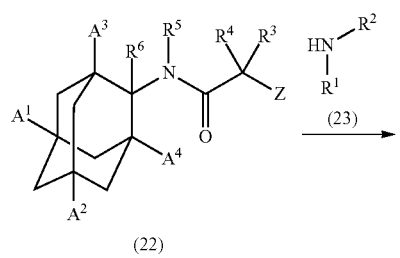

(22)

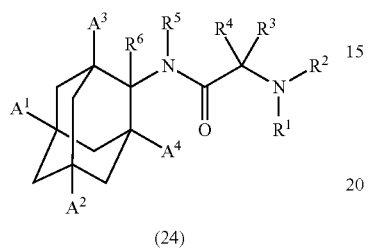

(24)

Substituted adamantanes of general formula (24), wherein $A^1$, $A^2$, $A^3$, $A^4$, $R^1$, $R^2$, $R^3$, $R^4$, $R^5$, and $R^6$ are as defined in formula I, may be prepared as in Scheme 6. Substituted adamantamines of general formula (19), wherein $A^1$, $A^2$, $A^3$, and $A^4$ are defined as in formula one I with the proviso that at least one is a hydroxyl group or a protected or masked hydroxyl group, may be purchased or prepared using methodology known to those in the art. Substituted adamantamines of general formula (19) may be treated with acylating agents such as chloroacetyl chloride or 2-bromopropionyl bromide of general formula (20), wherein X is chloro, bromo, or fluoro, Y is a leaving group such as Cl (or a protected or masked leaving group), and $R^3$ and $R^4$ are defined as in formula I, and a base such as diisopropylethylamine to provide amides of general formula (21). Alternatively, acids of general formula (20) wherein X=OH may be coupled to substituted adamantamines of general formula (19) with reagents such as EDGE and HOSt to provide amides of general formula (21) (after conversion of Y into a leaving group Z wherein Z is chloro, bromo, iodo, —O-tosyl, —O-mesyl, or —O-triflate). Hydroxyadamantanes, or protected or masked hydroxyl adamantanes which can be converted to the corresponding hydroxyadamantane, (21) may be carbonylated with reagents like oleum and formic acid to yield the corresponding adamantyl acid or ester (22), wherein $A^1$, $A^2$, $A^3$, and $A^4$ are defined as in formula one I with the proviso that at least one is a carboxy group or a protected carboxy group ($CO_2R^{17}$ wherein $R^{17}$ is defined as in formula I). Amides of general formula (22) may be treated with amines of general formula (23) wherein $R^1$ and $R^2$ are as defined in formula I to provide aminoamides of general formula (24). In some examples, $A^1$, $A^2$, $A^3$, and/or $A^4$ in amines of formula (24) may exist as a group further substituted with a protecting group such as carboxy protected as an alkyl ester. Examples containing a protected functional group may be required due to the synthetic schemes and the reactivity of said groups and could be later removed to provide the desired compound. Such protecting groups may be removed using methodology known to those skilled in the art or as described in T. W. Greene, P. G. M. Wuts "Protective Groups in Organic Synthesis" 3$^{rd}$ ed. 1999, Wiley & Sons, Inc.

Scheme 7

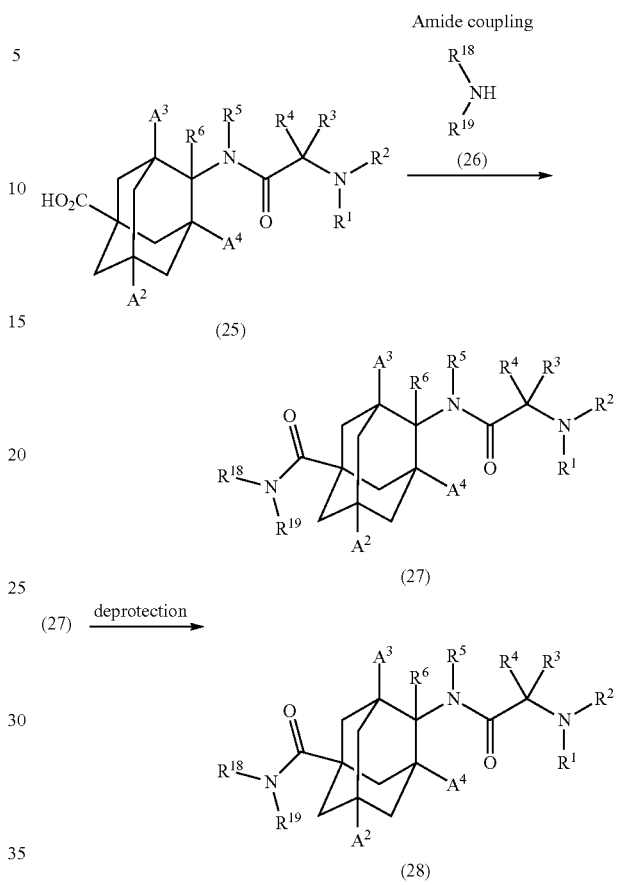

Substituted adamantanes of general formula (28), wherein $A^2$, $A^3$, $A^4$, $R^1$, $R^2$, $R^3$, $R^4$, $R^5$, $R^6$, $R^{18}$, and $R^{19}$ are as defined in formula I, may be prepared as in Scheme 7. Adamantyl acids of general formula (25) may be prepared as described herein or using methodology known to those in the art. The acids of general formula (25) may be coupled with amines of general formula (26) (wherein $R^{18}$ and $R^{19}$ are defined as in formula I) with reagents such as O-(Benzotrialzol-1-yl)-1,1,3,3-tetramethyluronium tetrafluoroborate (TBTU) to provide amides of general formula (27). In some examples, $A^2$, $A^3$, $A^4$, $R^1$, $R^2$, $R^3$, $R^4$, $R^5$, $R^6$, $R^{18}$, and $R^{19}$ in amines of formula (27) may contain a functional group covered with a protecting group such as carboxy protected as an ester. These protecting groups may be removed using methodology known to those in the art to provide amides of general formula (28).

Scheme 8

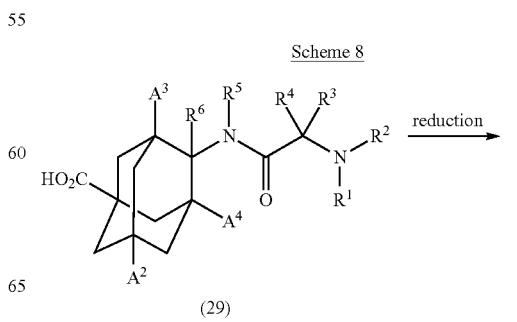

(29)

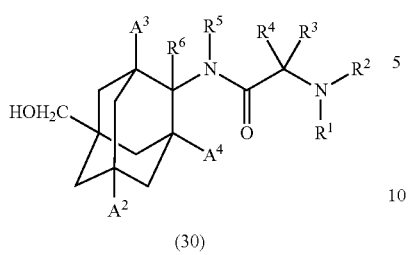

(30)

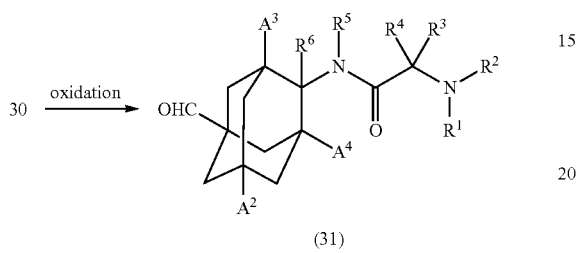

(31)

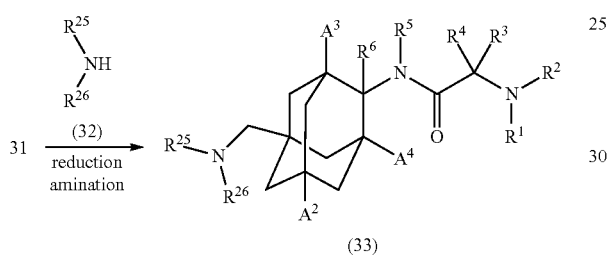

(33)

Substituted adamantanes of general formula (33), wherein $A^2, A^3, A^4, R^1, R^2, R^3, R^4, R^5, R^6, R^{25}$, and $R^{26}$ are as defined in formula I, may be prepared as in Scheme 8. Acids of general formula (29) may be prepared as detailed herein or by using methodology known to those in the art. Acids (29) may be reduced using a reagent like borane to alcohols of general formula (30). Alcohols of general formula (30) may be oxidized with reagents such as tetrapropylammonium perruthenate to aldehydes of general formula (31). Aldehydes of general formula (31) may be reductively aminated with an amine of general formula (32), wherein $R^{25}$ and $R^{26}$ are as defined in formula I, and a reducing agent such as sodium cyanoborohydride to provide amines of general formula (33). In some examples, $A^2, A^3, A^4, R^1, R^2, R^3, R^4, R^5, R^6, R^{25}$, and $R^{26}$ in amines of formula (33) may be and/or contain a functional group covered with a protecting group such as such as carboxy protected as an ester. These protecting groups may be removed using methodology known to those in the art.

Scheme 9

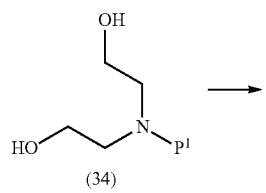

(34)

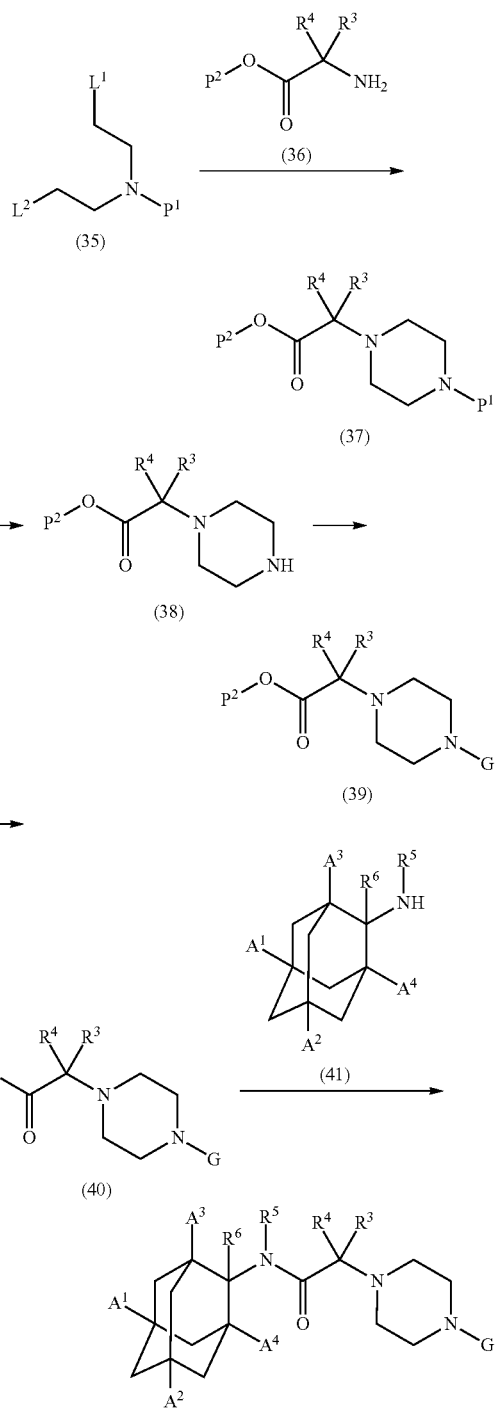

Substituted adamantanes of general formula (42), wherein $A^1, A^2, A^3, A^4, R^3, R^4, R^5$, and $R^6$ are as defined in formula I and G is as defined in formula V, may be prepared as in Scheme 9. Diethanolamines of general formula (34) wherein P' is an alkylsulfonyl or arylsulfonyl group may be purchased or prepared using methodology known to those in the art. Diethanolamines (34) wherein P' is an alkylsulfonyl or arylsulfonyl group can be prepared by reacting diethanolamine with a sulfonyl chloride like 2-nitrobenzenesulfonylchloride in the presence of a base like triethylamine in a solvent like methylene chloride. The diols of general formula (34) may be converted to sulfonamides of general formula (35) (wherein $L^1$ and $L^2$ are Cl, Br, I, OMs, or OTf) with reagents such as triflic anhydride. Sulfonamides of general formula (35) may be treated with aminoesters (36), wherein $R^3$ and $R^4$ are as defined in formula I and $P^2$ is an alkyl group, and a base like sodium carbonate to yield piperazines of general formula (37). Piperazine sulfonamides (37) can be deprotected to provide piperazines (38). Amines (38) can be arylated, or heteroarylated, with a reagent like 2-bromo-5-trifluoromethyl-pyridine to give piperazines of general formula (39). Esters (39) may be converted to acids of general formula (40). Acids (40) can be coupled to adamantly amines of general formula (41), wherein $A^1, A^2, A^3, A^4$, and $R^6$ are as defined in formula I, to give amides of general formula (42). In some examples, $A^1, A^2, A^3, A^4, R^3, R^4, R^5$, and/or $R^6$ in amines of formula (42) may contain a functional group covered with a protecting group such as such as carboxy protected as an ester. These protecting groups may be removed using methodology known to those in the art to give amides of general formula (43).

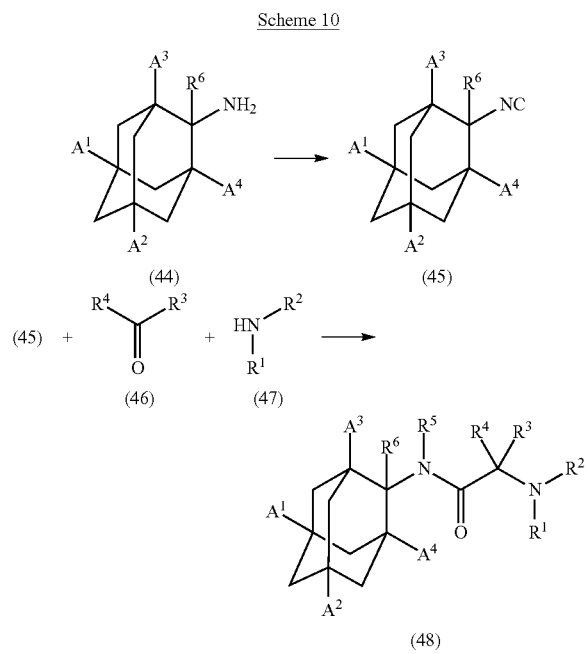

Substituted adamantanes of general formula (48), wherein $A^1, A^2, A^3, A^4, R^1, R^2, R^3, R^4, R^5$, and $R^6$ are as defined in formula I, may be prepared as in Scheme 10. Substituted adamantamines of general formula (44), wherein $A^1, A^2, A^3, A^4$, and $R^6$ are as defined in formula I, may be purchased or prepared using methodology known to those in the art. The amines of general formula (44) may be converted to isonitriles of general formula (45) with reagents such as methyl formate followed by treatment with phosphorous oxychloride in the presence of a base like triethylamine. Isonitriles of general formula (45) may be treated with aldehydes or ketones of general formula (46), amines of general formula (47), and an acid such as acetic acid to provide amides of general formula (48). In some examples, $A^1, A^2, A^3, A^4, R^1, R^2, R^3, R^4, R^5$, and/or $R^6$ in compounds of formula (48) may contain a functional group covered with a protecting group such as carboxy protected as an ester. These protecting groups may be removed using methodology known to those in the art in amides of general formula (48).

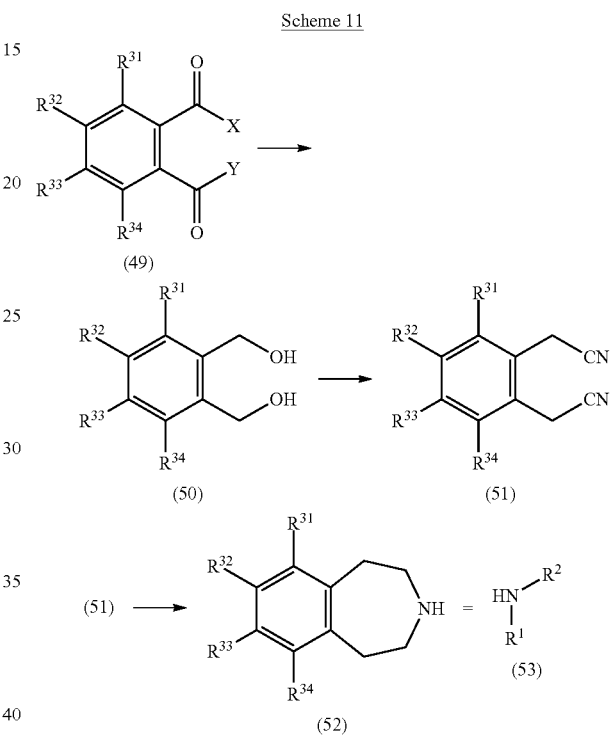

Substituted benzodiazepines of general formula (52), wherein $R^{31}, R^{32}, R^{33}$ and $R^{34}$ are defined as heterocycle substituents (and equivalent to benzodiazepines of general formula (53) wherein $R^1$ and $R^2$ are a subset of the substituents in formula (I)) may be prepared as in Scheme 11. Substituted arenes of general formula (49), wherein $R^{31}, R^{32}, R^{33}$, and $R^{34}$ are defined as heterocycle substituents and X and Y are independently halogen, —OH, or —Oalkyl, may be purchased or prepared using methodology known to those skilled in the art. Arenes of general formula (49) may be treated with reducing agents such as borane-tetrahydrofuran, to provide diols of general formula (50). Diols (50) may be converted to the corresponding dihalides with reagents like thionyl chloride and then treated with cyanide using reagents like sodium cyanide in solvents like dimethylsulfoxide to yield the corresponding dinitriles of general formula (51). Dinitriles of general formula (51) may be treated with ammonia under reducing conditions like Raney nickel in the presence of hydrogen gas at high pressure in a solvent such as but not limited to ethanol to provide benzodiazepines of general formula (52). Examples containing a protected functional group may be required due to the synthetic schemes and the reactivity of unprotected functional groups. The protecting group could be later removed to provide the desired compound. Such protecting groups may be added or removed using methodology known to those skilled in the art or as described in T. W. Greene, P. G. M. Wuts "Protective Groups in Organic Synthesis" 3rd ed. 1999, Wiley & Sons, Inc. Benozdiazepines of general formula (52) may be converted into compounds of general formula (I) using methods described herein and by methodology known to those skilled in the art.

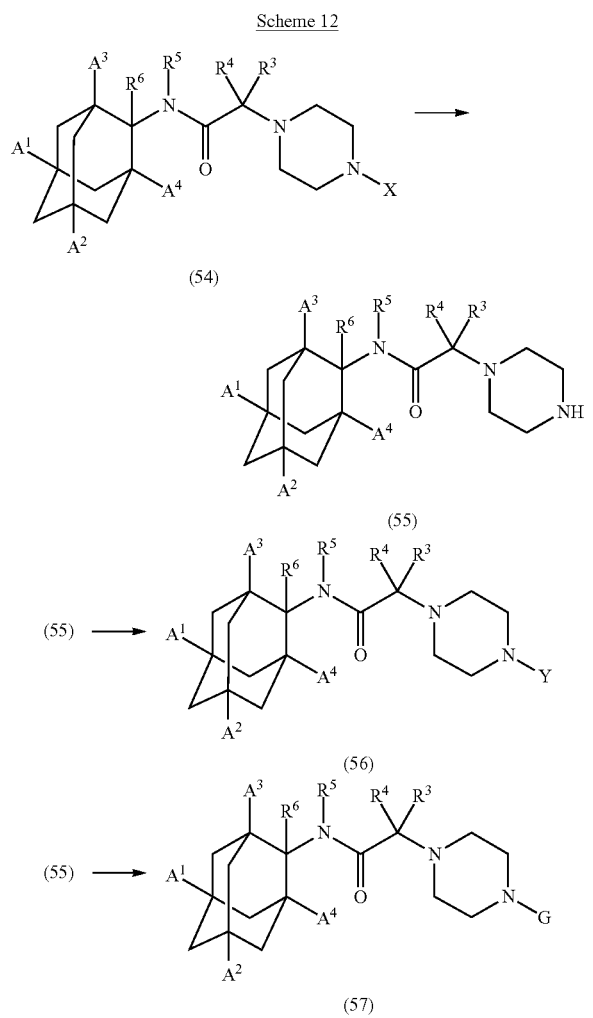

Substituted adamantanes of general formula (56) and (57), wherein $A^1$, $A^2$, $A^3$, $A^4$, $R^3$, $R^4$, $R^5$, and $R^6$ are as defined in formula (I), G is defined as in formula (V), and Y is an alkylcarbonyl, alkylsulfonyl, alkoxycarbonyl, alkylaminocarbonyl, arylcarbonyl, arylsulfonyl, aryloxycarbonyl, arylaminocarbonyl, heteroarylcarbonyl, heteroarylsulfonyl, heteroaryloxycarbonyl, heteroarylaminocarbonyl, arylalkylcarbonyl, arylalkylsulfonyl, arylalkoxycarbonyl, arylalkylaminocarbonyl, heteroarylalkylcarbonyl, heteroarylalkylsulfonyl, heteroarylalkoxycarbonyl, or a heteroarylalkylaminocarbonyl group may be prepared as in Scheme 12. Adamantyl piperazines of general formula (54) wherein X is an amine protecting group and $A^1$, $A^2$, $A^3$, $A^4$, $R^3$, $R^4$, $R^5$, and $R^6$ are as defined in formula (I) may be prepared as described herein or using methodology known to those skilled in the art. The protected piperazines of general formula (54) may be deprotected with reagents such as palladium on carbon in the presence of hydrogen when X is a benzyloxycarbonyl group to provide amines of general formula (55). Amines of general formula (55) can be treated with acid chlorides, sulfonylchlorides, chloroformates, isocyanates, and other compounds to provide piperazines of general formula (56). Amines of general formula (55) can also be treated with aryl or heteroaryl halides and other compounds to provide compounds of general formula (57). In some examples, $A^1$, $A^2$, $A^3$, $A^4$, $R^3$, $R^4$, $R^5$, $R^6$, G, and Y of piperazines containing compounds of formulas (56) and (57) may or may not contain a functional group substituted with a protecting group such as carboxy protected as an ester. These protecting groups may be removed using methodology known to those skilled in the art to provide piperazines of general formulas (56) and (57).

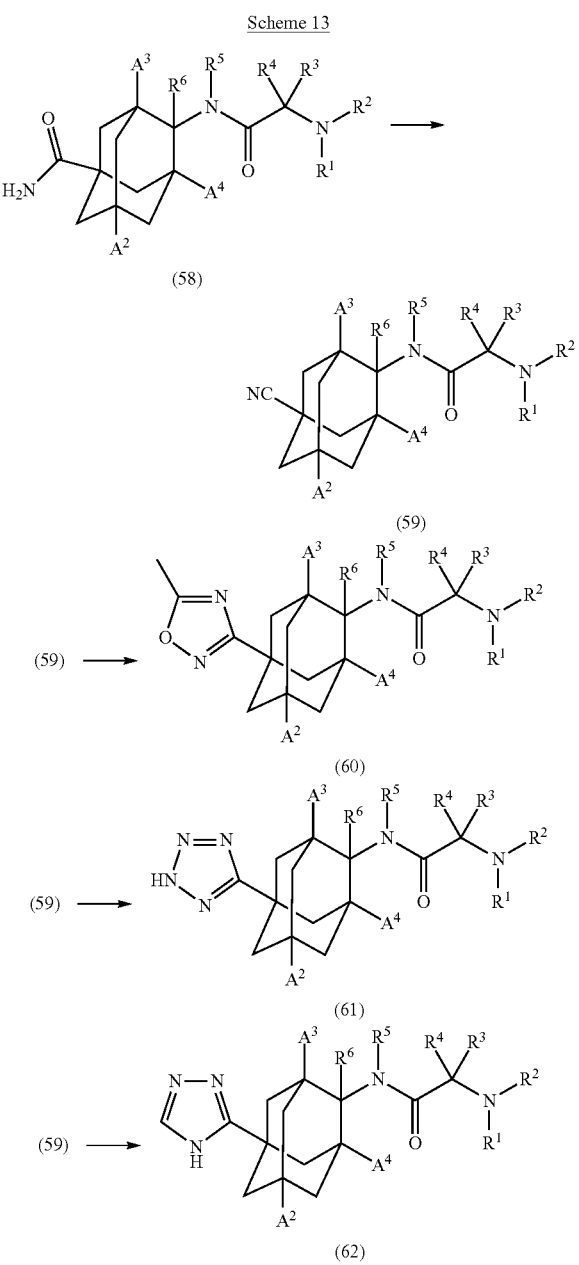

Substituted adamantanes of general formulas (60), (61), and (62), wherein $A^2$, $A^3$, $A^4$, $R^1$, $R^2$, $R^3$, $R^4$, $R^5$, and $R^6$ are as defined in formula (I), may be prepared as in Scheme 13. Amides of general formula (58), wherein $A^2$, $A^3$, $A^4$, $R^1$, $R^2$, $R^3$, $R^4$, $R^5$, and $R^6$ are as defined in formula (I), may be prepared as described herein or by using methodology known to those skilled in the art. Amides (58) may be dehydrated using a reagent such as but not limited to trifluoroacetic anhydride to provide nitriles of general formula (59). Nitriles of general formula (59) may be treated with reagents such as hydroxylamine hydrochloride and potassium carbonate in a solvent such as ethanol followed by treatment with acetyl chloride in a solvent such as pyridine to provide heterocycles of general formula (60). Nitriles of general formula (59) may also be treated with reagents such as sodium azide and a Lewis acid such as zinc bromide in a solvent such as water to provide tetrazoles of general formula (61). Nitriles of general formula (59) may also be treated with reagents such as dimethylformamide and dimethylacetamide followed by heating with hydrazine in acetic acid to provide triazoles of general formula (62). In some examples, $A^2$, $A^3$, $A^4$, $R^1$, $R^2$, $R^3$, $R^4$, $R^5$, and $R^6$ of adamantane containing compounds of formula (60), (61), and (62) may or may not contain a functional group substituted with a protecting group such as such as carboxy protected as an ester. These protecting groups may be removed using methodology known to those in the art.

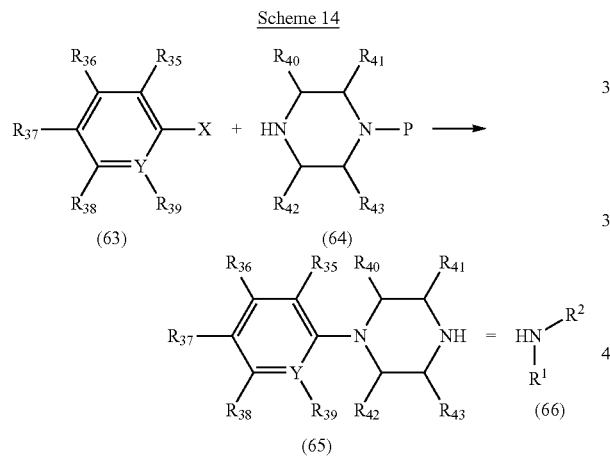

Piperazines of general formula (65) which are equivalent to compounds of general formula (66) wherein $R^{35}$, $R^{36}$, $R^{37}$, $R^{38}$, $R^{39}$, $R^{40}$, $R^{41}$, $R^{42}$, and $R^{43}$ are defined as aryl or heteroaryl substituents and Y is a carbon or a nitrogen, may be prepared as in Scheme 14. Arenes and heterocycles of general formula (63), wherein $R^{35}$, $R^{36}$, $R^{37}$, $R^{38}$, and $R^{39}$ are defined as aryl or heteroaryl substituents, X is a halogen, and Y is a carbon or a nitrogen may be purchased or prepared using methodology known to those skilled in the art. Piperazines of general formula (64) wherein $R^{40}$, $R^{41}$, $R^{42}$, and $R^{43}$ are defined as heterocycle substituents and P is a protecting group may be purchased or prepared using methodology known to those skilled in the art. Arenes and heterocycles of general structure (63) may be coupled with piperazines of general formula (64) by heating them together neat or in a solvent such as dimethylformamide in the presence of a base such as potassium carbonate to provide piperazines of general formula (65) following protecting group removal. Alternatively, this reaction may be conducted with palladium or other metal catalyst systems such as tris(dibenzylideneacetone)dipalladium and 2,2'-bis(diphenylphosphino)-1,1'-binaphthyl in the presence of a base such as sodium tert-butoxide in a solvent such as toluene. Examples containing a protected functional group may be required due to the synthetic schemes and the reactivity of other substituent groups which could be later removed to provide the desired compounds. Such protecting groups may be removed using methodology known to those skilled in the art or as described in T. W. Greene, P. G. M. Wuts "Protective Groups in Organic Synthesis" $3^{rd}$ ed. 1999, Wiley & Sons, Inc. piperazines of general formula (65) may be converted into compounds of general formula I using methods described herein and by methodology known to those skilled in the art.

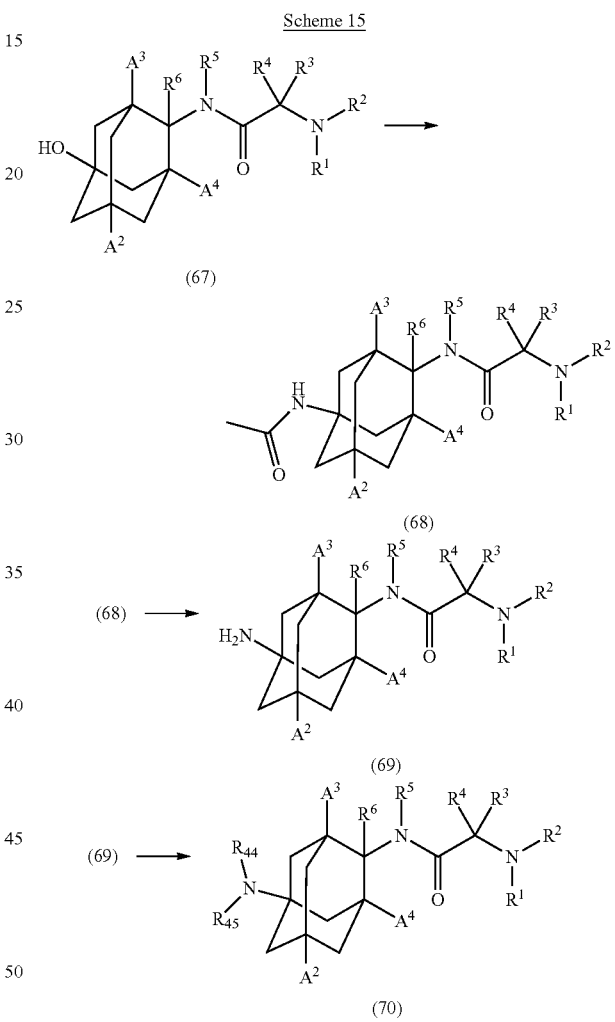

Substituted adamantanes of general formula (70), wherein $A^2$, $A^3$, $A^4$, $R^1$, $R^2$, $R^3$, $R^4$, $R^5$, and $R^6$ are as defined in formula (I) and $R^{44}$ and $R^{45}$ are independently defined as $R^7$, —[C($R^8R^9$)]$_n$—C(O)—$R^{10}$, $R^{15}$, and $R^{16}$ as defined in formula (I), may be prepared as in Scheme 15. Substituted adamantanols of general formula (67), wherein $A^2$, $A^3$, $A^4$, $R^1$, $R^2$, $R^3$, $R^4$, $R^5$, and $R^6$ are as defined in formula (I), may be purchased, prepared using procedures described herein, or made by methodology known to those skilled in the art. The adamantanols of general formula (67) may be converted to amides of general formula (68) with reagents such as acetonitrile in the presence of an acid such as trifluoroacetic acid. Amides of general formula (68) may be treated with another acid such as hydrochloric acid to provide amines of general formula (69). Amines of general formula (69) may undergo a variety of reactions such as acylation or sulfonylation with acetyl chloride or methanesulfonyl chloride in the presence of a base to provide substituted adamantanes of general formula (70). In some examples, $A^2, A^3, A^4, R^1, R^2, R^3, R^4, R^5$, and/or $R^6$ in compounds of formula (70) may contain a functional group substituted with a protecting group such as carboxy protected as an ester. These protecting groups may be removed using methodology known to those skilled in the art to provide compounds of general formula (70).

Scheme 16

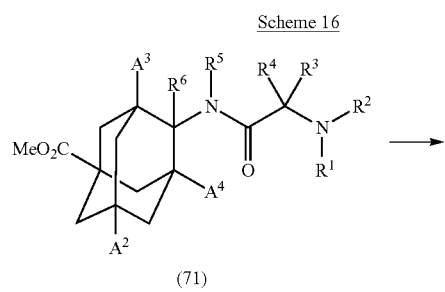

(71)

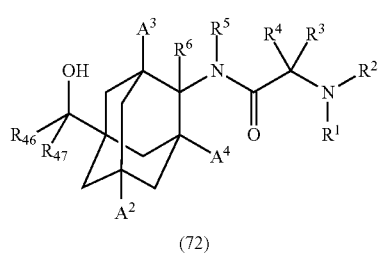

(72)

Substituted adamantanes of general formula (72), wherein $A^2, A^3, A^4, R^1, R^2, R^3, R^4, R^5$, and $R^6$ are as defined in formula I and $R^{46}$ and $R^{47}$ are alkyl, cycloalkyl, aryl or heterocyclic groups may be prepared as in Scheme 16. Substituted adamantane esters of general formula (71), wherein $A^2$, $A^3, A^4, R^1, R^2, R^3, R^4, R^5$, and $R^6$ are as defined in formula I may be purchased, synthesized as described herein, or prepared using methodology known to those skilled in the art. The esters of general formula (71) may be converted to alcohols of general formula (72) with reagents such as methyl lithium. In some examples, $A^2, A^3, A^4, R^3, R^4, R^5$, and/or $R^6$ in amines of formula (72) may contain a functional group substituted with a protecting group such as such as carboxy protected as an ester. These protecting groups may be removed using methodology known to those skilled in the art to provide adamantane alcohols of general formula (72).

Scheme 17

(73)

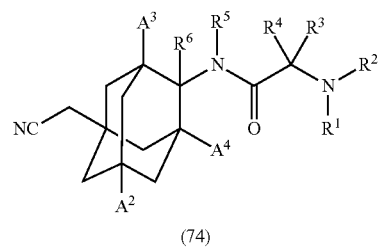

(74)

(74) →

(75)

Substituted adamantanes of general formula (75), wherein $A^2, A^3, A^4, R^1, R^2, R^3, R^4, R^5$, and $R^6$ are as defined in formula (I), may be prepared as in Scheme 17. Aldehydes of general formula (73), wherein $A^2, A^3, A^4, R^1, R^2, R^3, R^4, R^5$, and $R^6$ are as defined in formula (I) may be prepared by methods described herein or using methodology known to those skilled in the art. Aldehydes (73) may be converted to nitriles of general formula (74) with reagents such as p-tolylsulfonylmethyl isocyanide in solvents such as dimethoxyethane and ethanol in the presence of a base such as potassium tert-butoxide. Nitriles of general formula (74) may be treated with an acid such as hydrobromic acid in a solvent such as acetic acid to provide acids of general formula (75). In some examples, $A^2, A^3, A^4, R^3, R^4, R^5$, and/or $R^6$ in amines of formula (75) may contain a functional group substituted with a protecting group such as such as carboxy protected as an ester. These protecting groups may be removed using methodology known to those skilled in the art to provide acids of general formula (75).

Scheme 18

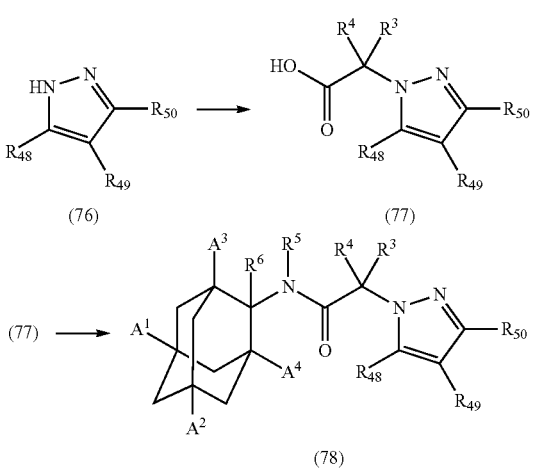

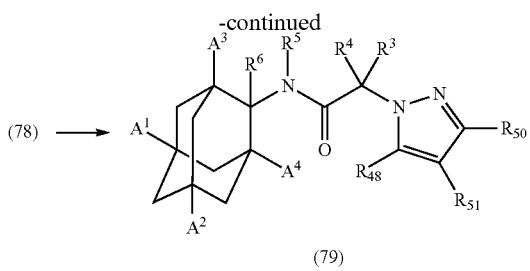

Substituted adamantanes of general formula (79), wherein $A^1, A^2, A^3, A^4, R^3, R^4, R^5$, and $R^6$ are as defined in formula (I), $R^{48}$ and $R^{50}$ are defined as heterocycle substituents, and $R^{51}$ is an aryl or heteroaryl group, may be prepared as in Scheme 18. Pyrazoles of general formula (76) wherein $R^{48}$ and $R^{50}$ are heterocycle substituents and $R^{49}$ is a halogen may be purchased or prepared using methodology known to those skilled in the art. Pyrazoles of general formula (76) may be alkylated with a reagent like 2-(trichloromethyl)-propan-2-ol in the presence of a base such as sodium hydroxide in a solvent such as acetone to provide acids of general formula (77). The acids of general formula (77) may be coupled with adamantamines as described in Scheme 4 to provide pyrazoles of general formula (78). Pyrazoles of general formula (78) may be coupled with boronic acids and related reagents such as 4-cyanophenylboronic acid in the presence of a catalyst such as but not limited to Pd(PPh$_3$)$_2$Cl$_2$ to provide pyrazoles of general formula (79). In some examples, $A^1, A^2, A^3, A^4, R^3, R^4, R^5, R^6, R^{48}, R^{50}$ and/or $R^{51}$ in amines of formula (79) may contain a functional group substituted with a protecting group such as such as carboxy protected as an ester. These protecting groups may be removed using methodology known to those skilled in the art to provide compounds of general formula (79).

The compounds and processes of the present invention will be better understood by reference to the following Examples, which are intended as an illustration of and not a limitation upon the scope of the invention. Further, all citations herein are incorporated by reference.

Compounds of the invention were named by ACD/Chem-Sketch version 5.01 (developed by Advanced Chemistry Development, Inc., Toronto, ON, Canada) or were given names consistent with ACD nomenclature. Adamantane ring system isomers were named according to common conventions. Two substituents around a single ring within an adamantane ring system are designated as being of Z or E relative configuration (for examples see C. D. Jones, M. Kaselj, R. N. Salvatore, W. J. le Noble J. Org. Chem. 63: 2758-2760, 1998).

EXAMPLE 1

N-[(Z)-5-Hydroxy-2-adamantyl]-2-{4-[5-(trifluoromethyl)pyridin-2-yl]piperazin-1-yl}acetamide

EXAMPLE 1A

Acetic acid 2-oxo-adamantan-5-yl ester

A solution of 5-hydroxy-2-adamantanone (2.6 g, 15.66 mmoles) in dichloromethane (DCM) (50 mL) was treated with dimethylaminopyridine (DMAP) (2.1 g, 17 mmoles) and acetic anhydride (2.3 mL, 23 mmoles) and stirred overnight at 50° C. The solvent was removed under reduced pressure and the residue was partitioned between water and ethyl acetate. The aqueous layer was extracted twice with ethyl acetate. Combined organic extracts were washed with water, dried (MgSO$_4$) and filtered. The filtrate was concentrated under reduced pressure to provide the title compound as an off-white solid.

EXAMPLE 1B (E)- and (Z)-Acetic acid 2-amino-adamantan-5-yl ester

A solution of acetic acid 2-oxo-adamantan-5-yl ester (3.124 g, 15 mmoles), from Example 1A, and 4 Å molecular seives (1 g) in methanolic ammonia (7N, 50 mL) was stirred overnight at room temperature. The mixture was cooled in an ice bath, treated portionwise with sodium borohydride (2.27 g, 60 mmoles) and stirred at room temperature for 2 hours. The suspension was filtered and concentrated under reduced pressure. The residue was taken into DCM (50 mL), acidified with 1N HCl to pH=3 and the layers separated. The aqueous layer was basified with 2N NaOH to pH=12 and extracted three times with 4:1 tetrahydrofuran:dichloromethane (THF:DCM). The combined organic extracts were dried (MgSO$_4$) and filtered. The filtrate was concentrated under reduced pressure to provide the title compound as a white solid.

EXAMPLE 1C (E)- and (Z)-Acetic acid 2-(2-chloroacetylamino)-adamantan-5-yl ester A solution of (E)- and (Z)-acetic acid 2-amino-adamantan-5-yl ester (1.82 g, 8.69 mmoles), from Example 1B, in DCM (30 mL) and diisopropylethylamine (DIPEA) (1.74 mL, 10 mmoles) was cooled in an ice bath and treated with chloroacetyl chloride (0.76 mL, 9.57 mmoles). The solution was stirred for 2 hours at room temperature and concentrated under reduced pressure. The residue was partitioned between water and ethyl acetate. The organic layer was washed with saturated aqueous sodium bicarbonate, water, dried (MgSO$_4$) and filtered. The filtrate was concentrated under reduced pressure to provide the title compound as dark beige solid.

EXAMPLE 1D

N-[(Z)-5-Hydroxy-2-adamantyl]-2-{4-[5-(trifluoromethyl)pyridin-2-yl]piperazin-1-yl}acetamide A solution of (E)- and (Z)-acetic acid 2-(2-chloroacetylamino)-adamantan-5-yl ester (2.1 g, 7.3 mmoles), from Example 1C, in MeOH (30 mL) and DIPEA (1.53 mL, 8.8 mmoles) was treated with 1-(5-trifluoromethyl-pyridin-2-yl)-piperazine (2.04 g, 8.8 mmoles) and stirred for 6 hours at 70° C. An aqueous solution of potassium carbonate (K$_2$CO$_3$) (15 mL) was added to the reaction and stirred overnight at 70° C. MeOH was removed under reduced pressure and the residue was partitioned with DCM. The aqueous layer was extracted with DCM and the combined organic extracts washed twice with water, dried (MgSO$_4$) and filtered. The filtrate was concentrated under reduced pressure to provide an off-white solid, which was purified by column chromatography (silica gel, 30-90% acetone in hexane) to provide the title compound as a white solid. $^1$H NMR (300 MHz, CDCl$_3$) δ 8.41 (s, 1H), 7.65 (dd, J=2.7, 9.1 Hz, 1H,), 7.6 (s, 1H), 6.65 (d, J=9.1 Hz, 1H), 3.98 (d, J=8.5 Hz, 1H), 3.69 (s, 4H), 3.09 (s, 2H), 2.67 (s, 4H), 2.19-2.15 (m, 3H), 1.79-1.38 (m, 10H); MS (APCI+) m/z 439 (M+H)$^+$.

EXAMPLE 2

N-[(E)-5-Hydroxy-2-adamantyl]-2-{4-[5-(trifluoromethyl)pyridin-2-yl]piperazin-1-yl}acetamide Purification of the concentrated filtrate from Example 1D by column chromatography (silica gel, 30-90% acetone in hexane) provided the title compound as a white solid. $^1$H NMR (300 MHz, CDCl$_3$) δ 8.41 (s, 1H), 7.67 (dd, J=2.1, 9.1 Hz, 1H), 7.6 (s, 1H), 6.67 (d, J=9.1 Hz, 1H), 4.07 (d, J=8.1 Hz, 1H), 3.69 (s, 4H), 3.1 (s, 2H), 2.68 (s, 4H), 2.12-2.17 (m, 3H), 1.91 (m, 2H), 1.79-1.75 (m, 4H), 1.67 (m, 2H), 1.57 (s, 1H), 1.36 (s, 1H); MS (APCI+) m/z 439 (M+H)$^+$.

EXAMPLE 3

N-[(E)-5-Hydroxy-2-adamantyl]-2-{4-[5-(trifluoromethyl)pyridin-2-yl]piperazin-1-yl}propanamide

EXAMPLE 3A

(E)- and (Z)-Acetic acid 2-(2-bromo-propionylamino)-adamantan-5-yl ester

A solution of (E)- and (Z)-acetic acid 2-amino-adamantan-5-yl ester (0.54 g, 2.58 mmoles), from Example 1B, in DCM (10 mL) and DIPEA (0.54 mL, 3.09 mmoles) was cooled in an ice bath and treated with 2-bromopropionyl chloride (0.26 mL, 2.6 mmoles). The solution was stirred for 2 hours at room temperature and DCM was removed under reduced pressure. The residue was partitioned between water and ethyl acetate. The organic layer was washed with saturated aqueous sodium bicarbonate, water, dried (MgSO$_4$) and filtered. The filtrate was concentrated under reduced pressure to provide the title compound as a dark beige solid.

EXAMPLE 3B

N-[(E)-5-Hydroxy-2-adamantyl]-2-{4-[5-(trifluoromethyl)pyridin-2-yl]piperazin-1-yl}propanamide A solution of (E)- and (Z)-acetic acid 2-(2-bromo-propionylamino)-adamantan-5-yl ester (0.746 g, 2.17 mmoles), from Example 3A, in MeOH (10 mL) and DIPEA (0.416 mL, 2.39 mmoles) was treated with 1-(5-trifluoromethyl-pyridin-2-yl)-piperazine (0.552 g, 2.39 mmoles) and stirred for 6 hours at 70° C. Saturated aqueous K$_2$CO$_3$ (5 mL) was added to the reaction mixture and the mixture stirred overnight at 70° C. The mixture was concentrated under reduced pressure and the residue partitioned by the addition of DCM. The aqueous layer was extracted with additional DCM (3×). The combined organic extracts were washed twice with water, dried (MgSO$_4$) and filtered. The filtrate was concentrated under reduced pressure to provide an off-white solid, which was purified by column chromatography (silica gel, 30-90% acetone in hexane) to provide the title compound as a white solid. $^1$H NMR (300 MHz, CDCl$_3$) δ 8.41 (s, 1H), 7.65 (m, 2H), 6.67 (d, J=8.8 Hz, 1H), 4.03 (d, J=8.5 Hz, 1H), 3.69 (m, 4H), 3.15 (q, J=7.1 Hz, 1H), 2.63 (m, 4H), 2.15 (m, 3H), 1.9 (m, 2H), 1.77 (m, 4H), 1.66 (m, 2H), 1.52 (s, 1H), 1.36 (s, 1H), 1.28 (d, J=7.1 Hz, 3H); MS (APCI+) m/z 453 (M+H)$^+$.

EXAMPLE 4

2-[(cis)-2,6-Dimethylmorpholin-4-yl]-N-[(E)-5-hydroxy-2-adamantyl]propanamide

EXAMPLE 4A

(E)- and (Z)-5-Chloro-2-adamantamine

A solution of 5-chloro-2-adamantanone (4.8 g, 26 mmoles) and 4 Å molecular sieves (2 g) in methanolic ammonia (7N, 50 mL) was stirred overnight at room temperature, cooled in an ice bath, treated with the portionwise addition of sodium borohydride (3.93 g, 104 mmoles) and stirred at room temperature for 2 hours. The suspension was filtered and concentrated under reduced pressure. The residue was taken into DCM (50 mL) and acidified with 1N HCl to pH=3. The layers were separated and the aqueous layer basified with 2N NaOH to pH=12 and extracted three times with 4:1 THF:DCM. The combined organic extracts were dried (MgSO$_4$), filtered and concentrated under reduced pressure to provide the title compound as a white solid.

EXAMPLE 4B

2-Bromo-N-[(E)- and (Z)-5-chloro-adamantan-2-yl]-propionamide

A solution of (E)- and (Z)-5-chloro-2-adamantamine (1 g, 5.38 mmoles), from Example 4A, in DCM (30 mL) and DIPEA (2.08 mL, 11.96 mmoles) was cooled in an ice bath and treated with 2-bromopropionyl chloride (0.65 mL, 6.46 mmoles) and the mixture stirred for 2 hours at room temperature. The mixture was concentrated under reduced pressure, partitioned between water and ethyl acetate. The organic layer was washed with aqueous saturated sodium bicarbonate (2×), water (2×), dried (MgSO$_4$) and filtered. The filtrate was concentrated under reduced pressure to provide the title compound as a tan solid.

EXAMPLE 4C

2-[(cis)-2,6-Dimethylmorpholin-4-yl]-N-[(E)-5-hydroxy-2-adamantyl]propanamide A solution of 2-bromo-N-[(E)- and (Z)-5-chloro-adamantan-2-yl]-propionamide (55 mg, 0.17 mmoles) from Example 4B in MeOH (1 mL) and DIPEA (0.1 mL) was treated with cis-2,6-dimethylmorpholine (23 mg, 0.2 mmoles) and the mixture stirred overnight at 70° C. The mixture was concentrated under reduced pressure. The residue dissolved in dioxane (0.1 mL) and 5N potassium hydroxide (0.4 mL) and irradiated by microwaves for 1 hour at 190° C. The mixture was filtered through a Celite cartridge and washed with 1:1 DMSO:MeOH (1.5 mL). The title compound was isolated by reverse phase HPLC (20-100% acetonitrile in 0.1% TFA in water) on a YMC ODS Guardpak column as a clear oil. $^1$H NMR (300 MHz, CDCl$_3$) δ 7.65 (d, J=8.3 Hz, 1H); 4.0 (d, J=8.6 Hz, 1H), 3.67 (m, 2H), 3.03 (q, J=7.0 Hz, 1H), 2.62 (t, J=11.2 Hz, 2H), 2.11 (m, 3H), 1.97-1.8 (m, 3H), 1.77-1.65 (m, 4H), 1.65-1.52 (m, 4H), 1.23 (d; J=7.1 Hz, 3H), 1.17 (dd, J=5.8, 6.1 Hz, 6H); MS (APCI+) m/z 337 (M+H)$^+$.

EXAMPLE 5

N-[(Z)-5-Hydroxy-2-adamantyl]-2-(4-hydroxypiperidin-1-yl)propanamide

The title compound was prepared according to the method of Example 4C substituting 4-hydroxypiperidine for cis-2,6- dimethylmorpholine. $^1$H NMR (300 MHz, CDCl$_3$) δ 7.75 (s, 1H), 3.9 (d, J=9.2 Hz, 1H), 3.74 (s, 1H), 3.12 (m, 1H), 2.77 (m, 2H), 2.43 (m, 1H), 2.25 (m, 2H), 2.15-1.93 (m, 10H), 1.75-1.6 (m, 8H), 1.23 (d, J=6.8 Hz, 3H); MS (APCI+) m/z 323 (M+H)$^+$.

EXAMPLE 6

N-[(E)-5-Hydroxy-2-adamantyl]-2-(4-hydroxypiperidin-1-yl)propanamide

The title compound was prepared according to the method of Example 4C substituting 4-hydroxypiperidine for cis-2,6-dimethylmorpholine. $^1$H NMR (300 MHz, CDCl$_3$) δ 7.76 (d, J=2.4 Hz, 1H), 4.0 (d, J=8.1 Hz, 1H), 3.74 (m, 1H), 3.13 (q, J=7.2 Hz, 1H), 2.78 (m, 2H), 2.44 (t, 12.2, 1H), 2.28 (t, J=9.6 Hz, 1H), 2.16-2.05 (m, 5H), 1.96-1.88 (m, 4H), 1.77-1.52 (m, 9H), 1.23 (d, J=7.2 Hz, 3H); MS (APCI+) m/z 323 (M+H)$^+$.

EXAMPLE 7

2-Azepan-1-yl-N-[(E)-5-hydroxy-2-adamantyl]propanamide

The title compound was prepared according to the method of Example 4C substituting hexamethyleneimine for cis-2,6-dimethylmorpholine. $^1$H NMR (300 MHz, CDCl$_3$) δ 7.84 (s, 1H), 3.99 (d, J=8.1 Hz, 1H), 3.35 (d, J=5.9 Hz, 1H), 2.71-2.65 (bd, 4H), 2.16-2.10 (m, 3H), 1.89 (d, J=11.9 Hz, 2H), 1.77-1.65 (m, 14H), 1.52 (d, J=12.8 Hz, 2H), 1.24 (d, J=6.9 Hz, 3H); MS (APCI+) m/z 321 (M+H)$^+$.

EXAMPLE 8

(E)-4-[({4-[5-(Trifluoromethyl)pyridin-2-yl]piperazin-1-yl}acetyl)amino]-1-adamantyl carbamate A solution of N-[(E)-5-hydroxy-2-adamantyl]-2-{4-[5-(trifluoromethyl)pyridin-2-yl]piperazin-1-yl}acetamide (44 mg, 0.1 mmoles) from Example 2 in DCM (1 mL) was treated with trichloroacetylisocyanate (13 µL, 0.11 mmoles) and stirred for 2 hours at room temperature. The solvent was removed under reduced pressure, the residue was dissolved in MeOH (1 mL) followed by the addition of saturated potassium carbonate (3 mL) and the mixture stirred overnight at 50° C. The mixture was concentrated under reduced pressure, partitioned with DCM and the aqueous layer extracted with additional DCM. The combined organic extracts were washed twice with water, dried (MgSO$_4$) and filtered. The filtrate was concentrated under reduced pressure to provide the title compound as a white solid. $^1$H NMR (300 MHz, CDCl$_3$) δ 8.42 (s, 1H), 7.64 (m, 2H), 6.67 (d, J=9.2 Hz, 1H), 4.4 (s, 2H), 4.12 (d, J=5.8 Hz, 1H), 3.68 (s, 4H), 3.09 (s, 2H), 2.68 (s, 4H), 2.19-2.17 (m, 9H), 1.64-1.63 (m, 4H); MS (APCI+) m/z 482 (M+H)$^+$.

EXAMPLE 9

(E)-4-[(2-{4-[5-(Trifluoromethyl)pyridin-2-yl]piperazin-1-yl}acetyl)amino]-1-adamantyl acetate A solution of N-[(E)-5-hydroxy-2-adamantyl]-2-{4-[5-(trifluoromethyl)pyridin-2-yl]piperazin-1-yl}acetamide (44 mg, 0.1 mmoles) from Example 2 in DCM (0.5 mL) and pyridine (0.5 mL) was treated with acetyl chloride (11 µL, 0.15 mmoles), catalytic amount of DMAP and stirred overnight at 50° C. Solvents were removed under reduced pressure and the residue was purified (silica gel, 10-30% acetone in hexane) to provide the title compound as a white solid. $^1$H NMR (300 MHz, CDCl$_3$) δ 8.41 (s, 1H), 7.64 (m, 2H), 6.65 (d, J=9.2 Hz, 1H), 4.12 (d, J=8.1 Hz, 1H), 3.68 (s, 4H), 3.09 (s, 2H), 2.68 (s, 4H), 2.21-2.14 (m, 7H), 1.98 (s, 3H), 1.64 (s, 2H), 1.26-1.22 (m, 4H); MS (APCI+) m/z 481 (M+H)$^+$.

EXAMPLE 10

N-[(E)-5-(Acetylamino)-2-adamantyl]-2-{4-[5-(trifluoromethyl)pyridin-2-yl]piperazin-1-yl}acetamide A solution of N-[(E)-5-hydroxy-2-adamantyl]-2-{4-[5-(trifluoromethyl)pyridin-2-yl]piperazin-1-yl}acetamide (44 mg, 0.1 mmoles) from Example 2 in TFA (0.5 mL) and acetonitrile (0.1 mL) was stirred overnight at 100° C. The mixture was adjusted to pH ~10 with 2N NaOH and extracted with DCM. The organic layer was washed with water (2×), dried (MgSO$_4$) and filtered. The filtrate was concentrated under reduced pressure and purified (silica gel, 10-35% acetone in hexane) to provide the title compound as a white solid.

$^1$H NMR (300 MHz, CDCl$_3$) δ 8.41 (s, 1H), 7.64 (m, 2H), 6.67 (d, J=9 Hz, 1H), 5.16 (s, 1H), 4.10 (d, J=8.4 Hz, 1H), 3.69 (s, 4H), 3.09 (s, 2H), 2.68 (s, 4H), 2.18-2.16 (d, 2H), 2.09 (d, 4H), 2.01 (d, 2H), 1.92 (s, 3H), 1.69-1.63 (m, 5H); MS (APCI+) m/z 480 (M+H)$^+$.

EXAMPLE 11

N-[(E)-5-Fluoro-2-adamantyl]-2-{4-[5-(trifluoromethyl)pyridin-2-yl]piperazin-1-yl}acetamide A solution of N-[(E)-5-hydroxy-2-adamantyl]-2-{4-[5-(trifluoromethyl)pyridin-2-yl]piperazin-1-yl}acetamide (66 mg, 0.15 mmoles) from Example 2 in DCM (0.5 mL) was cooled to −78° C., treated with (diethylamino)sulfur trifluoride (DAST) (0.020 mL, 0.16 mmoles) and slowly warmed to room temperature over 6 hours. The mixture was quenched with aqueous saturated sodium bicarbonate (0.1 mL), filtered through a Celite cartridge and purified (silica gel, 10-15% acetone in hexane) to provide the title compound as a white solid.
$^1$H NMR (300 MHz, CDCl$_3$) δ 8.42 (s, 1H), 7.63 (m, 2H), 6.68 (d, J=9.2 Hz, 1H), 4.09 (d, J=8.5 Hz, 1H), 3.69 (s, 4H), 3.09 (s, 2H), 2.69 (s, 4H), 2.27-2.22 (m, 3H), 2.06 (m, 2H), 1.94 (m, 4H), 1.58-1.54 (m, 4H); (APCI+) m/z 441 (M+H)$^+$.

EXAMPLE 12

N-[(Z)-5-Fluoro-2-adamantyl]-2-{4-[5-(trifluoromethyl)pyridin-2-yl]piperazin-1-yl}acetamide A solution of N-[(Z)-5-hydroxy-2-adamantyl]-2-{4-[5-(trifluoromethyl)pyridin-2yl]piperazin-1-yl}acetamide (66 mg, 0.15 mmoles) from Example 1D in DCM (0.5 mL) was cooled to −78° C., treated with DAST (0.020 mL, 0.16 mmoles) and slowly warmed to room temperature for 6 hours. The mixture was quenched by the addition of aqueous saturated sodium bicarbonate (0.1 mL), filtered through a Celite cartridge and purified (silica gel, 10-15% acetone in hexane) to provide the title compound as a white solid. $^1$H NMR (300 MHz, CDCl$_3$) δ 8.42 (s, 1H), 7.67 (m, 2H), 6.67 (d, J=9.1 Hz, 1H), 3.97 (s, 1H), 3.7 (s, 4H), 3.1 (s, 2H), 2.68 (s, 4H), 2.29-2.24 (m, 3H), 1.91-1.7 (m, 10H); MS (APCI+) m/z 441 (M+H)$^+$.

EXAMPLE 13

N-[(E)-5-Hydroxy-2-adamantyl]-2-[4-(5-methylpyridin-2-yl)piperazin-1-yl]propanamide

EXAMPLE 13A (E)- and (Z)-5-hydroxy-2-adamantamine

A solution of 5-hydroxy-2-adamantanone (10 g, 60.161 mmoles) and 4 Å molecular sieves (5 g) in methanolic ammonia (7N, 100 mL) was stirred overnight at room temperature. The mixture was cooled in an ice bath, treated by the portion-wise addition of sodium borohydride (9.1 g, 240.64 mmoles) and stirred at room temperature for 2 hours. The mixture was filtered and MeOH was removed under reduced pressure. The mixture was taken into DCM (100 mL), acidified with 1N HCl to pH=3 and the layers separated. The aqueous layer was treated with 2N NaOH solution to pH=12 and extracted three times with 4:1 THF:DCM. The combined organic extracts were dried (MgSO$_4$) and filtered. The filtrate was concentrated under reduced pressure to provide the title compound as a white solid.

EXAMPLE 13B

2-Bromo-N-[(E)- and (Z)-5-hydroxy-adamantan-2-yl]-propionamide

A solution of (E)- and (Z)-5-hydroxy-2-adamantamine (1 g, 5.98 mmoles) from Example 13A in DCM (30 mL) and DIPEA (2.08 mL, 11.96 mmoles) was cooled in an ice bath and treated with 2-bromopropionyl chloride (0.66 mL, 6.58 mmoles). The mixture was stirred for 2 hours at room temperature and DCM was removed under reduced pressure. The residue was partitioned between water and ethyl acetate. The organic layer was washed with saturated sodium bicarbonate, water, dried (MgSO$_4$) and filtered. The filtrate was concentrated under reduced pressure to provide the title compound as a dark beige solid. The isomers were separated by column chromatography (silica gel, 5-35% acetone in hexane) to furnish 2-bromo-N-[(E)-5-hydroxy-adamantan-2-yl]propionamide and 2-bromo-N-[(Z)-5-hydroxy-adamantan-2-yl]propionamide.

EXAMPLE 13C 1-(5-Methyl-pyridin-2-yl)-piperazine

A solution of piperazine (215 mg, 2.5 mmoles), 2-bromo-5-methyl-pyridine (172 mg, 1 mmoles) in dioxane (1 mL) and potassium carbonate (276 mg, 2 mmoles) was irradiated by microwaves for 60 minutes at 180° C. The dioxane was removed under reduced pressure and the residue partitioned between aqueous potassium carbonate and ethyl acetate. The aqueous layer was extracted with ethyl acetate and the combined organic extracts washed twice with water, dried (MgSO$_4$) and filtered. The filtrate was concentrated under reduced pressure and the residue was purified (silica gel, 0-10% methanol in dichloromethane) to provide the title compound as a white solid.

EXAMPLE 13D

N-[(E)-5-Hydroxy-2-adamantyl]-2-[4-(5-methylpyridin-2-yl)piperazin-1-yl]propanamide A solution of 2-bromo-N-[(E)-5-hydroxy-adamantan-2-yl]-propionamide (36 mg, 0.12 mmoles) from Example 13B and 1-(5-methyl-pyridin-2-yl)-piperazine (21 mg, 0.12 mmoles) from Example 13C in MeOH (0.5 mL) and DIPEA (0.1 mL) was stirred overnight at 70° C. The MeOH was removed under reduced pressure and the residue purified (silica gel, 10-40% acetone in hexane) to provide the title compound as a white solid. $^1$H NMR (300 MHz, CDCl$_3$) δ 8.06 (d, J=5.3, 1H), 7.71 (s, 1H), 6.51 (s, 2H), 4.02 (d, J=8.2 Hz, 1H), 3.56 (s, 4H), 3.12 (m, 1H), 2.68 (bd, 4H), 2.28 (s, 3H), 2.17-2.10 (m, 3H), 1.91-1.88 (d, J=11.5 Hz, 2H), 1.76 (s, 4H), 1.66 (d, J=12.5 Hz, 2H), 1.51 (m, 2H), 1.27 (m, 3H); MS (APCI+) m/z 399 (M+H)$^+$.

EXAMPLE 14

N-[(E)-5-Hydroxy-2-adamantyl]-2-methyl-2-{4-[5-(trifluoromethyl)pyridin-2-yl]piperazin-1-yl}propanamide

EXAMPLE 14A

2-[4-(5-Trifluoromethyl-pyridin-2-yl)-piperazin-1-yl]-propionic acid methyl ester A solution of 1-(5-trifluoromethyl-pyridin-2-yl)-piperazine (0.9 g, 3.9 mmoles) in MeOH (13 mL) and DIPEA (1.5 mL) was treated with 2-bromo-propionic acid methyl ester (0.48 mL, 4.3 mmoles) and stirred overnight at 70° C. The MeOH was removed under reduced pressure and the residue was purified (silica gel, 10-40% acetone in hexane) to provide the title compound as a yellowish solid.

EXAMPLE 14B

2-Methyl-2-[4-(5-trifluoromethyl-pyridin-2-yl)-piperazin-1-yl]-propionic acid methyl ester A solution of 2-[4-(5-trifluoromethyl-pyridin-2-yl)-piperazin-1-yl]-propionic acid methyl ester (1.23 g, 3.9 mmoles) from Example 14A in dry THF (3 mL) was added dropwise to a −65° C. solution of 1.8 N lithium diisopropylamine (LDA) in dry THF (2.4 mL) and stirred at this temperature for 1 hour. Methyl iodide (0.49 mL, 7.88 mmoles) was added and the mixture was allowed to slowly warm to room temperature and stir for 2 hours at room temperature. The mixture was quenched with ice/water and partitioned with ethyl acetate. The aqueous layer was extracted with ethyl acetate (3×) and the combined organic extracts washed with water, dried (MgSO$_4$), filtered and the filtrate concentrated under reduced pressure. The residue was purified (silica gel, 10-30% acetone in hexane) to provide the title compound as a yellowish solid.

EXAMPLE 14C

2-Methyl-2-[4-(5-trifluoromethyl-pyridin-2-yl)-piperazin-1-yl]-propionic acid

A solution of 2-methyl-2-[4-(5-trifluoromethyl-pyridin-2-yl)-piperazin-1-yl]-propionic acid methyl ester (1.05 g, 3.17 mmoles) from Example 14B in dioxane (10 mL) was treated with 5N potassium hydroxide (10 mL) and stirred for 4 hours at 60° C. The dioxane was removed under reduced pressure, the residue was neutralized with 1N HCl to pH=7 and extracted three times with 4:1 THF:DCM. The combined organic extracts were dried (MgSO$_4$), filtered and the filtrate concentrated under reduced pressure to provide the title compound as a white solid.

EXAMPLE 14D

N-[(E)-5-Hydroxy-2-adamantyl]-2-methyl-2-{4-[5-(trifluoromethyl)pyridin-2-yl]piperazin-1-yl}propanamide A solution of 2-methyl-2-[4-(5-trifluoromethyl-pyridin-2-yl)-piperazin-1-yl]-propionic acid (159 mg, 0.5 mmoles) from Example 14C in DCM (5 mL) and DIPEA (0.5 mL) was treated with hydroxybenzotriazole hydrate (HOBt) (84 mg, 0.6 mmoles), 5-hydroxy-2-adamantamine (100 mg, 0.6 mmoles) from Example 13A and 15 minutes later with (3-dimethylaminopropyl)-3-ethylcarbodiimide HCl (EDCI) (115 mg, 0.6 mmoles). The mixture was stirred overnight at room temperature after which the DCM was removed under reduced pressure and the residue was partitioned between water and ethyl acetate. The aqueous layer was extracted with ethyl acetate and the combined organic extracts washed with saturated sodium bicarbonate, water, dried (MgSO$_4$) and filtered. The filtrate was concentrated under reduced pressure and the crude product purified (silica gel, 10-40% acetone in hexane) to provide the title compound as a white solid. $^1$H NMR (300 MHz, CDCl$_3$) δ 8.41 (s, 1H), 7.67 (m, 2H), 6.66 (d, J=9.1 Hz, 1H), 4.0 (d, J=7.8 Hz, 1H), 3.66 (m, 4H), 2.64 (m, 4H), 2.23-2.1 (m, 3H), 1.9-1.63 (m, 10H), 1.25 (s, 6H); MS (APCI+) m/z 467 (M+H)$^+$.

EXAMPLE 15

(E)-4-{2-Methyl-2-[4-(5-trifluoromethyl-pyridin-2-yl)-piperazin-1-yl]-propionylamino}-adamantane-1-carboxylic acid

EXAMPLE 15A

Methyl 2-adamantanone-5-carboxylate

A solution of 5-hydroxy-2-adamantanone (2.0 g, 12.0 mmol) in 99% formic acid (12 mL) was added dropwise with vigorous gas evolution over 40 minutes to a rapidly stirred 30% oleum solution (48 mL) heated to 60° C. (W. J. le Noble, S. Srivastava, C. K. Cheung, J. Org. Chem. 48: 1099-1101, 1983). Upon completion of addition, more 99% formic acid (12 mL) was slowly added over the next 40 minutes. The mixture was stirred another 60 minutes at 60° C. and then slowly poured into vigorously stirred methanol (100 mL) cooled to 0° C. The mixture was allowed to slowly warm to 23° C. while stirring for 2 hours and then concentrated in vacuo. The residue was poured onto ice (30 g) and methylene chloride (100 mL) added. The layers were separated, and the aqueous phase extracted twice more with methylene chloride (100 mL aliquots). The combined methylene chloride solutions were concentrated in vacuo to 50 mL, washed with brine, dried over Na$_2$SO$_4$, filtered, and concentrated in vacuo to provide the title compound as a pale yellow solid. $^1$H NMR (300 MHz, DMSO-d$_6$) δ 3.61 (s, 3H), 2.47-2.40 (bs, 2H), 2.17-1.96 (m, 9H), 1.93-1.82 (m, 2H); MS (DCI) m/z 209 (M+H)$^+$.

EXAMPLE 15B

Methyl (E)- and (Z)-4-adamantamine-1-carboxylate

A solution of methyl 2-adamantanone-5-carboxylate (2.0 g, 9.6 mmoles) from Example 15A and 4 Å molecular sieves (1.0 g) in methanolic ammonia (7N, 17 mL) was stirred overnight at room temperature. The reaction mixture was cooled in an ice bath, treated portionwise with sodium borohydride (1.46 g, 38.4 mmoles) and stirred at room temperature for 2 hours. The suspension was filtered and MeOH was removed under reduced pressure. The residue was taken into methylene chloride (200 mL) and acidified with 10% citric acid. The pH of the solution was adjusted to neutral with saturated NaHCO$_3$ and then saturated with NaCl. The layers were separated and the aqueous extracted twice more with methylene chloride. The combined organic extracts were dried over Na$_2$SO$_4$ and filtered. The filtrate was concentrated under reduced pressure to provide the title compound as a light yellow solid. $^1$H NMR (300 MHz, CDCl$_3$) δ 3.66 (s, 3H), 3.16 (m, 1H), 2.27-1.46 (m, 13H); MS (DCI) m/z 210 (M+H)$^+$.

EXAMPLE 15C

Methyl (E)- and (Z)-4-{2-methyl-2-[4-(5-trifluoromethyl-pyridin-2-yl)-piperazin-1-yl]-propionylamino}-adamantane-1-carboxylate To a 0° C., heterogeneous solution of 2-methyl-2-[4-(5-trifluoromethyl-pyridin-2-yl)-piperazin-1-yl]-propionic acid (50 mg, 0.16 mmol) from Example 14C, methyl (E)- and (Z)-4-adamantamine-1-carboxylate (33 mg, 0.16 mmol) from Example 15B, tetrahydrofuran (1.3 mL), and Hunig's base (30 mg, 0.24 mmol) was added solid HATU (60 mg, 0.16 mmol). The stirred reaction mixture was allowed to slowly warm to 23° C. as the ice bath melted overnight (16 hours). LC/MS analysis of the homogenous reaction mixture revealed complete consumption of starting materials. The reaction mixture was concentrated under reduced pressure, and the residue purified with flash silica gel (ethyl acetate/hexanes, 20-80% gradient) to afford the title compound as a mixture of E/Z structural isomers. Carried on as a slightly impure E/Z mixture.

EXAMPLE 15D (E)-4-{2-Methyl-2-[4-(5-trifluoromethyl-pyridin-2-yl)-piperazin-1-yl]-propionylamino}-adamantane-1-carboxylic acid A stirred, 23° C., homogenous solution of methyl (E)- and (Z)-4-{2-methyl-2-[4-(5-trifluoromethyl-pyridin-2-yl)-piperazin-1-yl]-propionylamino}-adamantane-1-carboxylate (19 mg, 0.037 mmol) from Example 15C and methanol (0.5 mL) became cloudy upon addition of 10% aqueous NaOH (1 mL). After stirring for 1 hour at 23° C., the reaction mixture was heated to 50° C. for 1 hour. The mixture was diluted with sat. aqueous NaHCO$_3$ and extracted three times with a tetrahydrofuran/methylene chloride solution (4/1). The combined organic extracts were dried over Na$_2$SO$_4$, filtered, and concentrated under reduced pressure. The E/Z isomers were separated by radial chromatography with 2% methanol in ethyl acetate/hexanes (4/1) as the eluant to afford the title compound. $^1$H NMR (500 MHz, DMSO-d$_6$) δ 8.41 (s, 1H), 7.79 (dd, J=2.5, 9 Hz, 1H), 7.71 (d, J=7.5 Hz, 1H), 6.96 (d, J=9.5 Hz, 1H), 3.79 (m, 1H), 3.66 (m, 4H), 2.54 (m, 4H), 1.95-1.70 (m, 11H), 1.58-1.52 (m, 2H), 1.13 (s, 6H); MS (DCI) m/z 495 (M+H)$^+$.

EXAMPLE 16

(E)-4-({1-[4-(5-Trifluoromethyl-pyridin-2-yl)-piperazin-1-yl]-cyclopropanecarbonyl}-amino)-adamantane-1-carboxylic acid

EXAMPLE 16A

N,N-Bis-(2-hydroxy-ethyl)-2-nitrobenzenesulfonamide

A solution of 2-nitrobenzenesulfonyl chloride (10.5 g, 47.6 mmol) in anhydrous methylene chloride (25 mL) was added dropwise with stirring to a 0° C. solution of diethanolamine (5.00 g, 47.6 mmol) and triethylamine (4.92 g, 47.6 mmol) in anhydrous methylene chloride (50 mL). Reaction stirred three hours at 0° C. and then overnight at room temperature. Reaction mixture concentrated under reduced pressure. Residue dissolved in ethyl acetate, washed with 1 N NaOH, saturated NaHCO$_3$, and brine, dried over Na$_2$SO$_4$, filtered, and concentrated under reduced pressure. The residue was purified by normal phase HPLC on a Biotage pre-packed silica gel column eluting with ethyl acetate to afford the title compound. MS (ESI) m/z 291 (M+H)$^+$.

EXAMPLE 16B

N,N-Bis-(2-trifluoromethanesulfonyloxyethyl)-2-nitrobenzenesulfonamide

Triflic anhydride (13.6 g, 48.3 mmol) was added dropwise with stirring to a 0° C. solution of N,N-bis-(2-hydroxyethyl)-2-nitrobenzenesulfonamide (7.00 g, 24.1 mmol) from Example 16A and 2,4,6-collidine (5.85 g, 48.3 mmol) in anhydrous methylene chloride (50 mL) (J. A. Kozlowski, et al., Bioorg. Med. Chem. Lett. 12: 791-794, 2002). Reaction stirred two hours at 0° C. and then overnight at room temperature. Reaction diluted with chloroform, washed with saturated NaHCO$_3$ and brine, dried over Na$_2$SO$_4$, filtered, and concentrated under reduced pressure. The residue was purified by normal phase HPLC on a Biotage pre-packed silica gel column eluting with 3:1 hexane:ethyl acetate to afford the title compound. MS (ESI) m/z 555 (M+H)$^+$.

EXAMPLE 16C

Methyl 1-[4-(2-nitrobenzenesulfonyl)-piperazin-1-yl]-cyclopropanecarboxylate

A solution of N,N-bis-(2-trifluoromethanesulfonyloxyethyl)-2-nitrobenzenesulfonamide (1.83 g, 3.30 mmol) from Example 16B and methyl 1-aminocyclopropane-1-carboxylate HCl (0.50 g, 3.30 mmol) in anhydrous acetonitrile (10 mL) was treated with sodium carbonate (1.40 g, 13.2 mmol) and heated overnight at 60° C. (J. A. Kozlowski, et al., Bioorg. Med. Chem. Lett. 12: 791-794, 2002). Reaction diluted with ethyl acetate, washed with water and brine, dried over Na$_2$SO$_4$, filtered, and concentrated under reduced pressure. The residue was purified by normal phase HPLC on a Biotage pre-packed silica gel column eluting with 3:1 hexane:ethyl acetate to afford the title compound. MS (ESI) m/z 370 (M+H)$^+$.

EXAMPLE 16D

Methyl 1-[4-(5-trifluoromethylpyridin-2-yl)-piperazin-1-yl]-cyclopropanecarboxylate A solution of methyl 1-[4-(2-nitrobenzenesulfonyl)-piperazin-1-yl]-cyclopropanecarboxylate (0.60 g, 1.63 mmol) from Example 16C in anhydrous dimethylformamide (5 mL) was treated with potassium carbonate (0.67 g, 4.88 mmol) and thiophenol (0.21 g, 1.95 mmol) and stirred one hour at room temperature. This reaction mixture was then treated with 2-bromo-5-trifluoromethylpyridine (0.44 g, 1.95 mmol) and heated overnight at 80° C. Reaction diluted with ethyl acetate, washed with water and brine, dried over Na$_2$SO$_4$, filtered, and concentrated under reduced pressure. The residue was purified by normal phase HPLC on a Biotage pre-packed silica gel column eluting with 9:1 hexane:ethyl acetate to afford the title compound. MS (ESI) m/z 330 (M+H)$^+$.

EXAMPLE 16E

1-[4-(5-Trifluoromethylpyridin-2-yl)-piperazin-1-yl]-cyclopropanecarboxylic acid A solution of methyl 1-[4-(5-trifluoromethylpyridin-2-yl)-piperazin-1-yl]-cyclopropanecarboxylate (0.32 g, 0.96 mmol) from Example 16D in tetrahydrofuran (5 mL) and methanol (2 mL) was treated with 4 N sodium hydroxide (2.40 mL, 9.60 mmol) and stirred overnight at 60° C. Reaction mixture concentrated under reduced pressure and dissolved in water. Solution neutralized with 1 N phosphoric acid (pH 7) and extracted three times with chloroform. Extracts dried over Na$_2$SO$_4$, filtered, and concentrated under reduced pressure to afford the title compound without further purification. MS (ESI) m/z 316 (M+H)$^+$.

EXAMPLE 16F

Methyl (E)- and (Z)-4-({1-[4-(5-trifluoromethyl-pyridin-2-yl)-piperazin-1-yl]-cyclopropanecarbonyl}-amino)-adamantine-1-carboxylate A solution of 1-[4-(5-trifluoromethylpyridin-2-yl)-piperazin-1-yl]-cyclopropanecarboxylic acid (60 mg, 0.19 mmol) from Example 16E, methyl (E)- and (Z)-4-adamantamine-1-carboxylate (40 mg, 0.19 mmol) from Example 15B, and O-(1H-benzotriazol-1-yl)-N,N,N',N'-tetramethyluronium tetrafluoroborate (TBTU) (92 mg, 0.29 mmol) in dimethylformamide (3 mL) was treated, after stirring 5 minutes at room temperature, with N,N-diisopropylethylamine (50 mg, 0.38 mmol) and stirred overnight at room temperature. Reaction diluted with ethyl acetate, washed with water, saturated NaHCO$_3$, and brine, dried over Na$_2$SO$_4$, filtered, and concentrated under reduced pressure. The residue was purified by flash chromatography on silica gel eluting with 8:2 to 6:4 hexane:ethyl acetate to afford the title compound. MS (ESI) m/z 507 (M+H)$^+$.

EXAMPLE 16G (E)-4-({1-[4-(5-Trifluoromethyl-pyridin-2-yl)-piperazin-1-yl]-cyclopropanecarbonyl}-amino)-adamantane-1-carboxylic acid The title compound was prepared using the procedure described in Example 16E starting with methyl (E)- and (Z)-4-({1-[4-(5-trifluoromethyl-pyridin-2-yl)-piperazin-1-yl]-cyclopropanecarbonyl}-amino)-adamantane-1-carboxylate from Example 16F. The E and Z isomers were separated by flash chromatography on silica gel eluting with 20:1 to 10:1 methylene chloride:methanol to afford the title compound. $^1$H NMR (400 MHz, DMSO-d$_6$) δ 8.41 (s, 1H), 8.23 (d, J=7.5 Hz, 1H), 7.79 (dd, J=2.5, 9 Hz, 1H), 6.96 (d, J=9.5 Hz, 1H), 3.79 (m, 1H), 3.70 (m, 4H), 2.50 (m, 4H), 2.00-1.70 (m, 11H), 1.60-1.52 (m, 2H), 1.05 (m, 2H), 0.96 (m, 2H); MS (ESI) m/z 493 (M+H)+.

EXAMPLE 17

(E)-4-({1-[4-(5-Trifluoromethyl-pyridin-2-yl)-piperazin-1-yl]-cyclopropanecarbonyl}-amino)-adamantane-1-carboxamide The title compound was prepared according to the procedure outlined in Example 23 substituting (E)-4-({1-[4-(5-trifluoromethyl-pyridin-2-yl)-piperazin-1-yl]-cyclopropanecarbonyl}-amino)-adamantane-1-carboxylic acid from example 16G for (E)-4-{2-methyl-2-[4-(5-trifluoromethyl-pyridin-2-yl)-piperazin-1-yl]-propionylamino}-adamantane-1-carboxylic acid. $^1$H NMR (500 MHz, DMSO-d$_6$) δ 8.47 (s, 1H), 8.31 (d, J=9.5 Hz, 1H), 7.86 (dd, J=2.5, 9 Hz, 1H), 7.03 (d, J=9.5 Hz, 2H), 6.75 (bs, 1H), 3.88 (m, 1H), 3.77 (m, 4H), 2.57 (m, 4H), 2.05-1.80 (m, 11H), 1.61 (m, 2H), 1.12 (m, 2H), 1.03 (m, 2H); MS (ESI) m/z 492 (M+H)+.

EXAMPLE 18

(E)-4-{2-[4-(5-Trifluoromethyl-pyridin-2-yl)-piperazin-1-yl]-butyrylamino}-adamantane-1-carboxamide

EXAMPLE 18A

Methyl (E)- and (Z)-4-formylamino-adamantane-1-carboxylate

A solution of methyl (E)- and (Z)-4-adamantamine-1-carboxylate (12.7 g, 60.2 mmol) from Example 15B in methyl formate (60 mL) was treated with triethylamine (12.2 g, 120 mmol) and heated overnight at 50° C. in a high pressure tube. The reaction mixture was concentrated under reduced pressure. The residue was purified by normal phase HPLC on a Biotage pre-packed silica gel column eluting with 7:3 ethyl acetate:hexane to afford the title compound. MS (DCI) m/z 238 (M+H)+.

EXAMPLE 18B

Methyl (E)-4-isocyano-adamantane-1-carboxylate

A −10° C. solution of methyl (E)- and (Z)-4-formylamino-adamantane-1-carboxylate (6.00 g, 25.3 mmol) from Example 18A and triethylamine (12.8 g, 127 mmol) in anhydrous methylene chloride (30 mL) was treated dropwise with phosphorus oxychloride (5.82 g, 38.0 mmol) and reaction stirred one hour at −10° C. and then one hour at room temperature. Reaction cooled back down to 0° C. and quenched with saturated sodium bicarbonate. Organic layer separated and aqueous layer extracted two times with methylene chloride. Combined extracts dried over Na$_2$SO$_4$, filtered, and concentrated under reduced pressure. The E and Z isomers were separated by flash chromatography on silica gel eluting methylene chloride to provide the title compound. MS (DCI) m/z 220 (M+H)+.

EXAMPLE 18C

Methyl (E)-4-{2-[4-(5-trifluoromethyl-pyridin-2-yl)-piperazin-1-yl]-butyrylamino}-adamantane-1-carboxylate A heterogeneous solution of 1-[5-trifluoromethyl)-2-pyridyl]piperazine (106 mg, 0.46 mmol), propionaldehyde (14 mg, 0.23 mmol), acetic acid (27 mg, 0.46 mmol), and dried 4 Å molecular sieves (25 mg) in anhydrous methanol (2 mL) which had been stirring at room temperature for twenty minutes was treated with methyl (E)-4-isocyano-adamantane-1-carboxylate (50 mg, 0.23 mmol) from Example 18B and stirred two hours at room temperature and overnight at 70° C. The reaction mixture was concentrated under reduced pressure. The residue was purified by flash chromatography on silica gel eluting with 7:3 to 1:1 hexane:ethyl acetate to provide the title compound. MS (ESI) m/z 509 (M+H)+.

EXAMPLE 18D (E)-4-{2-[4-(5-Trifluoromethyl-pyridin-2-yl)-piperazin-1-yl]-butyrylamino}-adamantane-1-carboxylic acid The title compound was prepared using the procedure described in Example 16E starting with methyl (E)-4-{2-[4-(5-trifluoromethyl-pyridin-2-yl)-piperazin-1-yl]-butyrylamino}-adamantane-1-carboxylate from Example 18C. MS (ESI) m/z 495 (M+H)+.

EXAMPLE 18E (E)-4-{2-[4-(5-Trifluoromethyl-pyridin-2-yl)-piperazin-1-yl]-butyrylamino}-adamantane-1-carboxamide The title compound was prepared according to the procedure outlined in Example 23 substituting (E)-4-{2-[4-(5-trifluoromethyl-pyridin-2-yl)-piperazin-1-yl]-butyrylamino}-adamantane-1-carboxylic acid from example 18D for (E)-4-{2-methyl-2-[4-(5-trifluoromethyl-pyridin-2-yl)-piperazin-1-yl]-propionylamino}-adamantane-1-carboxylic acid. $^1$H NMR (500 MHz, DMSO-d$_6$) δ 8.39 (s, 1H), 7.77 (dd, J=2.5, 9 Hz, 1H), 7.68 (d, J=9.5 Hz, 1H), 6.97 (s, 1H), 6.94 (d, J=9.5 Hz, 1H), 6.71 (s, 1H), 3.82 (m, 1H), 3.58 (m, 4H), 3.12 (m, 1H), 2.65 (m, 2H), 2.56 (m, 2H), 1.95-1.70 (m, 11H), 1.65 (m, 1H), 1.55 (m, 1H), 1.41 (m, 2H), 0.83 (m, 3H); MS (ESI) m/z 494 (M+H)+.

EXAMPLE 19

(E)-4-{2-Cyclopropyl-2-[4-(5-trifluoromethyl-pyridin-2-yl)-piperazin-1-yl]-acetylamino}-adamantane-1-carboxamide

EXAMPLE 19A (E)-4-{2-Cyclopropyl-2-[4-(5-trifluoromethyl-pyridin-2-yl)-piperazin-1-yl]-acetylamino}-adamantane-1-carboxylic acid The title compound was prepared using the procedures described in Examples 18C-D substituting cyclopropanecarboxaldehyde for propionaldehyde.

EXAMPLE 19B (E)-4-{2-Cyclopropyl-2-[4-(5-trifluoromethyl-pyridin-2-yl)-piperazin-1-yl]-acetylamino}-adamantane-1-carboxamide The title compound was prepared using the procedures described in Examples 23 substituting (E)-4-{2-cyclopropyl-2-[4-(5-trifluoromethyl-pyridin-2-yl)-piperazin-1-yl]-acetylamino}-adamantane-1-carboxylic acid from example 19A for (E)-4-{2-methyl-2-[4-(5-trifluoromethyl-pyridin-2-yl)-piperazin-1-yl]-propionylamino}-adamantane-1-carboxylic acid. $^1$H NMR (500 MHz, DMSO-d$_6$) δ 8.39 (s, 1H), 7.78 (dd, J=2.5, 9 Hz, 1H), 7.56 (d, J=9.5 Hz, 1H), 6.98 (s, 1H), 6.93 (d, J=9.5 Hz, 1H), 6.72 (s, 1H), 3.82 (m, 1H), 3.62 (m, 4H), 2.79 (m, 2H), 2.53 (m, 2H), 2.22 (d, J=9.5 Hz, 1H), 1.95-1.70 (m, 11H), 1.43 (m, 2H), 0.99 (m, 1H), 0.60 (m, 1H), 0.41 (m, 1H), 0.27 (m, 2H); MS (ESI) m/z 506 (M+H)$^+$.

EXAMPLE 20

(E)-4-({1-[4-(5-Trifluoromethyl-pyridin-2-yl)-piperazin-1-yl]-cyclobutanecarbonyl}-amino)-adamantane-1-carboxamide

EXAMPLE 20A (E)-4-({1-[4-(5-Trifluoromethyl-pyridin-2-yl)-piperazin-1-yl]-cyclobutanecarbonyl}-amino)-adamantane-1-carboxylic acid The title compound was prepared using the procedures described in Examples 18C-D substituting cyclobutanone for propionaldehyde.

EXAMPLE 20B (E)-4-({1-[4-(5-Trifluoromethyl-pyridin-2-yl)-piperazin-1-yl]-cyclobutanecarbonyl}-amino)-adamantane-1-carboxamide The title compound was prepared using the procedures described in Examples 23 substituting (E)-4-({1-[4-(5-trifluoromethyl-pyridin-2-yl)-piperazin-1-yl]-cyclobutanecarbonyl}-amino)-adamantane-1-carboxylic acid for (E)-4-{2-methyl-2-[4-(5-trifluoromethyl-pyridin-2-yl)-piperazin-1-yl]-propionylamino}-adamantane-1-carboxylic acid. $^1$H NMR (500 MHz, DMSO-d$_6$) δ 8.41 (s, 1H), 7.80 (dd, J=2.5, 9 Hz, 1H), 7.36 (d, J=9.5 Hz, 1H), 6.99 (s, 1H), 6.97 (d, J=9.5 Hz, 1H), 6.73 (s, 1H), 3.82 (m, 1H), 3.63 (m, 4H), 2.53 (m, 4H), 2.22 (m, 2H), 2.14 (m, 2H), 1.95-1.60 (m, 13H), 1.46 (m, 2H); MS (ESI) m/z 506 (M+H)$^+$.

EXAMPLE 21

N-[(E)-5-Hydroxymethyl-adamantan-2-yl]-2-[4-(5-trifluoromethyl-pyridin-2-yl)-piperazin-1-yl]-isobutyramide A solution of (E)-4-{2-methyl-2-[4-(5-trifluoromethyl-pyridin-2-yl)-piperazin-1-yl]-propionylamino}-adamantane-1-carboxylic acid (494 mg, 1 mmoles) in THF (2 mL) was cooled to 0° C. and treated with 1N borane solution in THF (2 mL). The reaction was stirred at reflux for 20 hours and carefully quenched with water (4 mL) after cooling to room temperature. The reaction mixture extracted three times with a tetrahydrofuran/methylene chloride solution (4/1). The combined organic extracts were dried over Na$_2$SO$_4$, filtered, and concentrated under reduced pressure. The residue was purified with flash silica gel (acetone/hexanes, 10-40% gradient) to provide the title compound as a white solid. $^1$H NMR (300 MHz, CDCl$_3$) δ 8.41 (s, 1H), 7.77 (d, J=11.5 Hz, 1H), 7.64 (d, J=6.3 Hz, 1H), 6.66 (d, J=9.1 Hz, 1H), 6.76 (s, 1H), 3.96 (bd, 1H), 3.66 (s, 4H), 3.25 (d, J=5.4 Hz, 2H), 2.65 (s, 4H), 1.99 (s, 2H), 1.71-1.56 (m, 12H), 1.25 (s, 6H); MS (ESI+) m/z 481 (M+H)$^+$.

EXAMPLE 22

N-[(E)-5-Formyl-adamantan-2-yl]-2-[4-(5-trifluoromethyl-pyridin-2-yl)-piperazin-1-yl]-isobutyramide A solution of N-[(E)-hydroxymethyl-adamantan-2-yl]-2-[4-(5-trifluoromethyl-pyridin-2-yl)-piperazin-1-yl]-isobutyramide (400 mg, 0.83 mmoles) from Example 21 and 4 Å molecular sieves in DCE (3 mL) were treated with 4-methyl-morpholine-N-oxide (124 mg, 1.24 mmoles) and tetrapropylammonium perruthenate (15 mg, 0.04 mmoles). The reaction was stirred at room temperature for 20 hours, filtered and washed with DCM. DCM was concentrated under reduced pressure to afford the title compound as a white solid.

EXAMPLE 23

(E)-4-{2-Methyl-2-[4-(5-trifluoromethyl-pyridin-2-yl)-piperazin-1-yl]-propionylamino}-adamantane-1-carboxamide A solution of (E)-4-{2-methyl-2-[4-(5-trifluoromethyl-pyridin-2-yl)-piperazin-1-yl]-propionylamino}-adamantane-1-carboxylic acid (100 mg, 0.21 mmoles) from Example 15 in DCM (2 mL) was treated with HOBt (33 mg, 0.22 mmoles) and EDC (46 mg, 0.24 mmoles) and stirred at room temperature for 1 hour. Excess of aqueous (35%) ammonia (2 mL) was added and the reaction was stirred for additional 20 hours. The layers were separated and the aqueous extracted twice more with methylene chloride (2×2 mL). The combined organic extracts were dried over Na$_2$SO$_4$ and filtered. The filtrate was concentrated under reduced pressure to provide the crude title compound that was purified on reverse phase HPLC to provide the title compound. $^1$H NMR (400 MHz, DMSO-d$_6$) δ 8.47 (s, 1H), 7.83 (d, J=6.8 Hz, 1H), 7.76 (d, J=7.9 Hz, 1H), 7.02 (d, J=9.5 Hz, 2H), 6.76 (s, 1H), 3.86 (d, J=7.9 Hz, 1H), 3.71 (s, 4H), 2.59 (s, 4H), 1.98-1.90 (m, 7H), 1.81-1.77 (m, 4H), 1.58 (d, J=12.9 Hz, 2H), 1.18 (s, 6H); MS (ESI+) m/z 494 (M+H)$^+$.

EXAMPLE 24

(E)-4-{2-Methyl-2-[4-(5-trifluoromethyl-pyridin-2-yl)-piperazin-1-yl]-propionylamino}-adamantane-1-carboxylic acid hydroxyamide A solution of (E)-4-{2-methyl-2-[4-(5-trifluoromethyl-pyridin-2-yl)-piperazin-1-yl]-propionylamino}-adamantane-1-carboxylic acid (100 mg, 0.21 mmoles) from Example 15 in DCM (2 mL) was treated with HOBt (33 mg, 0.22 mmoles) and EDC (46 mg, 0.24 mmoles) and stirred at room temperature for 1 hour. Excess of aqueous hydroxylamine (2 mL) was added and the reaction was stirred for additional 20 hours. The layers were separated and the aqueous extracted twice more with methylene chloride (2×2 mL). The combined organic extracts were dried over Na$_2$SO$_4$ and filtered. The filtrate was concentrated under reduced pressure to provide the crude title compound that was purified on reverse phase HPLC to provide the title compound. $^1$H NMR (400 MHz, Py-d$_5$) δ 8.67 (s, 1H), 7.85 (d, J=8.3 Hz, 1H), 7.79 (d, J=9.2 Hz, 1H), 6.86 (d, J=8.9 Hz, 1H), 4.3 (d, J=8.3 Hz, 1H), 3.74 (s, 4H), 2.57 (s, 4H), 2.29 (s, 4H), 2.18 (s, 2H), 2.11 (s, 2H), 1.97 (s, 1H), 1.86 (d, J=13.5 Hz, 2H)), 1.62 (d, J=13.3 Hz, 2H), 1.31 (s, 6H); MS (ESI+) m/z 510 (M+H)$^+$.

EXAMPLE 25

(E)-4-{2-[4-(5-Trifluormethyl-pyridin-2-yl)-piperazin-1-yl]-acetylamino}-adamantane-1-carboxylic acid

EXAMPLE 25A

2-Chloro-N-[(E)- and (Z)-5-hydroxy-adamantan-2-yl]-acetamide

A solution of (E)- and (Z)-5-hydroxy-2-adamantamine (1.7 g, 10 mmoles) in DCM (33 mL) and DIPEA (1.47 g, 11.4 mmoles) was cooled in an ice bath and treated with 2-chloroacetyl chloride (0.88 mL, 11 mmoles). The mixture was stirred for 2.5 hours at room temperature and DCM was removed under reduced pressure. The residue was partitioned between water and ethyl acetate. The organic layer was washed with saturated 1 N HCl, water, brine, dried ($Na_2SO_4$), filtered, and concentrated in vacuo. The isomers were separated by column chromatography (silica gel, 10-30% acetone in hexane) to furnish 2-chloro-N-[(E)-5-hydroxy-adamantan-2-yl]acetamide and 2-chloro-N-[(Z)-5-hydroxy-adamantan-2-yl]acetamide.

EXAMPLE 25B

Methyl (E)-4-(2-chloro-acetylamino)-adamantane-1-carboxylate

A solution of 2-chloro-N-[(E)-5-hydroxy-adamantan-2-yl]acetamide (0.5 g, 2.1 mmol) from Example 25A in 99% formic acid (3 mL) was added dropwise by addition funnel with vigorous gas evolution to a rapidly stirred 30% oleum solution (13 mL) heated to 60° C. (W. J. le Noble, S. Srivastava, C. K. Cheung, J. Org. Chem. 48: 1099-1101, 1983). Upon completion of addition, more 99% formic acid (3 mL) was slowly added by addition funnel. The mixture was stirred another 60 minutes at 60° C. and then slowly poured into vigorously stirred ice water. The mixture was allowed to slowly warm to 23° C., filtered and washed with water to neutral pH. The precipitate was dried in a vacuum oven, taken into MeOH (3 mL) and treated with thionyl chloride at 0° C. (0.25 mL, 3.5 mmoles). The reaction mixture was stirring at room temperature for 3 hours and then MeOH was evaporated under reduced pressure to provide the title compound as an off-white solid.

EXAMPLE 25C (E)-4-{2-[4-(5-Trifluormethyl-pyridin-2-yl)-piperazin-1-yl]-acetylamino}-adamantane-1-carboxylic acid A solution of methyl (E)-4-(2-chloro-acetylamino)-adamantane-1-carboxylate (0.075 g, 0.26 mmoles) from Example 25B, in MeOH (1.5 mL) and DIPEA (0.05 mL, 0.29 mmoles) was treated with 1-(5-trifluoromethyl-pyridin-2-yl)-piperazine (0.091 g, 0.39 mmoles) and stirred for 2 hours at 80° C. The cooled reaction mixture was purified on reverse phase HPLC and hydrolyzed with 3N HCl at 60° C. over 6 hours. Drying of the reaction mixture under reduced pressure provided the title compound as a white solid. $^1$H NMR (300 MHz, DMSO-$d_6$) δ 10.48 (bs, 1H), 8.56 (d, J=7.2 Hz, 1H), 8.48 (bs, 1H), 7.92 (dd, J=2.4, 9.0 Hz, 1H), 7.07 (d, J=9.0 Hz, 1H), 4.51 (m, 2H), 4.06 (s, 2H), 3.89 (m, 1H), 3.56 (m, 2H), 3.41 (m, 2H), 3.21 (bs, 2H), 1.90 (m, 9H), 1.80 (m, 2H), 1.47 (m, 2H); MS (DCI+) m/z 467 (M+H)$^1$.

EXAMPLE 26

(E)-4-[2-(3,3-Difluoro-piperidin-1-yl)-acetylamino]-adamantane-1-carboxylic acid A solution of methyl (E)-4-(2-chloro-acetylamino)-adamantane-1-carboxylate (0.075 g, 0.26 mmoles) from Example 25B, in MeOH (1.5 mL) and DIPEA (0.05 mL, 0.29 mmoles) was treated with 3,3-difluoro-piperidine hydrochloride (0.062 g, 0.39 mmoles) and stirred for 2 hours at 80° C. The cooled reaction mixture was purified on reverse phase HPLC and hydrolyzed with 3N HCl at 60° C. over 6 hours. Drying of the reaction mixture under reduced pressure provided the hydrochloride salt of the title compound as a white solid. $^1$H NMR (300 MHz, DMSO-$d_6$) δ 8.45 (m, 1H), 3.97 (bs, 2H), 3.88 (m, 1H), 3.65 (m, 2H), 3.23 (m, 2H), 2.11 (m, 2H), 1.91 (m, 11H), 1.79 (m, 2H), 1.47 (m, 2H); MS (DCI+) m/z 357 (M+H)$^+$.

EXAMPLE 27

(E)-4-[2-(2-Trifluoromethyl-pyrrolidin-1-yl)-acetylamino]-adamantane-1-carboxylic acid A solution of methyl (E)-4-(2-chloro-acetylamino)-adamantane-1-carboxylate (0.075 g, 0.26 mmoles) from Example 25B, in MeOH (1.5 mL) and DIPEA (0.05 mL, 0.29 mmoles) was treated with 2-trifluoromethylpyrrolidine (0.055 g, 0.39 mmoles) and stirred for 2 hours at 80° C. The cooled reaction mixture was purified on reverse phase HPLC and hydrolyzed with 3N HCl at 60° C. over 6 hours. Drying of the reaction mixture under reduced pressure provided the hydrochloride salt of the title compound as a white solid. $^1$H NMR (300 MHz, DMSO-$d_6$) δ 7.72 (d, J=7.8 Hz, 1H), 3.79 (m, 2H), 3.54 (d, J=16.5 Hz, 1H), 3.36 (d, J=16.5 Hz, 1H), 3.07 (m, 1H), 2.72 (m, 1H), 2.10 (m, 1H), 1.82 (m, 14H), 1.48 (m, 2H); MS (DCI+) m/z 375 (M+H)$^+$.

EXAMPLE 28

(E)-4-{2-[4-(5-Trifluoromethyl-pyridin-2-yl)-piperazin-1-yl]-acetylamino}-adamantane-1-carboxamide A solution of (E)-4-{2-[4-(5-trifluoromethyl-pyridin-2-yl)-piperazin-1-yl]-acetylamino}-adamantane-1-carboxylic acid (100 mg, 0.21 mmoles) from Example 25C in DCM (2 mL) was treated with HOBt (32 mg, 0.21 mmoles) and EDC (46 mg, 0.24 mmoles) and stirred at room temperature for 1 hour. Excess of aqueous (35%) ammonia (2 mL) was added and the reaction was stirred for additional 20 hours. The layers were separated and the aqueous extracted twice more with methylene chloride (2×2 mL). The combined organic extracts were dried over $Na_2SO_4$ and filtered. The filtrate was concentrated under reduced pressure to provide the crude title compound that was purified on reverse phase HPLC to afford the title compound. $^1$H NMR (400 MHz, Py-$d_5$) δ 8.64 (s, 1H), 7.9 (d, J=7.6 Hz, 1H), 7.77 (d, J=9.2 Hz, 1H), 6.82 (d, J=9.2 Hz, 1H), 4.39 (d, J=8.3 Hz, 1H), 3.72 (t, J=4.9 Hz, 4H), 3.25 (s, 2H), 2.62 (t, J=4.9 Hz, 4H), 2.26 (m, 4H), 2.17 (s, 4H), 1.96 (m, 3H), 1.6 (d J=12.6 Hz, 2H); MS (ESI+) m/z 466 (M+H)$^+$.

EXAMPLE 29

(E)-4-[2-(2-Trifluoromethyl-pyrrolidin-1-yl)-acetylamino]-adamantane-1-carboxamide A solution of (E)-4-[2-(2-trifluoromethyl-pyrrolidin-1-yl)-acetylamino]-adamantane-1-carboxylic acid (74 mg, 0.2 mmoles) from Example 27 in DCM (2 mL) was treated with HOBt (33 mg, 0.22 mmoles) and EDC (46 mg, 0.24 mmoles) and stirred at room temperature for 1 hour. Excess of aqueous (35%) ammonia (2 mL) was added and the reaction was stirred for additional 20 hours. The layers were separated and the aqueous extracted twice more with methylene chloride (2×2 mL). The combined organic extracts were dried over $Na_2SO_4$ and filtered. The filtrate was concentrated under reduced pressure to provide the crude title compound which was purified on reverse phase HPLC to afford the title compound. $^1$H NMR (300 MHz, $CDCl_3$) δ 7.6 (d, J=6.4 Hz, 1H), 5.57-5.2 (bd, 2H), 4.05 (d, J=8.1 Hz, 1H), 3.56 (d, J=17 Hz, 1H), 3.32 (m, 2H), 3.22 (m, 1H), 2.58 (q, J=7.4 Hz, 1H), 2.08-1.90 (m, 13H), 1.77 (m, 2H), 1.65 (m, 2H); MS (ESI+) m/z 374 (M+H)$^+$.

EXAMPLE 30

(E)-4-[2-(3,3-Difluoro-piperidin-1-yl)-acetylamino]-adamantane-1-carboxamide

A solution of (E)-4-[2-(3,3-difluoro-piperidin-1-yl)-acetylamino]-adamantane-1-carboxylic acid (71 mg, 0.2 mmoles) from Example 26 in DCM (2 mL) was treated with HOBt (33 mg, 0.22 mmoles) and EDC (46 mg, 0.24 mmoles) and stirred at room temperature for 1 hour. Excess of aqueous (35%) ammonia (2 mL) was added and the reaction was stirred for additional 20 hours. The layers were separated and the aqueous extracted twice more with methylene chloride. The combined organic extracts were dried over $Na_2SO_4$ and filtered. The filtrate was concentrated under reduced pressure to provide the crude title compound which was purified on reverse phase HPLC to afford the title compound. $^1$H NMR (300 MHz, CDCl3) δ 7.74 (d, J=8.5 Hz, 1H), 5.54-5.18 (bd, 2H), 4.06 (d, J=8.5 Hz, 1H), 3.12 (s, 2H), 2.78 (t, J=11.2 Hz, 2H), 2.62 (bs, 2H), 2.08-1.80 (m, 15H), 1.6 (m, 2H); MS (ESI+) m/z 356 (M+H)$^+$.

EXAMPLE 31

(E)-4-(2-(3-Fluoropyrrolidin-1-yl)-propionylamino)-adamantane-1-carboxamide

EXAMPLE 31A (E)-4-(2-Bromo-propionylamino)-adamantane-1-carboxylic acid

A solution of 2-bromo-N-[(E)-5-hydroxy-adamantan-2-yl]-propionamide from Example 13B (4.0 g, 13.25 mmol) in 99% formic acid (13 mL) was added dropwise with vigorous gas evolution over 40 minutes to a rapidly stirred 30% oleum solution (40 mL) heated to 60° C. (W. J. le Noble, S. Srivastava, C. K. Cheung, J. Org. Chem. 48: 1099-1101, 1983). Upon completion of addition, more 99% formic acid (13 mL) was slowly added over the next 40 minutes. The mixture was stirred another 60 minutes at 60° C. and then slowly poured into vigorously stirred iced water (100 mL) cooled to 0° C. The mixture was allowed to slowly warm to 23° C. while stirring, filtered and washed with water to neutral pH (1 L). The precipitate was dried in a vacuum oven to provide the title compound as a white solid.

EXAMPLE 31B (E)-4-(2-Bromo-propionylamino)-adamantane-1-carboxamide

A solution of (E)-4-(2-bromo-propionylamino)-adamantane-1-carboxylic acid (330 mg, 1 mmol) from Example 31A in DCM (5 mL) was treated with HOBt (168 mg, 1.1 mmol) and EDC (230 mg, 1.2 mmoles) and stirred at room temperature for 1 hour. Excess of aqueous (35%) ammonia (5 nit) was added and the reaction was stirred for additional 2 hours. The layers were separated and the aqueous extracted twice more with methylene chloride (2×5 mL). The combined organic extracts were dried over $Na_2SO_4$ and filtered. The filtrate was concentrated under reduced pressure. The residue was taken into MeOH and formed a white precipitate that was filtered to provide the title compound as a white solid.

EXAMPLE 31C (E)-4-[2-(3-Fluoropyrrolidin-1-yl)-propionylamino]-adamantane-1-carboxamide A solution of (E)-4-(2-bromo-propionylamino)-adamantane-1-carboxamide (33 mg, 0.1 mmol) from Example 31B and the hydrochloride of (3R)-3-fluoropyrrolidine (15 mg, 0.12 mmol) in MeOH (0.5 mL) and DIPEA (0.1 mL) was stirred overnight at 70° C. The MeOH was removed under reduced pressure and the residue purified on reverse phase HPLC to provide the title compound as a mixture of 2 diastereomers. $^1$H NMR (400 MHz, Py-$d_5$) δ 7.7 (two d, 1H), 5.2-5.08 (bd, 2H), 4.32 (m, 1H), 3.56 (s, 4H), 3.29-2.95 (m, 2H), 2.6-2.5 (m, 2H), 2.25-2.0 (m, 10H), 1.95 (m, 3H), 1.37 (two d, 3H), 1.4 (t, 2H); MS (ESI+) m/z 338 (M+H)$^+$.

EXAMPLE 32

(E)-4-[2-(3,3-Difluoropiperidine-1-yl)-propionylamino]-adamantane-1-carboxamide

A solution of (E)-4-(2-bromo-propionylamino)-adamantane-1-carboxamide (33 mg, 0.1 mmoles) and the hydrochloride of 3,3-difluoropiperidine (19 mg, 0.12 mmol) from Example 31B in MeOH (0.5 mL) and DIPEA (0.1 mL) was stirred overnight at 70° C. The MeOH was removed under reduced pressure and the residue purified on reverse phase HPLC to provide the title compound as a white solid. $^1$H NMR (400 MHz, Py-$d_5$) δ 7.92 (d, J=7.7 Hz, 1H), 7.51 (s, 2H), 4.32 (d, J=7.7 Hz, 1H), 3.42 (q, J=7 Hz, 1H), 2.92 (q, J=10.7 Hz, 1H), 2.78 (q, J=11.6 Hz, 1H), 2.5 (m, 2H), 2.27-2.10 (m, 8H), 1.98-1.88 (m, 5H), 1.68 (m, 2H), 1.55 (m, 2H), 1.32 (d, 3H); MS (ESI+) m/z 370 (M+H)$^+$.

EXAMPLE 33

(E)-4-[2-(2-Trifluoromethylpyrrolidin-1-yl)-propionylamino]-adamantane-1-carboxamide A solution of (E)-4-(2-bromo-propionylamino)-adamantane-1-carboxamide (33 mg, 0.1 mmol) from Example 31B and the hydrochloride of 2-trifluoromethylpyrrolidine (21 mg, 0.12 mmol) in MeOH (0.5 mL) and DIPEA (0.1 mL) was stirred overnight at 70° C. The MeOH was removed under reduced pressure and the residue purified on reverse phase HPLC to provide the title compound as a mixture of 4 diastereomers. $^1$H NMR (400 MHz, Py-d$_5$) δ 7.81 (d, 1H), 4.32 (two d, 1H), 3.8 (two m, 2H), 3.2 (two m, 1H), 2.7 (two m, 1H), 2.48-1.5 (m, 17H), 1.47 (two d, 3H); MS (ESI+) m/z 388 (M+H)$^+$.

EXAMPLE 34

(E)-4-{2-[4-(5-Chloro-pyridin-2-yl)-piperazin-1-yl]-2-methyl-propionylamino}-adamantane-1-carboxylic acid

EXAMPLE 34A

2-Bromo-N-[(E)- and (Z)-5-hydroxy-adamantan-2-yl]-2-methyl-propionamide

A solution of (E)- and (Z)-5-hydroxy-2-adamantamine (8.7 g, 52 mmol) from Example 13A in DCM (150 mL) and DIPEA (25 mL) was cooled in an ice bath and treated with 2-bromoisobutyryl bromide (7.2 mL, 58 mmol) in DCM (25 mL). The mixture was stirred for 2 hours at room temperature and DCM was removed under reduced pressure. The residue was partitioned between water and ethyl acetate. The organic layer was washed with saturated sodium bicarbonate, water, dried (MgSO$_4$) and filtered. The filtrate was concentrated under reduced pressure to provide the title compound as a dark beige solid. The isomers were separated by column chromatography (silica gel, 5-35% acetone in hexane) to furnish 2-bromo-N-[(E)-5-hydroxy-adamantan-2-yl]-2-methyl-propionamide and 2-bromo-N-[(Z)-5-hydroxy-adamantan-2-yl]-2-methyl-propionamide.

EXAMPLE 34B

Methyl (E)-4-(2-bromo-2-methyl-propionylamino)-adamantane-1-carboxylate

A solution of 2-bromo-N-[(E)-5-hydroxy-adamantan-2-yl]-2-methyl-propionamide (7.84 g, 24.8 mmol) from Example 34A in 99% formic acid (25 mL) was added dropwise with vigorous gas evolution over 40 minutes to a rapidly stirred 30% oleum solution (75 mL) heated to 60° C. (W. J. le Noble, S. Srivastava, C. K. Cheung, J. Org. Chem. 48: 1099-1101, 1983). Upon completion of addition, more 99% formic acid (25 mL) was slowly added over the next 40 minutes. The mixture was stirred another 60 minutes at 60° C. and then slowly poured into vigorously stirred iced water (300 mL) cooled to 0° C. The mixture was allowed to slowly warm to 23° C., filtered and washed with water to neutral pH (1 L). The precipitate was dried in a vacuum oven, taken into MeOH and treated with thionyl chloride at 0° C. (2 mL, 28 mmol). The reaction mixture was stirring at room temperature for 3 hours and then MeOH was evaporated under reduced pressure to provide the title compound as an off-white solid.

EXAMPLE 34C (E)-4-{2-[4-(5-Chloro-pyridin-2-yl)-piperazin-1-yl]-2-methyl-propionylamino}-adamantane-1-carboxylic acid A two phase suspension of methyl (E)-4-(2-bromo-2-methyl-propionylamino)-adamantane-1-carboxylate (36 mg, 0.1 mmol) from Example 34B, 1-(5-chloro-2-pyridyl)piperazine (20 mg, 0.11 mmol) and tetrabutylammonium bromide (3 mg, 0.01 mmol) in DCM (0.2 mL) and 50% NaOH (0.2 mL) was stirred at room temperature for 20 hours. After that the reaction mixture was diluted with water and DCM and layers separated. Organic layer was washed with water (2×2 mL), dried (MgSO$_4$) and filtered. The filtrate was concentrated under reduced pressure to provide crude methyl ester of the title compound that was purified on reverse phase HPLC and hydrolyzed with 3N HCL at 60° C. over 6 hours. Drying of the reaction mixture under reduced pressure provided the title compound as a white solid. $^1$H NMR (400 MHz, Py-d$_5$) δ 8.38 (s, 1H), 7.87 (d, J=7.8 Hz, 1H), 6.8 (d, J=9 Hz, 1H), 4.31 (d, J=8.1 Hz, 1H), 3.64 (s, 4H), 2.59 (s, 4H), 2.25 (m, 4H), 2.17 (s, 2H), 2.11 (s, 2H), 1.96 (s, 1H), 1.87 (d, J=14.4 Hz, 2H), 1.62 (d, J=12.8 Hz, 2H), 1.31 (s, 6H); MS (ESI+) m/z 461 (M+H)$^+$.

EXAMPLE 35

(E)-4-[2-Methyl-2-(1,2,4,5-tetrahydro-benzo[d]azepin-3-yl)-propionylamino]-adamantane-1-carboxylic acid The title compound was prepared according to the procedure outlined in Example 34C substituting 2,3,4,5-tetrahydro-1H-benzo[d]azepine for 1-(5-chloro-2-pyridyl)piperazine. $^1$H NMR (400 MHz, Py-d$_5$) δ 7.85 (d, J=7.8 Hz, 1H), 7.24 (m, 4H), 4.33 (d, J=7.5 Hz, 1H), 2.9 (m, 4H), 2.56 (s, 4H), 2.32 (q, J=14 Hz, 4H), 2.22 (s, 1H), 2.16 (s, 1H), 2.01 (s, 1H), 1.88 (d, J=12.8 Hz, 2H), 1.78 (m, 2H), 1.65 (d, J=13.4 Hz, 2H), 1.28 (s, 6H); MS (ESI+) m/z 411 (M+H)$^+$.

EXAMPLE 36

(E)-4-[2-Methyl-2-(4-m-tolyl-[1,4]diazepan-1-yl)-propionylamino]-adamantane-1-carboxylic acid The title compound was prepared according to the procedure outlined in Example 34C substituting 1-m-tolyl-[1,4]diazepane for 1-(5-chloro-2-pyridyl)piperazine. $^1$H NMR (400 MHz, Py-d$_5$) δ 7.27 (t, J=7.7 Hz, 1H), 6.74 (s, 1H), 6.69 (d, J=6.4 Hz, 1H), 6.65 (d, J=8.6 Hz, 1H), 4.3 (d, J=7.3 Hz, 1H), 3.54 (t, J=8 Hz, 2H), 2.8 (s, 1H), 2.5 (s, 1H), 2.3 (s, 3H), 2.25 (m, 5H), 2.16 (m, 5H), 1.93 (m, 3H), 1.79 (m, 2H), 1.58 (m, 2H), 1.31 (s, 6H), 1.27 (t, J=7.4 Hz, 2H); MS (ESI+) m/z 454 (M+H)$^+$.

EXAMPLE 37

(E)-4-[2-Methyl-2-(4-phenyl-piperidin-1-yl)-propionylamino]-adamantane-1-carboxylic acid The title compound was prepared according to the method of procedure outlined in Example 34C substituting 4-phenyl-piperidine for 1-(5-chloro-2-pyridyl)piperazine. $^1$H NMR (400 MHz, Py-d$_5$) δ 7.96 (d, J=8.1 Hz, 1H), 7.41 (m, 4H), 7.29 (m, 1H), 4.3 (d, J=8.1 Hz, 1H), 2.93 (d, J=11.6 Hz, 2H), 2.53 (m, 1H), 2.31-2.12 (m, 10H), 1.90 (m, 5H), 1.77 (m, 2H), 1.6 (d, J=12.8 Hz, 2H), 1.35 (s, 6H); MS (ESI+) m/z 425 (M+H)$^+$.

EXAMPLE 38

(E)-4-{2-[4-(4-Chloro-phenyl)-piperidin-1-yl]-2-methyl-propionylamino}-adamantane-1-carboxylic acid The title compound was prepared according to the procedure outlined in Example 34C substituting 4-(4-chloro-phenyl)-piperidine for 1-(5-chloro-2-pyridyl)piperazine. $^1$H NMR (400 MHz, Py-d$_5$) δ 7.92 (d, J=8.1 Hz, 1H), 7.42 (d, J=8.5 Hz, 2H), 7.29 (d, J=8.7 Hz, 2H), 4.3 (d, J=8.1 Hz, 1H), 2.93 (d, J=11.6 Hz, 2H), 2.48 (m, 1H), 2.31-2.12 (m, 10H), 1.90 (m, 5H), 1.77 (m, 2H), 1.6 (d, J=13.1 Hz, 2H), 1.35 (s, 6H); MS (ESI+) m/z 459 (M+H)$^+$.

EXAMPLE 39

(E)-4-{2-[5-(6-Chloro-pyridin-3-yl)-hexahydro-pyrrolo[3,4-c]pyrrol-2-yl]-2-methyl-propionylamino}-adamantane-1-carboxamide

EXAMPLE 39A (E)-4-{2-[5-(6-Chloro-pyridin-3-yl)-hexahydro-pyrrolo[3,4-c]pyrrol-2-yl]-2-methyl-propionylamino}-adamantane-1-carboxylic acid The title compound was prepared according to the procedure outlined in Example 34C substituting 2,3,4,5-tetrahydro-1H-benzo[d]azepine for 1-(5-chloro-2-pyridyl)piperazine.

EXAMPLE 39B (E)-4-{2-[5-(6-Chloro-pyridin-3-yl)-hexahydro-pyrrolo[3,4-c]pyrrol-2-yl]-2-methyl-propionylamino}-adamantane-1-carboxamide The title compound was prepared according to the procedure outlined in Example 23 substituting (E)-4-{2-[5-(6-chloro-pyridin-3-yl)-hexahydro-pyrrolo[3,4-c]pyrrol-2-yl]-2-methyl-propionylamino}-adamantane-1-carboxylic acid for (E)-4-{2-methyl-2-[4-(5-trifluoromethyl-pyridin-2-yl)-piperazin-1-yl]-propionylamino}-adamantane-1-carboxylic acid. $^1$H NMR (400 MHz, Py-d$_5$) e) 7.98 (d, J=3.1 Hz, 1H), 7.73 (d, J=8.1 Hz, 1H), 7.32 (d, J=8.6 Hz, 1H), 6.98 (m, 1H), 4.23 (d, J=8.1 Hz, 1H), 3.32 (m, 2H), 3.12 (m, 2H), 2.76 (s, 2H), 2.59 (m, 4H), 2.16 (m, 4H), 2.01 (s, 4H), 1.6 (m, 3H), 1.38 (m, 2H), 1.31 (s, 6H); MS (ESI+) m/z 486 (M+H)$^+$.

EXAMPLE 40

(E)-4-{2-[4-(5-Fluoro-pyridin-3-yl)-[1,4]diazepan-1-yl]-2-methyl-propionylamino}-adamantane-1-carboxamide

EXAMPLE 40A (E)-4-{2-[4-(5-Fluoro-pyridin-3-yl)-[1,4]diazepan-1-yl]-2-methyl-propionylamino}-adamantane-1-carboxylic acid The title compound was prepared according to the procedure outlined in Example 34C substituting 1-(5-fluoro-pyridin-3-yl)-[1,4]diazepane for 1-(5-chloro-2-pyridyl)piperazine.

EXAMPLE 40B (E)-4-{2-[4-(5-Fluoro-pyridin-3-yl)-[1,4]diazepan-1-yl]-2-methyl-propionylamino}-adamantane-1-carboxamide The title compound was prepared according to the procedure outlined in Example 23 substituting (E)-4-{2-[4-(5-fluoro-pyridin-3-yl)-[1,4]diazepan-1-yl]-2-methyl-propionylamino}-adamantane-1-carboxylic acid for (E)-4-{2-methyl-2-[4-(5-trifluoromethyl-pyridin-2-yl)-piperazin-1-yl]-propionylamino}-adamantane-1-carboxylic acid. $^1$H NMR (400 MHz, Py-d$_5$) δ 8.28 (s, 1H), 8.13 (s, 1H), 7.44 (d, J=8 Hz, 1H), 7.0 (d, J=8 Hz, 1H), 4.25 (d, J=8.1 Hz, 1H), 3.5 (m, 4H), 2.73 (s, 2H), 2.45 (s, 2H), 2.23 (m, 4H), 2.14 (s, 2H), 2.06 (s, 2H), 1.9 (s, 1H), 1.79 (m, 2H), 1.66 (d, J=12.8 Hz, 2H), 1.55 (d, J=12.8 Hz, 2H), 1.29 (s, 6H); MS (ESI+) m/z 458 (M+H)$^+$.

EXAMPLE 41

(E)-4-[2-Methyl-2-(3-pyridin-3-yl-3,9-diaza-bicyclo[4.2.1]non-9-yl)-propionylamino]-adamantane-1-carboxamide

EXAMPLE 41A (E)-4-[2-Methyl-2-(3-pyridin-3-yl-3,9-diaza-bicyclo[4.2.1]non-9-yl)-propionylamino]-adamantane-1-carboxylic acid The title compound was prepared according to the procedure outline in Example 34C substituting 3-pyridin-3-yl-3,9-diaza-bicyclo[4.2.1]nonane for 1-(5-chloro-2-pyridyl)piperazine.

EXAMPLE 41B (E)-4-[2-Methyl-2-(3-pyridin-3-yl-3,9-diaza-bicyclo[4.2.1]non-9-yl)-propionylamino]-adamantane-1-carboxamide The title compound was prepared according to the procedure outlined in Example 23 substituting (E)-4-[2-methyl-2-(3-pyridin-3-yl-3,9-diaza-bicyclo[4.2.1]non-9-yl)-propionylamino]-adamantane-1-carboxylic acid for (E)-4-{2-methyl-2-[4-(5-trifluoromethyl-pyridin-2-yl)-piperazin-1-yl]-propionylamino}-adamantane-1-carboxylic acid. $^1$H NMR (300 MHz, CDCl$_3$) δ 7.84 (s, 1H), 3.99 (d, J=8.1 Hz, 1H), 3.35 (d, J=5.9 Hz, 1H), 2.71-2.65 (bd, 4H), 2.16-2.10 (m, 3H), 1.89 (d, J=11.9 Hz, 2H), 1.77-1.65 (m, 14H), 1.52 (d, J=12.8 Hz, 2H), 1.24 (d, J=6.9 Hz, 3H); MS (ESI+) m/z 466 (M+H)$^+$.

EXAMPLE 42

(E)-4-[2-Methyl-2-(2-trifluoromethyl-pyrrolidin-1-yl)-propionylamino]-adamantane-1-carboxamide

EXAMPLE 42A (E)-4-[2-Methyl-2-(2-trifluoromethyl-pyrrolidin-1-yl)-propionylamino]-adamantane-1-carboxylic acid The title compound was prepared according to the procedure outlined in Example 34C substituting 2-trifluoromethylpyrrolidine for 1-(5-chloro-2-pyridyl)piperazine.

EXAMPLE 42B (E)-4-[2-Methyl-2-(2-trifluoromethyl-pyrrolidin-1-yl)-propionylamino]-adamantane-1-carboxyamide The title compound was prepared according to the procedure outlined in Example 23 substituting (E)-4-[2-methyl-2-(2-trifluoromethyl-pyrrolidin-1-yl)-propionylamino]-adamantane-1-carboxylic acid for (E)-4-{2-methyl-2-[4-(5-trifluoromethyl-pyridin-2-yl)-piperazin-1-yl]-propionylamino}-adamantane-1-carboxylic acid. $^1$H NMR (400 MHz, Py-d$_5$) δ 7.43 (d, J=7.8 Hz, 1H), 5.54 (bs, 1H), 5.18 (bs, 1H), 3.99 (d, J=8.1 Hz, 1H), 3.68 (m, 1H), 3.05 (m, 1H), 2.82 (m, 1H), 2.05-1.9 (m, 12H), 1.77 (d, J=13.1 Hz, 3H), 1.65 (m, 2H), 1.35 (s, 3H); 1.21 (s, 3H); MS (ESI+) m/z 402 (M+H)$^+$.

EXAMPLE 43

(E)-4-[2-(3,3-Difluoro-piperidin-1-yl)-2-methyl-propionylamino]-adamantane-1-carboxamide

EXAMPLE 43A (E)-4-[2-(3,3-Difluoro-piperidin-1-yl)-2-methyl-propionylamino]-adamantane-1-carboxylic acid The title compound was prepared according to the procedure outlined in Example 34C substituting 3,3-difluoropiperidine for 1-(5-chloro-2-pyridyl)piperazine.

EXAMPLE 43B (E)-4-[2-(3,3-Difluoro-piperidin-1-yl)-2-methyl-propionylamino]-adamantane-1-carboxamide The title compound was prepared according to the procedure outlined in Example 23 substituting (E)-4-[2-(3,3-difluoro-piperidin-1-yl)-2-methyl-propionylamino]-adamantane-1-carboxylic acid for (E)-4-{2-methyl-2-[4-(5-trifluoromethyl-pyridin-2-yl)-piperazin-1-yl]-propionylamino}-adamantane-1-carboxylic acid. $^1$H NMR (400 MHz, Py-d$_5$) δ 7.71 (s, 1H), 5.55 (bs, 1H), 5.22 (bs, 1H), 3.96 (d, J=8.1 Hz, 1H), 2.71 (s, 2H), 2.54 (s, 2H), 2.05-1.9 (m, 11H), 1.8 (m, 4H), 1.6 (d, J=13.1 Hz, 2H), 1.23 (s, 6H); MS (ESI+) m/z 384 (M+H)$^+$.

EXAMPLE 44

(E)-4-[2-(3-Fluoro-pyrrolidin-1-yl)-2-methyl-propionylamino]-adamantane-1-carboxamide

EXAMPLE 44A (E)-4-(2-Bromo-2-methyl-propionylamino)-adamantane-1-carboxylic acid A solution of 2-bromo-N-[(E)-5-hydroxy-adamantan-2-yl]-2-methyl-propionamide (7.84 g, 24.8 mmol) from Example 34A in 99% formic acid (25 mL) was added dropwise with vigorous gas evolution over 40 minutes to a rapidly stirred 30% oleum solution (75 mL) heated to 60° C. (W. J. le Noble, S. Srivastava, C. K. Cheung, J. Org. Chem. 48: 1099-1101, 1983). Upon completion of addition, more 99% formic acid (25 mL) was slowly added over the next 40 minutes. The mixture was stirred another 60 minutes at 60° C. and then slowly poured into vigorously stirred iced water (300 mL) cooled to 0° C. The mixture was allowed to slowly warm to 23° C., filtered and washed with water to neutral pH (1 L). The precipitate was dried in a vacuum oven, to provide the title compound as an white solid.

EXAMPLE 44B (E)-4-(2-Bromo-2-methyl-propionylamino)-adamantane-1-carboxamide A solution of (1.72 g, 5 mmol) in (E)-4-(2-bromo-2-methyl-propionylamino)-adamantane-1-carboxylic acid from Example 44A in DCM (15 mL) was treated with HOBt (841 mg, 1.1 mmol) and EDC (1.15 g, 6 mmol) and stirred at room temperature for 1 hour. Excess of aqueous (35%) ammonia (15 mL) was added and the reaction was stirred for additional 2 hours. The layers were separated and the aqueous extracted twice more with methylene chloride (2×15 mL). The combined organic extracts were dried over Na$_2$SO$_4$ and filtered. The filtrate was concentrated under reduced pressure. The residue was taken into MeOH and formed a white precipitate that was filtered to provide the title compound as a white solid.

EXAMPLE 44C (E)-4-[2-(3-Fluoro-pyrrolidin-1-yl)-2-methyl-propionylamino]-adamantane-1- carboxamide A two phase suspension of (E)-4-(2-bromo-2-methyl-propionylamino)-adamantane-1-carboxamide (35 mg, 0.1 mmol) from Example 44B, (3R)-3-fluoropyrrolidine (14 mg, 0.11 mmol) and tetrabutylammonium bromide (3 mg, 0.01 mmol) in DCM (0.2 mL) and 50% NaOH (0.2 mL) was stirred at room temperature for 20 hours. After that the reaction mixture was diluted with water and DCM and layers separated. Organic layer was washed with water (2×2 mL), dried (MgSO$_4$) and filtered. The filtrate was concentrated under reduced pressure to provide the title compound as a white solid. $^1$H NMR (300 MHz, Py-d$_5$) δ 7.91 (d, J=7.7 Hz, 1H), 5.19-5.06 (bd, 1H), 4.29 (d, J=8.0 Hz, 1H), 3.0 (m, 1H), 2.91 (m, 1H), 2.58 (m, 1H), 2.39 (q, J=7.6 Hz, 1H), 2.27-2.01 (m, 7H), 1.96-1.85 (m, 6H), 1.53 (m, 3H), 1.35 (d, 6H); MS (ESI+) m/z 352 (M+H)$^+$.

EXAMPLE 45

(E)-4-{2-[4-(5-Trifluormethyl-pyridin-2-yl)-piperazin-1-yl]-acetylamino}-adamantane-1-carboxamide A solution of (E)-4-(2-bromo-propionylamino)-adamantane-1-carboxamide (0.075 g, 0.23 mmol) from Example 31B in MeOH (1.0 mL) and DIPEA (0.044 mL, 0.25 mmol) was treated with 1-(5-trifluoromethyl-pyridin-2-yl)-piperazine (0.058 g, 0.25 mmol) and stirred for 48 hours at 70° C. The cooled reaction mixture was purified on reverse phase HPLC and drying of the reaction mixture under reduced pressure provided the TFA salt of the title compound as a white solid. $^1$H NMR (400 MHz, Py-d$_5$) δ 8.66 (s, 1H), 7.93 (d, J=8 Hz, 1H), 7.77 (dd, J=2.8, 9.2 Hz, 1H), 7.62 (s, 1H), 6.84 (d, J=8.8 Hz, 1H), 4.36 (m, 1H), 3.74 (m, 4H), 3.33 (q, J=6.8 Hz, 1H), 2.67 (m, 2H), 2.57 (m, 2H), 2.27 (m, 4H), 2.16 (m, 5H), 1.94 (m, 3H), 1.60 (m, 2H), 1.34 (d, J=6.8 Hz, 3H); MS (DCI+) m/z 480 (M+H)$^+$.

EXAMPLE 46

(E)-4-[2-(3,3-Difluoro-piperidin-1-yl)-2-methyl-propionylamino]-adamantane-1-carboxylic acid 3,4-dimethoxy-benzylamide A solution of Example 43A (35.0 mg, 0.09 mmol) in DMA (5 mL) was treated with TBTU (0-(Benzotrialzol-1-yl)-1,1, 3,3-tetramethyluronium tetrafluoroborate) (43.3 mg, 0.135 mmol), 3,4-dimethoxy-benzylamine (18.0 mg, 0.108 mmol) and DIEA (Ethyl-diisopropyl-amine) (0.033 ml, 0.18 mmol). The mixture was stirred at room temperature for 12 hours. The reaction mixture was concentrated under reduced pressure. The residue was purified by reverse phase —HPLC to provide the title compound. $^1$H NMR (400 MHz, DMSO-D6) δ ppm 1.12 (s, 6H) 1.49-1.58 (m, 2H) 1.64-1.74 (m, 4H) 1.77-1.84 (m, 2H) 1.84-2.00 (m, 9H) 2.43-2.49 (m, 2H) 2.69 (m, 2H) 3.72 (s, 3H) 3.73 (s, 3H) 3.79 (m, 1H) 4.19 (d, J=5.83 Hz, 2H) 6.72 (dd, J=7.98 Hz, 1.53 Hz, 1H) 6.81 (d, J=1.53 Hz, 1H) 6.87 (d, J=7.98 Hz, 1H) 7.59 (d, J=7.98 Hz, 1H) 7.94 (t, J=5.83 Hz, 1H); MS (ESI+) m/z 534 (M+H)$^+$.

EXAMPLE 47

(E)-4-[({4-[2-(3,3-Difluoro-piperidin-1-yl)-2-methyl-propionylamino]-adamantane-1-carbonyl}-amino)-methyl]-benzoic acid A solution of Example 43A (71.0 mg, 0.18 mmol) in DMF (8 mL) was treated with TBTU (O-(Benzotrialzol-1-yl)-1,1,3,3-tetramethyluronium tetrafluoroborate) (77 mg, 0.27 mmol), 4-aminomethyl-benzoic acid methyl ester (36.0 mg, 0.216 mmol) and DIEA (Ethyl-diisopropyl-amine) (0.066 ml, 0.36 mmol). The mixture was stirred at room temperature for 12 hours. Then DCM (15 mL) and H2O (5 mL) were added to reaction mixture. The layers were separated and the organic phase were dried over Na$_2$SO$_4$ and filtered. The filtrate was concentrated under reduced pressure. The residue was purified by reverse phase —HPLC to provide white powder with MS (ESI+) m/z 532. The white powder was dissolved in THF (2 mL). H$_2$O (2 mL) and LiOH (24 mg, 1 mmol) were added to the THF solution. The reaction mixture was stirred for at room temperature for 12 hours. Then DCM (15 mL) and H$_2$O (5 mL) were added to reaction mixture. The layers were separated and the organic phase was dried over Na$_2$SO$_4$ and filtered. The filtrate was concentrated under reduced pressure. The residue was purified by reverse phase —HPLC to provide the title compound. $^1$H NMR (500 MHz, DMSO-D6) δ ppm 1.12 (s, 6H) 1.50-1.59 (m, J=12.79 Hz, 2H) 1.63-1.74 (m, 4H) 1.82 (d, J=2.18 Hz, 2H) 1.85-1.97 (m, 9H) 2.44-2.49 (m, 2H) 2.69 (t, J=11.07 Hz, 2H) 3.78 (d, J=7.49 Hz, 1H) 4.30 (d, J=5.93 Hz, 2H) 7.26 (d, J=8.11 Hz, 2H) 7.59 (d, J=8.11 Hz, 1H) 7.85 (d, J=8.11 Hz, 2H) 8.07 (t, J=5.93 Hz, 1H); MS (ESI+) m/z 518 (M+H)$^+$.

EXAMPLE 48

(E)-4-[2-(3,3-Difluoro-piperidin-1-yl)-2-methyl-propionylamino]-adamantane-1-carboxylic acid (furan-2-ylmethyl)-amide A solution of Example 43A (35.0 mg, 0.09 mmol) in DMF (5 mL) was treated with TBTU (O-(Benzotrialzol-1-yl)-1,1,3,3-tetramethyluronium tetrafluoroborate) (43.3 mg, 0.135 mmol), furfurylamine (10.5 mg, 0.108 mmol) and DIEA (Ethyl-diisopropyl-amine) (0.033 ml, 0.18 mmol). The mixture was stirred at room temperature for 12 hours. The reaction mixture was concentrated under reduced pressure. The residue was purified by reverse phase —HPLC to provide the title compound. $^1$H NMR (400 MHz, DMSO-D6) δ ppm 0.85-1.01 (s, 6H) 1.40-1.55 (m, 2H) 1.55-1.79 (m, 19H) 2.24-2.34 (m, 2H) 3.50-3.58 (m, 1H) 6.93-7.01 (m, 3H) 7.07 (t, J=7.67 Hz, 2H) 7.26 (t, J=5.52 Hz, 1H) 7.37 (d, J=7.98 Hz, 1H); MS (ESI+) m/z 464 (M+H)$^+$.

EXAMPLE 49

(E)-4-[2-(3,3-Difluoro-piperidin-1-yl)-2-methyl-propionylamino]-adamantane-1-carboxylic acid (thiazol-5-ylmethyl)-amide A solution of Example 43A (35.0 mg, 0.09 mmol) in DMA (5 mL) was treated with TBTU (O-(Benzotrialzol-1-yl)-1,1,3,3-tetramethyluronium tetrafluoroborate) (43.3 mg, 0.135 mmol), thiazol-5-yl-methylamine (12.0 mg, 0.108 mmol) and DIEA (Ethyl-diisopropyl-amine) (0.033 ml, 0.18 mmol). The mixture was stirred at room temperature for 12 hours. The reaction mixture was concentrated under reduced pressure. The residue was purified by reverse phase-HPLC to provide the title compound. $^1$H NMR (400 MHz, DMSO-D6) δ ppm 1.12 (s, 6H) 1.48-1.59 (m, 2H) 1.64-1.76 (m, 4H) 1.80-1.85 (m, 2H) 1.86-2.00 (m, 9H) 2.44-2.49 (m, 2H) 2.69 (t, J=11.51 Hz, 2H) 3.78 (d, J=7.67 Hz, 1H) 4.39 (d, J=6.14 Hz, 2H) 7.26 (s, 1H) 7.59 (d, J=7.67 Hz, 1H) 8.03 (t, J=6.14 Hz, 1H) 9.01-9.05 (m, 1H); MS (ESI+) m/z 481 (M+H)$^+$.

EXAMPLE 50

(E)-4-[2-(3,3-Difluoro-piperidin-1-yl)-2-methyl-propionylamino]-adamantane-1-carboxylic acid 2-methoxy-benzylamide A solution of Example 43A (35.0 mg, 0.09 mmol) in DMA (5 mL) was treated with TBTU (O-(Benzotrialzol-1-yl)-1,1,3,3-tetramethyluronium tetrafluoroborate) (43.3 mg, 0.135 mmol), 2-methoxy-benzylamine (15.0 mg, 0.108 mmol) and DIEA (Ethyl-diisopropyl-amine) (0.033 ml, 0.18 mmol). The mixture was stirred at room temperature for 12 hours. The reaction mixture was concentrated under reduced pressure. The residue was purified by reverse phase —HPLC to provide the title compound. $^1$H NMR (400 MHz, DMSO-D6) δ ppm 1.10-1.15 (m, 6H) 1.51-1.99 (m, 17H) 2.44-2.49 (m, 2H) 2.64-2.74 (m, 2H) 3.58-3.60 (m, 1H) 3.80 (s, 3H) 4.22 (d, J=5.83 Hz, 2H) 6.86-6.93 (m, 1H) 6.94-6.98 (m, 1H) 7.02-7.07 (m, 1H) 7.17-7.24 (m, 1H) 7.57-7.63 (m, 1H) 7.79-7.85 (m, 1H); MS (ESI+) m/z 504 (M+H)$^+$.

EXAMPLE 51

(E)-4-(2-Methyl-2-phenylamino-propionylamino)-adamantane-1-carboxamide (E)-4-(2-Methyl-2-phenylamino-propionylamino)-adamantane-1-carboxylic acid (MS (ESI+) m/z 357 (M+H)$^+$) was prepared according to the method of Example 34 substituting aniline for 1-(5-chloro-2-pyridyl)piperazine. A solution of (E)-4-(2-methyl-2-phenylamino-propionylamino)-adamantane-1-carboxylic acid (23.6 mg, 0.07 mmol) in DCM (1 mL) was treated with HOBt (10 mg, 0.073 mmol) and EDC (15.4 mg, 0.08 mmol) and stirred at room temperature for 1 hour. Excess of aqueous (30%) ammonia (1 mL) was added and the reaction was stirred at room temperature for additional 2 hours. The reaction mixture was concentrated under reduced pressure. The residue was purified by reverse phase —HPLC to provide the title compound. $^1$H NMR (300 MHz, DMSO-D6) δ ppm 1.24-1.34 (m, 2H) 1.37 (s, 6H) 1.38-1.48 (m, 2H) 1.59-1.89 (m, 9H) 3.78 (d, J=7.80 Hz, 1H) 5.81 (s, 1H) 6.53 (d, 2H) 6.60 (m, 1H) 6.69 (s, 1H) 6.95 (s, 1H) 7.03-7.13 (m, 2H) 7.26 (d, 1H); MS (ESI+) m/z 356 (M+H)$^+$.

EXAMPLE 52

(E)-4-[2-Methyl-2-(3-pyridin-3-yl-3,9-diaza-bicyclo[4.2.1]non-9-yl)-propionylamino]-adamantane-1-carboxamide

EXAMPLE 52A (E)-4-[2-Methyl-2-(3-pyridin-3-yl-3,9-diaza-bicyclo[4.2.1]non-9-yl)-propionylamino]-adamantane-1-carboxylic acid The title compound was prepared according to the method outlined in Example 34C substituting 3-pyridin-3-yl-3,9-diaza-bicyclo[4.2.1]nonane for 1-(5-chloro-2-pyridyl)piperazine.

EXAMPLE 52B (E)-4-[2-Methyl-2-(3-pyridin-3-yl-3,9-diaza-bicyclo[4.2.1]non-9-yl)-propionylamino]-adamantane-1-carboxamide The title compound was prepared according to the method outlined in Example 23 substituting (E)-4-[2-methyl-2-(3-pyridin-3-yl-3,9-diaza-bicyclo[4.2.1]non-9-yl)-propionylamino]-adamantane-1-carboxylic acid for (E)-4-{2-methyl-2-[4-(5-trifluoromethyl-pyridin-2-yl)-piperazin-1-yl]-propionylamino}-adamantane-1-carboxylic acid. $^1$H NMR (400 MHz, Py-$d_5$) δ 8.56 (d, J=2.4 Hz, 1H), 8.18 (d, J=3 Hz, 1H), 7.32 (d, J=7.7 Hz, 1H), 7.18 (m, 2H), 4.31 (d, J=7.7 Hz, 1H), 3.74 (d, J=13.5 Hz, 1H), 3.56 (m, 2H), 3.40 (m, 2H), 3.1 (d, J=13.5 Hz, 1H), 2.29-2.04 (m, 12H), 1.95-1.85 (m, 2H), 1.7701.74 (m, 2H), 1.57 (m, 2H), 1.4 (m, 1H), 1.31 (s, 6H); MS (ESI+) m/z 466 (M+H)$^+$.

EXAMPLE 53

(E)-4-{2-Methyl-2-[5-(3-trifluoromethyl-phenyl)-[1,5]diazocan-1-yl]-propionylamino}-adamantane-1-carboxylic acid The title compound was prepared according to the method outlined in Example 34C substituting 1-(3-trifluoromethyl-phenyl)-[1,5]diazocane for 1-(5-chloro-2-pyridyl)piperazine. $^1$H NMR (400 MHz, Py-$d_5$) δ 7.42 (t, J=7.8 Hz, 1H), 7.07 (d, J=7.6 Hz, 1H), 7.03 (s, 1H), 6.91 (d, J=8.6 Hz, 1H), 4.25 (s, 1H), 3.55 (s, 4H), 2.53 (s, 4H), 2.26 (m, 4H), 2.16 (s, 4H), 1.94 (m, 2H), 1.76 (s, 5H), 1.58 (m, 2H), 1.33 (s, 6H); MS (ESI+) m/z 522 (M+H)$^+$.

EXAMPLE 54

(E)-4-{2-[7-(5-Bromo-pyridin-2-yl)-3,7-diaza-bicyclo[3.3.1]non-3-yl]-2-methyl-propionylamino}-adamantane-1-carboxamide

EXAMPLE 54A (E)-4-{2-[7-(5-Bromo-pyridin-2-yl)-3,7-diaza-bicyclo[3.3.1]non-3-yl]-2-methyl-propionylamino}-adamantane-1-carboxylic acid The title compound was prepared according to the method outlined in Example 34C substituting 3-(5-bromo-pyridin-2-yl)-3,7-diaza-bicyclo[3.3.1]nonane for.

EXAMPLE 54B (E)-4-{2-[7-(5-Bromo-pyridin-2-yl)-3,7-diaza-bicyclo[3.3.1]non-3-yl]-2-methyl-propionylamino}-adamantane-1-carboxamide The title compound was prepared according to the method outlined in Example 23 substituting (E)-4-{2-[7-(5-bromo-pyridin-2-yl)-3,7 diaza-bicyclo[3.3.1]non-3-yl]-2-methyl-propionylamino}-adamantane-1-carboxylic acid for (E)-4-{2-methyl-2-[4-(5-trifluoromethyl-pyridin-2-yl)-piperazin-1-yl]-propionylamino}-adamantane-1-carboxylic acid. $^1$H NMR (400 MHz, Py-$d_5$) δ 8.48 (s, 1H), 7.69 (m, 1H), 7.14 (d, J=4.1 Hz, 1H), 6.55 (d, J=9.2 Hz, 1H), 4.03 (d, J=6.1 Hz, 1H), 3.8 (d, J=12.6 Hz, 2H), 3.18 (m, 2H), 2.75 (d, J=11 Hz, 2H), 2.32-2.14 (m, 9H), 2.04-2.0 (m, 4H), 1.69 (s, 1H), 1.5-1.39 (m, 3H), 1.20 (s, 6H), 1.15 (d, J=12.6 Hz, 2H); MS (ESI+) m/z 545 (M+H)$^+$.

EXAMPLE 56

N$^2$-[2-(4-Chlorophenyl)ethyl]-N$^1$-[(E)-5-hydroxy-2-adamantyl]alaninamide

The title compound was prepared according to the method of Example 13D substituting 2-(4-chloro-phenyl)-ethylamine for 1-(5-methyl-pyridin-2-yl)-piperazine. $^1$H NMR (500 MHz, Py-$d_5$) δ 8.42 (d, J=6.39 Hz, 1H), 7.30-7.27 (m, 2H), 7.23-7.20 (m, 2H), 4.36-4.25 (m, 1H), 4.10-3.99 (m, 1H), 3.34-3.15 (m, 2H), 3.13-2.92 (m, 2H), 2.30-2.21 (m, 2H), 2.17-2.02 (m, 3H), 2.01-1.95 (m, 5H), 1.94-1.81 (m, 2H), 1.61 (d, J=6.84 Hz, 3H), 1.50-1.43 (m, 2H); MS (ESI) m/z 377 (M+H)$^+$.

EXAMPLE 57

2-(4-Benzylpiperidin-1-yl)-N-[(E)-5-hydroxy-2-adamantyl]propanamide

The title compound was prepared according to the method of Example 13D substituting 4-benzyl-piperidine for 1-(5-methyl-pyridin-2-yl)-piperazine. $^1$H NMR (500 MHz, Py-$d_5$) δ 8.45 (m, 1H), 7.36 (dd, J=7.5, 7.5 Hz, 2H), 7.27 (m, 1H), 7.20 (m, 2H), 4.31 (m, 1H), 3.87 (bs, 1H), 3.13 (m, 2H), 2.66 (m, 1H), 2.51 (d, J=6.5 Hz, 2H), 2.42 (m, 1H), 2.28 (m, 1H), 2.24 (m, 1H), 2.10 (m, 3H), 1.98 (m, 6H), 1.65 (m, 3H), 1.54 (bs, 1H), 1.51 (bs, 1H), 1.47 (m, 2H), 1.44 (d, J=6.5 Hz, 3H); MS (ESI) m/z 397 (M+H)$^+$.

EXAMPLE 58

N-[(E)-5-Hydroxy-2-adamantyl]-2-(6,7,9,10-tetrahydro-8H-[1,3]dioxolo[4,5-g][3]benzazepin-8-yl)propanamide

EXAMPLE 58A (4-Hydroxymethyl-1,3-benzodioxol-5-yl)methanol

A solution of 1.0 M borane-tetrahydrofuran complex (200 mL, 200 mmoles) at 0° C. was treated portion-wise over 30 minutes with 5-formyl-benzo[1,3]dioxole-4-carboxylic acid (10 g, 51.5 mmoles) (F. E. Ziegler, K. W. Fowler, J. Org. Chem. 41: 1564-1566, 1976). Following the final addition, the mixture was stirred one hour at room temperature. The mixture was cooled to 0° C., quenched with water, and concentrated under reduced pressure to remove the tetrahydrofuran. The aqueous residue was acidified with 3N aqueous HCl, and the product extracted with chloroform. The combined extracts were dried over $Na_2SO_4$, filtered, and concentrated under reduced pressure to afford the title compound. MS (DCI) m/z 182 (M+H)$^+$.

EXAMPLE 58B 4,5-Bis(chloromethyl)-1,3-benzodioxole

A 0° C. solution of (4-hydroxymethyl-1,3-benzodioxol-5-yl)methanol (8.55 g, 47.0 mmoles) from Example 58A in anhydrous methylene chloride (50 mL) was treated dropwise with thionyl chloride (17 mL, 235 mmoles). The mixture was stirred one hour at room temperature and then concentrated under reduced pressure to afford the title compound. MS (DCI) m/z 218 (M+H)$^+$.

EXAMPLE 58C (5-Cyanomethyl-1,3-benzodioxol-4-yl)acetonitrile

A 0° C. suspension of sodium cyanide (7.4 g, 150 mmoles) in anhydrous dimethyl sulfoxide (80 mL) was treated portionwise with 4,5-bis(chloromethyl)-1,3-benzodioxole (10.2 g, 47.0 mmoles) from Example 58B. The mixture was stirred two hours at room temperature. Ice was added to the mixture, and the solids that formed were filtered off and washed with water. Solids were dissolved in chloroform, and solution washed with dilute aqueous NaOH, dried over $Na_2SO_4$, filtered, and concentrated under reduced pressure. The residue was purified by normal phase HPLC on a Biotage pre-packed silica gel column eluting with 7:3 hexane:ethyl acetate to afford the title compound. MS (DCI) m/z 201 (M+H)$^+$.

EXAMPLE 58D 7,8,9,10-Tetrahydro-6H-[1,3]dioxolo[4,5-g][3]benzazepine (5-Cyanomethyl-1,3-benzodioxol-4-yl)acetonitrile (6.00 g, 30.0 mmoles) from Example 58C was reductively cyclized with Raney-Nickel (1.21 g) under a hydrogen atmosphere and high pressure (1100 p.s.i.) in a 10% ammonia in ethanol solution (121 mL) at 100° C. for one hour. The mixture was cooled, and the catalyst filtered off and washed with hot ethanol. The mixture was concentrated under reduced pressure, and the residue purified by normal phase HPLC on a Biotage pre-packed silica gel column eluting with 7:3 methylene chloride:methanol to afford the title compound. MS (DCI) m/z 192 (M+H)$^+$.

EXAMPLE 58E

N-[(E)-5-Hydroxy-2-adamantyl]-2-(6,7,9,10-tetrahydro-8H-[1,3]dioxolo[4,5-g][3]benzazepin-8-yl)propanamide The title compound was prepared according to the method of Example 13D substituting 7,8,9,10-tetrahydro-6H-[1,3]dioxolo[4,5-g][3]benzazepine from example 58D for 1-(5-methyl-pyridin-2-yl)-piperazine. $^1$H NMR (400 MHz, DMSO-d$_6$) δ 7.75 (d, J=8 Hz, 1H), 6.60 (m, 2H), 5.93 (s, 2H), 3.77 (m, 1H), 3.39 (q, J=6.76 Hz, 1H), 2.80 (m, 4H), 2.65-2.50 (m, 4H), 2.05-1.90 (m, 3H), 1.80-1.55 (m, 8H), 1.40 (m, 2H), 1.03 (d, J=6.86 Hz, 3H); MS (ESI) m/z 413 (M+H)$^+$.

EXAMPLE 59

N-[(E)-5-Hydroxy-2-adamantyl]-2-(4-pyridin-2-ylpiperazin-1-yl)propanamide

The title compound was prepared according to the method of Example 13D substituting 1-pyridin-2-yl-piperazine for 1-(5-methyl-pyridin-2-yl)-piperazine. $^1$H NMR (500 MHz, Py-d$_5$) δ 8.40 (ddd, J=0.89, 2.00, 4.85 Hz, 1H), 7.89 (d, J=7.99 Hz, 1H), 7.53 (ddd, J=2.03, 7.10, 8.58 Hz, 1H), 6.81 (dt, J=0.80, 8.63 Hz, 1H), 6.68 (ddd, J=0.83, 4.85, 7.09 Hz, 1H), 5.81-6.00 (bs, 1H), 4.30-4.35 (m, 1H), 3.62-3.75 (m, 4H), 3.30 (q, J=6.98 Hz, 1H), 2.66-2.72 (m, 2H), 2.56-2.62 (m, 2H), 2.20-2.26 (m, 2H), 2.08-2.13 (m, 3H), 1.96-2.02 (m, 4H), 1.81-1.88 (m, 2H), 1.50-1.56 (m, 2H), 1.34 (d, J=6.98 Hz, 3H); MS (ESI) m/z 385 (M+H)$^+$.

EXAMPLE 60

2-[4-(4-Fluorophenyl)piperazin-1-yl]-N-[(E)-5-hydroxy-2-adamantyl]propanamide

The title compound was prepared according to the method of Example 13D substituting 1-(4-fluoro-phenyl)-piperazine for 1-(5-methyl-pyridin-2-yl)-piperazine. $^1$H NMR (500 MHz, Py-d$_5$) δ 7.86 (d, J=7.93 Hz, 1H), 7.12-7.16 (m, 2H), 6.98-7.02 (m, 2H), 4.29-4.38 (m, 1H), 3.32 (q, J=6.97 Hz, 1H), 3.11-3.25 (m, 4H), 2.71-2.81 (m, 2H), 2.59-2.69 (m, 2H), 2.21-2.28 (m, 2H), 2.07-2.15 (m, 3H), 1.96-2.03 (m, 4H), 1.81-1.89 (m, 2H), 1.50-1.59 (m, 2H), 1.37 (d, J=6.97 Hz, 3H); MS (ESI) m/z 402 (M+H)$^+$.

EXAMPLE 61

N-[(E)-5-Hydroxy-2-adamantyl]-2-[4-(4-methoxyphenyl)piperazin-1-yl]propanamide

The title compound was prepared according to the method of Example 13D substituting 1-(4-methoxy-phenyl)-piperazine for 1-(5-methyl-pyridin-2-yl)-piperazine. $^1$H NMR (500 MHz, Py-d$_5$) δ 7.89 (d, J=7.97 Hz, 1H), 7.00-7.10 (m, 4H), 5.89-5.92 (bs, 1H), 4.28-4.38 (m, 1H), 3.70 (s, 3H), 3.32 (q, J=6.97 Hz, 1H), 3.12-3.25 (m, 4H), 2.72-2.82 (m, 2H), 2.60-2.71 (m, 2H), 2.19-2.28 (m, 2H), 2.05-2.14 (m, 3H), 1.97-2.02 (m, 4H), 1.82-1.89 (m, 2H), 1.49-1.56 (m, 2H), 1.38 (d, J=6.97 Hz, 3H); MS (ESI) m/z 414 (M+H)$^+$.

EXAMPLE 62

2-[4-(5-Cyanopyridin-2-yl)piperazin-1-yl]-N-[(E)-5-hydroxy-2-adamantyl]propanamide The title compound was prepared according to the method of Example 13D substituting 6-piperazin-1-yl-nicotinonitrile for 1-(5-methyl-pyridin-2-yl)-piperazine. $^1$H NMR (500 MHz, Py-d$_5$) δ 8.64 (dd, J=0.72, 2.35 Hz, 1H), 7.88 (d, J=7.86 Hz, 1H), 7.74 (dd, J=2.38, 8.99 Hz, 1H), 6.77 (dd, J=0.82, 9.05 Hz, 1H), 4.28-4.37 (m, 1H), 3.65-3.82 (m, 4H), 3.35 (q, J=6.96 Hz, 1H), 2.63-2.73 (m, 2H), 2.55-2.60 (m, 2H), 2.20-2.29 (m, 2H), 2.07-2.15 (m, 3H), 1.96-2.04 (m, 4H), 1.82-1.92 (m, 2H), 1.52-1.59 (m, 2H), 1.34 (d, J=6.95 Hz, 3H); MS (ESI) m/z 410 (M+H)$^+$.

EXAMPLE 63

2-[4-(2-Furoyl)piperazin-1-yl]-N-[(E)-5-hydroxy-2-adamantyl]propanamide

The title compound was prepared according to the method of Example 13D substituting furan-2-yl-piperazin-1-yl-methanone for 1-(5-methyl-pyridin-2-yl)-piperazine.

$^1$H NMR (500 MHz, Py-$d_5$) δ 7.84 (d, J=7.86 Hz, 1H), 7.74 (dd, J=0.87, 1.75 Hz, 1H), 7.23 (dd, J=0.83, 3.39 Hz, 1H), 6.55 (dd, J=1.72, 3.43 Hz, 1H), 5.70-6.05 (bs, 1H), 4.30-4.37 (m, 1H), 3.79-3.94 (m, 4H), 3.32 (q, J=6.97 Hz, 1H), 2.55-2.67 (m, 2H), 2.49-2.55 (m, 2H), 2.19-2.28 (m, 2H), 2.09-2.14 (m, 2H), 1.98-2.03 (m, 4H), 1.92-1.98 (m, 1H), 1.81-1.88 (m, 2H), 1.50-1.58 (m, 2H), 1.31 (d, J=6.94 Hz, 3H); MS (ESI) m/z 402 (M+H)$^+$.

EXAMPLE 64

2-(1,3-Dihydro-2H-isoindol-2-yl)-N-[(E)-5-hydroxy-2-adamantyl]propanamide

The title compound was prepared according to the method of Example 13D substituting 2,3-dihydro-1H-isoindole for 1-(5-methyl-pyridin-2-yl)-piperazine. $^1$H NMR (500 MHz, Py-$d_5$) δ 7.62 (d, J=7.64 Hz, 1H), 7.24-7.30 (m, 4H), 4.32-4.40 (m, 1H), 4.09-4.13 (m, 2H), 4.00-4.04 (m, 2H), 3.51 (q, J=6.82 Hz, 1H), 2.23-2.28 (m, 2H), 2.08-2.12 (m, 2H), 1.98 (q, J=2.94 Hz, 1H), 1.95-1.97 (m, 2H), 1.93-1.95 (m, 2H), 1.74-1.83 (m, 2H), 1.49 (d, J=6.78 Hz, 3H), 1.39-1.45 (m, 2H); MS (ESI) m/z 341 (M+H)$^+$.

EXAMPLE 65

N-[(E)-5-Hydroxy-2-adamantyl]-2-{4-[4-(trifluoromethyl)phenyl]piperazin-1-yl}propanamide The title compound was prepared according to the method of Example 13D substituting 1-(4-trifluoromethyl-phenyl)-piperazine for 1-(5-methyl-pyridin-2-yl)-piperazine.

$^1$H NMR (500 MHz, Py-$d_5$) δ 7.87 (d, J=7.88 Hz, 1H), 7.62-7.66 (m, 2H), 7.07 (d, J=8.57 Hz, 2H), 4.29-4.39 (m, 1H), 3.29-3.40 (m, 5H), 2.71-2.77 (m, 2H), 2.62-2.68 (m, 2H), 2.20-2.30 (m, 2H), 2.11-2.14 (m, 3H), 1.95-2.06 (m, 4H), 1.80-1.92 (m, 2H), 1.53-1.58 (m, 2H), 1.37 (d, J=6.97 Hz, 3H); MS (ESI) m/z 452 (M+H)$^+$.

EXAMPLE 66 and EXAMPLE 67

(2S)-N-[(E)-5-Hydroxy-2-adamantyl]-2-{4-[5-(trifluoromethyl)pyridin-2-yl]piperazin-1-yl}propanamide and (2R)-N-[(E)-5-Hydroxy-2-adamantyl]-2-{4-[5-(trifluoromethyl)pyridin-2-yl]piperazin-1-yl}propanamide The two enantiomers of Example 3, N-[(E)-5-hydroxy-2-adamantyl]-2-{4-[5-(trifluoromethyl)pyridin-2-yl]piperazin-1-yl}propanamide, were separated by chiral chromatography (Chiralcel OD Chiral Technologies Column; Isocratic mobile phase, 12% ethanol in hexanes, 1.0 mL/minutes, 10 minutes runtime; 254 nm and 210 nm UV detection; retention times: 6.8 min and 8.3 min.). Spectral information is identical as with earlier racemic material. $^1$H NMR (300 MHz, CDCl$_3$) δ 8.41 (s, 1H), 7.65 (m, 2H), 6.67 (d, J=8.8 Hz, 1H), 4.03 (d, J=8.5 Hz, 1H), 3.69 (m, 4H), 3.15 (q, J=7.1 Hz, 1H), 2.63 (m, 4H), 2.15 (m, 3H), 1.9 (m, 2H), 1.77 (m, 4H), 1.66 (m, 2H), 1.52 (s, 1H), 1.36 (s, 1H), 1.28 (d, J=7.1 Hz, 3H); MS(APCI+) m/z 453 (M+H)$^+$.

EXAMPLE 68

2-[3-(4-Chlorophenoxy)azetidin-1-yl]-N-[(E)-5-hydroxy-2-adamantyl]propanamide

The title compound was prepared according to the method of Example 13D substituting 3-(4-chloro-phenoxy)-azetidine for 1-(5-methyl-pyridin-2-yl)-piperazine. $^1$H NMR (500 MHz, Py-$d_5$) δ 7.37-7.42 (m, 1H), 7.34-7.37 (m, 2H), 6.89-6.94 (m, 2H), 5.88-5.89 (bs, 1H), 4.24-4.32 (m, 1H), 3.92-3.96 (m, 1H), 3.76-3.80 (m, 1H), 3.32 (dd, J=5.20, 7.79 Hz, 1H), 3.27 (dd, J=5.25, 7.83 Hz, 1H), 3.18 (q, J=6.76 Hz, 1H), 2.19-2.29 (m, 2H), 2.06-2.13 (m, 2H), 2.02-2.05 (m, 1H), 1.94-2.00 (m, 4H), 1.80-1.88 (m, 2H), 1.44-1.52 (m, 2H), 1.30 (d, J=6.78 Hz, 3H); MS(ESI) m/z 405 (M+H)$^+$.

EXAMPLE 69

2-[4-(2-Fluorophenoxy)piperidin-1-yl]-N-[(E)-5-hydroxy-2-adamantyl]propanamide

The title compound was prepared according to the method of Example 13D substituting 4-(2-fluoro-phenoxy)-piperidine for 1-(5-methyl-pyridin-2-yl)-piperazine. $^1$H NMR (300 MHz, CDCl$_3$) δ 1.25 (d, J=7.04 Hz, 3H), 1.55-1.58 (m, 1H), 1.63-1.72 (m, 2H), 1.75-1.80 (m, 4H), 1.82-1.97 (m, 5H), 1.98-2.14 (m, 4H), 2.14-2.23 (m, 2H), 2.29-2.40 (m, 1H), 2.48 (ddd, J=11.72, 9.01, 2.90 Hz, 1H), 2.77-2.90 (m, 2H), 3.12 (q, J=7.01 Hz, 1H), 3.98-4.04 (m, 1H), 4.24-4.34 (m, 1H), 6.89-7.13 (m, 4H), 7.73 (d, J=8.31 Hz, 1H); MS(APCI+) m/z 417 (M+H)$^+$.

EXAMPLE 70

2-[3-(2-Fluorophenoxy)piperidin-1-yl]-N-[(E)-5-hydroxy-2-adamantyl]propanamide

The title compound was prepared according to the method of Example 13D substituting 3-(2-fluoro-phenoxy)-piperidine for 1-(5-methyl-pyridin-2-yl)-piperazine. $^1$H NMR (500 MHz, CDCl$_3$) δ 1.20-1.30 (m, 4H), 1.45-1.48 (m, 2.5H), 1.65-1.67 (m, 1.5H), 1.68-1.73 (m, 5H), 1.80-1.90 (m, 4H), 1.99 (m, 1H), 2.00-2.09 (m, 2H), 2.48 (m, 0.5H), 2.6 (m, 1H), 2.7 (m, 0.5H), 2.8 (m, 1H), 3.09-3.17 (m, 0.5H), 3.25 (m, 0.5H), 3.65-3.70 (m, 0.5H), 3.87-3.90 (m, 0.5H), 3.95 (m, 1H), 4.00-4.04 (m, 0.5H), 4.28-4.34 (m, 0.5H), 6.87-7.09 (m, 4H), 7.83 (m, 1H); MS(APCI+) m/z 417 (M+H)$^+$.

EXAMPLE 71

2-[3-(3-Fluorophenoxy)pyrrolidin-1-yl]-N-[(E)-5-hydroxy-2-adamantyl]propanamide

The title compound was prepared according to the method of Example 13D substituting 3-(3-fluorophenoxy)-pyrrolidine for 1-(5-methyl-pyridin-2-yl)-piperazine. $^1$H NMR (500 MHz, CDCl$_3$) δ 1.29-1.35 (m, 4H), 1.55-1.58 (m, 2H), 1.70-1.76 (m, 6H), 1.87 (m, 2H), 2.07 (m, 3H), 2.14 (m, 1H), 2.3 (m, 1H), 2.40 (m, 0.5H), 2.6 (m, 1.5H), 2.90 (m, 1H), 2.97 (m, 0.5H), 3.05 (m, 0.5H), 3.13 (m, 1H), 3.98-4.04 (m, 1H), 4.78 (s, 1H), 6.5-6.63 (m, 2H) 6.64 (m, 0.5H), 6.77 (m, 0.5H), 6.95

EXAMPLE 72

N²-[2-(3,4-Dichlorophenyl)ethyl]-N¹-[(E)-5-hydroxy-2-adamantyl]-N²-methylalaninamide The title compound was prepared according to the method of Example 13D substituting [2-(3,4-dichloro-phenyl)-ethyl]-methyl-amine for 1-(5-methyl-pyridin-2-yl)-piperazine. $^1$H NMR (500 MHz, CDCl$_3$) δ 7.35 (d, J=8.12 Hz, 1H), 7.27-7.33 (m, 1H), 7.04 (dd, J=2.05, 8.16 Hz, 1H), 3.87-3.95 (m, 1H), 3.16-3.29 (m, 1H), 2.71-2.84 (m, 4H), 2.24-2.26 (m, 3H), 2.04-2.12 (m, 1H), 1.96-2.02 (m, 1H), 1.91-1.96 (m, 1H), 1.80-1.88 (m, 2H), 1.69-1.75 (m, 4H), 1.37-1.49 (m, 4H), 1.27-1.34 (m, 1H), 1.17-1.24 (m, 3H); MS(APCI+) m/z 426 (M+H)$^+$.

EXAMPLE 73

N²-[2-(4-Chlorophenyl)-1-methylethyl]-N¹-[(E)-5-hydroxy-2-adamantyl]-N²-methylalaninamide The title compound was prepared according to the method of Example 13D substituting [2-(4-chloro-phenyl)-1-methylethyl]-methyl-amine for 1-(5-methyl-pyridin-2-yl)-piperazine. $^1$H NMR (500 MHz, CDCl$_3$) δ 7.4 (d, 0.5H), 7.24 (d, 2H), 7.15 (d, 0.5H), 7.11 (m, 2H), 3.88 (t, 1H), 3.32 (m, 0.5H), 3.26 (m, 0.5H), 3.18 (m, 0.5H), 3.12 (m, 0.5H), 2.84 (m, 0.5H), 2.75 (m, 0.5H), 2.65 (m, 0.5H), 2.6 (m, 0.5H), 2.2 (d, 3H), 2.06 (m, 1H), 1.88-1.94 (m, 1H), 1.84 (m, 2H), 1.68-1.73 (m, 4H), 1.36-1.41 (m, 3H), 1.33-1.32 (m, 1.5H), 1.29 (m, 1H), 1.21-1.26 (m, 2.5H), 1.02-1.07 (dd, 3H); MS(APCI+) m/z 405 (M+H)$^+$.

EXAMPLE 74

2-(5-Chloro-2,3-dihydro-1H-indol-1-yl)-N-[(E)-5-hydroxy-2-adamantyl]propanamide

The title compound was prepared according to the method of Example 13D substituting 5-chloro-2,3-dihydro-1H-indole for 1-(5-methyl-pyridin-2-yl)-piperazine. $^1$H NMR (500 MHz, CDCl$_3$) δ 7.08-7.09 (m, 1H), 7.01 (dd, J=2.17, 8.30 Hz, 1H), 6.90-6.99 (m, 1H), 6.35 (d, J=8.32 Hz, 1H), 4.00-4.05 (m, 1H), 3.87 (q, J=7.09 Hz, 1H), 3.37-3.51 (m, 2H), 2.99 (t, J=8.15 Hz, 2H), 2.02-2.11 (m, 3H), 1.84-1.90 (m, 2H), 1.72-1.76 (m, 2H), 1.71-1.72 (m, 1H), 1.44-1.48 (m, 2H), 1.40-1.43 (m, 2H), 1.40 (d, J=7.09 Hz, 3H); MS(APCI+) m/z 375 (M+H)$^+$.

EXAMPLE 75

2-[4-(6-Chloropyridin-3-yl)piperazin-1-yl]-N-[(E)-5-hydroxy-2-adamantyl]propanamide

EXAMPLE 75A

Benzyl 4-(2-{[(E)-5-hydroxy-2-adamantyl]amino}-1-methyl-2-oxoethyl)piperazine-1-carboxylate The title compound was prepared and used in the next step according to the method of Example 13D substituting piperazine-1-carboxylic acid benzyl ester for 1-(5-methyl-pyridin-2-yl)-piperazine. MS(APCI+) m/z 442 (M+H)$^+$.

EXAMPLE 75B

N-[(E)-5-Hydroxy-2-adamantyl]-2-piperazin-1-yl-propanamide

A suspension of the product from Example 75A and 5% Pd/C in MeOH (0.5 mL) was stirred under hydrogen atmosphere at room temperature overnight. The mixture was filtered, concentrated and carried on to the next step. MS(APCI+) m/z 308 (M+H)$^+$.

EXAMPLE 75C

2-[4-(6-Chloropyridin-3-yl)piperazin-1-yl]-N-[(E)-5-hydroxy-2-adamantyl]propanamide A suspension of N-[(E)-5-hydroxy-2-adamantyl]-2-piperazin-1-ylpropanamide from Example 75B (21.5 mg, 0.07 mmoles), 2-chloro-5-iodopyridine (20.5 mg, 0.07 mmoles), copper iodide (I) (2 mg, 0.01 mmoles), ethylene glycol (0.008 mL, 0.14 mmoles), potassium phosphate (32.7 mg, 0.154 mmoles) in isopropanol (0.7 mL) was stirred for 48 hours at 80° C. The mixture was filtered, taken into DCM and purified by column chromatography (silica gel, 10-50% acetone in hexane) to provide the title compound. $^1$H NMR (400 MHz, CDCl$_3$) δ 8.03 (s, 1H), 7.57 (d, J=9.2 Hz, 1H), 7.19 (s, 1H), 4.02 (d, J=8 Hz 1H), 3.23 (m, 4H), 3.13 (q, J=7.1 Hz, 1H), 2.54 (m, 4H), 1.95-1.89 (m, 3H), 1.77 (m, 6H), 1.58 (m, 4H) 1.13 (d, J=7 Hz, 3H); MS(APCI+) m/z 419 (M+H)$^+$.

EXAMPLE 76

N-[(E)-5-Hydroxy-2-adamantyl]-2-(3-phenylazetidin-1-yl)propanamide

The title compound was prepared according to the method of Example 13D substituting 3-phenyl azetidine for 1-(5-methyl-pyridin-2-yl)-piperazine. $^1$H NMR (500 MHz, DMSO-d$_6$) δ 7.32-7.36 (m, 3H), 7.29-7.32 (m, 2H), 7.18-7.22 (m, 1H), 3.71-3.75 (m, 1H), 3.57-3.67 (m, 3H), 3.16-3.20 (m, 2H), 2.94 (q, J=6.76 Hz, 1H), 1.98-2.02 (m, 1H), 1.90-1.96 (m, 2H), 1.70-1.76 (m, 2H), 1.64-1.69 (m, 2H), 1.57-1.63 (m, 4H), 1.34-1.41 (m, 2H), 1.03 (d, J=6.86 Hz, 3H); MS(ESI) m/z 355 (M+H)$^+$.

EXAMPLE 77

(E)-N-Methyl-4-[(2-methyl-2-{4-[5-(trifluoromethyl)pyridin-2-yl]piperazin-1-yl}propanoyl)amino]adamantane-1-carboxamide The title compound was prepared according to the method of Example 24 substituting methylamine for hydroxylamine. $^1$H NMR (400 MHz, CDCl$_3$) δ 8.36-8.45 (m, 1H), 7.71-7.81 (m, 1H), 7.64 (dd, J=2.38, 8.98 Hz, 1H), 6.66 (d, J=8.96 Hz, 1H), 5.53-5.61 (m, 1H), 3.95-4.11 (m, 1H), 3.61-3.69 (m, 4H), 2.80 (d, J=4.74 Hz, 3H), 2.59-2.70 (m, 4H), 2.00-2.08 (m, 3H), 1.96-1.99 (m, 4H), 1.85-1.91 (m, 2H), 1.69-1.78 (m, 2H), 1.59-1.67 (m, 2H), 1.25 (s, 6H); MS(APCI+) m/z 508 (M+H)$^+$.

EXAMPLE 78

(E)-N-Methoxy-4-[(2-methyl-2-{4-[5-(trifluoromethyl)pyridin-2-yl]piperazin-1-yl}propanoyl)amino]adamantane-1-carboxamide The title compound was prepared according to the method of Example 24 substituting methoxyamine for hydroxylamine. ¹H NMR (400 MHz, CDCl₃) δ 8.41 (s, 1H), 7.78 (d, J=8.3 Hz, 1H), 7.64 (d, J=6.5 Hz, 1H), 6.66 (d, J=8.9 Hz, 1H), 4.0 (d, J=8.3 Hz, 1H), 3.75 (s, 3H), 3.65 (s, 4H), 2.65 (s, 4H), 2.03 (s, 4H), 1.99 (s, 3H), 1.90 (s, 2H), 1.73 (d, J=13.5 Hz, 2H)), 1.62 (d, J=13.5 Hz, 2H), 1.25 (s, 6H); MS(APCI+) m/z 524 (M+H)⁺.

EXAMPLE 79

N-[(E)-5-(Aminomethyl)-2-adamantyl]-2-methyl-2-{4-[5-(trifluoromethyl)pyridin-2-yl]piperazin-1-yl}propanamide A solution of N-[(E)-5-formyl-adamantan-2-yl]-2-[4-(5-trifluoromethyl-pyridin-2-yl)-piperazin-1-yl]-isobutyramide (48 mg, 0.1 mmoles) from Example 22, and 4 Å molecular seives (50 mg) in methanolic ammonia (7N, 2 mL) was stirred overnight at room temperature. The mixture was cooled in an ice bath, treated portionwise with sodium borohydride (15 mg, 0.4 mmoles) and stirred at room temperature for 2 hours. The suspension was filtered and concentrated under reduced pressure. The residue was taken into DCM (2 mL), acidified with 1N HCl to pH=3 and the layers separated. The aqueous layer was basified with 2N NaOH to pH=12 and extracted three times with DCM. The combined organic extracts were dried (MgSO₄) and filtered. The filtrate was concentrated under reduced pressure and purified on reverse phase HPLC to provide the title compound. ¹H NMR (500 MHz, Py-d₅) δ 8.67 (s, 1H), 7.82 (d, J=8.1 Hz, 1H), 7.79 (d, J=2.5, 9.1 Hz, 1H), 6.86 (d, J=8.9 Hz, 1H), 4.22 (d, J=8.1 Hz, 1H), 3.73 (s, 4H), 3.05 (s, 2H), 2.57 (m, 4H), 2.07 (s, 2H), 1.96 (s, 1H), 1.82-1.92 (m, 8H), 1.55-1.58 (d, J=13.1 Hz, 2H), 1.30 (s, 6H); MS(ESI+) m/z 480 (M+H)⁺.

EXAMPLE 80

N-[(E)-5-Hydroxy-2-adamantyl]-1-{[4-(trifluoromethyl)benzyl]amino}cyclopropanecarboxamide

EXAMPLE 80A tert-Butyl 1-({[(E)-5-hydroxy-2-adamantyl]amino}carbonyl)cyclopropylcarbamate The title compound was prepared according to the method of Example 16F using a mixture of (E)- and (Z)-5-hydroxy-2-adamantamine from example 13A and 1-(N-t-Boc-amino)cyclopropanecarboxylic acid. The (E)-isomer was isolated by normal phase HPLC on a Biotage pre-packed silica gel column eluting with 4:1 ethyl acetate:hexane to afford the title compound. MS(ESI) m/z 351 (M+H)⁺.

EXAMPLE 80B

1-Amino-N-[(E)-5-hydroxy-2-adamantyl]cyclopropanecarboxamide

A solution of text-butyl 1-({[(E)-5-hydroxy-2-adamantyl]amino}carbonyl)cyclopropylcarbamate (0.50 g, 1.43 mmoles) from Example 80A in methylene chloride (3 mL) was treated with trifluoroacetic acid (1 mL) and stirred two hours at room temperature. The mixture was concentrated under reduced pressure. The residue was dissolved in saturated NaHCO₃, and the product extracted with chloroform. The combined extracts were dried over Na₂SO₄, filtered, and concentrated under reduced pressure to afford the title compound. MS(ESI) m/z 251 (M+H)⁺.

EXAMPLE 80C

N-[(E)-5-Hydroxy-2-adamantyl]-1-{[4-trifluoromethyl)benzyl]amino}cyclopropanecarboxamide A solution of 1-amino-N-[(E)-5-hydroxy-2-adamantyl]cyclopropanecarboxamide from example 80B (0.050 g, 0.20 mmoles), 4-(trifluoromethyl)benzaldehyde (0.034 g, 0.20 mmoles), and acetic acid (0.048 g, 0.80 mmoles) in dichloroethane (2 mL) was treated, after stirring two hours at room temperature, with sodium triacetoxyborohydride (0.085 g, 0.40 mmoles). The mixture was stirred overnight at room temperature. The mixture was quenched with saturated NaHCO₃, and the product extracted into ethyl acetate. The combined extracts were washed with saturated NaHCO₃ and brine, dried over Na₂SO₄, filtered, and concentrated under reduced pressure. The residue was purified by reverse phase HPLC (20-100% acetonitrile in 0.1% TFA in water) on a YMC ODS Guardpak column to afford the title compound. ¹H NMR (400 MHz, DMSO-d₆) δ 8.72 (m, 1H), 8.22 (m, 1H), 7.80-7.70 (m, 2H), 7.60-7.40 (m, 2H), 4.15 (m, 1H), 4.03 (m, 2H), 1.90 (m, 2H), 1.70-1.50 (m, 5H), 1.40-1.20 (m, 4H), 1.08 (m, 2H), 0.89 (t, J=6 Hz, 2H), 0.76 (t, J=6 Hz, 2H); MS(ESI) m/z 409 (M+H)⁺.

EXAMPLE 82

N-[(E)-5-Hydroxy-2-adamantyl]-1-piperidin-1-ylcyclopropanecarboxamide

EXAMPLE 82A

Methyl 1-piperidin-1-ylcyclopropanecarboxylate

A mixture of methyl 1-aminocyclopropane-1-carboxylate (0.50 g, 4.35 mmoles), powdered potassium carbonate (2.40 g, 17.4 mmoles), and tetrabutylammonium bromide (0.140 g, 0.43 mmoles) in anhydrous acetonitrile (12 mL) was treated with 1,5-diiodopentane (1.70 g, 5.22 mmoles). The mixture was stirred for three days at 90° C. The mixture was cooled to room temperature and filtered. The filtrate was concentrated under reduced pressure. The residue was purified on an Alltech pre-packed silica gel column eluting with ethyl acetate to afford the title compound. MS(DCI) m/z 184 (M+H)⁺. Vaidyanathan, G.; Wilson, J. W. *J. Org. Chem.* 1989, 54, 1810-1815.

EXAMPLE 82B

1-Piperidin-1-ylcyclopropanecarboxylic acid

The title compound was prepared according to the method of Example 16E substituting methyl 1-piperidin-1-ylcyclopropanecarboxylate from example 82A for methyl 1-[4-(5-trifluoromethylpyridin-2-yl)-piperazin-1-yl]-cyclopropanecarboxylate. MS(DCI) m/z 170 (M+H)⁺.

EXAMPLE 82C

N-[(E)-5-Hydroxy-2-adamantyl]-1-piperidin-1-ylcyclopropanecarboxamide

The title compound was prepared according to the method of Example 16F using (E)- and (Z)-5-hydroxy-2-adamantamine from Example 13A and 1-piperidin-1-ylcyclopropan-ecarboxylic acid from Example 82B. The (E)-isomer was isolated on an Alltech pre-packed silica gel column eluting with ethyl acetate to afford the title compound. $^1$H NMR (500 MHz, DMSO-$d_6$) δ 8.32 (m, 1H), 4.44 (m, 1H), 3.75 (m, 1H), 2.32 (m, 2H), 2.06 (m, 1H), 1.91 (m, 2H), 1.80-1.40 (m, 15H), 1.39 (m, 2H), 1.00 (m, 2H), 0.76 (m, 2H); MS(ESI) m/z 319 (M+H)$^+$.

EXAMPLE 83

2-Methyl-N-[(E)-5-(5-methyl-1,2,4-oxadiazol-3-yl)-2-adamantyl]-2-{4-[5-(trifluoromethyl)pyridin-2-yl]piperazin-1-yl}propanamide

EXAMPLE 83A

2-Bromo-N-[(E)-5-cyano-2-adamantyl]-2-methyl-propanamide

A solution of (E)-4-(2-bromo-2-methyl-propionylamino)-adamantane-1-carboxamide (343 mg, 1 mmoles) from Example 44B in dioxane (7 mL) and pyridine (0.7 mL) was cooled to 0° C., treated with trifluoroacetic acid anhydride (0.1 mL) and stirred at room temperature for 4 hours. Solvents were removed under reduced pressure and the residue partitioned between water and DCM. Organics were washed with water, dried (MgSO$_4$) and filtered. The filtrate was concentrated under reduced pressure to provide the title compound.

EXAMPLE 83B

N-[(E)-5-Cyano-2-adamantyl]-2-methyl-2-{4-[5-(trifluoromethyl)pyridin-2-yl]piperazin-1-yl}propanamide A two phase suspension of 2-bromo-N-[(E)-5-cyano-2-adamantyl]-2-methylpropanamide (300 mg, 0.92 mmoles) from Example 83A, 1-(5-trifluoromethyl-pyridin-2-yl)piperazine (34 mg, 1 mmoles) and tetrabutylammonium bromide (30 mg, 0.1 mmoles) in DCM (7 mL) and 50% NaOH (7 mL) was stirred at room temperature for 20 hours. After that the mixture was diluted with water and DCM and layers separated. Organic layer was washed with water (2×2 mL), dried (MgSO$_4$) and filtered. The filtrate was concentrated under reduced pressure to provide crude material that was purified by column chromatography (silica gel, 10-40% acetone in hexane) to provide the title compound. MS(ESI+) m/z 476 (M+H)$^+$.

EXAMPLE 83C

2-Methyl-N-[(E)-5-(5-methyl-1,2,4-oxadiazol-3-yl)-2-adamantyl]-2-{4-[5-(trifluoromethyl)pyridin-2-yl]piperazin-1-yl}propanamide A solution of N-[(E)-5-cyano-2-adamantyl]-2-methyl-2-{4-[5-(trifluoromethyl)pyridin-2-yl]piperazin-1-yl}propanamide (95 mg, 0.2 mmoles) from Example 83B, hydroxylamine hydrochloride (70 mg, 1 mmoles) and potassium carbonate (138 mg, 1 mmoles) in ethanol (1 mL) was refluxed overnight, filtered hot, and washed with hot ethanol. The solvent was concentrated under reduced pressure; the residue was taken into pyridine (1 mL), treated at 80° C. with acetyl chloride (28 μL, 0.4 mmoles) and stirred at 100° C. overnight. The solvent was concentrated under reduced pressure and the residue purified by reverse phase HPLC to provide the title compound. $^1$H NMR (300 MHz, Py-$d_5$) δ 8.68 (s, 1H), 7.88 (d, J=8 Hz, 1H), 7.79 (d, J=8.9 Hz, 1H), 6.87 (d, J=8.2 Hz, 1H), 4.33 (d, J=8.0 Hz, 1H), 3.76 (s, 4H), 2.59 (m, 4H), 2.41 (s, 3H), 2.27-1.86 (m, 11H), 1.65 (m, 2H), 1.32 (d, 6H); MS(ESI+) m/z 533 (M+H)$^+$.

EXAMPLE 84

2-Methyl-N-[(E)-5-(2H-tetraazol-5-yl)-2-adamantyl]-2-{4-[5-(trifluoromethyl)pyridin-2-yl]piperazin-1-yl}propanamide A suspension of N-[(E)-5-cyano-2-adamantyl]-2-methyl-2-{4-[5-(trifluoromethyl)pyridin-2-yl]piperazin-1-yl}propanamide (95 mg, 0.2 mmoles) from Example 83B, sodium azide (14.3 mg, 0.22 mmoles) and zinc bromide (45 mg, 0.2 mmoles) in water (0.5 mL) with a drop of isopropanol was stirred at 120° C. for 72 hours. The solvent was concentrated under reduced pressure and the residue purified by reverse phase HPLC to provide the title compound. $^1$H NMR (300 MHz, Py-$d_5$) δ 8.69 (s, 1H), 7.89 (d, J=7.9 Hz, 1H), 7.8 (d, J=9.1 Hz, 1H), 6.89 (d, J=8.8 Hz, 1H), 4.36 (d, J=7.7 Hz, 1H), 3.76 (s, 4H), 2.58 (m, 4H), 2.39 (m, 4H), 2.26 (s, 2H), 2.16 (s, 2H), 2.02 (s, 1H), 1.92 (d, J=12.9 Hz, 2H), 1.65 (d, J=12.9 Hz, 2H), 1.32 (s, 6H); MS(ESI+) m/z 519 (M+H)$^+$.

EXAMPLE 85

(E)-4-[(2-{4-[[(4-Chlorophenyl)sulfonyl](cyclopropyl)amino]piperidin-1-yl}propanoyl)amino]adamantane-1-carboxamide A solution of (E)-4-(2-bromo-propionylamino)-adamantane-1-carboxamide (33 mg, 0.1 mmoles) from Example 31B, 4-chloro-N-cyclopropyl-N-piperidin-4-yl-benzenesulfonamide (12 mg, 0.12 mmoles) in MeOH (0.5 mL) and DIPEA (0.1 mL) was stirred overnight at 70° C. The MeOH was removed under reduced pressure and the residue purified on reverse phase HPLC to provide the title compound. $^1$H NMR (500 MHz, CDCl$_3$) δ 7.96 (d, J=6.6 Hz, 1H), 5.54-5.34 (m, 2H), 4.68-4.78 (m, 1H), 4.00 (d, J=7.8 Hz, 1H), 3.2 (q, J=7.2 Hz, 1H), 2.8 (m, 1H), 2.53-2.59 (m, 3H), 1.55-2.07 (m, 17H), 1.22 (d, J=7.2 Hz, 3H); MS(ESI+) m/z 352 (M+H)$^+$.

EXAMPLE 86

N-[(E)-5-Hydroxy-2-adamantyl]-2-methyl-2-[2-(trifluoromethyl)pyrrolidin-1-yl]propanamide A two phase suspension of 2-bromo-N-[(E)-5-hydroxy-adamantan-2-yl]-2-methyl-propionamide (32 mg, 0.1 mmoles) from Example 34A, hydrochloride of 2-trifluoromethylpyrrolidine (21 mg, 0.12 mmoles) and tetrabutylammonium bromide (3 mg, 0.01 mmoles) in DCM (0.2 mL) and 50% NaOH (0.2 mL) was stirred at room temperature for 20 hours. The mixture was diluted with water and DCM and the layers separated. The organic layer was washed with water (2×2 mL), dried (MgSO$_4$) and filtered. The filtrate was concentrated under reduced pressure, and the residue was purified on reverse phase HPLC to provide the title compound. $^1$H NMR (400 MHz, Py-$d_5$) δ 7.33-7.43 (m, 1H), 5.87-5.91 (bs, 1H), 4.21-4.31 (m, 1H), 3.97 (qd, J=7.93, 4.80 Hz, 1H), 3.06 (ddd, J=10.70, 7.46, 5.92 Hz, 1H), 2.82 (dt, J=10.69, 6.94 Hz, 1H), 2.20-2.25 (m, 1H), 2.14-2.19 (m, 1H), 2.04-2.13 (m, 3H), 1.89-2.03 (m, 5H), 1.70-1.87 (m, 4H), 1.58-1.70 (m, 1H), 1.48-1.58 (m, 2H), 1.48 (s, 3H), 1.34 (s, 3H); MS(ESI+) m/z 375 (M+H)$^+$.

EXAMPLE 87

(E)-4-({2-[(3S)-3-Fluoropyrrolidin-1-yl]-2-methylpropanoyl}amino)adamantane-1-carboxamide The title compound was prepared according to the method of Example 44C substituting (3S)-3-fluoropyrrolidine for (3R)-3-fluoropyrrolidine. $^1$H NMR (300 MHz, Py-d5) δ 7.91 (d, J=7.7 Hz, 1H), 5.19-5.06 (m, 1H), 4.29 (d, J=8.0 Hz, 1H), 3.0 (m, 1H), 2.91 (m, 1H), 2.58 (m, 1H), 2.39 (q, J=7.6 Hz, 1H), 2.27-2.01 (m, 7H), 1.96-1.85 (m, 6H), 1.53 (m, 2H), 1.35 (m, 6H); MS(ESI+) m/z 352 (M+H)$^+$.

EXAMPLE 88

Methyl (E)-4-{[2-methyl-2-(4-pyridin-2-ylpiperazin-1-yl)propanoyl]amino}adamantane-1-carboxylate The title compound was prepared according to the method of Example 34C substituting 1-pyridin-2-yl-piperazine for 1-(5-chloro-2-pyridyl)piperazine and isolating the ester before hydrolysis. $^1$H NMR (500 MHz, Py-d$_5$) δ 8.38-8.46 (m, 1H), 7.88 (d, J=8.10 Hz, 1H), 7.55 (ddd, J=1.83, 7.02, 8.62 Hz, 1H), 6.85 (d, J=8.56 Hz, 1H), 6.70 (dd, J=5.03, 6.87 Hz, 1H), 4.18-4.26 (m, 1H), 3.68 (s, 4H), 3.62 (s, 3H), 2.55-2.64 (m, 4H), 1.98-2.08 (m, 6H), 1.92-1.94 (m, 2H), 1.86-1.90 (m, 1H), 1.75-1.84 (m, 2H), 1.48-1.56 (m, 2H), 1.30 (s, 6H); MS(ESI+) m/z 441 (M+H)$^+$.

EXAMPLE 89

(E)-4-[2-Methyl-2-(4-pyridin-2-ylpiperazin-1-yl) propanoyl]amino adamantane-1-carboxylic acid The title compound was prepared according to the procedure outlined in Example 34C substituting 1-pyridin-2-yl-piperazine for 1-(5-chloro-2-pyridyl)piperazine. $^1$H NMR (500 MHz, Py-d$_5$) δ 14.49-15.26 (bs, 1H), 8.39-8.46 (m, 1H), 7.91 (d, J=8.10 Hz, 1H), 7.53-7.57 (m, 1H), 6.85 (d, J=8.54 Hz, 1H), 6.70 (t, J=5.96 Hz, 1H), 4.27-4.35 (m, 1H), 3.63-3.76 (m, 4H), 2.57-2.65 (m, 4H), 2.26-2.33 (m, 2H), 2.20-2.26 (m, 2H), 2.15-2.17 (m, 2H), 2.09-2.12 (m, 2H), 1.94-1.96 (m, 1H), 1.81-1.90 (m, 2H), 1.56-1.65 (m, 2H), 1.31 (s, 6H); MS(ESI+) m/z 427 (M+H)$^+$.

EXAMPLE 90

(E)-4-({2-Methyl-2-[(2S)-2-methyl-4-pyridin-2-ylpiperazin-1-yl]propanoyl}amino)adamantane-1-carboxylic acid The title compound was prepared according to the procedure outlined in Example 34C substituting (3S)-3-methyl-1-pyridin-2-yl-piperazine for 1-(5-chloro-2-pyridyl)piperazine. $^1$H NMR (500 MHz, Py-d$_5$) δ 8.37-8.43 (m, 1H), 8.13-8.23 (m, 1H), 7.53 (ddd, J=1.87, 6.94, 8.67 Hz, 1H), 6.84 (d, J=8.58 Hz, 1H), 6.68 (dd, J=4.94, 7.12 Hz, 1H), 4.25-4.30 (m, 1H), 4.19-4.23 (m, 1H), 4.05-4.12 (m, 1H), 3.31-3.42 (m, 2H), 3.17-3.27 (m, 1H), 2.96-3.07 (m, 1H), 2.40-2.52 (m, 1H), 2.20-2.31 (m, 4H), 2.08-2.17 (m, 4H), 1.93-1.98 (m, 1H), 1.86-1.93 (m, 2H), 1.57-1.63 (m, 2H), 1.42 (s, 6H), 1.16 (d, J=6.24 Hz, 3H); MS(ESI+) m/z 441 (M+H)$^+$.

EXAMPLE 91

(E)-4-{[2-Methyl-2-(4-pyridin-2-ylpiperazin-1-yl) propanoyl]amino}adamantane-1-carboxamide The title compound was prepared according to the method of Example 23 substituting (E)-4-[2-methyl-2-(4-pyridin-2-yl-piperazin-1-yl)-propionylamino]-adamantane-1-carboxylic acid for (E)-4-{2-methyl-2-[4-(5-trifluoromethyl-pyridin-2-yl)-piperazin-1-yl]-propionylamino}-adamantane-1-carboxylic acid. $^1$H NMR (500 MHz, Py-d$_5$) δ 8.41-8.44 (m, 1H), 7.90 (d, J=8.14 Hz, 1H), 7.68-7.70 (bs, 1H), 7.61-7.63 (bs, 1H), 7.55 (ddd, J=1.81, 6.98, 8.62 Hz, 1H), 6.85 (d, J=8.53 Hz, 1H), 6.70 (dd, J=4.83, 7.08 Hz, 1H), 4.25-4.34 (m, 1H), 3.67-3.70 (m, 4H), 2.55-2.63 (m, 4H), 2.21-2.31 (m, 4H), 2.15 (s, 2H), 2.07-2.12 (m, 2H), 1.95 (s, 1H), 1.79-1.88 (m, 2H), 1.54-1.63 (m, 2H), 1.30 (s, 6H); MS(ESI+) m/z 426 (M+H)$^+$.

EXAMPLE 92

2-Methyl-N-[(E)-5-(4H-1,2,4-triazol-3-yl)-2-adamantyl]-2-{4-[5-(trifluoromethyl)pyridin-2-yl]piperazin-1-yl}propanamide A solution of (E)-4-{2-methyl-2-[4-(5-trifluoromethyl-pyridin-2-yl)-piperazin-1-yl]-propionylamino}-adamantane-1-carboxamide (28 mg, 0.06 mmoles) from Example 23 in DMF-DMA (1 mL, 1/1 mixture) was heated at 100° C. for 3 hours. The mixture was cooled and concentrated under reduced pressure. The residue was heated in acetic acid (2 mL) to 90° C. and treated with 9 µL of hydrazine. The mixture was cooled and the solvent was removed under reduced pressure. The residue was partitioned between water and ethyl acetate. The aqueous layer was extracted twice with ethyl acetate. The combined organic extracts were washed with water, dried (MgSO$_4$) and filtered. The filtrate was concentrated under reduced pressure to provide an off-white solid that was purified by reverse phase HPLC to provide the title compound. $^1$H NMR (500 MHz, Py-d$_5$) δ 8.67-8.68 (m, 1H), 8.46 (s, 1H), 7.89 (d, J=8.11 Hz, 1H), 7.79 (dd, J=2.57, 9.12 Hz, 1H), 6.87 (d, J=9.00 Hz, 1H), 4.36-4.42 (m, 1H), 3.70-3.81 (m, 4H), 2.55-2.64 (m, 4H), 2.37-2.49 (m, 4H), 2.31-2.32 (m, 2H), 2.16-2.23 (m, 2H), 2.00-2.07 (m, 1H), 1.88-1.97 (m, 2H), 1.65-1.74 (m, 2H), 1.32 (s, 6H); MS(APCI+) m/z 518 (M+H)$^+$.

EXAMPLE 93

(E)-4-{[2-(3,3-Difluoropiperidin-1-yl)-2-methylpropanoyl]amino}-N-(pyridin-4-ylmethyl)adamantane-1-carboxamide A solution of Example 43A (35.0 mg, 0.09 mmoles) in DMF (5 mL) was treated with TBTU (O-(benzotriazol-1-yl)-1,1,3,3-tetramethyluronium tetrafluoroborate) (43.3 mg, 0.135 mmoles), 4-(aminomethyl)pyridine (12.1 mg, 0.108 mmoles) and DIEA (ethyl-diisopropyl-amine) (0.033 mL, 0.18 mmoles). The mixture was stirred at room temperature for 12 hours. The mixture was concentrated under reduced pressure. The residue was purified by reverse phase HPLC to provide the title compound. $^1$H NMR (300 MHz, DMSO-d$_6$) δ 8.76 (d, J=6.44 Hz, 2H) 8.33 (t, J=5.93 Hz, 1H) 7.71 (d, J=6.44 Hz, 2H) 7.61 (d, J=7.80 Hz, 1H) 4.45 (d, J=5.76 Hz, 2H) 3.80 (d, J=7.80 Hz, 1H) 2.73 (m, 2H) 1.88-1.98 (m, 10H) 1.84 (m, 2H) 1.66-1.78 (m, 5H) 1.50-1.61 (m, 2H) 1.15 (s, 6H); MS(ESI+) m/z 464 (M+H)$^+$.

EXAMPLE 94

(E)-4-[(2-Methyl-2-{4-[4-(trifluoromethyl)phenyl] piperazin-1-yl}propanoyl)amino]adamantane-1-carboxylic acid The title compound was prepared according to the procedure outlined in Example 34C substituting 1-(4-trifluoromethyl-phenyl)-piperazine for 1-(5-chloro-2-pyridyl)piperazine. $^1$H NMR (400 MHz, Py-d$_5$) δ 7.85 (d, J=7.98 Hz, 1H), 7.66 (d, J=8.51 Hz, 2H), 7.11 (d, J=8.44 Hz, 2H), 4.27-4.37 (m, 1H), 3.31-3.38 (m, 4H), 2.59-2.68 (m, 4H), 2.19-2.35 (m, 4H), 2.09-2.19 (m, 4H), 1.94-1.99 (m, 1H), 1.84-1.90 (m, 2H), 1.59-1.66 (m, 2H), 1.34 (s, 6H); MS(ESI+) m/z 494 (M+H)$^+$.

EXAMPLE 95

(E)-4-({2-Methyl-2-[(2R)-2-methyl-4-(5-methylpyridin-2-yl)piperazin-1-yl]propanoyl}amino)adamantane-1-carboxylic acid

EXAMPLE 95A (3R)-3-Methyl-1-(5-methylpyridin-2-yl)piperazine

A solution of 2-chloro-5-methyl-pyridine (127 mg, 1 mmoles), (2R)-2-methyl-piperazine (200 mg, 2 mmoles) in EtOH (3 mL) was heated in microwave to 180° C. for 5 minutes. The mixture was cooled, concentrated under reduced pressure and partitioned with DCM and the saturated aqueous sodium bicarbonate layer. The aqueous solution was extracted three times with additional DCM. The combined organic extracts were washed twice with water, dried (MgSO$_4$) and filtered. The filtrate was concentrated under reduced pressure to provide the crude title compound.

EXAMPLE 95B (E)-4-({2-Methyl-2-[(2R)-2-methyl-4-(5-methylpyridin-2-yl)piperazin-1-yl]propanoyl}amino)adamantane-1-carboxylic acid The title compound was prepared according to the procedure outlined in Example 34C substituting (3R)-3-methyl-1-(5-methylpyridin-2-yl)piperazine from Example 95A for 1-(5-chloro-2-pyridyl)piperazine. $^1$H NMR (400 MHz, Py-d$_5$) δ 8.27 (s, 1H), 8.2 (d, J=7.3 Hz, 1H), 7.37 (d, J=9.7 Hz, 1H), 6.83 (d, J=8.5 Hz, 1H), 4.28 (d, J=4.6 Hz, 1H), 4.18 (d, J=7.3 Hz, 1H), 4.03 (d, J=6.7 Hz, 1H), 3.18 (t, J=10.1 Hz, 1H), 2.45 (d, J=11.6 Hz, 1H), 2.26 (m, 4H), 2.14 (s, 3H), 2.12 (m, 5H), 1.94 (s, 1H), 1.87 (d, J=12.5 Hz, 2H), 1.60 (m, 4H), 1.43 (s, 6H), 1.18 (d, J=6.4 Hz, 3H); MS(ESI+) m/z 455 (M+H)$^+$.

EXAMPLE 96

(E)-4-({2-[(3S)-3-Fluoropiperidin-1-yl]propanoyl}amino)adamantane-1-carboxamide

A solution of (E)-4-(2-bromo-propionylamino)-adamantane-1-carboxamide (33 mg, 0.1 mmoles) from Example 31B and the hydrochloride of (3S)-3-fluoropiperidine (12 mg, 0.12 mmoles) in MeOH (0.5 mL) and DIPEA (0.1 mL) was stirred overnight at 70° C. The McOH was removed under reduced pressure and the residue purified on reverse phase HPLC to provide the title compound. $^1$H NMR (500 MHz, CDCl$_3$) δ 7.96 (d, J=6.6 Hz, 1H), 5.54-5.34 (m, 2H), 4.68-4.78 (m, 1H), 4.00 (d, J=7.8 Hz, 1H), 3.2 (q, J=7.2 Hz, 1H), 2.8 (m, 1H), 2.53-2.59 (m, 3H), 1.55-2.07 (m, 17H), 1.22 (d, J=7.2 Hz, 3H); MS(ESI+) m/z 352 (M+H)$^+$.

EXAMPLE 97

(E)-4-[((2S)-2-{4-[5-(Trifluoromethyl)pyridin-2-yl]piperazin-1-yl}propanoyl)amino]adamantane-1-carboxamide

EXAMPLE 97A (2S)-2-{4-[5-(Trifluoromethyl)pyridin-2-yl]piperazin-1-yl}propanoic acid A solution of 1-(5-trifluoromethyl-pyridin-2-yl)-piperazine (2.77 g, 11.99 mmoles) in DCM (42 mL) and TEA (4.2 mL) was treated with (2R)-2-bromo-propionic acid (1.19 mL, 13.2 mmoles) and stirred overnight at 35° C. The DCM was removed under reduced pressure to provide crude title compound as a yellowish solid that was used in the next step. MS(APCI+) m/z 304 (M+H)$^+$.

EXAMPLE 97B

Methyl (E)-4-[((2S)-2-{4-[5-(trifluoromethyl)pyridin-2-yl]piperazin-1-yl}propanoyl)amino]adamantane-1-carboxylate The title compound was prepared according to the method of Example 15C substituting (2S)-2-{4-[5-(trifluoromethyl)pyridin-2-yl]piperazin-1-yl}propanoic acid for 2-methyl-2-[4-(5-trifluoromethyl-pyridin-2-yl)-piperazin-1-yl]-propionic acid. MS(APCI+) m/z 495 (M+H)$^+$.

EXAMPLE 97C (E)-4-[((2S)-2-{4-[5-(Trifluoromethyl)pyridin-2-yl]piperazin-1-yl}propanoyl)amino]adamantane-1-carboxylic acid The title compound was prepared according to the method of Example 15D substituting methyl (E)-4-[((2S)-2-{4-[5-(trifluoromethyl)pyridin-2-yl]piperazin-1-yl}propanoyl)amino]adamantane-1-carboxylate for methyl (E)-4-{2-methyl-2-[4-(5-trifluoromethyl-pyridin-2-yl)-piperazin-1-yl]-propionylamino}-adamantane-1-carboxylate. MS(APCI+) m/z 481 (M+H)$^+$.

EXAMPLE 97D (E)-4-[((2S)-2-{4-[5-(Trifluoromethyl)pyridin-2-yl]piperazin-1-yl}propanoyl)amino]adamantane-1-carboxamide The title compound was prepared according to the method of Example 23 substituting (E)-4-[((2S)-2-{4-[5-(trifluoromethyl)pyridin-2-yl]piperazin-1-yl}propanoyl)amino]adamantane-1-carboxylic acid for (E)-4-{2-methyl-2-[4-(5-trifluoromethyl-pyridin-2-yl)-piperazin-1-yl]-propionylamino}-adamantane-1-carboxylic acid. $^1$H NMR (400 MHz, Py-d$_5$) δ 8.66 (s, 1H), 7.94 (d, J=7.88 Hz, 1H), 7.78 (dd, J=2.59, 9.02 Hz, 1H), 7.61-7.64 (bs, 1H), 7.58-7.61 (bs, 1H), 6.84 (d, J=8.96 Hz, 1H), 4.34-4.39 (m, 1H), 3.66-3.81 (m, 4H), 3.34 (q, J=6.96 Hz, 1H), 2.64-2.72 (m, 2H), 2.55-2.62 (m, 2H), 2.27-2.33 (m, 2H), 2.21-2.27 (m, 2H), 2.16-2.18 (m, 2H), 2.12-2.19 (m, 2H), 1.96-2.00 (m, 1H), 1.89-1.96 (m, 2H), 1.57-1.64 (m, 2H), 1.35 (d, J=7.06 Hz, 3H); MS(DCI+) m/z 480 (M+H)$^+$.

EXAMPLE 98

(E)-4-[((2R)-2-{4-[5-(Trifluoromethyl)pyridin-2-yl]piperazin-1-yl}propanoyl)amino]adamantane-1-carboxamide

EXAMPLE 98A (2R)-2-{4-[5-(Trifluoromethyl)pyridin-2-yl]piperazin-1-yl}propanoic acid A solution of 1-(5-trifluoromethyl-pyridin-2-yl)-piperazine (2.77 g, 11.99 mmoles) in DCM (42 mL) and TEA (4.2 mL) was treated with (2S)-2-bromo-propionic acid (1.19 mL, 13.2 mmoles) and stirred overnight at 35° C. The DCM was removed under reduced pressure to provide crude title compound.

EXAMPLE 98B

Methyl (E)-4-[((2R)-2-{4-[5-(trifluoromethyl)pyridin-2-yl]piperazin-1-yl}propanoyl)amino]adamantane-1-carboxylate The title compound was prepared according to the method of Example 15C substituting (2R)-2-{4-[5-(trifluoromethyl)pyridin-2-yl]piperazin-1-yl}propanoic acid for 2-methyl-2-[4-(5-trifluoromethyl-pyridin-2-yl)-piperazin-1-yl]-propionic acid. MS(APCI+) m/z 495 (M+H)$^+$.

EXAMPLE 98C (E)-4-[((2R)-2-{4-[5-(Trifluoromethyl)pyridin-2-yl]piperazin-1-yl}propanoyl)amino]adamantane-1-carboxylic acid The title compound was prepared according to the method of Example 15D substituting methyl (E)-4-[((2R)-2-{4-[5-(trifluoromethyl)pyridin-2-yl]piperazin-1-yl}propanoyl)amino]adamantane-1-carboxylate for methyl (E)-4-{2-methyl-2-[4-(5-trifluoromethyl-pyridin-2-yl)-piperazin-1-yl]-propionylamino}-adamantane-1-carboxylate. MS(APCI+) m/z 481 (M+H)$^+$.

EXAMPLE 98D (E)-4-[((2R)-2-{4-[5-(Trifluoromethyl)pyridin-2-yl]piperazin-1-yl}propanoyl)amino]adamantane-1-carboxamide The title compound was prepared according to the method of Example 23 substituting (E)-4-[((2R)-2-{4-[5-(trifluoromethyl)pyridin-2-yl]piperazin-1yl}propanoyl)amino]adamantane-1-carboxylic acid for (E)-4-{2-methyl-2-[4-(5-trifluoromethyl-pyridin-2-yl)-piperazin-1-yl]-propionylamino}-adamantane-1-carboxylic acid. $^1$H NMR (400 MHz, Py-d$_5$) δ 8.63-8.65 (m, 1H), 7.93 (d, J=7.94 Hz, 1H), 7.76 (dd, J=2.59, 9.04 Hz, 1H), 7.58-7.66 (m, 2H), 6.83 (d, J=9.03 Hz, 1H), 4.32-4.37 (m, 1H), 3.64-3.79 (m, 4H), 3.32 (q, J=6.94 Hz, 1H), 2.61-2.74 (m, 2H), 2.50-2.61 (m, 2H), 2.18-2.35 (m, 4H), 2.08-2.18 (m, 4H), 1.94-1.98 (m, 1H), 1.87-1.94 (m, 2H), 1.53-1.65 (m, 2H), 1.33 (d, J=6.95 Hz, 3H); MS(DCI+) m/z 480 (M+H)$^+$.

EXAMPLE 99

(E)-4-[({2-(Trifluoromethyl)-4-[5-(trifluoromethyl)pyridin-2-yl]piperazin-1-yl}acetyl)amino]adamantane-1-carboxamide

EXAMPLE 99A

1-Benzyl-3-(trifluoromethyl)piperazine

The title compound was prepared according to the method described in the following reference, Jenneskens, Leonardus W.; Mahy, Jan; Berg, Ellen M. M. de Brabander-van.; Hoef, Ineke van der; Lugtenburg, Johan; Recl. Tray. Chim. Pays-Bas; 114; 3; 1995; 97-102. Purification by reverse phase HPLC afforded the trifluoroacetic acid salt of the title compound. MS(DCI+) m/z 245 (M+H)$^+$.

EXAMPLE 99B

Methyl (E)-4-({[4-benzyl-2-(trifluoromethyl)piperazin-1-yl]acetyl}amino adamantane-1-carboxylate A solution of the trifluoroacetic acid salt of 1-benzyl-3-(trifluoromethyl)piperazine from Example 99A (100 mg), methyl (E)-4-(2-chloro-acetylamino)-adamantane-1-carboxylate from Example 25B (55 mg, 0.19 mmoles), and methanol (1.5 mL) was treated with DIEA (100 pt), and the reaction mixture warmed to 80 C for 24 h. The reaction mixture was concentrated under reduced pressure and purified by reverse phase HPLC to afford the title compound. MS(APCI+) m/z 494 (M+H)$^+$.

EXAMPLE 99C

Methyl (E)-4-({[2-(trifluoromethyl)piperazin-1-yl]acetyl}amino)adamantane-1-carboxylate To a solution of methyl (E)-4-({[4-benzyl-2-(trifluoromethyl)piperazin-1-yl]acetyl}amino)adamantane-1-carboxylate from Example 99B (50 mg, 0.10 mmoles), cyclohexene (1 mL), and methanol (1 mL) was added 10% Pd/C (30 mg), and the reaction mixture heated to 70 C for 16 h. The reaction mixture was cooled to 23 C, additional cyclohexene (1 mL) and 10% Pd/C (30 mg) was added, and the reaction mixture heated to 80 C for 2 h. The reaction mixture was cooled to 23 C and filtered through Celite. The filtrate was concentrated under reduced pressure to afford the title compound that was carried on crude. See also reference in 99A. MS(APCI+) m/z 404 (M+H)$^+$.

EXAMPLE 99D

Methyl (E)-4-[({2-(trifluoromethyl)-4-[5-(trifluoromethyl)pyridin-2-yl]piperazin-1-yl}acetyl)amino]adamantane-1-carboxylate Solid methyl (E)-4-({[2-(trifluoromethyl)piperazin-1-yl]acetyl}amino)adamantane-1-carboxylate from Example 99C (20 mg, 0.05 mmoles) and solid 2-bromo-5-trifluoromethyl-pyridine (160 mg, 0.71 mmoles) were combined in a small vial with a stirring bar. The vial was gently warmed until the two solids melted between 45-50 C, and then the temperature was raised to 120 C for 14 h. The reaction mixture was cooled to 23 C, and the residue was purified using radial chromatography (0-100% acetone/hexanes) to afford the title compound. MS(APCI+) m/z 549 (M+H)+.

EXAMPLE 99E (E)-4-[({2-(Trifluoromethyl)-4-[5-(trifluoromethyl)pyridin-2-yl]piperazin-1-yl}acetyl)amino]adamantane-1-carboxylic acid A slightly heterogeneous solution of methyl (E)-4-[({2-(trifluoromethyl)-4-[5-(trifluoromethyl)pyridin-2-yl]piperazin-1-yl}acetyl)amino]adamantane-1-carboxylate from Example 99D (14 mg), dioxane (0.1 mL), and 3N HCl (0.75 mL) was warmed to 50 C for 20 h. The reaction mixture was cooled and concentrated under reduced pressure to afford the title compound as the hydrochloride salt. MS(DCI+) m/z 535 (M+H)+.

EXAMPLE 99F (E)-4-[({2-(Trifluoromethyl)-4-[5-(trifluoromethyl)pyridin-2-yl]piperazin-1-yl}acetyl)amino]adamantane-1-carboxamide The hydrochloride salt of (E)-4-[({2-(trifluoromethyl)-4-[5-(trifluoromethyl)pyridin-2-yl]piperazin-1-yl}acetyl)amino]adamantane-1-carboxylic acid from Example 99E (12 mg, 0.023 mmoles), EDCI (5.7 mg, 0.030 mmoles), HOBt (33 mg, 0.025 mmoles), methylene chloride (1.7 mL), 1,4-dioxane (50 µL) and triethylamine (50 µL) were combined and stirred at 23 C for 1 h. Aqueous NH$_4$OH (1 mL, 30%) was added, and the reaction mixture stirred another 16 hours. The layers were separated and the aqueous phase extracted additionally with methylene chloride (2×). The combined methylene chloride extracts were dried (Na$_2$SO$_4$), filtered, and concentrated under reduced pressure. The residue was purified using radial chromatography (80% acetone/hexanes) to afford the title compound. $^1$H NMR (400 MHz, Py-d$_5$) δ 8.63 (s, 1H), 8.01 (d, J=7.36 Hz, 1H), 7.77 (d, J=6.75 Hz, 2H), 7.68 (s, 1H), 6.75 (d, J=9.21 Hz, 1H), 4.79 (d, J=11.35 Hz, 1H), 4.42 (d, J=7.36 Hz, 1H), 3.98-4.11 (m, 2H), 3.79-3.92 (m, 2H), 3.70-3.79 (m, 1H), 3.47-3.57 (m, 1H), 3.24-3.35 (m, 1H), 3.09-3.21 (m, 1H), 2.30-2.39 (m, 2H), 2.12-2.30 (m, 6H), 1.90-2.03 (m, 3H), 1.58 (m, 2H); MS(DCI+) m/z 480 (M+H)+.

EXAMPLE 100

(E)-4-[(Cyclopropyl{4-[5-(trifluoromethyl)pyridin-2-yl]piperazin-1-yl}acetyl)amino]adamantane-1-carboxylic acid The title compound was prepared according to the methods of Examples 18C-D substituting cyclopropanecarboxaldehyde for propionaldehyde. $^1$H NMR (500 MHz, DMSO-d$_6$) δ 8.39 (bs, 1H), 7.78 (dd, J=2.5, 9 Hz, 1H), 7.49 (d, J=9.5 Hz, 1H), 6.97 (s, 1H), 3.78 (m, 1H), 3.62 (m, 4H), 2.79 (m, 2H), 2.55 (m, 2H), 2.21 (d, J=9.5 Hz, 1H), 1.90-1.65 (m, 11H), 1.42 (m, 2H), 0.99 (m, 1H), 0.60 (m, 1H), 0.42 (m, 1H), 0.27 (m, 2H); MS(ESI) m/z 507 (M+H)+.

EXAMPLE 101

(E)-4-{[(1-{4-[5-(Trifluoromethyl)pyridin-2-yl]piperazin-1-yl}cyclobutyl)carbonyl]amino}adamantane-1-carboxylic acid The title compound was prepared according to the methods of Examples 18C-D substituting cyclobutanone for propionaldehyde. $^1$H NMR (500 MHz, DMSO-d$_6$) δ 8.41 (bs, 1H), 7.79 (dd, J=2.5, 9 Hz, 1H), 7.36 (d, J=9.5 Hz, 1H), 6.97 (d, J=9.5 Hz, 1H), 3.78 (m, 1H), 3.65 (m, 4H), 2.53 (m, 4H), 2.22 (m, 2H), 2.12 (m, 2H), 1.90-1.60 (m, 13H), 1.43 (m, 2H); MS(ESI) m/z 507 (M+H)+.

EXAMPLE 102

(E)-4-({2-[9-(6-Chloropyridin-3-yl)-3,9-diazabicyclo[4.2.1]non-3-yl]-2-methylpropanoyl}amino)adamantane-1-carboxamide

EXAMPLE 102A (E)-4-({2-[9-(6-Chloropyridin-3-yl)-3,9-diazabicyclo[4.2.1]non-3-yl]-2-methylpropanoyl}amino)adamantane-1-carboxylic acid The title compound was prepared according to the method of Example 34C substituting 9-(6-chloropyridin-3-yl)-3,9-diazabicyclo[4.2.1]nonane for 1-(5-chloro-2-pyridyl)piperazine. MS(ESI+) m/z 501 (M+H)+.

EXAMPLE 102B (E)-4-({2-[9-(6-Chloropyridin-3-yl)-3,9-diazabicyclo[4.2.1]non-3-yl]-2-methylpropanoyl}amino)adamantane-1-carboxamide The title compound was prepared according to the method of Example 23 substituting (E)-4-({2-[9-(6-chloropyridin-3-yl)-3,9-diazabicyclo[4.2.1]non-3-yl]-2-methylpropanoyl}amino)adamantane-1-carboxylic acid from Example 102A for (E)-4-{2-methyl-2-[4-(5-trifluoromethyl-pyridin-2-yl)-piperazin-1-yl]-propionylamino}-adamantane-1-carboxylic acid. $^1$H NMR (400 MHz, CDCl$_3$) δ 7.78 (s, 1H), 7.10 (d, J=8.6 Hz, 1H), 7.02 (d, 1H), 6.98 (m, 1H), 5.54-5.19 (d, 2H), 4.33 (m, 2H), 3.95 (d, J=8.1 Hz, 1H), 2.99 (m, 1H), 1.88-2.58 (m, 18H), 1.13-1.21 (d, 6H) 6 MS(ESI+) m/z 500 (M+H)+.

EXAMPLE 103

(E)-4-({2-[4-(2,3-Dichlorophenyl)piperazin-1-yl]-2-methylpropanoyl}amino)adamantane-1-carboxylic acid The title compound was prepared according to the method of Example 34C substituting 1-(2,3-dichloro-phenyl)-piperazine for 1-(5-chloro-2-pyridyl)piperazine. $^1$H NMR (500 MHz, Py-d$_5$) δ 7.89 (d, J=8.09 Hz, 1H), 7.28 (dd, J=1.43, 7.96 Hz, 1H), 7.21 (d, J=6.71 Hz, 1H), 7.07 (dd, J=1.48, 8.04 Hz, 1H), 4.29-4.37 (m, 1H), 3.05-3.18 (m, 4H), 2.70-2.72 (m, 4H), 2.21-2.35 (m, 4H), 2.11-2.19 (m, 4H), 1.95-2.01 (m, 1H), 1.85-1.93 (m, 2H), 1.60-1.69 (m, 2H), 1.36 (s, 6H); MS(ESI) m/z 494 (M+H)+.

EXAMPLE 104

(E)-4-{[2-Methyl-2-(4-phenylpiperazin-1-yl)propanoyl]amino}adamantane-1-carboxylic acid The title compound was prepared according to the method of Example 34C substituting 1-phenyl-piperazine for 1-(5-chloro-2-pyridyl)piperazine. $^1$H NMR (500 MHz, Py-d$_5$) δ 7.89 (d, J=8.11 Hz, 1H), 7.36-7.42 (m, 2H), 7.10-7.14 (m, 2H), 6.95-6.99 (m, 1H), 4.30-4.38 (m, 1H), 3.23-3.30 (m, 4H), 2.61-2.66 (m, 4H), 2.30-2.41 (m, 4H), 2.23-2.27 (m, 2H), 2.09-2.15 (m, 2H), 1.91-1.98 (m, 1H), 1.83-1.87 (m, 2H), 1.58-1.66 (m, 2H), 1.32 (s, 6H); MS(ESI) m/z 426 (M+H)$^+$.

EXAMPLE 105

(E)-4-({2-Methyl-2-[4-(4-methylphenyl)piperazin-1-yl]propanoyl}amino adamantane-1-carboxylic acid The title compound was prepared according to the method of Example 34C substituting 1-p-tolyl-piperazine for 1-(5-chloro-2-pyridyl)piperazine. $^1$H NMR (500 MHz, Py-d$_5$) δ 7.91 (d, J=8.12 Hz, 1H), 7.20 (d, J=8.55 Hz, 2H), 7.06 (d, J=8.09 Hz, 2H), 4.27-4.36 (m, 1H), 3.22-3.29 (m, 4H), 2.63-2.71 (m, 4H), 2.20-2.34 (m, 7H), 2.15-2.16 (m, 2H), 2.09-2.14 (m, 2H), 1.90-1.95 (m, 1H), 1.81-1.89 (m, 2H), 1.56-1.63 (m, 2H), 1.34 (s, 6H); MS(ESI) m/z 440 (M+H)$^+$.

EXAMPLE 106

(E)-4-({2-[4-(1,3-Benzothiazol-2-yl)piperazin-1-yl]-2-methylpropanoyl}amino)adamantane-1-carboxylic acid The title compound was prepared according to the method of Example 34C substituting 2-piperazin-1-yl-benzothiazole for 1-(5-chloro-2-pyridyl)piperazine. $^1$H NMR (500 MHz, Py-d$_5$) δ 7.88 (d, J=7.96 Hz, 1H), 7.83 (d, J=7.76 Hz, 1H), 7.78 (d, J=8.02 Hz, 1H), 7.42 (t, J=7.53 Hz, 1H), 7.19 (t, J=7.46 Hz, 1H), 4.27-4.35 (m, 1H), 3.69-3.76 (m, 4H), 2.54-2.61 (m, 4H), 2.20-2.34 (m, 4H), 2.14-2.19 (m, 2H), 2.10-2.12 (m, 2H), 1.96-2.00 (m, 1H), 1.80-1.90 (m, 2H), 1.58-1.67 (m, 2H), 1.31 (s, 6H); MS(ESI) m/z 483 (M+H)$^+$.

EXAMPLE 107

(E)-4-({2-[4-(3,4-Dichlorophenyl)piperazin-1-yl]-2-methylpropanoyl}amino)adamantane-1-carboxylic acid The title compound was prepared according to the method of Example 34C substituting 1-(3,4-dichloro-phenyl)-piperazine for 1-(5-chloro-2-pyridyl)piperazine. $^1$H NMR (500 MHz, Py-d$_5$) δ 7.85 (d, J=8.05 Hz, 1H), 7.43 (d, J=8.88 Hz, 1H), 7.24 (d, J=2.80 Hz, 1H), 6.94 (dd, J=2.87, 8.94 Hz, 1H), 4.28-4.37 (m, 1H), 3.21-3.30 (m, 4H), 2.61-2.68 (m, 4H), 2.20-2.34 (m, 4H), 2.16-2.17 (m, 2H), 2.10-2.15 (m, 2H), 1.93-1.98 (m, 1H), 1.83-1.92 (m, 2H), 1.58-1.67 (m, 2H), 1.34 (s, 6H); MS(ESI) m/z 494 (M+H)$^+$.

EXAMPLE 108

(E)-4-({2-Methyl-2-[4-(3-methylphenyl)piperazin-1-yl]propanoyl}amino adamantane-1-carboxylic acid The title compound was prepared according to the method of Example 34C substituting 1-m-tolyl-piperazine for 1-(5-chloro-2-pyridyl)piperazine. $^1$H NMR (500 MHz, Py-d$_5$) δ 7.92 (d, J=8.09 Hz, 1H), 7.31 (t, J=7.73 Hz, 1H), 6.92-7.02 (m, 2H), 6.80 (d, J=7.35 Hz, 1H), 4.28-4.36 (m, 1H), 3.28-3.31 (m, 4H), 2.64-2.72 (m, 4H), 2.32 (s, 3H), 2.26-2.31 (m, 2H), 2.20-2.26 (m, 2H), 2.09-2.18 (m, 4H), 1.91-1.95 (m, 1H), 1.81-1.89 (m, 2H), 1.56-1.63 (m, 2H), 1.34 (s, 6H); MS(ESI) m/z 440 (M+H)$^+$.

EXAMPLE 109

(E)-4-[(2-Methyl-2-{4-[2-(trifluoromethyl)phenyl]piperazin-1-yl}propanoyl)amino]adamantane-1-carboxylic acid The title compound was prepared according to the method of Example 34C substituting 1-(2-trifluoromethyl-phenyl)-piperazine for 1-(5-chloro-2-pyridyl)piperazine. $^1$H NMR (500 MHz, Py-d$_5$) δ 7.94 (d, J=8.06 Hz, 1H), 7.74 (d, J=7.67 Hz, 1H), 7.58-7.60 (m, 1H), 7.55 (t, J=8.77 Hz, 1H), 7.28 (t, J=7.40 Hz, 1H), 4.28-4.37 (m, 1H), 3.01-3.08 (m, 4H), 2.66-2.73 (m, 4H), 2.28-2.35 (m, 2H), 2.23-2.26 (m, 2H), 2.16-2.20 (m, 2H), 2.13-2.15 (m, 2H), 1.97-1.99 (m, 1H), 1.88-1.95 (m, 2H), 1.60-1.69 (m, 2H), 1.34 (s, 6H); MS(ESI) m/z 494 (M+H)$^+$.

EXAMPLE 110

(E)-4-({2-[4-(2,4-Difluorophenyl)piperazin-1-yl]-2-methylpropanoyl}amino)adamantane-1-carboxylic acid The title compound was prepared according to the method of Example 34C substituting 1-(2,4-difluoro-phenyl)-piperazine for 1-(5-chloro-2-pyridyl)piperazine. $^1$H NMR (500 MHz, Py-d$_5$) δ 7.89 (d, J=8.07 Hz, 1H), 7.14 (ddd, J=2.72, 8.65, 11.87 Hz, 1H), 7.05 (td, J=5.88, 9.23 Hz, 1H), 6.94-7.01 (m, 1H), 4.28-4.37 (m, 1H), 3.09-3.17 (m, 4H), 2.65-2.72 (m, 4H), 2.27-2.35 (m, 2H), 2.20-2.27 (m, 2H), 2.16-2.18 (m, 2H), 2.07-2.15 (m, 2H), 1.94-1.98 (m, 1H), 1.84-1.92 (m, 2H), 1.58-1.68 (m, 2H), 1.34 (s, 6H); MS(ESI) m/z 462 (M+H)$^+$.

EXAMPLE 111

(E)-4-({2-Methyl-2-[4-(6-methylpyridin-2-yl)piperazin-1-yl]propanoyl}amino)adamantane-1-carboxylic acid The title compound was prepared according to the method of Example 34C substituting 1-(6-methyl-pyridin-2-yl)-piperazine for 1-(5-chloro-2-pyridyl)piperazine. $^1$H NMR (500 MHz, Py-d$_5$) δ 7.93 (d, J=8.10 Hz, 1H), 7.47 (t, J=7.80 Hz, 1H), 6.68 (d, J=8.41 Hz, 1H), 6.59 (d, J=7.20 Hz, 1H), 4.27-4.36 (m, 1H), 3.70 (s, 4H), 2.58-2.66 (m, 4H), 2.48 (s, 3H), 2.26-2.34 (m, 2H), 2.20-2.26 (m, 2H), 2.13-2.19 (m, 3H), 2.09-2.12 (m, 2H), 1.91-1.97 (m, 1H), 1.81-1.88 (m, 2H), 1.55-1.64 (m, 2H), 1.31 (s, 6H); MS(ESI) m/z 441 (M+H)$^+$.

EXAMPLE 112

(E)-4-{[2-Methyl-2-(4-pyrimidin-2-ylpiperazin-1-yl)propanoyl]amino}adamantane-1-carboxylic acid The title compound was prepared according to the method of Example 34C substituting 2-piperazin-1-yl-pyrimidine for 1-(5-chloro-2-pyridyl)piperazine. $^1$H NMR (500 MHz, Py-d$_5$) δ 8.47 (d, J=4.68 Hz, 2H), 7.90 (d, J=8.17 Hz, 1H), 6.53 (t, J=4.68 Hz, 1H), 4.26-4.34 (m, 1H), 3.95-4.02 (m, 4H), 2.52-2.59 (m, 4H), 2.25-2.31 (m, 2H), 2.21-2.25 (m, 2H), 2.15-2.17 (m, 2H), 2.09-2.13 (m, 2H), 1.96-2.00 (m, 1H), 1.83-1.90 (m, 2H), 1.58-1.67 (m, 2H), 1.30 (s, 6H); MS(ESI) m/z 428 (M+H)$^+$.

EXAMPLE 113

(E)-4-({2-[4-(4-Fluorophenyl)piperazin-1-yl]-2-methylpropanoyl}amino)adamantane-1-carboxylic acid The title compound was prepared according to the method of Example 34C substituting 1-(4-fluoro-phenyl)-piperazine for 1-(5-chloro-2-pyridyl)piperazine. $^1$H NMR (500 MHz, Py-d$_5$) δ 7.88 (d, J=8.07 Hz, 1H), 7.14-7.19 (m, 2H), 7.02-7.08 (m, 2H), 4.27-4.35 (m, 1H), 3.17-3.24 (m, 4H), 2.62-2.71 (m, 4H), 2.26-2.33 (m, 2H), 2.21-2.25 (m, 2H), 2.14-2.18 (m, 2H), 2.10-2.14 (m, 2H), 1.91-1.97 (m, 1H), 1.83-1.89 (m, 2H), 1.56-1.65 (m, 2H), 1.34 (s, 6H); MS(ESI) m/z 444 (M+H)$^+$.

EXAMPLE 114

(E)-4-[(2-Methyl-2-{4-[3-(trifluoromethyl)phenyl]piperazin-1-yl}propanoyl)amino]adamantane-1-carboxylic acid The title compound was prepared according to the method of Example 34C substituting 1-(3-trifluoromethyl-phenyl)-piperazine for 1-(5-chloro-2-pyridyl)piperazine. $^1$H NMR (500 MHz, Py-d$_5$) δ 7.86 (d, J=8.06 Hz, 1H), 7.43 (t, J=8.01 Hz, 1H), 7.39-7.40 (m, 1H), 7.22-7.26 (m, 1H), 7.19-7.21 (m, 1H), 4.28-4.36 (m, 1H), 3.28-3.35 (m, 4H), 2.63-2.72 (m, 4H), 2.26-2.34 (m, 2H), 2.21-2.25 (m, 2H), 2.14-2.16 (m, 2H), 2.10-2.14 (m, 2H), 1.92-1.98 (m, 1H), 1.82-1.90 (m, 2H), 1.56-1.66 (m, 2H), 1.35 (s, 6H); MS(ESI) m/z 494 (M+H)$^+$.

EXAMPLE 115

(E)-4-[(2-Methyl-2-{4-[3-(trifluoromethyl)pyridin-2-yl]piperazin-1-yl}propanoyl)amino]adamantane-1-carboxylic acid The title compound was prepared according to the method of Example 34C substituting 1-(3-trifluoromethyl-pyridin-2-yl)-piperazine for 1-(5-chloro-2-pyridyl)piperazine. $^1$H NMR (500 MHz, Py-d$_5$) δ 8.54 (dd, J=1.25, 4.52 Hz, 1H), 7.96 (dd, J=1.84, 7.72 Hz, 1H), 7.91 (d, J=8.09 Hz, 1H), 7.02 (dd, J=4.76, 7.41 Hz, 1H), 4.25-4.35 (m, 1H), 3.47 (s, 4H), 2.68-2.74 (m, 4H), 2.25-2.33 (m, 2H), 2.20-2.23 (m, 2H), 2.14 (s, 2H), 2.08-2.13 (m, 2H), 1.92 (s, 1H), 1.83-1.90 (m, 2H), 1.55-1.61 (m, 2H), 1.34 (s, 6H); MS(ESI) m/z 495 (M+H)$^+$.

EXAMPLE 116

(E)-4-({2-[4-(3-Chlorophenyl)piperazin-1-yl]-2-methylpropanoyl}-amino)adamantane-1-carboxylic acid The title compound was prepared according to the method of Example 34C substituting 1-(3-chloro-phenyl)-piperazine for 1-(5-chloro-2-pyridyl)piperazine. $^1$H NMR (500 MHz, Py-d$_5$) δ 7.86 (d, J=8.06 Hz, 1H), 7.26 (t, J=8.06 Hz, 1H), 7.17 (t, J=2.15 Hz, 1H), 6.96 (dd, J=2.13, 8.05 Hz, 2H), 4.27-4.35 (m, 1H), 3.22-3.30 (m, 4H), 2.60-2.68 (m, 4H), 2.26-2.31 (m, 2H), 2.21-2.26 (m, 2H), 2.14-2.17 (m, 2H), 2.10-2.14 (m, 2H), 1.92-1.98 (m, 1H), 1.91 (s, 2H), 1.57-1.66 (m, 2H), 1.33 (s, 6H); MS(ESI) m/z 460 (M+H)$^+$.

EXAMPLE 117

(E)-4-({2-[4-(4-Acetylphenyl)piperazin-1-yl]-2-methylpropanoyl}amino)adamantane-1-carboxylic acid The title compound was prepared according to the method of Example 34C substituting 1-(4-piperazin-1-yl-phenyl)-ethanone for 1-(5-chloro-2-pyridyl)piperazine. $^1$H NMR (500 MHz, Py-d$_5$) δ 8.09-8.22 (m, 2H), 7.80-7.89 (m, 1H), 7.09 (d, J=8.90 Hz, 1H), 4.28-4.36 (m, 1H), 3.38-3.45 (m, 4H), 2.57-2.67 (m, 4H), 2.55 (s, 3H), 2.21-2.34 (m, 4H), 2.09-2.20 (m, 4H), 1.93-1.99 (m, 2H), 1.82-1.91 (m, 2H), 1.58-1.67 (m, 2H), 1.33 (s, 6H); MS(ESI) m/z 468 (M+H)$^+$.

EXAMPLE 118

(E)-N,N-Dimethyl-4-[(2-methyl-2-{4-[5-(trifluoromethyl)pyridin-2-yl]piperazin-1-yl}propanoyl)amino]adamantane-1-carboxamide From Example 15D (E)-4-{2-methyl-2-[4-(5-trifluoromethyl-pyridin-2-yl)-piperazin-1-yl]-propionylamino}-adamantane-1-carboxylic acid (0.04 mmoles) dissolved in DMA (0.7 mL) was mixed with TBTU (0.04 mmoles) dissolved in DMA (0.7 mL). Dimethylamine hydrochloride (0.05 mmoles) dissolved in DMA (0.3 mL) was added, followed by addition of DIEA (0.08 mmoles) dissolved in DMA (0.7 mL). The mixture was shaken at room temperature overnight. The solvent was stripped down and the crude mixture was purified using reverse phase HPLC. $^1$H NMR (500 MHz, Py-d$_5$) δ 8.68 (s, 1H), 7.88 (d, J=8.24 Hz, 1H), 7.80 (dd, J=2.29, 9.00 Hz, 1H), 6.89 (d, J=9.15 Hz, 1H), 4.26 (d, J=7.93 Hz, 1H), 3.76 (s, 4H), 2.95 (s, 6H), 2.59 (t, J=4.73 Hz, 4H), 2.19-2.26 (m, 2H), 2.07-2.19 (m, 6H), 1.97 (s, 1H), 1.81-1.91 (m, 2H), 1.61 (d, J=12.82 Hz, 2H), 1.32 (s, 6H); MS(ESI) m/z 522 (M+H)$^+$.

EXAMPLE 119

N-[(E)-5-(Acetylamino)-2-adamantyl]-2-{4-[5-(trifluoromethyl)pyridin-2-yl]piperazin-1-yl}propanamide The title compound was prepared according to the method of Example 10 substituting N-[(E)-5-hydroxy-2-adamantyl]-2-{4-[5-(trifluoromethyl)pyridin-2-yl]piperazin-1-yl}propanamide for N-[(E)-5-hydroxy-2-adamantyl]-2-{4-[5-(trifluoromethyl)pyridin-2-yl]piperazin-1-yl}acetamide. $^1$H NMR (300 MHz, DMSO-d$_6$) δ 8.40 (d, J=2.55 Hz, 1H), 7.78 (dd, J=2.61, 9.14 Hz, 1H), 7.69 (d, J=7.69 Hz, 1H), 7.35 (s, 1H), 6.95 (d, J=9.11 Hz, 1H), 3.74-3.88 (m, 1H), 3.55-3.70 (m, 4H), 3.25 (q, J=6.82 Hz, 1H), 2.49-2.69 (m, 4H), 1.86-2.00 (m, 9H), 1.77-1.85 (m, 2H), 1.74 (s, 3H), 1.36-1.52 (m, 2H), 1.11 (d, J=6.83 Hz, 3H); MS(APCI) m/z 494 (M+H)$^+$.

EXAMPLE 120

(E)-4-{[2-Methyl-2-(4-pyrimidin-2-ylpiperazin-1-yl)propanoyl]amino}adamantane-1-carboxamide The title compound was prepared according to the procedure outlined in Example 23 substituting (E)-4-[2-methyl-2-(4-pyrimidin-2-yl-piperazin-1-yl)-propionylamino]-adamantane-1-carboxylic acid for (E)-4-{2-methyl-2-[4-(5-trifluoromethyl-pyridin-2-yl)-piperazin-1-yl]-propionylamino}-adamantane-1-carboxylic acid. $^1$H NMR (500 MHz, Py-d$_5$) δ 7.35 (d, J=4.67 Hz, 2H), 6.81 (d, J=7.93

Hz, 1H), 6.57-6.61 (bs, 2H), 5.43 (t, J=4.68 Hz, 1H), 3.11-3.20 (m, 1H), 2.76-2.93 (m, 4H), 1.40-1.44 (m, 4H), 1.13-1.19 (m, 2H), 1.08-1.12 (m, 2H), 1.03 (d, J=−0.21 Hz, 2H), 0.93-0.99 (m, 2H), 0.81-0.86 (m, 1H), 0.68-0.76 (m, 2H), 0.43-0.49 (m, 2H), 0.17 (s, 6H); MS(ESI) m/z 427

EXAMPLE 121

(E)-4-{[2-Methyl-2-(4-pyrazin-2-ylpiperazin-1-yl)propanoyl]amino}adamantane-1-carboxamide

EXAMPLE 121A (E)-4-{[2-Methyl-2-(4-pyrazin-2-ylpiperazin-1-yl)propanoyl]amino}adamantane-1-carboxylic acid The title compound was prepared according to the method of Example 34C substituting 3,4,5,6-tetrahydro-2H-[1,2]bipyrazinyl for 1-(5-chloro-2-pyridyl)piperazine.

EXAMPLE 121B (E)-4-{[2-Methyl-2-(4-pyrazin-2-ylpiperazin-1-yl)propanoyl]amino}adamantane-1-carboxamide The title compound was prepared according to the procedure outlined in Example 23 substituting (E)-4-{[2-methyl-2-(4-pyrazin-2-ylpiperazin-1-yl)propanoyl]amino}adamantane-1-carboxylic acid from Example 121A for (E)-4-{2-methyl-2-[4-(5-trifluoromethyl-pyridin-2-yl)-piperazin-1-yl]-propionylamino}-adamantane-1-carboxylic acid. $^1$H NMR (500 MHz, Py-d$_5$) δ 8.51-8.51 (m, 1H), 8.22-8.23 (m, 1H), 8.06-8.07 (m, 1H), 7.86 (d, J=8.12 Hz, 1H), 7.69-7.72 (bs, 1H), 7.62-7.65 (bs, 1H), 4.26-4.35 (m, 1H), 3.67-3.71 (m, 4H), 2.56-2.61 (m, 4H), 2.27-2.32 (m, 2H), 2.22-2.27 (m, 2H), 2.16-2.18 (m, 2H), 2.10-2.13 (m, 2H), 2.01 (s, 1H), 1.81-1.91 (m, 3H), 1.56-1.65 (m, 2H), 1.31 (s, 6H); MS(ESI) m/z 427 (M+H)$^+$.

EXAMPLE 122

(E)-4-({2-[4-(4-Fluorophenyl)piperazin-1-yl]-2-methylpropanoyl}amino)adamantane-1-carboxamide The title compound was prepared according to the method of Example 23 substituting (E)-4-{2-[4-(4-fluoro-phenyl)-piperazin-1-yl]-2-methyl-propionylamino}-adamantane-1-carboxylic acid for (E)-4-{2-methyl-2-[4-(5-trifluoromethyl-pyridin-2-yl)-piperazin-1-yl]-propionylamino}-adamantane-1-carboxylic acid. $^1$H NMR (500 MHz, Py-d$_5$) δ 7.88 (d, J=8.11 Hz, 1H), 7.69-7.71 (bs, 1H), 7.62-7.66 (bs, 1H), 7.13-7.20 (m, 2H), 7.01-7.08 (m, 2H), 4.26-4.34 (m, 1H), 3.18-3.21 (m, 4H), 2.61-2.69 (m, 4H), 2.20-2.33 (m, 4H), 2.15-2.16 (m, 2H), 2.08-2.14 (m, 2H), 1.92-1.96 (m, 1H), 1.81-1.88 (m, 2H), 1.55-1.61 (m, 2H), 1.33 (s, 6H); MS(ESI) m/z 443 (M+H)$^+$.

EXAMPLE 123

(E)-4-({2-[4-(3-Cyanopyridin-2-yl)piperazin-1-yl]-2-methylpropanoyl}amino)adamantane-1-carboxamide

EXAMPLE 123A (E)-4-({2-[4-(3-Cyanopyridin-2-yl)piperazin-1-yl]-2-methylpropanoyl}amino)adamantane-1-carboxylic acid The title compound was prepared according to the method of Example 34C substituting 2-piperazin-1-yl-nicotinonitrile for 1-(5-chloro-2-pyridyl)piperazine.

EXAMPLE 123B (E)-4-({2-[4-(3-Cyanopyridin-2-yl)piperazin-1-yl]-2-methylpropanoyl}amino)adamantane-1-carboxamide The title compound was prepared according to the method of Example 23 substituting (E)-4-({2-[4-(3-cyanopyridin-2-yl)piperazin-1-yl]-2-methylpropanoyl}amino)adamantane-1-carboxylic acid from Example 123A for (E)-4-{2-methyl-2-[4-(5-trifluoromethyl-pyridin-2-yl)-piperazin-1-yl]-propionylamino}-adamantane-1-carboxylic acid. $^1$H NMR (500 MHz, Py-d$_5$) δ 8.44 (dd, J=1.83, 4.73 Hz, 1H), 7.92 (dd, J=1.94, 7.58 Hz, 1H), 7.84 (d, J=8.13 Hz, 1H), 7.69-7.72 (bs, 1H), 7.63-7.66 (bs, 1H), 6.78 (dd, J=4.75, 7.55 Hz, 1H), 4.25-4.33 (m, 1H), 3.82 (s, 4H), 2.60-2.72 (m, 4H), 2.26-2.33 (m, 2H), 2.21-2.26 (m, 2H), 2.15-2.17 (m, 2H), 2.08-2.11 (m, 2H), 1.95 (s, 1H), 1.79-1.87 (m, 2H), 1.54-1.63 (m, 2H), 1.30 (s, 6H); MS(ESI) m/z 451 (M+H)$^+$.

EXAMPLE 124

(E)-4-({2-Methyl-2-[4-(6-methylpyridin-3-yl)-1,4-diazepan-1-yl]propanoyl}amino)adamantane-1-carboxamide The title compound was prepared according to the method of Example 44C substituting 1-(6-methyl-pyridin-3-yl)-[1,4]diazepane for (3R)-3-fluoropyrrolidine. $^1$H NMR (400 MHz, Py-d$_5$) δ 8.03 (s, 1H), 7.38 (d, J=8 Hz, 1H), 7.03 (m, 2H), 3.95 (d, J=8.1 Hz, 1H), 3.56 (m, 4H), 2.82 (s, 2H), 2.57 (s, 2H), 2.48 (s, 3H), 1.98 (m, 8H), 1.89 (s, 5H), 1.65 (m, 2H), 1.29 (s, 6H); MS(ESI+) m/z 454 (M+H)$^+$.

EXAMPLE 125

(E)-4-[(2-{4-[3-Chloro-5-(trifluoromethyl)pyridin-2-yl]piperazin-1-yl}-2-methylpropanoyl)amino]adamantane-1-carboxylic acid The title compound was prepared according to the method of Example 34C substituting 1-(3-chloro-5-trifluoromethyl-pyridin-2-yl)-piperazine for 1-(5-chloro-2-pyridyl)piperazine. $^1$H NMR (400 MHz, Py-d$_5$) δ 8.57 (d, J=2.02 Hz, 1H), 8.05 (d, J=2.18 Hz, 1H), 7.88 (d, J=8.12 Hz, 1H), 4.27-4.38 (m, 1H), 3.61-3.70 (m, 4H), 2.65-2.76 (m, 4H), 2.20-2.36 (m, 4H), 2.14-2.18 (m, 2H), 2.09-2.14 (m, 2H), 1.93-2.00 (m, 1H), 1.85-1.91 (m, 2H), 1.58-1.66 (m, 2H), 1.36 (s, 6H).

EXAMPLE 126

4-(2-{[((E)-4-{[2-(3,3-Difluoropiperidin-1-yl)-2-methylpropanoyl]amino}-1-adamantyl)carbonyl]amino}ethyl)benzoic acid A solution of (E)-4-[2-(3,3-difluoro-piperidin-1-yl)-2-methyl-propionylamino]-adamantane-1-carboxylic acid from Example 43A (71.0 mg, 0.18 mmoles) in DMF (8 mL) was treated with TBTU (0-(benzotrialzol-1-yl)-1,1,3,3-tetramethyluronium tetrafluoroborate) (77 mg, 0.27 mmoles), 4-(2-amino-ethyl)-benzoic acid methyl ester (41.0 mg, 0.22 mmoles) and DIEA (ethyl-diisopropyl-amine) (0.066 mL, 0.36 mmoles). The mixture was stirred at room temperature for 12 hours. DCM (15 mL) and H$_2$O (5 mL) were added to the mixture, the layers were separated and the organic phase was dried over Na$_2$SO$_4$ and filtered. The filtrate was concentrated under reduced pressure. The residue was purified by reverse phase HPLC to provide a white powder with MS(ESI+) m/z 546. The white powder was dissolved in THF (2 mL) and H$_2$O (2 mL) and then LiOH (24 mg, 1 mmoles) was added. The mixture was stirred at room temperature for 12 hours. The mixture was neutralized (pH=6) with HCl (2.0 N). DCM (15 mL) and H$_2$O (5 mL) were added to the reaction mixture. The layers were separated and the organic phase was dried over Na$_2$SO$_4$ and filtered. The filtrate was concentrated under reduced pressure. The residue was purified by reverse phase HPLC to provide the title compound. $^1$H NMR (300 MHz, DMSO-d$_6$) δ 7.81-7.90 (m, 2H) 7.58 (d, J=7.80 Hz, 1H) 7.50 (t, J=5.59 Hz, 1H) 7.29 (d, J=8.48 Hz, 2H) 3.70-3.80 (m, 1H) 3.23-3.34 (m, 2H) 2.78 (t, J=7.12 Hz, 2H) 2.62-2.74 (m, 2H) 1.83-2.03 (m, 7H) 1.80 (s, 4H) 1.72 (d, J=2.37 Hz, 6H) 1.43-1.57 (m, 2H) 1.12 (s, 6H); MS(ESI+) m/z 532 (M+H)$^+$.

EXAMPLE 129

N-{(E)-5-[(Methylsulfonyl)amino]-2-adamantyl}-2-{4-[5-(trifluoromethyl)pyridin-2-yl]piperazin-1-yl}propanamide

EXAMPLE 129A

N-[(E)-5-Amino-2-adamantyl]-2-{4-[5-(trifluoromethyl)pyridin-2-yl]piperazin-1-yl}propanamide N-[(E)-5-(Acetylamino)-2-adamantyl]-2-{4-[5-(trifluoromethyl)pyridin-2-yl]piperazin-1-yl}propanamide from Example 119 (45 mg) was treated with 5N HCl at 100 C for 48 h. The mixture was cooled and concentrated in vacuo to afford the title compound as the dihydrochloride salt. MS(DCI+) m/z 452 (M+H)$^+$.

EXAMPLE 129B

N-{(E)-5-[(Methylsulfonyl)amino]-2-adamantyl}-2-{4-[5-(trifluoromethyl)pyridin-2-yl]piperazin-1-yl}propanamide A 0° C. solution of N-[(E)-5-amino-adamantan-2-yl]-2-[4-(5-trifluoromethyl-pyridin-2-yl)-piperazin-1-yl]-propionamide from Example 129A (13 mg, 0.029 mmoles) and DIEA (6 μL) in methylene chloride (1 mL) was treated with methane sulfonyl chloride (2.5 μL). After 5 minutes, the reaction was warmed to 23° C. for 16 hours. The mixture was filtered through a silica gel plug (0-100% acetone/hexanes) and the resultant solution concentrated under reduced pressure. The residue was purified by radial chromatography (0-100% acetone/hexanes) to afford the title compound. $^1$H NMR (400 MHz, Py-d$_5$) δ 8.66 (s, 1H), 8.26 (s, 1H), 7.91 (d, J=7.98 Hz, 1H), 7.78 (dd, J=2.03, 9.05 Hz, 1H), 6.84 (d, J=8.90 Hz, 1H), 4.33 (d, J=7.67 Hz, 1H), 3.66-3.82 (m, 4H), 3.34 (q, J=7.06 Hz, 1H), 3.14 (s, 3H), 2.64-2.73 (m, 2H), 2.54-2.64 (m, 2H), 2.16-2.35 (m, 8H), 2.05 (s, 1H), 1.88 (m, 2H), 1.57 (m, 2H), 1.35 (d, J=7.06 Hz, 3H); MS(DCI) m/z 530 (M+H)$^+$.

EXAMPLE 131

N-[(E)-5-(1-Hydroxy-1-methylethyl)-2-adamantyl]-2-methyl-2-{-4-[5-(trifluoromethyl)pyridin-2-yl]piperazin-1-yl}propanamide A solution of methyl 4-{2-methyl-2-[4-(5-trifluoromethyl-pyridin-2-yl)-piperazin-1-yl]-propionylamino}-adamantane-1-carboxylate from Example 15C (70 mg, 0.138 mmoles) and tetrahydrofuran (5 mL) cooled to –78° C. was treated with methyl lithium (0.26 mL, 1.6 M solution in ether). The mixture was slowly warmed to 23° C. and stirred for 16 hours. The mixture was quenched with saturated NH$_4$Cl solution, and the tetrahydrofuran was removed under reduced pressure. The aqueous solution was extracted with methylene chloride (3×), and the combined extracts concentrated under reduced pressure. The residue was purified by silica gel chromatography (0-100% acetone/hexanes) to afford the title compound. $^1$H NMR (400 MHz, Py-d$_5$) δ 8.67 (s, 1H), 7.88 (d, J=7.67 Hz, 1H), 7.79 (d, J=9.21 Hz, 1H), 6.87 (d, J=8.90 Hz, 1H), 4.26 (d, J=8.29 Hz, 1H), 3.76 (s, 4H), 2.59 (s, 4H), 2.08-2.17 (m, 2H), 1.81-2.04 (m, 10H), 1.60 (m, 2H), 1.33 (s, 6H), 1.29 (s, 6H); MS(DCI) m/z 509 (M+H)$^+$.

EXAMPLE 132

(E)-4-{[2-Methyl-2-(4-phenylpiperazin-1-yl)propanoyl]amino}adamantane-1-carboxamide The title compound was prepared according to the procedure outlined in Example 23 substituting (E)-4-[2-methyl-2-(4-phenyl-piperazin-1-yl)-propionylamino]-adamantane-1-carboxylic acid for (E)-4-{2-methyl-2-[4-(5-trifluoromethyl-pyridin-2-yl)-piperazin-1-yl]-propionylamino}-adamantane-1-carboxylic acid. $^1$H NMR (500 MHz, Py-d$_5$) δ 7.88 (d, J=8.11 Hz, 1H), 7.67-7.72 (m, 1H), 7.61-7.65 (m, 1H), 7.35-7.43 (m, 2H), 7.11 (d, J=8.07 Hz, 2H), 6.97 (t, J=7.22 Hz, 1H), 4.26-4.34 (m, 1H), 3.26 (s, 4H), 2.62-2.66 (m, 4H), 2.26-2.32 (m, 2H), 2.21-2.26 (m, 2H), 2.13-2.18 (m, 2H), 2.08-2.13 (m, 2H), 1.93 (s, 1H), 1.78-1.88 (m, 2H), 1.56-1.60 (m, 2H), 1.32 (s, 6H); MS(ESI) m/z 425 (M+H)$^+$.

EXAMPLE 133

(E)-4-({2-[4-(2-Methoxyphenyl)piperazin-1-yl]-2-methylpropanoyl}amino)adamantane-1-carboxamide The title compound was prepared according to the method of Example 44C substituting 1-(2-methoxy-phenyl)-piperazine for (3R)-3-fluoropyrrolidine. $^1$H NMR (300 MHz, Py-d$_5$) δ 7.96 (d, J=8.2 Hz, 1H), 6.98-7.12 (m, 4H), 4.32 (d, J=8.2 Hz, 1H), 3.82 (s, 3H), 3.22 (s, 4H), 2.71 (s, 4H), 2.23-2.31 (m, 4H), 2.14-2.16 (m, 3H), 1.87-1.98 (m, 4H), 1.6 (d, J=12.5 Hz, 2H), 1.33 (s, 6H); MS(ESI+) m/z 455 (M+H)$^+$.

EXAMPLE 134

(E)-4-[(N,2-Dimethyl-N-phenylalanyl)amino]adamantane-1-carboxamide

EXAMPLE 134A (E)-4-[(N,2-Dimethyl-N-phenylalanyl)amino]adamantane-1-carboxylic acid The title compound was prepared according to the method of Example 34C substituting N-methylaniline for 1-(5-chloro-2-pyridyl)piperazine. MS(ESI+) m/z 371 (M+H)+.

EXAMPLE 134B (E)-4-[(N,2-Dimethyl-N-phenylalanyl)amino]adamantane-1-carboxamide The title compound was prepared according to the procedure outlined in Example 23 substituting (E)-4-[(N,2-dimethyl-N-phenylalanyl)amino]adamantane-1-carboxylic acid for (E)-4-{2-[5-(6-chloro-pyridin-3-yl)-hexahydro-pyrrolo[3,4-c]pyrrol-2-yl]-2-methyl-propionylamino}-adamantane-1-carboxylic acid. The product was purified by reverse phase HPLC to provide the title compound as a TFA salt. $^1$H NMR (400 MHz, DMSO-$d_6$) δ 7.38 (d, J=7.98 Hz, 1H) 7.23 (t, J=7.98 Hz, 2H) 7.03 (d, 2H) 6.90-6.98 (m, 2H) 6.68 (s, 1H) 3.77 (d, 1H) 2.81 (s, 3H) 1.74-1.85 (m, 7H) 1.70 (s, 2H) 1.54 (d, 2H) 1.39 (d, 2H) 1.20-1.29 (s, 6H); MS(ESI+) m/z 370 (M+H)+.

EXAMPLE 135

(E)-4-({2-[4-(2,4-Dimethoxyphenyl)piperazin-1-yl]-2-methylpropanoyl}amino)adamantane-1-carboxamide The title compound was prepared according to the method of Example 44C substituting 1-(2,4-dimethoxy-phenyl)-piperazine for (3R)-3-fluoropyrrolidine. $^1$H NMR (300 MHz, Py-$d_5$) δ 7.98 (d, J=8.2 Hz, 1H), 7.05 (d, J=8.3 Hz, 1H), 6.79 (s, 1H), 6.65 (d, J=8.3 Hz, 1H), 4.32 (d, J=8.2 Hz, 1H), 3.82 (s, 3H), 3.74 (s, 3H), 3.18 (s, 4H), 2.72 (s, 4H), 2.23-2.31 (m, 4H), 2.14-2.16 (m, 3H), 1.87-1.98 (m, 4H), 1.62 (d, J=12.5 Hz, 2H)), 1.33 (s, 6H); MS(ESI+) m/z 485 (M+H)+.

EXAMPLE 136

(E)-4-({2-[4-(2,3-Dicyanophenyl)piperazin-1-yl]-2-methylpropanoyl}amino)adamantane-1-carboxamide The title compound was prepared according to the method of Example 44C substituting 1-(2,3-dicyano-phenyl)-piperazine for (3R)-3-fluoropyrrolidine. $^1$H NMR (300 MHz, Py-$d_5$) δ 7.75 (m, 1H), 7.4-7.54 (m, 2H), 7.17 (m, 1H), 4.32 (d, J=8.2 Hz, 1H), 3.39 (s, 4H), 2.72 (s, 4H), 2.23-2.31 (m, 2H), 2.04-2.17 (m, 6H), 1.82-1.98 (m, 3H), 1.62 (d, J=12.5 Hz, 2H)), 1.32 (s, 6H); MS(ESI+) m/z 475 (M+H)+.

EXAMPLE 137

N-[(E)-5-(Cyanomethyl)-2-adamantyl]-2-methyl-2-{4-[5-(trifluoromethyl)pyridin-2-yl]piperazin-1-yl}propanamide A solution of N-[(E)-5-formyl-adamantan-2-yl]-2-[4-(5-trifluoromethyl-pyridin-2-yl)-piperazin-1-yl]-isobutyramide (230 mg, 0.48 mmoles) from Example 22 and (p-tolylsulfonyl)methyl isocyanide (TosMIC, 121 mg, 0.624 mmoles) in DME (2 mL) and EtOH (0.5 mL) was cooled to 0° C. and treated portion-wise with solid potassium tert-butoxide (134.7 mg, 1.2 mmoles) while maintaining the temperature at 5-10° C. The mixture was stirred at room temperature for 0.5 hour and at 35-40° C. for another 0.5 hour before filtration and washing with DME. The filtrate was concentrated under reduced pressure, loaded onto a short aluminium oxide column and washed with 500/100 mL of hexane/DCM. The solvent was concentrated under reduced pressure to provide the title compound. $^1$H NMR (400 MHz, CDCl$_3$) δ 8.40-8.42 (bs, 1H), 7.71-7.79 (m, 1H), 7.65 (dd, J=2.52, 9.03 Hz, 1H), 6.66 (d, J=8.98 Hz, 1H), 3.95-4.00 (m, 1H), 3.62-3.70 (m, 4H), 2.59-2.70 (m, 4H), 2.15 (s, 2H), 2.01-2.06 (m, 2H), 1.74-1.76 (m, 4H), 1.65-1.73 (m, 4H), 1.56-1.65 (m, 3H), 1.25 (s, 6H); MS(ESI+) m/z 490 (M+H)+.

EXAMPLE 138

(E)-4-({2-Methyl-2-[4-(4-nitrophenyl)piperazin-1-yl]propanoyl}amino)adamantane-1-carboxylic acid A two phase suspension of (E)-4-(2-bromo-2-methyl-propionylamino)-adamantane-1-carboxamide (36 mg, 0.1 mmoles) from Example 44B, 1-(5-chloro-2-pyridyl)piperazine (20 mg, 0.11 mmoles) and tetrabutylammonium bromide (3 mg, 0.01 mmoles) in DCM (0.2 mL) and 50% NaOH (0.2 mL) was stirred at room temperature for 20 hours. The mixture was diluted with water and DCM and the layers separated. The organic layer was washed with water (2×2 mL), dried (MgSO$_4$) and filtered. The filtrate was concentrated under reduced pressure. The crude methyl ester of the title compound that was purified on reverse phase HPLC and hydrolyzed with 3N HCL at 60° C. for 20 hours. Drying of the mixture under reduced pressure provided the hydrochloride of the title compound. $^1$H NMR (500 MHz, Py-$d_5$) δ 8.38-8.46 (m, 1H), 7.88 (d, J=8.10 Hz, 1H), 7.55 (ddd, J=1.83, 7.02, 8.62 Hz, 1H), 6.85 (d, J=8.56 Hz, 1H), 6.70 (dd, J=5.03, 6.87 Hz, 1H), 4.18-4.26 (m, 1H), 3.68 (s, 4H), 3.62 (s, 3H), 2.55-2.64 (m, 4H), 1.98-2.08 (m, 6H), 1.92-1.94 (m, 2H), 1.86-1.90 (m, 1H), 1.75-1.84 (m, 2H), 1.48-1.56 (m, 2H), 1.30 (s, 6H); MS(ESI+) m/z 461 (M+H)+.

EXAMPLE 139

(E)-4-({2-[4-(2,4-Dichlorophenyl)piperazin-1-yl]-2-methylpropanoyl}amino)adamantane-1-carboxylic acid The title compound was prepared according to the method of Example 34C substituting 1-(2,4-dichloro-phenyl)-piperazine for 1-(5-chloro-2-pyridyl)piperazine. $^1$H NMR (400 MHz, Py-$d_5$) δ 7.83-7.96 (m, 1H), 7.31 (dd, J=2.30, 8.59 Hz, 1H), 7.10 (d, J=8.57 Hz, 1H), 4.28-4.38 (m, 1H), 3.07-3.15 (m, 4H), 2.71-2.75 (m, 4H), 2.27-2.36 (m, 2H), 2.21-2.27 (m, 2H), 2.15-2.18 (m, 1H), 2.10-2.15 (m, 2H), 1.95-2.01 (m, 1H), 1.85-1.95 (m, 2H), 1.57-1.69 (m, 4H), 1.36 (s, 6H); MS(ESI+) m/z 495 (M+H)+.

EXAMPLE 140

{(E)-4-[(2-Methyl-2-{4-[5-(trifluoromethyl)pyridin-2-yl]piperazin-1-yl}propanoyl)amino]-1-adamantyl}acetic acid A solution of (E)-N-(5-cyanomethyl-adamantan-2-yl)-2-[4-(5-trifluoromethyl-pyridin-2-yl)-piperazin-1-yl]-isobutyramide (25 mg, 0.05 mmoles) from Example 137 in acetic acid (0.5 mL) and 48% HBr (2.5 mL) was stirred overnight at 120° C. The solvents were concentrated and the residue was purified on reverse phase HPLC to provide the title compound. $^1$H NMR (400 MHz, Py-d$_6$) δ 8.67 (s, 1H), 7.83 (d, J=8.3 Hz, 1H), 7.78 (d, J=7.1 Hz, 1H), 6.86 (d, J=8.9 Hz, 1H), 4.23 (d, J=8.3 Hz, 1H), 3.75 (s, 4H), 2.59 (s, 4H), 2.31 (s, 2H), 2.08 (s, 3H), 1.92-1.84 (m, 7H), 1.73 (s, 1H), 1.62 (m, 3H), 1.31 (s, 6H); MS(ESI+) m/z 508 (M+H)$^+$.

EXAMPLE 141

(E)-4-({2-[4-(4-Chloro-2-fluorophenyl)piperazin-1-yl]-2-methylpropanoyl}amino)adamantane-1-carboxylic acid The title compound was prepared according to the procedure outlined in Example 34C substituting 1-(4-chloro-2-fluoro-phenyl)-piperazine for 1-(5-chloro-2-pyridyl)piperazine. $^1$H NMR (500 MHz, Py-d$_5$) δ 7.87 (d, J=8.09 Hz, 1H), 7.30 (dd, J=2.40, 12.30 Hz, 1H), 7.17-7.20 (m, 1H), 7.01 (t, J=8.96 Hz, 1H), 4.29-4.35 (m, 1H), 3.11-3.18 (m, 4H), 2.63-2.70 (m, 4H), 2.21-2.35 (m, 4H), 2.10-2.19 (m, 4H), 1.95-1.98 (bs, 1H), 1.85-1.91 (m, 2H), 1.58-1.67 (m, 2H), 1.34 (s, 6H); MS(ESI+) m/z 479 (M+H)$^+$.

EXAMPLE 142

(E)-4-[(2-Methyl-2-{4-[4-(trifluoromethyl)pyrimidin-2-yl]piperazin-1-yl}propanoyl)amino]adamantane-1-carboxylic acid The title compound was prepared according to the method of Example 34C substituting 2-piperazin-1-yl-4-trifluoromethyl-pyrimidine for 1-(5-chloro-2-pyridyl)piperazine. $^1$H NMR (500 MHz, Py-d$_5$) δ 8.67 (d, J=4.76 Hz, 1H), 7.87 (d, J=8.10 Hz, 1H), 6.89 (d, J=4.77 Hz, 1H), 4.28-4.36 (m, 1H), 3.84-4.04 (m, 4H), 2.49-2.58 (m, 4H), 2.22-2.34 (m, 4H), 2.17-2.19 (m, 2H), 2.09-2.15 (m, 2H), 1.98-2.00 (bs, 1H), 1.82-1.90 (m, 2H), 1.60-1.67 (m, 2H), 1.31 (s, 6H); MS(ESI) m/z 496 (M+H)$^+$.

EXAMPLE 143

(E)-4-({2-[4-(3-Chloro-4-fluorophenyl)piperazin-1-yl]-2-methylpropanoyl}amino)adamantane-1-carboxylic acid The title compound was prepared according to the method of Example 34C substituting 1-(3-chloro-4-fluoro-phenyl)-piperazine for 1-(5-chloro-2-pyridyl)piperazine. $^1$H NMR (500 MHz, Py-d$_5$) δ 7.87 (d, J=8.07 Hz, 1H), 7.19-7.23 (m, 2H), 6.90-7.00 (m, 1H), 4.28-4.37 (m, 1H), 3.13-3.27 (m, 4H), 2.62-2.71 (m, 4H), 2.27-2.34 (m, 2H), 2.22-2.26 (m, 2H), 2.15-2.17 (m, 2H), 2.10-2.15 (m, 2H), 1.93-1.97 (m, 1H), 1.83-1.91 (m, 2H), 1.57-1.65 (m, 2H), 1.34 (s, 6H); MS(ESI) m/z 478 (M+H)$^+$.

EXAMPLE 144

(E)-4-({2-[4-(4-Cyanophenyl)piperazin-1-yl]-2-methylpropanoyl}amino)adamantane-1-carboxylic acid The title compound was prepared according to the method of Example 34C substituting 4-piperazin-1-yl-benzonitrile for 1-(5-chloro-2-pyridyl)piperazine. $^1$H NMR (500 MHz, Py-d$_5$) δ 7.83 (d, J=8.07 Hz, 1H), 7.64 (d, J=8.57 Hz, 2H), 7.02 (d, J=8.62 Hz, 2H), 4.28-4.36 (m, 1H), 3.36 (s, 4H), 2.56-2.65 (m, 4H), 2.27-2.34 (m, 2H), 2.23-2.26 (m, 2H), 2.17 (s, 2H), 2.13 (s, 2H), 1.97 (s, 1H), 1.81-1.91 (m, 2H), 1.58-1.67 (m, 2H), 1.33 (s, 6H); MS(ESI) m/z 451 (M+H)$^+$.

EXAMPLE 145

(E)-4-({2-[4-(4-Bromophenyl)piperazin-1-yl]-2-methylpropanoyl}amino)adamantane-1-carboxylic acid The title compound was prepared according to the method of Example 34C substituting 1-(4-bromo-phenyl)-piperazine for 1-(5-chloro-2-pyridyl)piperazine. $^1$H NMR (500 MHz, Py-d$_5$) δ 7.87 (d, J=8.08 Hz, 1H), 7.51-7.54 (m, 2H), 6.96-7.00 (m, 2H), 4.28-4.35 (m, 1H), 3.19-3.27 (m, 4H), 2.59-2.68 (m, 4H), 2.26-2.34 (m, 2H), 2.20-2.26 (m, 2H), 2.15-2.17 (m, 2H), 2.11-2.13 (m, 2H), 1.94-1.96 (m, 1H), 1.82-1.89 (m, 2H), 1.58-1.65 (m, 2H), 1.33 (s, 6H); MS(ESI) m/z 504 (M+H)$^+$.

EXAMPLE 146

(E)-4-({2-[4-(5-Chloro-2-methoxyphenyl)piperazin-1-yl]-2-methylpropanoyl}amino)adamantane-1-carboxylic acid The title compound was prepared according to the method of Example 34C substituting 1-(5-chloro-2-methoxy-phenyl)-piperazine for 1-(5-chloro-2-pyridyl)piperazine. $^1$H NMR (500 MHz, Py-d$_5$) δ 7.92 (d, J=8.12 Hz, 1H), 7.10-7.12 (m, 2H), 6.90 (d, J=8.67 Hz, 1H), 4.29-4.37 (m, 1H), 3.80 (s, 3H), 2.99-3.33 (m, 4H), 2.66-2.74 (m, 4H), 2.29-2.35 (m, 2H), 2.24-2.29 (m, 2H), 2.17-2.20 (m, 2H), 2.12-2.15 (m, 2H), 1.94-1.97 (bs, 1H), 1.87-192 (m, 2H), 1.58-1.66 (m, 2H), 1.34 (s, 6H); MS(ESI) m/z 490 (M+H)$^+$.

EXAMPLE 147

(E)-4-({2-[4-(2-Chlorophenyl)piperazin-1-yl]-2-methylpropanoyl}amino)adamantane-1-carboxylic acid The title compound was prepared according to the method of Example 34C substituting 1-(2-chloro-phenyl)-piperazine for 1-(5-chloro-2-pyridyl)piperazine. $^1$H NMR (500 MHz, Py-d$_5$) δ 7.91 (d, J=8.10 Hz, 1H), 7.52 (d, J=7.82 Hz, 1H), 7.29 (t, J=7.59 Hz, 1H), 7.17 (d, J=7.85 Hz, 1H), 7.05 (t, J=7.54 Hz, 1H), 4.29-4.37 (m, 1H), 2.98-3.26 (m, 4H), 2.69-2.74 (m, 4H), 2.21-2.36 (m, 4H), 2.10-2.20 (m, 4H), 1.95-1.99 (m, 1H), 1.85-1.92 (m, 2H), 1.59-1.68 (m, 2H), 1.35 (s, 6H); MS(ESI) m/z 460 (M+H)$^+$.

EXAMPLE 148

(E)-4-({2-[4-(2-Cyanophenyl)piperazin-1-yl]-2-methylpropanoyl}amino)adamantane-1-carboxylic acid The title compound was prepared according to the method of Example 34C substituting 2-piperazin-1-yl-benzonitrile for 1-(5-chloro-2-pyridyl)piperazine. $^1$H NMR (500 MHz, Py-d$_5$) δ 7.84 (d, J=8.09 Hz, 1H), 7.69 (dd, J=1.48, 7.70 Hz, 1H), 7.47-7.52 (m, 1H), 7.10 (d, J=8.29 Hz, 1H), 7.03 (t, J=7.50 Hz, 1H), 4.28-4.36 (m, 1H), 3.23-3.42 (m, 4H), 2.69-2.77 (m, 4H), 2.27-2.35 (m, 2H), 2.23-2.26 (m, 2H), 2.15-

2.19 (m, 2H), 2.09-2.15 (m, 2H), 1.96-1.98 (bs, 1H), 1.83-1.92 (m, 2H), 1.58-1.67 (m, 2H), 1.31 (s, 6H); MS(ESI) m/z 451 (M+H)+.

EXAMPLE 149

(E)-4-({2-[4-(2-Fluorophenyl)piperazin-1-yl]-2-methylpropanoyl}amino)adamantane-1-carboxylic acid The title compound was prepared according to the method of Example 34C substituting 1-(2-fluoro-phenyl)-piperazine for 1-(5-chloro-2-pyridyl)piperazine. $^1$H NMR (500 MHz, Py-d$_5$) δ 7.89 (d, J=8 Hz, 1H), 7.21 (m, 1H), 7.15 (dd, J=7.5, 7.5 Hz, 1H), 7.09 (dd, J=8, 8 Hz, 1H), 7.02 (m, 1H), 4.32 (bd, J=8.5 Hz, 1H), 3.19 (bs, 4H), 2.68 (m, 4H), 2.27 (m, 4H), 2.17 (bs, 2H), 2.13 (bs, 2H), 1.96 (bs, 1H), 1.88 (bd, J=13.5 Hz, 2H), 1.62 (bd, J=12.5 Hz, 2H), 1.34 (s, 6H); MS(ESI) m/z 444 (M+H)+.

EXAMPLE 150

(E)-4-({2-Methyl-2-[4-(2-methylphenyl)piperazin-1-yl]propanoyl}amino)adamantane-1-carboxylic acid The title compound was prepared according to the method of Example 34C substituting 1-o-tolyl-piperazine for 1-(5-chloro-2-pyridyl)piperazine. $^1$H NMR (500 MHz, Py-d$_5$) δ 7.94 (d, J=8.10 Hz, 1H), 7.26-7.32 (m, 2H), 7.17 (d, J=8.24 Hz, 1H), 7.11 (t, J=7.31 Hz, 1H), 4.29-4.37 (m, 1H), 2.97-3.01 (m, 4H), 2.66-2.70 (m, 4H), 2.39 (s, 3H), 2.28-2.35 (m, 2H), 2.22-2.28 (m, 2H), 2.17 (s, 2H), 2.14 (s, 2H), 1.96 (s, 1H), 1.86-1.93 (m, 2H), 1.58-1.68 (m, 2H), 1.37 (s, 6H); MS(ESI) m/z 440 (M+H)+.

EXAMPLE 151

(E)-4-({2-[4-(4-Chlorophenyl)piperazin-1-yl]-2-methylpropanoyl}amino)adamantane-1-carboxylic acid The title compound was prepared according to the method of Example 34C substituting 1-(4-chloro-phenyl)-piperazine for 1-(5-chloro-2-pyridyl)piperazine. $^1$H NMR (500 MHz, Py-d$_5$) δ 7.87 (d, J=8.07 Hz, 1H), 7.37-7.42 (m, 2H), 7.01-7.05 (m, 2H), 4.28-4.36 (m, 1H), 3.23 (s, 4H), 2.60-2.68 (m, 4H), 2.26-2.34 (m, 2H), 2.22-2.25 (m, 2H), 2.15-2.17 (m, 2H), 2.10-2.14 (m, 2H), 1.93-1.97 (m, 1H), 1.81-1.89 (m, 2H), 1.58-1.64 (m, 2H), 1.33 (s, 6H); MS(ESI) m/z 460 (M+H)+.

EXAMPLE 152

(E)-4-({2-[4-(3-Chloropyridin-2-yl)piperazin-1-yl]-2-methylpropanoyl}amino)adamantane-1-carboxylic acid The title compound was prepared according to the method of Example 34C substituting 1-(3-chloro-pyridin-2-yl)-piperazine for 1-(5-chloro-2-pyridyl)piperazine. $^1$H NMR (500 MHz, Py-d$_5$) δ 8.30 (dd, J=0.92, 4.58 Hz, 1H), 7.71 (dd, J=1.55, 7.64 Hz, 1H), 6.89 (dd, J=4.64, 7.71 Hz, 1H), 4.31-4.36 (m, 1H), 3.46-3.83 (m, 4H), 2.76-3.02 (m, 4H), 2.26-2.31 (m, 2H), 2.20-2.25 (m, 2H), 2.14-2.16 (m, 4H), 1.98-2.08 (m, 2H), 1.92-1.98 (m, 1H), 1.56-1.63 (m, 2H), 1.44 (s, 6H); MS(ESI+) m/z 462 (M+H)+.

EXAMPLE 153

(E)-4-[(2-{4-[2-Chloro-4-(trifluoromethyl)phenyl]piperazin-1-yl}-2-methylpropanoyl)amino]adamantane-1-carboxylic acid The title compound was prepared according to the method of Example 34C substituting 1-(2-chloro-4-trifluoromethyl-phenyl)-piperazine for 1-(5-chloro-2-pyridyl)piperazine. $^1$H NMR (500 MHz, Py-d$_5$) δ 7.88-8.10 (m, 1H), 7.85 (d, J=2.18 Hz, 1H), 7.55-7.61 (m, 1H), 7.18-7.25 (m, 1H), 4.30-4.39 (m, 1H), 3.06-3.49 (m, 4H), 2.57-2.97 (m, 4H), 2.28-2.34 (m, 2H), 2.22-2.28 (m, 2H), 2.17-2.18 (m, 2H), 2.12-2.17 (m, 2H), 197-2.04 (m, 1H), 1.85-1.97 (m, 2H), 1.60-1.69 (m, 2H), 1.39 (s, 6H); MS(ESI+) m/z 529 (M+H)+.

EXAMPLE 154

(E)-4-({2-[(3R)-3-Fluoropyrrolidin-1-yl]-2-methylpropanoyl}amino)-N-(pyridin-3-ylmethyl)adamantane-1-carboxamide

EXAMPLE 154A (E)-4-({2-[(3R)-3-Fluoropyrrolidin-1-yl]-2-methylpropanoyl}amino)adamantane-1-carboxylic acid The title compound was prepared according to the method of Example 34C substituting (3R)-3-fluoro-pyrrolidine (356.0 mg, 4 mmoles) for 1-(5-chloro-2-pyridyl)piperazine. $^1$H NMR (300 MHz, DMSO-d$_6$) δ 10.83-11.15 (m, 1H), 7.69-7.86 (d, J=4.80 Hz, 1H), 3.78-3.90 (m, 1H), 3.60 (d, J=4.75 Hz, 1H), 2.16-2.37 (m, 2H), 1.92-2.09 (m, 4H), 1.76-1.94 (m, 8H), 1.54-1.66 (m, 6H), 1.38-1.51 (m, 3H), 1.21-1.33 (m, 1H); MS(ESI+) m/z 353 (M+H)+.

EXAMPLE 154B (E)-4-({2-[(3R)-3-Fluoropyrrolidin-1-yl]-2-methylpropanoyl}amino)-N-(pyridin-3-ylmethyl)adamantane-1-carboxamide A solution of (E)-4-({2-[(3R)-3-fluoropyrrolidin-1-yl]-2-methylpropanoyl}amino)adamantane-1-carboxylic acid from Example 154A (21.0 mg, 0.06 mmoles) in DMF (5 mL) was treated with TBTU (O-(benzotrialzol-1-yl)-1,1,3,3-tetramethyluronium tetrafluoroborate) (26.0 mg, 0.08 mmoles), 3-(aminomethyl)pyridine (8.0 mg, 0.07 mmoles) and DIEA (ethyl-diisopropyl-amine) (0.02 mL, 0.11 mmoles). The mixture was stirred at room temperature for 12 hours. The mixture was concentrated under reduced pressure. The residue was purified by reverse phase HPLC to provide the title compound. $^1$H NMR (400 MHz, DMSO-d$_6$) δ 8.39-8.49 (m, 2H), 8.09 (t, J=6.10 Hz, 1H), 7.71 (d, J=8.29 Hz, 1H), 7.59 (d, J=7.67 Hz, 1H), 7.33 (dd, J=7.67, 4.91 Hz, 1H), 4.27 (d, J=6.14 Hz, 2H), 3.79 (d, J=7.98 Hz, 1H), 2.81-2.93 (m, 2H), 2.65-2.74 (m, 1H), 2.41-2.49 (m, 1H), 2.03-2.22 (m, 1H), 1.85-1.99 (m, 8H), 1.80 (s, 2H), 1.66-1.76 (m, 2H), 1.46-1.57 (m, 2H), 1.17 (s, 6H); MS(ESI+) m/z 443 (M+H)+.

EXAMPLE 155

(E)-4-[2-Methyl-2-(3-phenylpiperidin-1-yl)propanoyl]amino adamantane-1-carboxamide The title compound was prepared according to the method of Example 44C substituting 3-phenyl-piperidine for (3R)-3- fluoropyrrolidine. ¹H NMR (300 MHz, Py-d₅) δ 7.94 (s, 1H), 7.35-7.42 (m, 2H), 7.28-7.33 (m, 3H), 4.27 (d, J=8.0 Hz, 1H), 3.0 (m, 1H), 2.91 (m, 1H), 2.04-2.34 (m, 11H), 1.93 (m, 4H), 1.74 (m, 1H), 1.50-1.68 (m, 4H), 1.33 (d, J=5.8 Hz, 6H); MS(ESI+) m/z 424 (M+H)⁺.

EXAMPLE 156

(E)-4-({2-[4-(2-Chloro-4-methylphenyl)piperazin-1-yl]-2-methylpropanoyl}amino)adamantane-1-carboxylic acid The title compound was prepared according to the method of Example 34C substituting 1-(2-chloro-4-methyl-phenyl)-piperazine for 1-(5-chloro-2-pyridyl)piperazine. ¹H NMR (500 MHz, Py-d₅) δ 7.94-8.12 (bs, 1H), 7.31 (s, 1H), 7.06-7.12 (m, 2H), 4.30-4.39 (m, 1H), 3.04-3.34 (m, 4H), 2.67-2.92 (m, 4H), 2.28-2.35 (m, 2H), 2.22-2.28 (m, 2H), 2.11-2.21 (m, 7H), 1.87-2.04 (m, 3H), 1.57-1.68 (m, 2H), 1.39 (s, 6H); MS(ESI+) m/z 475 (M+H)⁺.

EXAMPLE 157

(E)-4-({2-[4-(2-Fluorophenyl)piperidin-1-yl]-2-methylpropanoyl}amino)adamantane-1-carboxylic acid The title compound was prepared according to the method of Example 34C substituting 4-(2-fluoro-phenyl)-piperidine for 1-(5-chloro-2-pyridyl)piperazine. ¹H NMR (500 MHz, Py-d₅) δ 1.45 (s, 6H), 1.59-1.63 (m, 2H), 1.89-1.99 (m, 3H), 2.15-2.30 (m, 10H), 2.99-3.05 (m, 2H), 3.15-3.25 (m, 1H), 4.34 (m, 1H), 7.14-7.245 (m, 4H), 7.95 (m, 1H); MS(ESI+) m/z 443 (M+H)⁺.

EXAMPLE 158

(E)-4-({2-Methyl-2-[4-(2-methylphenyl)piperidin-1-yl]propanoyl}amino adamantane-1-carboxylic acid The title compound was prepared according to the method of Example 34C substituting 1-(3-chloro-pyridin-2-yl)-piperazine for 1-(5-chloro-2-pyridyl)piperazine. ¹H NMR (500 MHz, Py-d₅) δ 8.30 (dd, J=0.92, 4.58 Hz, 1H), 7.71 (dd, J=1.55, 7.64 Hz, 1H), 6.89 (dd, J=4.64, 7.71 Hz, 1H), 4.31-4.36 (m, 1H), 3.46-3.83 (m, 4H), 2.76-3.02 (m, 4H), 2.26-2.31 (m, 2H), 2.20-2.25 (m, 2H), 2.14-2.16 (m, 4H), 1.98-2.08 (m, 2H), 1.92-1.98 (m, 1H), 1.56-1.63 (m, 2H), 1.44 (s, 6H); MS(ESI+) m/z 462 (M+H)⁺.

EXAMPLE 159

(E)-4-({2-[4-(2-Chloro-4-fluorophenyl)piperazin-1-yl]-2-methylpropanoyl}amino)adamantane-1-carboxamide

EXAMPLE 159A 1-(2-Chloro-4-fluorophenyl)piperazine

A suspension of 1-bromo-2-chloro-4-fluorobenzene (4.19 g, 20 mmoles), piperazine (10.32 g, 120 mmoles), sodium tert-butoxide (2.3 g, 1.5 mmoles), tris(dibenzylideneacetone)dipalladium (366 mg, 0.4 mmoles) and racemic (±)-2,2'-bis(diphenylphosphino)-1,1'-binaphthyl (747 mg, 1.2 mmoles) in toluene (2 mL) was heated to 120° C. overnight. The mixture was cooled, filtered and the filtrate concentrated under reduced pressure. The crude residue was purified by column chromatography (silica gel, 0-5% 2N methanolic ammonia in DCM) to provide the title compound.

EXAMPLE 159B (E)-4-({2-[4-(2-Chloro-4-fluorophenyl)piperazin-1-yl]-2-methylpropanoyl}amino)adamantane-1-carboxamide The title compound was prepared according to the method of Example 44C substituting 1-(2-chloro-4-fluorophenyl)piperazine from Example 159A for (3R)-3-fluoropyrrolidine ¹H NMR (400 MHz, Py-d₅) δ 7.83-7.93 (m, 1H), 7.58-7.66 (m, 2H), 7.33-7.41 (m, 1H), 7.04-7.18 (m, 2H), 4.26-4.34 (m, 1H), 3.03-3.13 (m, 4H), 2.67-2.75 (m, 4H), 2.27-2.33 (m, 2H), 2.22-2.27 (m, 2H), 2.11-2.18 (m, 4H), 1.94-2.00 (m, 1H), 1.85-1.93 (m, 2H), 1.58-1.66 (m, 2H), 1.35 (s, 6H); MS(ESI+) m/z 477 (M+H)⁺.

EXAMPLE 160

(E)-4-({2-[4-(2-Furoyl)piperazin-1-yl]-2-methylpropanoyl}amino)adamantane-1-carboxylic acid

EXAMPLE 160A

Methyl (E)-4-({2-[4-(2-furoyl)piperazin-1-yl]-2-methylpropanoyl}amino)adamantane-1-carboxylate The hydrochloride salt of methyl (E)-4[2-(4-piperazin-1-yl)-2-methyl-propionyl-amino]-adamantane-1-carboxylate (70 mg, 0.18 mmoles), TBTU (62 mg, 0.193 mmoles), and furoic acid (22 mg, 0.192 mmoles) were suspended in dimethylacetamide (0.5 mL). Diisopropylamine (525 mg, 4.07 mmoles) was added and the solution was kept at room temperature for 18 hours. To the mixture was added toluene and the solution concentrate under reduced pressure. More toluene was added and the solution was washed with $H_3PO_4$, water, and finally $KHCO_3$ before drying ($MgSO_4$) and removing the solvents in vacuum to afford the title compound. MS(ESI) m/z 458 (M+H)⁺.

EXAMPLE 160B (E)-4-({2-[4-(2-Furoyl)piperazin-1-yl]-2-methylpropanoyl}amino)adamantane-1-carboxylic acid The title compound was prepared according to the method of Example 164B substituting methyl (E)-4-({2-[4-(2-furoyl)piperazin-1-yl]-2-methylpropanoyl}amino)adamantane-1-carboxylate from Example 160A for methyl (E)-4-[(2-{4-[(4-chlorophenyl)sulfonyl]piperazin-1-yl}-2-methylpropanoyl)amino]adamantane-1-carboxylate. ¹H NMR (300 MHz, CDCl₃) δ 7.73 (d, J=8 Hz, 1H), 7.49 (d, J=1 Hz, 1H), 7.02 (d, J=3 Hz, 1H), 6.49 (dd, J=3 Hz, 1 Hz, 1H), 4.01 (d, J=8 Hz, 1H), 3.82 (br. s, 4H), 2.60 (m, 4H), 1.93-2.10 (m, 9H), 1.73 (d, J=12 Hz, 2H), 1.65 (d, J=12 Hz, 2H), 1.22 (s, 6H); MS(ESI+) m/z 444 (M+H)⁺.

EXAMPLE 161

(E)-4-({2-[4-(2-Chloro-4-cyanophenyl)piperazin-1-yl]-2-methylpropanoyl}amino)adamantane-1-carboxylic acid

EXAMPLE 161A

3-Chloro-4-piperazin-1-ylbenzonitrile

A solution of 3-chloro-4-fluoro-benzonitrile (236 mg, 1.52 mmoles), piperazine (784 mg, 9.1 mmoles) and potassium carbonate (276 mg, 2 mmoles) in acetonitrile (5 mL) was heated to 100° C. overnight. The mixture was cooled, filtered and the filtrate concentrated under reduced pressure. The crude residue was purified by column chromatography (silica gel, 0-5% 2N methanolic ammonia in DCM) to provide the title compound. MS(APCI+) m/z 222 (M+H)$^+$.

EXAMPLE 161B (E)-4-({2-[4-(2-Chloro-4-cyanophenyl)piperazin-1-yl]-2-methylpropanoyl}amino)adamantane-1-carboxylic acid The title compound was prepared according to the procedure outlined in Example 34C substituting 3-chloro-4-piperazin-1-ylbenzonitrile from Example 161A for 1-(5-chloro-2-pyridyl)piperazine. $^1$H NMR (400 MHz, Py-d$_5$) δ 7.84-7.85 (m, 1H), 7.82-7.85 (m, 1H), 7.58-7.63 (m, 1H), 7.13 (d, J=8.34 Hz, 1H), 4.28-4.38 (m, 1H), 3.10-3.33 (m, 4H), 2.71 (s, 4H), 2.20-2.36 (m, 4H), 2.11-2.19 (m, 4H), 1.97 (s, 1H), 1.83-1.93 (m, 2H), 1.59-1.69 (m, 2H), 1.36 (s, 6H); MS(ESI+) m/z 486 (M+H)$^+$.

EXAMPLE 162

(E)-4-({2-[4-(2-Chloro-4-fluorophenyl)piperazin-1-yl]-2-methylpropanoyl}amino)adamantane-1-carboxylic acid A sample of (E)-4-{2-[4-(2-chloro-4-fluoro-phenyl)-piperazin-1-yl]-2-methyl-propionylamino}-adamantane-1-carboxamide (10 mg, 0.02 mmoles) from Example 159B was hydrolyzed with 3N HCL at 60° C. overnight. Drying of the mixture under reduced pressure provided the title compound. $^1$H NMR (500 MHz, Py-d$_5$) δ 14.59-15.48 (bs, 1H), 7.90 (d, J=8.13 Hz, 1H), 7.39 (dd, J=2.82, 8.47 Hz, 1H), 7.15 (dd, J=5.65, 8.85 Hz, 1H), 7.11 (ddd, J=2.92, 7.79, 8.87 Hz, 1H), 4.29-4.38 (m, 1H), 2.98-3.21 (m, 4H), 2.67-2.79 (m, 4H), 2.28-2.37 (m, 2H), 2.21-2.28 (m, 2H), 2.16-2.20 (m, 2H), 2.12-2.16 (m, 2H), 1.93-2.11 (m, 1H), 1.86-1.93 (m, 2H), 1.60-1.67 (m, 2H), 1.36 (s, 6H); MS(ESI+) m/z 478 (M+H)$^+$.

EXAMPLE 163

(E)-4-[(2-Methyl-2-{4-[5-(trifluoromethyl)pyridin-2-yl]piperazin-1-yl}propanoyl)amino]-1-adamantyl carbamate A solution of N-[(E)-5-hydroxy-2-adamantyl]-2-methyl-2-{4-[5-(trifluoromethyl)pyridin-2-yl]piperazin-1-yl}propanamide (466 mg, 1 mmoles) from Example 14 in DCM (3 mL) was treated with trichloroacetylisocyanate (131 µL, 1.1 mmoles) and stirred for 2 hours at room temperature. The solvent was removed under reduced pressure; the residue was dissolved in MeOH (10 mL) followed by the addition of saturated potassium carbonate (20 mL) and the mixture stirred overnight at room temperature. The mixture was concentrated under reduced pressure, partitioned with DCM and the aqueous layer extracted with additional DCM. The combined organic extracts were washed twice with water, dried (MgSO$_4$) and filtered. The filtrate was concentrated under reduced pressure to provide the title compound. $^1$H NMR (400 MHz, CDCl$_3$) δ 8.40-8.41 (bs, 1H), 7.69 (d, J=8.21 Hz, 1H), 7.64 (dd, J=2.53, 8.95 Hz, 1H), 6.66 (d, J=8.98 Hz, 1H), 4.36-4.48 (m, 2H), 3.98-4.09 (m, 1H), 3.63-3.67 (m, 4H), 2.59-2.70 (m, 4H), 1.58-1.70 (m, 5H), 1.24 (s, 6H); MS(APCI+) m/z 510 (M+H)$^+$.

EXAMPLE 164

(E)-4-[(2-{4-[(4-Chlorophenyl)sulfonyl]piperazin-1-yl}-2-methylpropanoyl)amino]adamantane-1-carboxylic acid

EXAMPLE 164A tert-Butyl 4-(2-{[(E)-5-(methoxycarbonyl)-2-adamantyl]amino}-1,1-dimethyl-2-oxoethyl)piperazine-1-carboxylate The title compound was prepared according to the method of Example 34C substituting piperazine-1-carboxylic acid tert-butyl ester for 1-(5-chloro-2-pyridyl)piperazine and isolating the ester before hydrolysis. MS(DCI+) m/z 464 (M+H)$^+$.

EXAMPLE 164B

Methyl (E)-4-[(2-methyl-2-piperazin-1-ylpropanoyl)amino]adamantane-1-carboxylate A 0° C. solution of tert-butyl 4-(2-{[(E)-5-(methoxycarbonyl)-2-adamantyl]amino}-1,1-dimethyl-2-oxoethyl)piperazine-1-carboxylate from Example 164A (250 mg, 0.54 mmoles) in methanol (3 mL) was slowly treated with acetyl chloride (0.15 mL). After 5 minutes, the solution was warmed to 23° C. and stirred for 16 hours. The mixture was concentrated in vacuo to afford the title compound as the hydrochloride salt. MS(DCI+) m/z 364 (M+H)$^+$.

EXAMPLE 164C

Methyl (E)-4-[(2-{4-[(4-chlorophenyl)sulfonyl]piperazin-1-yl}-2-methylpropanoyl)amino]adamantane-1-carboxylate The hydrochloride salt of methyl (E)-4-[(2-methyl-2-piperazin-1-ylpropanoyl)amino]adamantane-1-carboxylate from Example 164B (70 mg, 0.18 mmoles) was suspended in CHCl$_3$ (0.5 mL) in a 4 mL vial with rapid stirring. Diisopropylethylamine (70 mg, 0.54 mmoles) was added followed by 4-chlorobenzene sulfonyl chloride (44 mg, 0.208 mmoles). The solution was stirred at room temperature for 15 hours. Toluene was added, and the solution was washed with KHCO$_3$ and then dilute H$_3$PO$_4$. After drying (Na$_2$SO$_4$), the toluene was removed under reduced pressure and the residue crystallized from 1:1 ether:heptane to afford the title compound. MS(ESI) m/z 538 (M+H)$^+$.

EXAMPLE 164D (E)-4-[(2-{4-[(4-Chlorophenyl)sulfonyl]piperazin-1-yl}-2-methylpropanoyl)amino]adamantane-1-carboxylic acid A solution of methyl (E)-4-[(2-{4-[(4-chlorophenyl)sulfonyl]piperazin-1-yl}-2-methylpropanoyl)amino]adamantane-1-carboxylate from Example 164C (50 mg) in 50% aqueous NaOH (30 mg), methanol (0.8 mL), and water (0.25 mL) was stirred and heated at 55° C. for 1 hour. The solution was cooled and concentrated under reduced pressure, and the residue dissolved in water (1 mL). The solution was acidified by addition of solid $KH_2PO_4$. The resultant mixture was extracted with $CHCl_3$, dried ($Na_2SO_4$), and filtered. The filtrate was concentrated and the residue crystallized from ether to afford the title compound. $^1H$ NMR (500 MHz, $CDCl_3$) δ 7.73 (d, J=9 Hz, 2H), 7.55 (d, J=9 Hz, 2H), 7.40 (d, J=8 Hz, 1H), 3.93 (d, J=8 Hz, 1H), 3.05 (br.s, 4H), 2.60 (m, 4H), 2.02 (d, J=12 Hz, 2H), 1.95 (d, J=12 Hz, 2H), 1.92 (m, 5H), 1.55 (d, J=13 Hz, 2H), 1.44 (d, J=13 Hz, 2H), 1.18 (s, 6H); MS(ESI+) m/z 524 (M+H)$^+$.

EXAMPLE 165

(E)-4-({2-[4-(2,4-Difluorophenyl)piperidin-1-yl]-2-methylpropanoyl}amino)adamantane-1-carboxylic acid The title compound was prepared according to the procedure outlined in Example 34C substituting 4-(2,4-difluorophenyl)piperidine for 1-(5-chloro-2-pyridyl)piperazine. $^1H$ NMR (500 MHz, Py-$d_5$) δ 7.96 (d, J=8.07 Hz, 1H), 7.37 (td, J=6.46, 8.60 Hz, 1H), 7.10 (ddd, J=2.40, 8.82, 11.03 Hz, 1H), 6.97-7.06 (m, 1H), 4.27-4.35 (m, 1H), 2.89-2.98 (m, 2H), 2.79-2.88 (m, 1H), 2.26-2.34 (m, 2H), 2.10-2.26 (m, 8H), 1.75-1.96 (m, 7H), 1.57-1.65 (m, 2H), 1.35 (s, 6H); MS(ESI+) m/z 461 (M+H)$^+$.

EXAMPLE 166

(E)-4-({2-[4-(4-Cyano-2-fluorophenyl)piperazin-1-yl]-2-methylpropanoyl}amino)adamantane-1-carboxylic acid

EXAMPLE 166A

3-Fluoro-4-piperazin-1-ylbenzonitrile

A solution of 4-chloro-3-fluoro-benzonitrile (236 mg, 1.52 mmoles), piperazine (784 mg, 9.1 mmoles) and potassium carbonate (276 mg, 2 mmoles) in acetonitrile (5 mL) was heated to 100° C. overnight. The mixture was cooled and filtered, and the filtrate was concentrated under reduced pressure. The crude residue was purified by column chromatography (silica gel, 0-5% 2N methanolic ammonia in DCM) to provide the title compound. MS(APCI+) m/z 206 (M+H)$^+$.

EXAMPLE 166B (E)-4-({2-[4-(4-Cyano-2-fluorophenyl)piperazin-1-yl]-2-methylpropanoyl}amino)adamantane-1-carboxylic acid The title compound was prepared according to the procedure outlined in Example 34C substituting 3-fluoro-4-piperazin-1-ylbenzonitrile from Example 166A for 1-(5-chloro-2-pyridyl)piperazine. $^1H$ NMR (400 MHz, Py-$d_5$) δ 7.84-7.85 (m, 1H), 7.82-7.85 (m, 1H), 7.58-7.63 (m, 1H), 7.13 (d, J=8.34 Hz, 1H), 4.28-4.38 (m, 1H), 3.10-3.33 (m, 4H), 2.71 (s, 4H), 2.20-2.36 (m, 4H), 2.11-2.19 (m, 4H), 1.97 (s, 1H), 1.83-1.93 (m, 2H), 1.59-1.69 (m, 2H), 1.36 (s, 6H); MS(ESI+) m/z 486 (M+H)$^+$.

EXAMPLE 167

(E)-4-[(2-Methyl-2-{3-methyl-4-[5-(trifluoromethyl)pyridin-2-yl]piperazin-1-yl}propanoyl)amino]adamantane-1-carboxylic acid

EXAMPLE 167A

2-Methyl-1-[5-(trifluoromethyl)pyridin-2-yl]piperazine

A suspension of 3-methyl-piperazine-1-carboxylic acid tert-butyl ester (200 mg, 1 mmoles), 2-bromo-5-trifluoromethyl-pyridine (339 mg, 1.5 mmoles), sodium tert-butoxide (144 mg, 1.5 mmoles), tris(dibenzylideneacetone)dipalladium (4.6 mg, 0.005 mmoles) and tri-t-butylphosphine (8 mg, 0.04 mmoles) in toluene (2 mL) was heated to 120° C. overnight. The mixture was cooled, filtered and the filtrate concentrated under reduced pressure. The crude residue was purified by column chromatography (silica gel, 0-20% acetone in hexane), and the ester was hydrolyzed stirring in 4N HCl in dioxane (5 mL) for 4 hours at room temperature. The solvent was concentrated under reduced pressure to provide the hydrochloride of the title compound. MS(APCI+) m/z 246 (M+H)$^+$.

EXAMPLE 167B (E)-4-[(2-Methyl-2-{3-methyl-4-[5-(trifluoromethyl)pyridin-2-yl]piperazin-1-yl}propanoyl)amino]adamantane-1-carboxylic acid The title compound was prepared according to the procedure outlined in Example 34C substituting 2-methyl-1-[5-(trifluoromethyl)pyridin-2-yl]piperazine from Example 167A for 1-(5-chloro-2-pyridyl)piperazine. $^1H$ NMR (400 MHz, Py-$d_5$) δ 8.7 (s, 1H), 7.8 (d, J=8.8 Hz, 1H), 7.73 (d, J=7.6 Hz, 1H), 6.85 (d, J=8.9 Hz, 1H), 4.32 (d, J=7.7 Hz, 1H), 3.22 (t, J=12.5 Hz, 1H), 2.86 (d, J=10.7 Hz, 1H), 2.76 (d, J=11.3 Hz, 1H), 2.45 (d, J=9 Hz, 1H), 2.15-2.3 (m, 8H), 2.1 (s, 1H), 1.97 (s, 1H), 1.89 (d, J=12.5 Hz, 2H), 1.63 (d, J=12.5 Hz, 2H), 1.34 (d, J=6.7 Hz, 3H), 1.32 (s, 6H); MS(ESI+) m/z 509 (M+H)$^+$.

EXAMPLE 168

(E)-4-({2-[4-(4-Cyanophenyl)-3,5-dimethyl-1H-pyrazol-1-yl]-2-methylpropanoyl}amino)adamantane-1-carboxylic acid

EXAMPLE 168A 2-(4-Bromo-3,5-dimethyl-1H-pyrazol-1-yl)-2-methylpropanoic acid To a cold (0° C.), well stirred suspension of NaOH (1.6 g, 40 mmoles) and 4-bromo-3,5-dimethylpyrazole (1.75 g, 10 mmoles) in acetone (100 mL), was added 2-(trichloromethyl)-propan-2-ol (3.54 g, 20 mmoles) portion-wise over 1 hour. The mixture was allowed to warm to room temperature overnight. The solvent was evaporated under reduced pressure. The residue was dissolved in water (100 mL) and washed with ether (50 mL). The aqueous phase was separated and acidified with conc. HCl to pH=3. The mixture was extracted with $CH_2Cl_2$ (3×50 mL) and the combined organics dried over $Na_2SO_4$. A colorless oil was obtained after the removal of the solvent under reduced pressure. MS(DCI+) m/z 263 (M+H)$^+$.

EXAMPLE 168B

Methyl (E)-4-{[2-(4-bromo-3,5-dimethyl-1H-pyrazol-1-yl)-2-methylpropanoyl]amino}adamantane-1-carboxylate To a DMF (20 mL) solution of 2-(4-bromo-3,5-dimethyl-1H-pyrazol-1-yl)-2-methylpropanoic acid from Example 168A (2.00 g, 7.66 mmoles) and methyl 4-adamantamine-1-carboxylate from Example 15B (1.71 g, 7.66 mmoles), was added O-(1H-benzotriazol-1-yl)-N,N,N'N'-tetramethyluronium tetrafluoroborate (TBTU 3.36 g, 10.47 mmoles) followed by N,N-diisopropylethylamine (DIEA, 6.1 mL, 34.9 mmoles). The mixture was stirred at room temperature overnight and then diluted with ethyl acetate (150 mL). The organic layer was washed with water (3×30 mL), brine (30 mL), dried over $Na_2SO_4$, filtered, concentrated under reduced pressure to provide the crude product as dark brown oil. The residue was chromatographed on a Biotage flash 40 M eluting with 70:30 hexane/ethyl acetate to afford the title compound. MS(ESI) m/z 452 (M+H)$^+$.

EXAMPLE 168C

Methyl (E)-4-({2-[4-(4-cyanophenyl)-3,5-dimethyl-1H-pyrazol-1-yl]-2-methylpropanoyl}amino)adamantane-1-carboxylate To a solution of methyl (E)-4-{[2-(4-bromo-3,5-dimethyl-1H-pyrazol-1-yl)-2-methylpropanoyl]amino}adamantane-1-carboxylate from Example 168B (91 mg, 0.2 mmoles) in isopropanol (1 mL) was added 4-cyanophenylboronic acid (36 mg, 0.24 mmoles), Pd(PPh$_3$)$_2$Cl$_2$ (15 mg, 0.02 mmoles), and K$_2$CO$_3$ (83 mg, 0.6 mmoles). The mixture was heated to 85° C. for 3 hours in sealed tube. It was diluted with ethyl acetate (10 mL) and washed with water (2×1 mL) and brine. The organic layer was dried over sodium sulfate, filtered, concentrated under reduced pressure and purified by flash chromatography with 30% ethyl acetate/hexane to provide the title compound. MS(ESI) m/z 475 (M+H)$^+$.

EXAMPLE 168D (E)-4-({2-[4-(4-Cyanophenyl)-3,5-dimethyl-1H-pyrazol-1-yl]-2-methylpropanoyl}amino)adamantane-1-carboxylic acid To a solution of methyl (E)-4-({2-[4-(4-cyanophenyl)-3,5-dimethyl-1H-pyrazol-1-yl]-2-methylpropanoyl}amino)adamantane-1-carboxylate from Example 168C (50 mg, 0.11 mmoles) in THF (0.2 mL) and water (0.1 mL) at room temperature was added lithium hydroxide (27 mg, 0.66 mmoles). The resultant mixture was stirred at room temperature overnight. The reaction was acidified with a 1N HCl solution to pH=3 and extracted with $CH_2Cl_2$ (3×10 mL). The combined organic layers were dried over sodium sulfate, filtered, and concentrated to provide the title compound. $^1$H NMR (300 MHz, CD$_3$OD) δ 7.79 (d, J=8.24 Hz, 2H), 7.43 (d, J=8.24 Hz, 2H), 6.14 (m, 1H), 3.92 (m, 1H), 2.24 (s, 3H), 2.22 (s, 3H), 1.87-1.99 (m, 9H), 1.86 (s, 6H), 1.51-1.57 (m, 4H); MS(ESI) m/z 461 (M+H)$^+$.

EXAMPLE 169

(E)-4-({2-[4-(4-Cyanophenyl)-3,5-dimethyl-1H-pyrazol-1-yl]-2-methylpropanoyl}amino)adamantane-1-carboxamide To a DMF (0.2 mL) solution of (E)-4-({2-[4-(4-cyanophenyl)-3,5-dimethyl-1H-pyrazol-1-yl]-2-methylpropanoyl}amino)adamantane-1-carboxylic acid from Example 168D (30 mg, 0.065 mmoles), was added O-(1H-benzotriazol-1-yl)-N,N,N'N'-tetramethyluronium tetrafluoroborate (32 mg, 0.098 mmoles) followed by N,N-diisopropylethylamine (0.057 mL, 0.326 mmoles) and ammonium hydroxide (0.018 mL, 0.13 mmoles). The mixture was stirred at room temperature overnight. It was diluted with ethyl acetate (10 mL), washed with water (2×2 mL) and brine (3 mL), dried over $Na_2SO_4$. The crude product was obtained after concentration. The residue was purified by HPLC to afford the title compound. $^1$H NMR (500 MHz, CDCl$_3$) δ 7.71 (d, J=8.24 Hz, 2H), 7.29 (d, J=8.24 Hz, 2H), 6.09 (s, 1H), 5.67 (s, 1H), 5.56 (m, 1H), 3.97 (d, J=7.93 Hz, 1H), 2.27 (s, 3H), 2.23 (s, 3H), 1.91-1.97 (m, 7H), 1.90 (s, 6H), 1.83-1.86 (m, 2H), 1.52 (m, 2H), 1.36 (m, 2H); MS(ESI) m/z 460 (M+H)$^+$.

EXAMPLE 171

(E)-4-{[2-Methyl-N-(3-methylphenyl)alanyl]amino}adamantane-1-carboxamide

The title compound was prepared according to the method of Example 51 substituting m-tolylamine for phenylamine. $^1$H NMR (500 MHz, DMSO-d6) δ 7.26 (d, J=8.24 Hz, 1H), 6.92-6.99 (m, 2H), 6.70 (s, 1H), 6.44 (d, J=7.32 Hz, 1H), 6.32-6.37 (m, 2H), 5.71 (s, 1H), 3.78 (d, J=7.93 Hz, 1H), 2.15 (s, 3H), 1.73-1.85 (m, 6H), 1.71 (s, 1H), 1.67 (s, 2H), 1.44 (s, 1H), 1.39-1.42 (m, 1H), 1.36 (s, 6H), 1.32 (s, 1H), 1.30 (s, 1H); MS(ESI+) m/z 370 (M+H)$^+$.

EXAMPLE 172 tert-Butyl-4-(2-{[(E)-5-(aminocarbonyl)-2-adamantyl]amino}-1,1-dimethyl-2-oxo ethyl)piperazine-1-carboxylate A solution of piperazine-1-carboxylic acid tert-butyl ester (20.0 mg, 0.11 mmoles) in anhydrous toluene (2 mL) was treated with sodium hydride (3.6 mg, 1.5 mmoles). The reaction mixture was stirred at room temperature under nitrogen for 2 hours. Then (E)-4-(2-bromo-2-methyl-propionylamino)-adamantane-1-carboxamide (35.0 mg, 0.1 mmol) from Example 44B was added to the mixture. This reaction mixture was stirred at 100° C. under a nitrogen atmosphere for 12 hours. The reaction mixture was concentrated under reduced pressure. The residue was purified by reverse phase HPLC to provide the title compound. $^1$H NMR (500 MHz, DMSO-d$_6$) δ 7.63 (d, J=8.24 Hz, 1H), 7.00 (s, 1H), 6.72 (s, 1H), 3.76 (d, J=8.24 Hz, 1H), 2.34-2.41 (m, 4H), 1.92 (m, 2H), 1.86 (m, 3H), 1.81-1.84 (m, 4H), 1.73-1.78 (m, 3H), 1.67-1.72 (m, 2H), 1.52-1.55 (m, 1H), 1.49-1.52 (m, 2H), 1.39 (s, 9H), 1.07-1.12 (s, 6H); MS(ESI+) m/z 449 (M+H)$^+$.

EXAMPLE 173

(2R)-2-[(3R)-3-Fluoropyrrolidin-1-yl]-N-[(E)-5-hydroxy-2-adamantyl]propanamide

EXAMPLE 173A (2S)-2-Bromo-N-[(E)-5-hydroxy-2-adamantyl]propanamide

A solution of (2S)-2-bromo-propionic acid (1.53 g, 10 mmoles) in DCM (100 mL) was treated with hydroxybenzotriazole hydrate (HOBt) (1.68 g, 11 mmoles), (E)- and (Z)-5-hydroxy-2-adamantamine (1.67 g, 10 mmoles) from Example 13A and 15 minutes later with (3-dimethylaminopropyl)-3-ethylcarbodiimide HCl (EDCI) (2.4 g, 12 mmoles). The mixture was stirred overnight at room temperature after which the DCM was removed under reduced pressure and the residue was partitioned between water and ethyl acetate. The aqueous layer was extracted with ethyl acetate and the combined organic extracts washed with saturated sodium bicarbonate, water, dried (MgSO$_4$) and filtered. The filtrate was concentrated under reduced pressure and the crude product purified (silica gel, 10-40% acetone in hexane) to provide the title compound. MS(APCI+) m/z 302, 304 (M+H)$^+$.

EXAMPLE 173B (2R)-2-[(3R)-3-Fluoropyrrolidin-1-yl]-N-[(E)-5-hydroxy-2-adamantyl]propanamide A solution of (2S)-2-bromo-N-[(E)-5-hydroxy-2-adamantyl]propanamide (100 mg, 0.33 mmoles) from Example 173A and the hydrochloride of (3R)-3-fluoropyrrolidine (41 mg, 0.33 mmoles) in DCM (1 mL) and TEA (0.1 mL) was stirred overnight at 50° C. The DCM was removed under reduced pressure, and the residue was purified on reverse phase HPLC to provide the title compound. $^1$H NMR (300 MHz, CDCl$_3$) δ 7.42 (s, 1H), 5.12-5.23 (d, J=55 Hz, 1H), 4.01 (d, J=8.5 Hz, 1H), 2.93-3.16 (m, 3H), 2.20-2.50 (m, 2H), 2.23-2.1 (m, 5H), 1.9-1.88 (m, 2H), 1.7-1.8 (m, 6H), 1.5-1.53 (m, 2H) 1.33 (d, J=5.2 Hz, 3H); MS(APCI+) m/z 311 (M+H)$^+$.

EXAMPLE 174

(E)-4-({2-[4-(2-Bromophenyl)piperazin-1-yl]-2-methylpropanoyl}amino)adamantane-1-carboxylic acid

EXAMPLE 174A

Methyl (E)-4-({2-[4-(2-bromophenyl)piperazin-1-yl]-2-methylpropanoyl}amino)adamantane-1-carboxylate The title compound was prepared according to the method of Example 34C substituting 1-(2-bromo-phenyl)-piperazine for 1-(5-chloro-2-pyridyl)piperazine and isolating the ester before hydrolysis to the acid. MS(DCI) m/z 518 (M+H)$^+$.

EXAMPLE 174B (E)-4-({2-[4-(2-Bromophenyl)piperazin-1-yl]-2-methylpropanoyl}amino)adamantane-1-carboxylic acid A solution of methyl (E)-4-({2-[4-(2-bromophenyl)piperazin-1-yl]-2-methylpropanoyl}amino)adamantane-1-carboxylate (50 mg, 0.10 mmol) in tetrahydrofuran (1 mL) was treated with potassium trimethylsilanolate (25 mg, 0.19 mmol, tech. 90%), and the reaction mixture warmed to 40° C. for sixteen hours. The reaction mixture was cooled to 23° C., diluted with methylene chloride, and quenched with 1N HCl (190 µL). The layers were separated and the aqueous phase extracted additionally with methylene chloride (2×). The combined organic phases were dried (Na$_2$SO$_4$), filtered, and concentrated under reduced pressure. The solid residue was triturated with diethyl ether to afford the title compound. $^1$H NMR (400 MHz, Py-d$_5$) δ 7.90 (d, J=7.98 Hz, 1H), 7.71 (d, J=7.98 Hz, 1H), 7.33 (dd, J=7.67 Hz, 1H), 7.15-7.20 (m, 1H), 6.98 (dd, J=7.52 Hz, 1H), 4.32 (d, J=7.67 Hz, 1H), 3.05-3.22 (m, 4H), 2.67-2.80 (m, 4H), 2.20-2.35 (m, 4H), 2.15 (d, J=13.20 Hz, 4H), 1.84-2.00 (m, 3H), 1.63 (d, J=12.58 Hz, 2H), 1.35 (s, 6H); MS(DCI) m/z 504 (M+H)$^+$.

EXAMPLE 175

(E)-4-{[N-(3-Chlorophenyl)-2-methylalanyl]amino}adamantane-1-carboxamide

The title compound was prepared according to the method of Example 51 substituting 3-chloro-phenylamine for phenylamine. $^1$H NMR (400 MHz, DMSO-d$_6$) δ 7.18 (d, J=7.98 Hz, 1H), 7.08 (t, J=8.13 Hz, 1H), 6.94 (s, 1H), 6.67 (d, J=1.84 Hz, 1H), 6.62 (dd, J=7.98, 1.23 Hz, 1H), 6.51 (t, J=2.15 Hz, 1H), 6.45-6.49 (m, 1H), 6.13 (s, 1H), 3.75-3.81 (m, 1H), 1.76-1.82 (m, J=4.91, 4.30 Hz, 5H), 1.70-1.76 (m, 2H), 1.65-1.69 (m, J=3.07 Hz, 2H), 1.44-1.47 (m, 1H), 1.40-1.44 (m, J=1.23 Hz, 1H), 1.38 (s, 6H), 1.31-1.34 (m, 1H), 1.27-1.31 (m, 1H); MS(ESI+) m/z 390 (M+H)$^+$.

EXAMPLE 176

(E)-4-{[N-(3-Methoxyphenyl)-2-methylalanyl]amino}adamantane-1-carboxamide

The title compound was prepared according to the method of Example 51 substituting 3-methoxy phenylamine for phenylamine. $^1$H NMR (400 MHz, DMSO-d6) δ 6.91-7.04 (m, 2H), 6.68 (d, J=5.52 Hz, 1H), 6.20 (dd, J=8.13, 1.99 Hz, 1H), 6.07-6.17 (m, 2H), 5.81 (s, 1H), 3.76 (t, J=6.14 Hz, 2H), 3.64 (s, 3H), 1.98 (s, 2H), 1.88 (s, 2H), 1.70-1.84 (m, 2H), 1.68 (s, 2H), 1.46 (s, 1H), 1.43 (s, 1H), 1.36 (s, 6H), 1.33 (s, 1H), 1.30 (s, 1H); MS(ESI+) m/z 386 (M+H)$^+$.

EXAMPLE 177

(E)-4-({2-[4-(4-Cyanophenyl)-3,5-dimethyl-1H-pyrazol-1-yl]-2-methylpropanoyl}amino)-N-(1,3-thiazol-5-ylmethyl)adamantane-1-carboxamide The title compound was prepared according to the method of Example 169 substituting C-thiazol-5-yl-methylamine for ammonium hydroxide. $^1$H NMR (300 MHz, CDCl$_3$) δ 8.87 (s, 1H), 7.70 (d, J=8.24 Hz, 2H), 7.30 (s, 1H), 7.29 (d, J=8.24 Hz, 2H), 6.55 (s, 1H), 5.53 (m, 1H), 4.56-4.62 (m, 2H), 3.96 (m, 1H), 2.26 (s, 3H), 2.22 (s, 3H), 1.91-2.01 (m, 7H), 1.89 (s, 6H), 1.82-1.87 (m, 2H), 1.46-1.55 (m, 2H), 1.30-1.39 (m, 2H); MS(ESI) m/z 557 (M+H)$^+$.

EXAMPLE 178

(E)-4-({2-[4-(6-Chloropyrimidin-4-yl)piperazin-1-yl]-2-methylpropanoyl}amino)adamantane-1-carboxylic acid A solution of methyl (E)-4-(2-methyl-2-piperazin-1-yl-propionylamino)-adamantane-1-carboxylate from Example 164B (1.0 mmole), 4,6-dichloro-pyrimidine (1.2 mmoles), and dioxane (0.8 mL) was heated in a microwave reactor to 130° C. for 1 hour. The cooled reaction mixture was directly purified by HPLC. The methyl ester was hydrolyzed with aq. LiOH in methanol to afford the title compound. $^1$H NMR (300 MHz, CD$_3$OD), δ 8.28 (s, 1H), 6.83 (s, 1H), 3.93 (bs, 1H), 3.75 (bs, 4H), 2.62 (t, J=6 Hz, 4H), 2.02-1.63 (m, 14H), 1.22 (s, 6H); MS(ESI) m/z 462 (M+H)$^+$.

EXAMPLE 179

(E)-4-({2-[4-(6-Chloropyridazin-3-yl)piperazin-1-yl]-2-methylpropanoyl}amino)adamantane-1-carboxylic acid The title compound was prepared according to the method of Example 178 substituting 3,6-dichloro-pyridazine for 4,6-dichloro-pyrimidine. $^1$H NMR (300 MHz, CD$_3$OD), δ 7.44 (d, J=9 Hz, 1H), 7.53 (d, J=9 Hz, 1H), 3.93 (bs, 1H), 3.65 (bs, 4H), 2.66 (t, J=6 Hz, 4H), 2.02-1.63 (m, 14H), 1.24 (s, 6H); MS(ESI), m/z 462 (M+H)$^+$.

EXAMPLE 180

(E)-4-({2-[4-(2-Chloropyrimidin-4-yl)piperazin-1-yl]-2-methylpropanoyl}amino)adamantane-1-carboxylic acid The title compound was prepared according to the method of Example 178 substituting 2,4-dichloro-pyrimidine for 4,6-dichloro-pyrimidine. $^1$H NMR (300 MHz, CD$_3$OD), δ 8.00 (d, J=6 Hz, 1H), 6.72 (d, J=6 Hz, 1H), 3.93 (bs, 1H), 3.75 (bs, 4H), 2.63 (t, J=6 Hz, 4H), 2.07-1.63 (m, 14H), 1.24 (s, 6H); MS(ESI), m/z 462 (M+H)$^+$.

EXAMPLE 181

N-[({[E]-4-[(2-Methyl-2-{4-[5-(trifluoromethyl)pyridin-2-yl]piperazin-1-yl}propanoyl)amino]-1-adamantyl}amino)carbonyl]glycine

EXAMPLE 181A

N-[(E)-5-Isocyanato-2-adamantyl]-2-methyl-2-{4-[5-(trifluoromethyl)pyridin-2-yl]piperazin-1-yl}propanamide A solution of (E)-4-{2-methyl-2-[4-(5-trifluoromethyl-pyridin-2-yl)-piperazin-1-yl]-propionylamino}-adamantane-1-carboxylic acid (1.48 g, 3 mmoles) from Example 15D in toluene (10 mL) was treated with diphenylphosphoryl azide (991 mg, 3.6 mmoles) and TEA (0.54 mL), and the reaction mixture was stirred at 90° C. overnight. The solvent was removed under reduced pressure to provide the crude title compound. MS(APCI+) m/z 492 (M+H)$^+$.

EXAMPLE 181B

N-[({[E]-4-[(2-Methyl-2-{4-[5-(trifluoromethyl)pyridin-2-yl]piperazin-1-yl}propanoyl)amino]-1-adamantyl}amino)carbonyl]glycine A solution of N-[(E)-5-isocyanato-2-adamantyl]-2-methyl-2-{4-[5-(trifluoromethyl)pyridin-2-yl]piperazin-1-yl}propanamide (250 mg, 0.51 mmoles) from Example 181A in dioxane (0.5 mL) was treated with the hydrochloride salt of glycine methyl ester (125.6 mg, 1 mmole), and the reaction mixture was stirred at 70° C. overnight. The dioxane was concentrated under reduced pressure. The crude product was purified (silica gel, 10-40% acetone in hexane) to provide methyl ester of the title that was hydrolyzed by stirring in 3N HCl at 60° C. overnight. The reaction mixture was cooled to 23° C. and concentrated under reduced pressure to provide the hydrochloride salt of the title compound. $^1$H NMR (500 MHz, Py-d$_5$) δ 8.68 (s, 1H), 7.79 (ddd, J=6.10, 2.90, 2.59 Hz, 2H), 6.87 (d, J=9.15 Hz, 1H), 6.65 (s, 1H), 4.45 (s, 2H), 4.28 (d, J=7.93 Hz, 1H), 3.73 (s, 4H), 2.55 (t, J=4.73 Hz, 4H), 2.28-2.37 (m, 6H), 2.12 (s, 2H), 2.00 (s, 1H), 1.79 (m, 2H), 1.58 (m, 2H), 1.29 (s, 6H); MS(ESI+) m/z 567 (M+H)$^+$.

EXAMPLE 182

(E)-4-({2-[4-(5-Cyanopyridin-2-yl)piperazin-1-yl]-2-methylpropanoyl}amino)adamantane-1-carboxylic acid The title compound was prepared according to the method of Example 34C substituting 6-piperazin-1-yl-nicotinonitrile for 1-(5-chloro-2-pyridyl)piperazine. $^1$H NMR (500 MHz, Py-d5) δ 8.68 (d, J=2.44 Hz, 1H), 7.84 (d, J=7.93 Hz, 1H), 7.77 (dd, J=8.85, 2.44 Hz, 1H), 6.82 (d, J=9.15 Hz, 1H), 4.32 (d, J=8.24 Hz, 1H), 3.74 (s, 4H), 2.55 (t, J=4.88 Hz, 4H), 2.22-2.31 (m, 4H), 2.18 (s, 2H), 2.12 (d, J=1.83 Hz, 2H), 1.99 (s, 1H), 1.87 (m, 2H), 1.64 (m, 2H), 1.31 (s, 6H), MS(ESI+) m/z 452 (M+H)$^+$.

EXAMPLE 183

(E)-4-({2-[4-(3-Chloro-5-cyanopyridin-2-yl)piperazin-1-yl]-2-methylpropanoyl}amino)adamantane-1-carboxylic acid

EXAMPLE 183A 5,6-Dichloronicotinamide

The title compound was prepared according to the method of Example 31B substituting 5,6-dichloro-nicotinic acid for (E)-4-(2-bromo-propionylamino)-adamantane-1-carboxylic acid. MS(APCI+) m/z 192 (M+H)$^+$.

EXAMPLE 183B 5,6-Dichloronicotinonitrile

The title compound was prepared according to the method of Example 83A substituting 5,6-dichloronicotinamide from Example 183A for (E)-4-(2-bromo-2-methyl-propionylamino)-adamantane-1-carboxamide.

EXAMPLE 183C

5-Chloro-6-piperazin-1-ylnicotinonitrile

The title compound was prepared according to the method of Example 161A substituting 5,6-dichloronicotinonitrile from Example 183B for 3-chloro-4-fluoro-benzonitrile. MS(APCI+) m/z 223 (M+H)$^+$.

EXAMPLE 183D (E)-4-({2-[4-(3-Chloro-5-cyanopyridin-2-yl)piperazin-1-yl]-2-methylpropanoyl}amino)adamantane-1-carboxylic acid The title compound was prepared according to the method of Example 34C substituting 5-chloro-6-piperazin-1-ylnicotinonitrile from Example 183C for 1-(5-chloro-2-pyridyl) piperazine. $^1$H NMR (500 MHz, Py-d5) δ 8.59 (d, J=1.83 Hz, 1H), 8.06 (d, J=1.83 Hz, 1H), 7.86 (d, J=8.24 Hz, 1H), 4.33 (d, J=8.24 Hz, 1H), 3.69 (s, 4H), 2.64-2.72 (m, 4H), 2.22-2.32 (m, 4H), 2.17 (s, 2H), 2.12 (s, 2H), 1.96 (s, 1H), 1.86 (m, 2H), 1.62 (m, 2H), 1.35 (s, 6H); MS(ESI+) m/z 486 (M+H)$^+$.

EXAMPLE 184

(E)-4-({2-Methyl-2-[4-(1,3-thiazol-2-yl)piperazin-1-yl]propanoyl}amino)adamantane-1-carboxylic acid The title compound was prepared according to the method of Example 34C substituting 1-thiazol-2-yl-piperazine for 1-(5-chloro-2-pyridyl)piperazine. $^1$H NMR (400 MHz, CDCl$_3$) δ 7.72 (d, J=8.0 Hz, 1H), 7.16 (d, J=3.7 Hz, 1H), 6.55 (d, J=3.7 Hz, 1H), 3.38 (bs, 4H), 2.99 (ap t, J=5.1 Hz, 1H), 2.61 (bs, 4H), 1.79-1.94 (m, 9H), 1.51-1.61 (m, 4H), 1.18 (s, 6H); MS(ESI) m/z 433 (M+H)$^+$.

EXAMPLE 185

(E)-4-{[N-(4-Methoxyphenyl)-2-methylalanyl]amino}adamantane-1-carboxamide

A solution of 4-methoxy-phenylamine (25.0 mg, 0.2 mmoles) in anhydrous toluene (3 mL) was treated with sodium hydride (7.2 mg, 3.0 mmoles). The reaction mixture was stirred at room temperature under nitrogen for 2 hours. Then (E)-4-(2-bromo-2-methyl-propionylamino)-adamantane-1-carboxamide (35.0 mg, 0.1 mmol) from Example 44B was added to the mixture. This reaction mixture was stirred at 100° C. under nitrogen for 12 hours. The reaction mixture was concentrated under reduced pressure. The residue was purified by reverse phase HPLC to provide the title compound. $^1$H NMR (500 MHz, DMSO-d$_6$) δ 7.41 (d, J=8.01 Hz, 1H) 6.97 (s, 1H) 6.67-6.77 (m, J=8.85 Hz, 3H) 6.51 (d, J=8.85 Hz, 2H) 5.44 (s, 1H) 3.79 (d, J=7.94 Hz, 1H) 3.63 (s, 3H) 1.73-1.86 (m, 7H) 1.69 (s, 2H) 1.47 (m, 2H) 1.34-1.38 (m, 2H) 1.32 (s, 6H); MS(ESI+) m/z 386 (M+H)$^+$.

EXAMPLE 186

(E)-4-({N-[4-(Dimethylamino)phenyl]-2-methylalanyl}amino)adamantane-1-carboxamide The title compound was prepared according to the method of Example 185 substituting N,N-dimethyl-benzene-1,4-diamine (27.0 mg, 0.2 mmoles) for 4-methoxy-phenylamine. $^1$H NMR (500 MHz, DMSO-d$_6$) δ 7.48 (s, 1H), 6.97 (s, 1H), 6.71 (s, 1H), 6.58-6.69 (m, 2H), 6.44-6.59 (m, 2H), 5.19-5.40 (m, 1H), 3.80 (s, 1H), 2.74 (s, 6H), 1.94-2.09 (m, 1H), 1.72-1.91 (m, 6H), 1.69 (s, 2H), 1.43-1.56 (m, 2H), 1.33-1.41 (m, 1H), 1.31 (s, 6H), 1.21-1.27 (m, 1H); MS(ESI+) m/z 399 (M+H)$^+$.

EXAMPLE 187

(E)-4-({2-Methyl-N-[4-(trifluoromethyl)phenyl]alanyl}amino)adamantane-1-carboxamide The title compound was prepared according to the method of Example 185 substituting 4-trifluoromethyl-phenylamine (32.2 mg, 0.2 mmoles) for 4-methoxy-phenylamine. $^1$H NMR (500 MHz, DMSO-d$_6$) δ 7.40 (d, J=8.54 Hz, 2H), 7.14 (d, J=7.93 Hz, 1H), 6.96 (s, 1H), 6.70 (s, 1H), 6.62 (d, J=8.54 Hz, 2H), 6.49 (s, 1H), 3.78 (d, J=7.81 Hz, 1H), 1.93-2.10 (m, 1H), 1.72-1.85 (m, 6H), 1.62-1.72 (m, 3H), 1.42 (s, 6H), 1.38 (s, 1H), 1.21-1.31 (m, 2H); MS(ESI+) m/z 424 (M+H)$^+$.

EXAMPLE 188

(E)-4-({2-Methyl-N-[3-(trifluoromethyl)phenyl]alanyl}amino)adamantane-1-carboxamide The title compound was prepared according to the method of Example 185 substituting 3-trifluoromethyl-phenylamine (32.2 mg, 0.2 mmoles) for 4-methoxy-phenylamine. $^1$H NMR (500 MHz, DMSO-d$_6$) δ 7.29 (t, J=7.93 Hz, 1H), 6.96 (s, 1H), 6.91 (d, J=7.63 Hz, 1H), 6.79 (d, J=8.24 Hz, 1H), 6.75 (s, 1H), 6.70 (s, 1H), 6.32 (s, 1H), 3.78 (d, J=7.63 Hz, 1H), 1.71-1.85 (m, 7H), 1.63-1.71 (m, 2H), 1.40 (s, 6H), 1.37 (s, 2H), 1.23-1.31 (m, 2H); MS(ESI+) m/z 424 (M+H)$^+$.

EXAMPLE 189

(E)-4-({2-[4-(2-Hydroxyphenyl)piperazin-1-yl]-2-methylpropanoyl}amino)adamantane-1-carboxylic acid

EXAMPLE 189A

Methyl (E)-4-({2-[4-(2-methoxyphenyl)piperazin-1-yl]-2-methylpropanoyl}amino)adamantane-1-carboxylate The title compound was prepared according to the method of Example 34C substituting 1-(2-methoxy-phenyl)-piperazine for 1-(5-chloro-2-pyridyl)piperazine and isolating the ester before hydrolysis to the acid. MS(DCI) m/z 470 (M+H)$^+$.

EXAMPLE 189B

Methyl (E)-4-({2-[4-(2-hydroxyphenyl)piperazin-1-yl]-2-methylpropanoyl}amino)adamantane-1-carboxylate To a 0° C. solution of methyl (E)-4-({2-[4-(2-methoxyphenyl)piperazin-1-yl]-2-methylpropanoyl}amino)adamantane-1-carboxylate from Example 189A (20 mg, 0.043 mmoles) in methylene chloride (2 mL) was added boron tribromide (0.26 mL, 1.0 M solution in methylene chloride), and the reaction mixture warmed to 23° C. for 1 hour and 45° C. for 16 hours. The reaction mixture was cooled to 0° C. and methanol (1 mL) was slowly added. The reaction was warmed to 40° C. for 4 hours, cooled to 23° C., and concentrated under reduced pressure. The residue was taken up in ethyl acetate and washed with saturated aqueous NaHCO$_3$ and brine. The ethyl acetated solution was dried (Na$_2$SO$_4$), filtered, and concentrated under reduced pressure. The residue was purified (flash silica gel, 0-40% methanol in methylene chloride) to provide the title compound. MS(DCI) m/z 456 (M+H)$^+$.

EXAMPLE 189C (E)-4-({2-[4-(2-Hydroxyphenyl)piperazin-1-yl]-2-methylpropanoyl}amino)adamantane-1-carboxylic acid The title compound was prepared according to the method of Example 174B substituting methyl (E)-4-({2-[4-(2-hydroxyphenyl)piperazin-1-yl]-2-methylpropanoyl}amino)adamantane-1-carboxylate for methyl (E)-4-({2-[4-(2-bromophenyl)piperazin-1-yl]-2-methylpropanoyl}amino) adamantane-1-carboxylate. $^1$H NMR (500 MHz, Py-d$_5$) δ ppm 7.98 (d, J=8.24 Hz, 1H), 7.28 (dd, J=7.93, 1.53 Hz, 1H), 7.22-7.24 (m, 1H), 7.10-7.15 (m, 1H), 7.00-7.05 (m, 1H), 4.31 (d, J=7.93 Hz, 1H), 3.27 (s, 4H), 2.68 (s, 4H), 2.20-2.33 (m, 4H), 2.10-2.19 (m, J=20.14 Hz, 4H), 1.93-1.98 (m, 1H), 1.87-1.93 (m, J=13.12 Hz, 2H), 1.58-1.65 (m, 2H), 1.31 (s, 6H); MS(APCI) m/z 442 (M+H)$^+$.

EXAMPLE 190

4-(2-{[(E)-5-(Aminocarbonyl)-2-adamantyl]amino}-1,1-dimethyl-2-oxoethyl)-N-(tert-butyl)piperazine-1-carboxamide

EXAMPLE 190A

Methyl (E)-4-[(2-{4-[(tert-butylamino)carbonyl] piperazin-1-yl}-2-methylpropanoyl)amino]adamantane-1-carboxylate To a 23° C. solution of methyl (E)-4-(2-methyl-2-piperazin-1-yl-propionylamino)-adamantane-1-carboxylate from Example 164B (50 mg, 0.114 mmoles) and methylene chloride (1 mL) was added tert-butyl isocyanate (12 mg, 0.114 mmoles) and DIEA (37 mg, 0.285 mmoles). The reaction mixture was stirred for 1 hour. The reaction mixture was purified (flash silica gel, 0-50% acetone in methylene chloride) to afford the title compound. MS(DCI) m/z 463 (M+H)$^+$.

EXAMPLE 190B (E)-4-[(2-{4-[(tert-Butylamino)carbonyl]piperazin-1-yl}-2-methylpropanoyl)amino]adamantane-1-carboxylic acid The title compound was prepared according to the method of Example 174B substituting methyl (E)-4-[(2-{4-[(tert-butylamino)carbonyl]piperazin-1-yl}-2-methylpropanoyl) amino]adamantane-1-carboxylate for methyl (E)-4-({2-[4-(2-bromophenyl)piperazin-1-yl]-2-methylpropanoyl}amino)adamantane-1-carboxylate. MS(DCI) m/z 449 (M+H)$^+$.

EXAMPLE 190C 4-(2-{[(E)-5-(Aminocarbonyl)-2-adamantyl]amino}-1,1-dimethyl-2-oxoethyl)-N-(tert-butyl)piperazine-1-carboxamide The title compound was prepared according to the method of Example 23 substituting (E)-4-[(2-{4-[(tert-butylamino) carbonyl]piperazin-1-yl}-2-methylpropanoyl)amino]adamantane-1-carboxylic acid from Example 190B for (E)-4-{2-methyl-2-[4-(5-trifluoromethyl-pyridin-2-yl)-piperazin-1-yl]-propionylamino}-adamantane-1-carboxylic acid. $^1$H NMR (400 MHz, Py-d$_5$) δ 7.80 (d, J=7.98 Hz, 1H), 7.59-7.65 (m, 2H), 6.09 (s, 1H), 4.23 (d, J=7.98 Hz, 1H), 3.59-3.68 (m, 4H), 2.45 (t, J=4.60 Hz, 4H), 2.16-2.29 (m, 4H), 2.11-2.16 (m, 2H), 2.00-2.06 (m, 2H), 1.87-1.93 (m, 1H), 1.72-1.80 (m, 2H), 1.49-1.57 (m, 11H), 1.22 (s, 6H); MS(DCI) m/z 448 (M+H)$^+$.

EXAMPLE 191

N-[(E)-5-(Formylamino)-2-adamantyl]-2-methyl-2-{4-[5-(trifluoromethyl)pyridin-2-yl]piperazin-1-yl}propanamide

EXAMPLE 191A

N-[(E)-5-amino-2-adamantyl]-2-methyl-2-{4-[5-(trifluoromethyl)pyridin-2-yl]piperazin-1-yl}propanamide A solution of N-[(E)-5-isocyanato-adamantan-2-yl]-2-[4-(5-trifluoromethyl-pyridin-2-yl)-piperazin-1-yl]-isobutyramide (1.47 g, 1.5 mmoles) from Example 181A in dioxane (5 mL) was treated with 5N HCl and stirred at 70° C. overnight. The solvents were concentrated under reduced pressure to provide the crude hydrochloride of the title compound. MS(APCI+) m/z 466 (M+H)$^+$.

EXAMPLE 191B

N-[(E)-5-(Formylamino)-2-adamantyl]-2-methyl-2-{4-[5-(trifluoromethyl)pyridin-2-yl]piperazin-1-yl}propanamide A solution of N-[(E)-5-amino-adamantan-2-yl]-2-[4-(5-trifluoromethyl-pyridin-2-yl)-piperazin-1-yl]-isobutyramide (83 mg, 0.1 mmoles) in ethyl formate (0.5 mL) and TEA (0.1 mL) was stirred at 70° C. for 3 days. The solvents were removed under reduced pressure, and the residue was purified by reverse phase HPLC to provide the title compound. $^1$H NMR (500 MHz, Py-d$_5$) δ 8.68 (s, 2H), 7.85 (d, J=7.93 Hz, 1H), 7.80 (dd, J=8.85, 2.44 Hz, 1H), 6.88-6.92 (m, 1H), 4.30 (d, J=7.63 Hz, 1H), 3.76 (s, 4H), 2.54-2.61 (m, 4H), 2.29-2.38 (m, 4H), 2.14 (s, 2H), 2.02 (s, 2H), 1.88-1.95 (m, 1H), 1.82 (m, 2H), 1.61 (m, 2H), 1.29-1.34 (m, 6H); MS(ESI+) m/z 494 (M+H)$^+$.

Biological Data

Measurement of Inhibition Constants:

The ability of test compounds to inhibit human 11β-HSD-1 enzymatic activity in vitro was evaluated in a Scintillation Proximity Assay (SPA). Triatiated-cortisone substrate, NADPH cofactor and titrated compound were incubated with truncated human 11β-HSD-1 enzyme (24-287AA) at room temperature to allow the conversion to cortisol to occur. The reaction was stopped by adding a non-specific 11β-HSD inhibitor, 18β-glycyrrhetinic acid. The tritiated cortisol was captured by a mixture of an anti-cortisol monoclonal antibody and SPA beads coated with anti-mouse antibodies. The reaction plate was shaken at room temperature and the radioactivity bound to SPA beads was then measured on a β-scintillation counter. The 11β-HSD-1 assay was carried out in 96-well microtiter plates in a total volume of 220 μl. To start the assay, 188 μl of master mix which contained 17.5 nM $^3$H-cortisone, 157.5 nM cortisone, and 181 mM NADPH was added to the wells. In order to drive the reaction in the forward direction, 1 mM G-6-P was also added. Solid compound was dissolved in DMSO to make a 10 mM stock followed by a subsequent 10-fold dilution with 3% DMSO in Tris/EDTA buffer (pH 7.4). 22 μl of titrated compounds was then added in triplicate to the substrate. Reactions were initiated by the addition of 10 μl of 0.1 mg/ml E. coli lysates overexpressing 11β-HSD-1 enzyme. After shaking and incubating plates for 30 minutes at room temperature, reactions were stopped by adding 10 µl of 1 mM glycyrrhetinic acid. The product, tritiated cortisol, was captured by adding 10 µl of 1 µM monoclonal anti-cortisol antibodies and 100 µl SPA beads coated with anti-mouse antibodies. After shaking for 30 minutes, plates were read on a liquid scintillation counter Topcount. Percent inhibition was calculated based on the background and the maximal signal. Wells that contained substrate without compound or enzyme were used as the background, while the wells that contained substrate and enzyme without any compound were considered as maximal signal. Percent of inhibition of each compound was calculated relative to the maximal signal and $IC_{50}$ curves were generated. This assay was applied to 11β-HSD-2 as well, whereby tritiated cortisol and $NAD^+$ were used as substrate and cofactor, respectively.

Compounds of the present invention are active in the 11β-HSD-1 assay described above, and show selectivity for human 11β-HSD-1 over human 11β-HSD-2, as indicated in Table 1.

TABLE 1

Human 11β-HSD-1 and 11β-HSD-2 enzymatic SPA assay.

| Compound | 11β-HSD-1 $IC_{50}$ (nM) | 11β-HSD-2 $IC_{50}$ (nM) |
| --- | --- | --- |
| A | 110 | >10,000 |
| B | 92 | >10,000 |
| C | 150 | >10,000 |
| D | 140 | >10,000 |
| E | 82 | >10,000 |
| F | 53 | >30,000 |
| G | 37 | >30,000 |
| H | 35 | >30,000 |
| I | 67 | >30,000 |
| J | 80 | >10,000 |
| K | 58 | >10,000 |
| L | 200 | >10,000 |
| M | 160 | >30,000 |

The data in Table 1 indicates that the compounds of the present invention are active in the human 11β-HSD-1 enzymatic SPA assay described above, and show selectivity for 11β-HSD-1 over 11β-HSD-2. The 11β-HSD-1 inhibitors of this invention generally have an inhibition constant $IC_{50}$ of less than 600 nM, and preferably less than 50 nM. The compounds preferably are selective, having an inhibition constant $IC_{50}$ against 11β-HSD-2 greater than 1000 nM, and preferably greater than 10,000 nM. Generally, the $IC_{50}$ ratio for 11β-HSD-2 to 11β-HSD-1 of a compound is at least 10 or greater, and preferably 100 or greater.

Mouse Dehydrocorticosterone Challenge Model

Male CD-1 (18-22 g) mice (Charles River, Madison, Wis.) were group housed and allowed free access to food and water. Mice are brought into a quiet procedure room for acclimation the night before the study. Animals are dosed with vehicle or compound at various times (pretreatment period) before being challenged with 11-dehydrocorticosterone (Steraloids Inc., Newport, R.I.). Thirty minutes after challenge, the mice are euthanized with $CO_2$ and blood samples (EDTA) are obtained by cardiac puncture and immediately placed on ice. Blood samples were then spun, the plasma was removed, and the samples frozen until further analysis was performed. Corticosterone levels were obtained by ELISA (American Laboratory Prod., Co., Windham, N.H.) or HPLC/mass spectroscopy.

TABLE 2

Plasma corticosterone levels following vehicle, 11 dehydrocorticosterone (11-DHC), or Compounds N, O and P (followed by 11-DHC) treatment.

| Pretreatment Period | Time (hours) | vehicle | 11-DHC | Compound dose at 30 mpk | Compound dose at 100 mpk |
| --- | --- | --- | --- | --- | --- |
| Compound N | 0.5 | 231 ± 51 | 1478 ± 180 | 1297 ± 121 | 742 ± 119 |
| | 16 | 151 ± 23 | 1200 ± 86 | 1402 ± 99 | 1422 ± 129 |
| Compound O | 0.5 | 359 ± 67 | 1648 ± 151 | 1095 ± 33 | |
| | 16 | 253 ± 45 | 2003 ± 260 | 1167 ± 211 | |
| Compound P | 1.0 | 90 ± 18 | 1521 ± 150 | 100 ± 18 | |
| | 16 | 191 ± 33 | 1963 ± 170 | 1924 ± 148 | | ob/ob Mouse Model of Type 2 Diabetes.

Male B6.VLep$^{ob(-/-)}$ (ob/ob) mice and their lean littermates (Jackson Laboratory, Bar Harbor, Me.) were group housed and allowed free access to food (Purina 5015) and water. Mice were 6-7 weeks old at the start of each study. On day 0, animals were weighed and postprandial glucose levels determined (Medisense Precision-X™ glucometer, Abbott Laboratories). Mean postprandial glucose levels did not differ significantly from group to group (n=10) at the start of the studies. Animals were weighed, and postprandial glucose measurements were taken weekly throughout the study. On the last day of the study, 16 hours post dose (unless otherwise noted) the mice were euthanized via $CO_2$, and blood samples (EDTA) were taken by cardiac puncture and immediately placed on ice. Whole blood measurements for HbA1c were taken with hand held meters (A1c NOW, Metrika Inc., Sunnyvale Calif.). Blood samples were then spun and plasma was removed and frozen until further analysis. The plasma triglyceride levels were determined according to instructions by the manufacturer (Infinity kit, Sigma Diagnostics, St. Louis Mo.).

TABLE 3

Plasma glucose, HbA1c, and triglyceride levels following three weeks of twice daily dosing with vehicle or Compounds N, O and P.

| | | Control ob/ob | Compound dose at 30 mpk | Compound dose at 100 mpk |
| --- | --- | --- | --- | --- |
| Compound N | Glucose mg/dL | 338 ± 13 | 295 ± 31 | 263 ± 21 |
| | % HbA1c | 6.9 ± 0.3 | 7.6 ± 0.6 | 6.4 ± 0.5 |
| | Triglycerides mg/dL | 348 ± 31 | 255 ± 22 | 282 ± 36 |
| Compound O | Glucose mg/dL | 359 ± 14 | 193 ± 19 | |
| | % HbA1c | 9.0 ± 0.3 | 6.7 ± 0.3 | |
| | Triglycerides mg/dL | 390 ± 24 | 143 ± 19 | |
| | FFA mEq/L | 1.74 ± .13 | 1.16 ± .15 | |
| Compound P | Glucose mg/dL | 359 ± 14 | 259 ± 34 | 146 ± 9 |
| | % HbA1c | 9.0 ± 0.3 | 7.0 ± 1.0 | 6.0 ± 0.4 |
| | Triglycerides mg/dL | 390 ± 24 | 186 ± 24 | 117 ± 14 |
| | FFA mEq/L | 1.74 ± .13 | 1.56 ± .13 | 0.97 ± .11 |

Mouse Model of High Fat Diet Induced Obesity.

Male C57BL/6J. mice were placed on a high fat diet (Research Diets D12492i, 60 kcal % fat) for 16 weeks, starting at 5-6 weeks age, with free access to food and water. Age-matched mice on low fat diet (Research Diets D12450Bi) served as lean controls. Individually housed mice were 22-23 weeks old at the start of each study, and conditioned for 7 days to daily oral gavage with vehicle at 15:00 h. On day 0, prior to the start of the studies, mean body weights did not differ significantly from group to group (n=10), except for the group on low fat diet. Additional mice (n=8 per group) were used for evaluation of insulin sensitivity by insulin tolerance test (ITT). Animals and food were weighed, and postprandial glucose measurements were taken twice each week throughout the 28 day study. Mice were dosed twice a day at 08:00 h and 15:00 h by oral gavage. On day 28, 16 hours post dose (unless otherwise noted) the mice were euthanized via $CO_2$, and blood samples (EDTA) were taken by cardiac puncture and immediately placed on ice. Blood samples were centrifuged and plasma was removed and frozen until further analysis. The plasma insulin levels were determined according to instructions by the manufacturer (Mouse Insulin Elisa, Alpco Diagnostics, Windham N.H.). On day 26, starting at approximately 06:00 h, 8 mice from Compound F 30 mg/kg, DIO and lean vehicle groups were fasted for 4 h in clean cages, with water available ad libitum. Blood glucose was determined by tail snip (time 0), and regular human insulin (Lilly Humulin-R™, 0.25 U/kg, 10 ml/kg IP diluted in sterile saline containing 1% bovine serum albumin) was given. Blood glucose was determined (Medisense Precision-X™ glucometer, Abbott Laboratories) at 30, 60, 90 and 120 min post-injection, and the area under the blood glucose vs time response curve (AUC) was reported.

range that prefers NADPH/$NADP^+$ (nicotinamide adenine dinucleotide phosphate) as cofactors. 11β-HSD-1 is widely expressed and particularly high expression levels are found in liver, brain, lung, adipose tissue, and vascular smooth muscle cells. In vitro studies indicate that 11β-HSD-1 is capable of acting both as a reductase and a dehydrogenase. However, many studies have shown that it functions primarily as a reductase in vivo and in intact cells. It converts inactive 11-ketoglucocorticoids (i.e., cortisone or dehydrocorticosterone) to active 11-hydroxyglucocorticoids (i.e., cortisol or corticosterone), and thereby amplifies glucocorticoid action in a tissue-specific manner.

With only 20% homology to 11β-HSD-1, the 11β-hydroxysteroid dehydrogenases type 2 enzyme (11β-HSD-2) is a $NAD^+$-dependent (nicotinamide adenine dinucleotide-dependent), high affinity dehydrogenase with a $K_m$ for cortisol in the nanomolar range. 11β-HSD-2 is found primarily in mineralocorticoid target tissues, such as kidney, colon, and placenta. Glucocorticoid action is initiated by the binding of glucocorticoids to receptors, such as glucocorticoid receptors and mineralocorticoid receptors. Through binding to its receptor, the main mineralocorticoid aldosterone controls the water and electrolyte balance in the body. However, the mineralocorticoid receptors have a high affinity for both cortisol and aldosterone. 11β-HSD-2 converts cortisol to inactive cortisone, therefore preventing the exposure of non-selective

TABLE 4

Body weight loss, plasma insulin level and insulin sensitivity following four weeks of twice daily dosing with vehicle or Compounds O and P.

|  | Control DIO Mice | Compound O 10 mpk | Compound O 30 mpk | Compound P 30 mpk | Control Lean Mice |
| --- | --- | --- | --- | --- | --- |
| Body Weight Change (g) | 2.78 ± 0.49 | −0.99 ± 0.61 | −7.53 ± 1.01 | −1.14 ± 0.95 | −0.04 ± 0.34 |
| Insulin (ng/ml) | 3.58 ± 0.52 | 2.44 ± 0.25 | 1.12 ± 0.24 | 2.52 ± 0.36 | 0.94 ± 0.11 |
| ITT AUC (mg/dl * min) | −4288 ± 1080 | nd | −8582 ± 1816 | nd | −9574 ± 929 |

(nd = not determined)

The compounds of this invention are selective inhibitors of the 11β-HSD-1 enzyme. Their utility in treating or prophylactically treating type 2 diabetes, high blood pressure, dyslipidemia, obesity, metabolic syndrome, and other diseases and conditions is believed to derive from the biochemical mechanism described below.

Biochemical Mechanism

Glucocorticoids are steroid hormones that play an important role in regulating multiple physiological processes in a wide range of tissues and organs. For example, glucocorticoids are potent regulators of glucose and lipid metabolism. Excess glucocorticoid action may lead to insulin resistance, type 2 diabetes, dyslipidemia, visceral obesity and hypertension. Cortisol and cortisone are the major active and inactive forms of glucocorticoids in humans, respectively, while corticosterone and dehydrocorticosterone are the major active and inactive forms in rodents.

Previously, the main determinants of glucocorticoid action were thought to be the circulating hormone concentration and the density of receptors in the target tissues. In the last decade, it was discovered that tissue glucocorticoid levels may also be controlled by 11β-hydroxysteroid dehydrogenases enzymes (11β-HSDs). There are two 11β-HSD isozymes which have different substrate affinities and cofactors. The 11β-hydroxysteroid dehydrogenases type 1 enzyme (11β-HSD-1) is a low affinity enzyme with $K_m$ for cortisone in the micromolar mineralocorticoid receptors to high levels of cortisol. Mutations in the gene encoding 11β-HSD-2 cause Apparent Mineralocorticoid Excess Syndrome (AME), which is a congenital syndrome resulting in hypokaleamia and severe hypertension. Patients have elevated cortisol levels in mineralocorticoid target tissues due to reduced 11β-HSD-2 activity. The AME symptoms may also be induced by administration of the 11β-HSD-2 inhibitor glycyrrhetinic acid. The activity of 11β-HSD-2 in placenta is probably important for protecting the fetus from excess exposure to maternal glucocorticoids, which may result in hypertension, glucose intolerance and growth retardation.

The effects of elevated levels of cortisol are also observed in patients who have Cushing's syndrome (D. N. Orth, N. Engl. J. Med. 332:791-803, 1995, M. Boscaro, et al., Lancet, 357: 783-791, 2001, X. Bertagna, et al, Cushing's Disease. In: Melmed S., Ed. The Pituitary. $2^{nd}$ ed. Malden, Mass.: Blackwell; 592-612, 2002), which is a disease characterized by high levels of cortisol in the blood stream. Patients with Cushing's syndrome often develop many of the symptoms of type 2 diabetes, obesity, metabolic syndrome and dyslipidemia including insulin resistance, central obesity, hypertension, glucose intolerance, etc.

The compounds of this invention are selective inhibitors of 11β-HSD-1 when comparing to 11β-HSD-2. Previous studies (B. R. Walker et al., J. of Clin. Endocrinology and Met., 80: 3155-3159, 1995) have demonstrated that administration of 11β-HSD-1 inhibitors improves insulin sensitivity in humans. However, these studies were carried out using the nonselective 11β-HSD-1 inhibitor carbenoxolone. Inhibition of 11β-HSD-2 by carbenoxolone causes serious side effects, such as hypertension.

Although cortisol is an important and well-recognized anti-inflammatory agent (J. Baxer, Pharmac. Ther., 2:605-659, 1976), if present in large amount, it also has detrimental effects. For example, cortisol antagonizes the effects of insulin in the liver resulting in reduced insulin sensitivity and increased gluconeogenesis. Therefore, patients who already have impaired glucose tolerance have a greater probability of developing type 2 diabetes in the presence of abnormally high levels of cortisol.

Since glucocorticoids are potent regulators of glucose and lipid metabolism, excessive glucocorticoid action may lead to insulin resistance, type 2 diabetes, dyslipidemia, visceral obesity and hypertension. The present invention relates to the administration of a therapeutically effective dose of an 11β-HSD-1 inhibitor for the treatment, control, amelioration, and/or delay of onset of diseases and conditions that are mediated by excess or uncontrolled, amounts or activity of cortisol and/or other corticosteroids. Inhibition of the 11β-HSD-1 enzyme limits the conversion of inactive cortisone to active cortisol. Cortisol may cause, or contribute to, the symptoms of these diseases and conditions if it is present in excessive amounts.

Dysregulation of glucocorticoid activity has been linked to metabolic disorders, including type 2 diabetes, metabolic syndrome, Cushing's Syndrome, Addison's Disease, and others. Glucocorticoids upregulate key glucoeneogenic enzymes in the liver such as PEPCK and G6Pase, and therefore lowering local glucocorticoid levels in this tissue is expected to improve glucose metabolism in type 2 diabetics. 11β-HSD-1 receptor whole-body knockout mice, and mice overexpressing 11β-HSD-2 in fat (resulting in lower levels of active glucocorticoid in fat) have better glucose control than their wild type counterparts (Masuzaki, et al.; *Science.* 294: 2166-2170, 2001; Harris, et al.; *Endocrinology.* 142: 114-120, 2001; Kershaw et al.; *Diabetes.* 54: 1023-1031, 2005). Therefore, specific 11β-HSD-1 inhibitors could be used for the treatment or prevention of type 2 diabetes and/or insulin resistance.

By reducing insulin resistance and maintaining serum glucose at normal concentrations, compounds of this invention may also have utility in the treatment and prevention of the numerous conditions that often accompany type 2 diabetes and insulin resistance, including the metabolic syndrome, obesity, reactive hypoglycemia, and diabetic dyslipidemia. The following diseases, disorders and conditions are related to type 2 diabetes, and some or all of these may be treated, controlled, prevented and/or have their onset delayed, by treatment with the compounds of this invention: hyperglycemia, low glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, pancreatitis, abdominal obesity, neurodegenerative disease, retinopathy, nephropathy, neuropathy, metabolic syndrome and other disorders where insulin resistance is a component. Abdominal obesity is closely associated with glucose intolerance (C. T. Montague et al., Diabetes, 49: 883-888, 2000), hyperinsulinemia, hypertriglyceridemia, and other factors of metabolic syndrome (also known as Syndrome X), such as high blood pressure, elevated LDL, and reduced HDL. Animal data supporting the role of HSD1 in the pathogenesis of the metabolic syndrome is extensive (Masuzaki, et al.; *Science.* 294: 2166-2170, 2001; Paterson et al.; *Proc Natl. Acad. Sci. USA.* 101: 7088-93, 2004; Montague and O'Rahilly; *Diabetes.* 49: 883-888, 2000). Thus, administration of an effective amount of an 11β-HSD-1 inhibitor may be useful in the treatment or control of the metabolic syndrome. Furthermore, administration of an 11β-HSD-1 inhibitor may be useful in the treatment or control of obesity by controlling excess cortisol, independent of its effectiveness in treating or prophylactically treating NIDDM. Long-term treatment with an 11β-HSD-1 inhibitor may also be useful in delaying the onset of obesity, or perhaps preventing it entirely if the patients use an 11β-HSD-1 inhibitor in combination with controlled diet and exercise. Potent, selective 11β-HSD-1 inhibitors should also have therapeutic value in the treatment of the glucocorticoid-related effects characterizing the metabolic syndrome, or any of the following related conditions: hyperglycemia, low glucose tolerance, insulin resistance, obesity, lipid disorders, dyslipidemia, hyperlipidemia, hypertriglycidemia, hypercholesterolemia, low HDL levels, high LDL levels, atherosclerosis, vascular restenosis, pancreatitis, obesity, neurodegenerative disease, retinopathy, nephropathy, hepatic steatosis or related liver diseases, and Syndrome X, and other disorders where insulin resistance is a component.

11β-HSD-1 is expressed in pancreatic islet cells, where active glucocorticoids have a negative effect on glucose stimulated insulin secretion (Davani et al.;. *Biol. Chem.* 10: 34841-34844, 2000; Tadayyon and Smith. *Expert Opin. Investig. Drugs.* 12: 307-324, 2003; Billaudel and Sutter. *J. Endocrinol.* 95: 315-20, 1982.). It has been reported that the conversion of dehydrocorticosterone to corticosterone by 11β-HSD-1 inhibits insulin secretion from isolated murine pancreatic beta cells. Incubation of isolated islets with an 11β-HSD-1 inhibitor improves glucose stimulated insulin secretion. An earlier study suggested that glucocorticoids reduce insulin secretion in vivo. (B. Billaudel et al., Horm. Metab. Res. 11: 555-560, 1979). Therefore, inhibition of 11β-HSD-1 enzyme in the pancreas may improve glucose stimulated insulin release.

Glucocorticoids may bind to and activate glucocorticoid receptors (and possibly mineralocorticoid receptors) to potentiate the vasoconstrictive effects of both catecholamines and angiotensin II (M. Pirpiris et al., Hypertension, 19:567-574, 1992, C. Kornel et al., Steroids, 58: 580-587, 1993, B. R. Walker and B. C. Williams, Clin. Sci. 82:597-605, 1992). The 11β-HSD-1 enzyme is present in vascular smooth muscle, which is believed to control the contractile response together with 11β-HSD-2. High levels of cortisol in tissues where the mineralocorticoid receptor is present may lead to hypertension. Therefore, administration of a therapeutic dose of an 11β-HSD-1 inhibitor should be effective in treating or prophylactically treating, controlling, and ameliorating the symptoms of hypertension.

11β-HSD-1 is expressed in mammalian brain, and published data indicates that glucocorticoids may cause neuronal degeneration and dysfunction, particularly in the aged (de Quervain et al.; *Hum Mol. Genet.* 13: 47-52, 2004; Belanoff et al. *J. Psychiatr Res.* 35: 127-35, 2001). Evidence in rodents and humans suggests that prolonged elevation of plasma glucocorticoid levels impairs cognitive function that becomes more profound with aging. (See, A. M. Issa et al., J. Neurosci., 10:3247-3254, 1990, S. J. Lupien et. al., Nat. Neurosci., 1:69-73 1998, J. L. Yau et al., Neuroscience, 66: 571-581, 1995). Chronic excessive cortisol levels in the brain may result in neuronal loss and neuronal dysfunction. (See, D. S. Kerr et al., Psychobiology 22: 123-133, 1994, C. Woolley, Brain Res. 531: 225-231, 1990, P. W. Landfield, Science, 272: 1249-

1251, 1996). Furthermore, glucocorticoid-induced acute psychosis exemplifies a more pharmacological induction of this response, and is of major concern to physicians when treating patients with these steroidal agents (Wolkowitz et al.; *Ann NY Acad Sci.* 1032: 191-4, 2004). Thekkapat et al have recently shown that 11β-HSD-1 mRNA is expressed in human hippocampus, frontal cortex and cerebellum, and that treatment of elderly diabetic individuals with the non-selective 11β-HSD-1 and 11β-HSD-2 inhibitor carbenoxolone improved verbal fluency and memory (*Proc Natl Acad Sci USA.* 101: 6743-9, 2004). Therefore, administration of a therapeutic dose of an 11β-HSD-1 inhibitor may reduce, ameliorate, control and/or prevent the cognitive impairment associated with aging, neuronal dysfunction, dementia, and steroid-induced acute psychosis.

Cushing's syndrome is a life-threatening metabolic disorder characterized by chronically elevated glucocorticoid levels caused by either excessive endogenous production of cortisol from the adrenal glands, or by the administration of high doses of exogenous glucocorticoids, such as prednisone or dexamethasone, as part of an anti-inflammatory treatment regimen. Typical Cushingoid characteristics include central obesity, diabetes and/or insulin resistance, dyslipidemia, hypertension, reduced cognitive capacity, dementia, osteoporosis, atherosclerosis, moon faces, buffalo hump, skin thinning, and sleep deprivation among others (Principles and Practice of Endocrinology and Metabolism. Edited by Kenneth Becker, Lippincott Williams and Wilkins Publishers, Philadelphia, 2001; pg 723-8). It is therefore expected that potent, selective 11β-HSD-1 inhibitors would be effective for the treatment of Cushing's disease.

As previously described above, 11β-HSD-1 inhibitors may be effective in the treatment of many features of the metabolic syndrome including hypertension and dyslipidemia. The combination of hypertension and dyslipidemia contribute to the development of atherosclerosis, and therefore it would be expected that administration of a therapeutically effective amount of an 11β-HSD-1 inhibitor would treat, control, delay the onset of, and/or prevent atherosclerosis and other metabolic syndrome-derived cardiovascular diseases.

One significant side effect associated with topical and systemic glucocorticoid therapy is corticosteroid-induced glaucoma. This condition results in serious increases in intraocular pressure, with the potential to result in blindness (Armaly et al.; *Arch Ophthalmol.* 78: 193-7, 1967; Stokes et al.; *Invest Ophthalmol Vis Sci.* 44: 5163-7, 2003.). The cells that produce the majority of aqueous humor in the eye are the non-pigmented epithelial cells (NPE). These cells have been demonstrated to express 11β-HSD-1, and consistent with the expression of 11β-HSD-1, is the finding of elevated ratios of cortisol:cortisone in the aqueous humor (Rauz et al.; *Invest Ophthalmol Vis Sci.* 42: 2037-2042, 2001). Furthermore, it has been shown that patients who have glaucoma, but who are not taking exogenous steroids, have elevated levels of cortisol vs. cortisone in their aqueous humor (Rauz et al.; *QJM.* 96: 481-490, 2003.) Treatment of patients with the nonselective 11β-HSD-1 and 11β-HSD-2 inhibitor carbenoxolone for 4 and 7 days significantly lowered intraocular pressure by 10% and 17% respectively, and lowered local cortisol generation within the eye (Rauz et al.; *QJM.* 96: 481-490, 2003). Therefore, administration of 11β-HSD-1 specific inhibitors could be used for the treatment of glaucoma.

In certain disease states, such as tuberculosis, psoriasis, and stress in general, high glucocorticoid activity shifts the immune response to a humoral response, when in fact a cell based response may be more beneficial to the patients. Inhibition of 11β-HSD-1 activity may reduce glucocorticoid levels, thereby shifting the immuno response to a cell based response. (D. Mason, Immunology Today, 12: 57-60, 1991, G. A. W. Rook, Baillier's Clin. Endocrinol. Metab. 13: 576-581, 1999). Therefore, administration of 11β-HSD-1 specific inhibitors could be used for the treatment of tuberculosis, psoriasis, stress in general, and diseases or conditions where high glucocorticoid activity shifts the immune response to a humoral response.

Glucocorticoids are known to cause a variety of skin related side effects including skin thinning, and impairment of wound healing (Anstead, G. M. *Adv Wound Care.* 11: 277-85, 1998; Beer, et al.; *Vitam Horn.* 59: 217-39, 2000). 11β-HSD-1 is expressed in human skin fibroblasts, and it has been shown that the topical treatment with the non-selective 11β-HSD-1 and 11β-HSD-2 inhibitor glycerrhetinic acid increases the potency of topically applied hydrocortisone in a skin vasoconstrictor assay (Hammami, M M, and Siiteri, P K. *J. Clin. Endocrinol. Metab.* 73: 326-34, 1991). Advantageous effects of selective 11β-HSD-1 inhibitors on wound healing have also been published (WO 2004/11310). It is therefore expected that potent, selective 11β-HSD-1 inhibitors would treat wound healing or skin thinning due to excessive glucocorticoid activity.

Excess glucocorticoids decrease bone mineral density and increase fracture risk. This effect is mainly mediated by inhibition of osteoblastic bone formation, which results in a net bone loss (C. H. Kim et al. J. Endocrinol. 162: 371-379, 1999, C. G. Bellows et al. 23: 119-125, 1998, M. S. Cooper et al., Bone 27: 375-381, 2000). Glucocorticoids are also known to increase bone resorption and reduce bone formation in mammals (Turner et al.; *Calcif Tissue Int.* 54: 311-5, 1995; Lane, N E et al. *Med Pediatr Oncol.* 41: 212-6, 2003). 11β-HSD-1 mRNA expression and reductase activity have been demonstrated in primary cultures of human osteoblasts in homogenates of human bone (Bland et al.; *J. Endocrinol.* 161: 455-464, 1999; Cooper et al.; *Bone,* 23: 119-125, 2000; Cooper et al.; *J. Bone Miner Res.* 17: 979-986, 2002). In surgical explants obtained from orthopedic operations, 11β-HSD-1 expression in primary cultures of osteoblasts was found to be increased approximately 3-fold between young and old donors (Cooper et al.; *J. Bone Miner Res.* 17: 979-986, 2002). Glucocorticoids such as prednisone and dexamethasone are also commonly used to treat a variety of inflammatory conditions including arthritis, inflammatory bowl disease, and asthma. These steroidal agents have been shown to increase expression of 11β-HSD-1 mRNA and activity in human osteoblasts (Cooper et al.; *J. Bone Miner Res.* 17: 979-986, 2002). Similar results have been shown in primary osteoblast cells and MG-63 osteosarcoma cells where the inflammatory cytokines TNF alpha and IL-1 beta increase 11β-HSD-1 mRNA expression and activity (Cooper et al.; *J. Bone Miner Res.* 16: 1037-1044, 2001). These studies suggest that 11β-HSD-1 plays a potentially important role in the development of bone-related adverse events as a result of excessive glucocorticoid levels or activity. Bone samples taken from healthy human volunteers orally dosed with the non-selective 11β-HSD-1 and 11β-HSD-2 inhibitor carbenoxolone showed a significant decrease in markers of bone resorption (Cooper et al.; *Bone.* 27: 375-81, 2000). Therefore, administration of an 11β-HSD-1 specific inhibitor may be useful for preventing bone loss due to glucocorticoid-induced or age-dependent osteoporosis.

Therapeutic Compositions-Administration-Dose Ranges

Therapeutic compositions of the present compounds comprise an effective amount of the same formulated with one or more therapeutically suitable excipients. The term "therapeutically suitable excipient," as used herein, generally refers to pharmaceutically suitable, solid, semi-solid or liquid fillers, diluents, encapsulating material, formulation auxiliary and the like. Examples of therapeutically suitable excipients include, but are not limited to, sugars, cellulose and derivatives thereof, oils, glycols, solutions, buffers, colorants, releasing agents, coating agents, sweetening agents, flavoring agents, perfuming agents, and the like. Such therapeutic compositions may be administered parenterally, intracisternally, orally, rectally, intraperitoneally or by other dosage forms known in the art.

Liquid dosage forms for oral administration include, but are not limited to, emulsions, microemulsions, solutions, suspensions, syrups, and elixirs. Liquid dosage forms may also contain diluents, solubilizing agents, emulsifying agents, inert diluents, wetting agents, emulsifiers, sweeteners, flavorants, perfuming agents and the like.

Injectable preparations include, but are not limited to, sterile, injectable, aqueous, oleaginous solutions, suspensions, emulsions and the like. Such preparations may also be formulated to include, but are not limited to, parenterally suitable diluents, dispersing agents, wetting agents, suspending agents and the like. Such injectable preparations may be sterilized by filtration through a bacterial-retaining filter. Such preparations may also be formulated with sterilizing agents that dissolve or disperse in the injectable media or other methods known in the art.

The absorption of the compounds of the present invention may be delayed using a liquid suspension of crystalline or amorphous material having poor water solubility. The rate of absorption of the compounds generally depends upon the rate of dissolution and crystallinity. Delayed absorption of a parenterally administered compound may also be accomplished by dissolving or suspending the compound in oil. Injectable depot dosage forms may also be prepared by microencapsulating the same in biodegradable polymers. The rate of drug release may also be controlled by adjusting the ratio of compound to polymer and the nature of the polymer employed. Depot injectable formulations may also prepared by encapsulating the compounds in liposomes or microemulsions compatible with body tissues.

Solid dosage forms for oral administration include, but are not limited to, capsules, tablets, gels, pills, powders, granules and the like. The drug compound is generally combined with at least one therapeutically suitable excipient, such as carriers, fillers, extenders, disintegrating agents, solution retarding agents, wetting agents, absorbents, lubricants and the like. Capsules, tablets, and pills may also contain buffering agents. Suppositories for rectal administration may be prepared by mixing the compounds with a suitable non-irritating excipient that is solid at ordinary temperature but fluid in the rectum.

The present drug compounds may also be microencapsulated with one or more excipients. Tablets, dragees, capsules, pills, and granules may also be prepared using coatings and shells, such as enteric and release or rate controlling polymeric and nonpolymeric materials. For example, the compounds may be mixed with one or more inert diluents. Tableting may further include lubricants and other processing aids. Similarly, capsules may contain opacifying agents that delay release of the compounds in the intestinal tract.

Transdermal patches have the added advantage of providing controlled delivery of the present compounds to the body. Such dosage forms are prepared by dissolving or dispensing the compounds in suitable medium. Absorption enhancers may also be used to increase the flux of the compounds across the skin. The rate of absorption may be controlled by employing a rate controlling membrane. The compounds may also be incorporated into a polymer matrix or gel.

For a given dosage form, disorders of the present invention may be treated, prophylatically treated, or have their onset delayed in a patient by administering to the patient a therapeutically effective amount of compound of the present invention in accordance with a suitable dosing regimen. In other words, a therapeutically effective amount of any one of compounds of formulas I thru IX is administered to a patient to treat and/or prophylatically treat disorders modulated by the 11-beta-hydroxysteroid dehydrogenase type 1 enzyme. The specific therapeutically effective dose level for a given patient population may depend upon a variety of factors including, but not limited to, the specific disorder being treated, the severity of the disorder; the activity of the compound, the specific composition or dosage form, age, body weight, general health, sex, diet of the patient, the time of administration, route of administration, rate of excretion, duration of the treatment, drugs used in combination, coincidental therapy and other factors known in the art.

The present invention also includes therapeutically suitable metabolites formed by in vivo biotransformation of any of the compounds of formula I thru IX. The term "therapeutically suitable metabolite", as used herein, generally refers to a pharmaceutically active compound formed by the in vivo biotransformation of compounds of formula (I-IX). For example, pharmaceutically active metabolites include, but are not limited to, compounds made by adamantane hydroxylation or polyhydroxylation of any of the compounds of formulas (I-IX). A discussion of biotransformation is found in Goodman and Gilman's, The Pharmacological Basis of Therapeutics, seventh edition, MacMillan Publishing Company, New York, N.Y., (1985).

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing diabetes mellitus and/or hyperglycemia or hypertriglyceridemia or other diseases for which compounds of Formula (I) are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

It is understood that the foregoing detailed description and accompanying examples are merely illustrative and are not to be taken as limitations upon the scope of the invention, which is defined solely by the appended claims and their equivalents. Various changes and modifications to the disclosed aspects will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

We claim:
1. A compound according to formula (I),

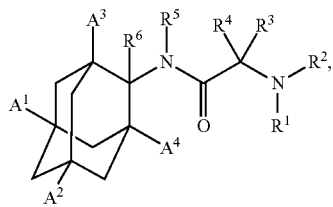

wherein
$A^1$ is aryl, halogen or —$OR^{14}$;
$A^2$, $A^3$, and $A^4$ are each independently selected from the group consisting of hydrogen, alkyl, alkyl-NH-alkyl, alkylcarbonyl, alkylsulfonyl, cycloalkyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heterocycle, heterocyclealkyl, heterocycleoxyalkyl, —$NR^7$—[C($R^8R^9$)]—C(O)—$R^{10}$, —O—[C($R^{11}R^{12}$)]$_p$—C(O)—$R^{13}$, —$OR^{14}$, —N($R^{15}R^{16}$), —$CO_2R^{17}$, —C(O)—N($R^{18}R^{19}$), —C($R^{20}R^{21}$)—$OR^{22}$, and —C($R^{23}R^{24}$)—N($R^{25}R^{26}$);
n is 0 or 1;
p is 0 or 1;
$R^1$ and $R^2$ are each independently selected from the group consisting of hydrogen, alkyl, alkoxyalkyl, alkyl-NH-alkyl, aryloxyalkyl, aryl-NH-alkyl, carboxyalkyl, carboxycycloalkyl, heterocycleoxyalkyl, heterocycle-NH-alkyl, cycloalkyl, aryl, arylalkyl, haloalkyl, heterocycle, heterocyclealkyl, heterocycle-heterocycle, and aryl-heterocycle;
$R^3$ and $R^4$ are each independently hydrogen, alkyl, carboxycycloalkyl, cycloalkyl, haloalkyl, or heterocycle, or $R^3$ and $R^4$ together with the atom to which they are attached form a ring selected from the group consisting of cycloalkyl and non-aromatic heterocycle;
$R^5$ and $R^6$ are hydrogen;
$R^7$ is selected from the group consisting of hydrogen, alkyl, carboxyalkyl, cycloalkyl, carboxycycloalkyl, aryl, arylalkyl, aryloxyalkyl, aryloxy, hydroxy, alkoxy, cycloalkyloxy, heterocycleoxy, heterocycle, heterocyclealkyl, and heterocycleoxyalkyl;
$R^8$ and $R^9$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or $R^8$ and $R^9$ together with the atom to which they are attached form a ring selected from the group consisting of cycloalkyl and non-aromatic heterocycle;
$R^{10}$ is selected from the group consisting of hydrogen, alkyl, carboxy, carboxyalkyl, cycloalkyl, carboxycycloalkyl, aryl, aryloxy, arylalkyl, aryloxyalkyl, hydroxy, alkoxy, cycloalkyloxy, heterocycleoxy, heterocycle, heterocyclealkyl, heterocycleoxyalkyl, and —N($R^{27}R^{28}$);
$R^{11}$ and $R^{12}$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or $R^{11}$ and $R^{12}$ together with the atom to which they are attached form a ring selected from the group consisting of cycloalkyl and non-aromatic heterocycle;
$R^{13}$ is selected from the group consisting of hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heterocycleoxy, heterocycle, heterocyclealkyl, heterocycleoxyalkyl, and —N($R^{29}R^{30}$);
$R^{14}$ is selected from the group consisting of hydrogen, alkyl, carboxyalkyl, cycloalkyl, carboxycycloalkyl, aryl, arylalkyl, aryloxyalkyl, haloalkyl, heterocycle, heterocyclealkyl, and heterocycleoxyalkyl;
$R^{15}$ and $R^{16}$ are each independently selected from the group consisting of hydrogen, alkyl, carboxyalkyl, cycloalkyl, carboxycycloalkyl, aryl, arylalkyl, aryloxyalkyl, heterocycle, heterocyclealkyl, heterocycleoxyalkyl, alkylsulfonyl, cycloalkylsulfonyl, arylsulfonyl, and heterocyclesulfonyl, or $R^{15}$ and $R^{16}$ together with the atom to which they are attached form a heterocycle;
$R^{17}$ is selected from the group consisting of hydrogen, alkyl, carboxyalkyl, cycloalkyl, carboxycycloalkyl, aryl, arylalkyl, aryloxyalkyl, heterocycle, heterocyclealkyl, and heterocycleoxyalkyl;
$R^{18}$ and $R^{19}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{18}$ and $R^{19}$ together with the atom to which they are attached form a non-aromatic heterocycle;
$R^{20}$, $R^{21}$ and $R^{22}$ are each independently selected from the group consisting of hydrogen, alkyl, carboxyalkyl, carboxycycloalkyl, cycloalkyl, haloalkyl, aryl, and heterocycle;
$R^{23}$ and $R^{24}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, cycloalkyl, aryl, and heterocycle;
$R^{25}$ and $R^{26}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, hydroxy, alkoxy, cycloalkyloxy, aryloxy, heterocycleoxy, cycloalkyl, aryl, and heterocycle, or $R^{25}$ and $R^{26}$ together with the atom to which they are attached form a heterocycle;
$R^{27}$ and $R^{28}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{27}$ and $R^{28}$ together with the atom to which they are attached form a non-aromatic heterocycle; and
$R^{29}$ and $R^{30}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{29}$ and $R^{30}$ together with the atom to which they are attached form a non-aromatic heterocycle;

or a therapeutically acceptable salt thereof.

2. The compound according to claim 1 that is
N²-[2-(4-chlorophenyl)ethyl]-N¹-[(E)-5—hydroxy-2-adamantyl]alaninamide;
N²-[2-(3,4-dichlorophenyl)ethyl]-N¹-[(E)-5-hydroxy-2-adamantyl]-N²-methylalaninamide;
N²-[2-(4-chlorophenyl)-1-methylethyl]-N¹-[(E)-5-hydroxy-2-adamantyl]-N²-methylalaninamide; or
N-[(E)-5-hydroxy-2-adamantyl]-1- {[4-trifluoromethyl)benzyl]amino}cyclopropane carboxamide;

or a therapeutically acceptable salt thereof.

3. A pharmaceutical composition comprising a therapeutically effective amount of the compound according to claim 1 in combination with a pharmaceutically suitable carrier.

4. A method of inhibiting 11-beta-hydroxysteroid dehydrogenase Type I enzyme, comprising administering to a mammal, a therapeutically effective amount of a compound of formula I of claim 1 for treating a disorder selected from the group consisting of non insulin dependent type 2 diabetes, obesity, hypertension, and cognitive impairment associated with aging.

5. A compound according to formula (I),

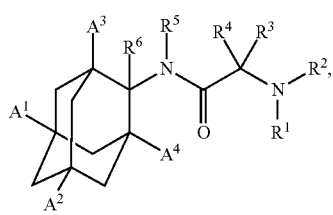

(I)

wherein
$A^1$ is aryl, halogen or —$OR^{14}$;
$A^2$, $A^3$, and $A^4$ are each independently selected from the group consisting of hydrogen, alkyl, alkyl-NH-alkyl, alkylcarbonyl, alkylsulfonyl, cycloalkyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heterocycle, heterocyclealkyl, heterocycleoxyalkyl, —$NR^7$—[$C(R^8R^9)$]$_n$—$C(O)$—$R^{10}$, —$O$—[$C(R^{11}R^{12})$]$_p$—$C(O)$—$R^{13}$, —$OR^{14}$—$N(R^{15}R^{16})$, —$CO_2R^{17}$, —$C(O)$—$N(R^{18}R^{19})$, —$C(R^{20}R^{21})$—$OR^{22}$, —$C(R^{23}R^{24})$—$N(R^{25}R^{26})$;
n is 0 or 1;
p is 0 or 1;
$R^1$ and $R^2$ together with the atom to which they are attached form a heterocycle selected from the group consisting of azepinyl, azetedinyl, dihydro-indolyl, dihydro-isoindolyl, morpholinyl, and pyrrolidinyl, said heterocycle optionally substituted with 0, 1, 2 or 3 substituents independently selected from alkenyl, alkenylthio, alkenyloxy, alkoxy, alkoxyalkoxy, alkoxyalkoxyalkoxy, alkoxyalkoxyalkyl, alkoxyalkyl, alkoxycarbonyl, alkoxycarbonylalkoxy, alkoxycarbonylalkyl, alkoxysulfonyl, alkyl, alkylcarbonyl, alkylcarbonylalkoxy, alkyl carbonyl alkyl, alkyl carbonylalkylthio, alkylcarbonyloxy, alkylcarbonylthio, alkylsulfinyl, alkylsulfinylalkyl, alkyl sulfonyl, alkylsulfonylalkyl, alkylthio, alkylthioalkyl, alkylthioalkoxy, alkynyl, alkynyloxy, alkynylthio, aryl, arylcarbonyl, aryloxy, arylsulfonyl, carboxy, carboxyalkoxy, carboxyalkyl, cyano, cyanoalkoxy, cyanoalkyl, cyanoalkylthio, ethylenedioxy, formyl, formylalkoxy, formylalkyl, haloalkenyl, haloalkenyloxy, haloalkoxy, haloalkyl, haloalkynyl, haloalkynyloxy, halogen, heterocycle, heterocyclecarbonyl, heterocycleoxy, heterocyclesulfonyl, hydroxy, hydroxyalkoxy, hydroxyalkyl, mercapto, mercaptoalkoxy, mercaptoalkyl, methylenedioxy, nitro, $R_fR_gN$—, $R_fR_g$Nalkyl, $R_fR_g$Ncarbonyl and $R_fR_g$Nsulfonyl, wherein $R_f$ and $R_g$ are members independently selected from the group consisting of hydrogen, alkyl, alkoxyalkyl, alkylcarbonyl, alkylsulfonyl, alkoxycarbonyl, cycloalkyl, cycloalkylalkyl, cycloalkylcarbonyl and cycloalkylsulfonyl, and wherein substituent aryl, the aryl of arylcarbonyl, the aryl of aryloxy, the aryl of arylsulfonyl, the substituent heterocycle, the heterocycle of heterocyclecarbonyl, the heterocycle of heterocycleoxy, the heterocycle of heterocyclesulfonyl may be optionally substituted with 0, 1, 2 or 3 substituents independently selected from the group consisting of alkenyl, alkenylthio, alkenyloxy, alkoxy, alkoxyalkoxy, alkoxyalkoxyalkoxy, alkoxyalkoxyalkyl, alkoxyalkyl, alkoxycarbonyl, alkoxycarbonylalkoxy, alkoxycarbonylalkyl, alkoxysulfonyl, alkyl, alkylcarbonyl, alkylcarbonylalkoxy, alkylcarbonylalkyl, alkylcarbonylalkylthio, alkylcarbonyloxy, alkylcarbonylthio, alkylsulfinyl, alkylsulfinylalkyl, alkyl sulfonyl, alkylsulfonylalkyl, alkylthio, alkylthioalkyl, alkylthioalkoxy, alkynyl, alkynyloxy, alkynylthio, carboxy, carboxyalkoxy, carboxyalkyl, cyano, cyanoalkoxy, cyanoalkyl, cyanoalkylthio, ethylenedioxy, formyl, formylalkoxy, formylalkyl, haloalkenyl, haloalkenyloxy, haloalkoxy, haloalkyl, haloalkynyl, haloalkynyloxy, halogen, hydroxy, hydroxyalkoxy, hydroxyalkyl, mercapto, mercaptoalkoxy, mercaptoalkyl, methyl enedioxy, oxo, nitro, $R_fR_gN$—, $R_fR_g$Nalkyl, $R_fR_g$Ncarbonyl and $R_fR_g$Nsulfonyl;
$R^3$ is hydrogen, alkyl, carboxyalkyl, carboxycycloalkyl, cycloalkyl, haloalkyl, aryl, or heterocycle;
$R^4$ is alkyl, carboxyalkyl, carboxycycloalkyl, cycloalkyl, haloalkyl, aryl, or heterocycle, or $R^3$and $R^4$ together with the atom to which they are attached form a ring selected from the group consisting of cycloalkyl and non-aromatic heterocycle;
$R^5$ is hydrogen, alkyl, carboxyalkyl, carboxycycloalkyl, cycloalkyl, aryl, arylalkyl, aryloxyalkyl, heterocycle, heterocyclealkyl, or heterocycleoxyalkyl;
$R^6$ is selected from the group consisting of hydrogen, alkyl, or carboxy;
$R^7$ is selected from the group consisting of hydrogen, alkyl, carboxyalkyl, cycloalkyl, carboxycycloalkyl, aryl, arylalkyl, aryloxyalkyl, aryloxy, hydroxy, alkoxy, cycloalkyloxy, heterocycleoxy, heterocycle, heterocyclealkyl, and heterocycleoxyalkyl;
$R^8$ and $R^9$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or $R^8$ and $R^9$ together with the atom to which they are attached form a ring selected from the group consisting of cycloalkyl and non-aromatic heterocycle;
$R^{10}$ is selected from the group consisting of hydrogen, alkyl, carboxy, carboxyalkyl, cycloalkyl, carboxycycloalkyl, aryl, aryloxy, arylalkyl, aryloxyalkyl, hydroxy, alkoxy, cycloalkyloxy, heterocycleoxy, heterocycle, heterocyclealkyl, heterocycleoxyalkyl, and —N(R$^{27}$R$^{28}$);

R$^{11}$ and R$^{12}$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or R$^{11}$ and R$^{12}$ together with the atom to which they are attached form a ring selected from the group consisting of cycloalkyl and non-aromatic heterocycle;

R$^{13}$ is selected from the group consisting of hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heterocycleoxy, heterocycle, heterocyclealkyl, heterocycleoxyalkyl, and —N(R$^{29}$R$^{30}$);

R$^{14}$ is selected from the group consisting of hydrogen, alkyl, carboxyalkyl, cycloalkyl, carboxycycloalkyl, aryl, arylalkyl, aryloxyalkyl, haloalkyl, heterocycle, heterocyclealkyl, and heterocycleoxyalkyl;

R$^{15}$ and R$^{16}$ are each independently selected from the group consisting of hydrogen, alkyl, carboxyalkyl, cycloalkyl, carboxycycloalkyl, aryl, arylalkyl, aryloxyalkyl, heterocycle, heterocyclealkyl, heterocycleoxyalkyl, alkylsulfonyl, cycloalkylsulfonyl, arylsulfonyl, and heterocyclesulfonyl, or R$^{15}$ and R$^{16}$ together with the atom to which they are attached form a heterocycle;

R$^{17}$ is selected from the group consisting of hydrogen, alkyl, carboxyalkyl, cycloalkyl, carboxycycloalkyl, aryl, arylalkyl, aryloxyalkyl, heterocycle, heterocyclealkyl, and heterocycleoxyalkyl;

R$^{18}$ and R$^{19}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or R$^{18}$ and R$^{19}$ together with the atom to which they are attached form a non-aromatic heterocycle;

R$^{20}$, R$^{21}$ and R$^{22}$ are each independently selected from the group consisting of hydrogen, alkyl, carboxyalkyl, carboxycycloalkyl, cycloalkyl, haloalkyl, aryl, and heterocycle;

R$^{23}$ and R$^{24}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, cycloalkyl, aryl, and heterocycle;

R$^{25}$ and R$^{26}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, hydroxy, alkoxy, cycloalkyloxy, aryloxy, heterocycleoxy, cycloalkyl, aryl, and heterocycle, or R$^{25}$ and R$^{26}$ together with the atom to which they are attached form a heterocycle;

R$^{27}$ and R$^{28}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or R$^{27}$ and R$^{28}$ together with the atom to which they are attached form a non-aromatic heterocycle; and R$^{29}$ and R$^{30}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or R$^{29}$ and R$^{30}$ together with the atom to which they are attached form a non-aromatic heterocycle;

or a therapeutically acceptable salt thereof.

6. The compound according to claim 5 that is
2-[(cis)-2,6-dimethylmorpholin-4-yl]-N-[(E)-5-hydroxy-2-adamantyl]propanamide;
2-azepan-1-yl-N-[(E)-5-hydroxy-2-adamantyl] propanamide;
N-[(E)-5-hydroxy-2-adamantyl]-2-(6,7,9,10-tetrahydro-8H-[1,3]dioxolo[4,5-g][3]benzazepin-8-yl)propanamide;
2-(1,3-dihydro-2H-isoindol-2-yl)-N-[(E)-5-hydroxy-2-adamantyl]propanamide;
2-[3-(4-chlorophenoxy)azetidin-1-yl]-N-[(E)-5-hydroxy-2-adamantyl]propanamide;
2-(5-chloro-2,3-dihydro-1H-indol-1-yl)-N-[(E)-5-hydroxy-2-adamantyl]propanamide;
N-[(E)-5-hydroxy-2-adamantyl]-2-(3-phenylazetidin-1-yl)propanamide;
2-[3-(3-fluorophenoxy)pyrrolidin-1-yl]-N-[(E)-5-hydroxy-2-adamantyl]propanamide; or
N-[(E)-5-hydroxy-2-adamantyl]-2-methyl-2-[2-(trifluoromethyl)pyrrolidin-1-yl]propanamide;

or a therapeutically acceptable salt thereof.

7. A pharmaceutical composition comprising a therapeutically effective amount of the compound according to claim 5 in combination with a pharmaceutically suitable carrier.

8. A method of inhibiting 11-beta-hydroxysteroid dehydrogenase Type I enzyme, comprising administering to a mammal, a therapeutically effective amount of a compound of formula I of claim 5 for treating a disorder selected from the group consisting of non insulin dependent type 2 diabetes, obesity, hypertension, and cognitive impairment associated with aging.

9. A compound according to formula (I),

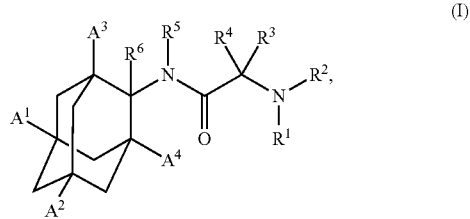

wherein

A$^1$ is aryl, halogen or —OR$^{14}$;

A$^2$, A$^3$, and A$^4$ are each independently selected from the group consisting of hydrogen, alkyl, alkyl-NH-alkyl, alkylcarbonyl, alkylsulfonyl, cycloalkyl, cycloalkylcarbonyl, cycloalkylsulfonyl, arylcarbonyl, arylsulfonyl, heterocyclecarbonyl, heterocyclesulfonyl, aryl, arylalkyl, aryloxyalkyl, carboxyalkyl, carboxycycloalkyl, halogen, haloalkyl, heterocycle, heterocyclealkyl, heterocycleoxyalkyl, —NR$^7$—[C(R$^8$R$^9$)]$_n$—C(O)—R$^{10}$, —O—[C(R$^{11}$R$^{12}$)]$_p$—C(O)—R$^{13}$, —OR$^{14}$, —N(R$^{15}$R$^{16}$), —CO$_2$R$^{17}$, —C(O)—N(R$^{18}$R$^{19}$), —C(R$^{20}$R$^{21}$)—OR$^{22}$, and —C(R$^{23}$R$^{24}$)—N(R$^{25}$R$^{26}$);

n is 0 or 1;

p is 0 or 1;

$R^1$ and $R^2$ together with the atom to which they are attached form a heterocycle, wherein the heterocycle is piperazinyl or piperidinyl, being substituted with one or more substituents independently selected from the group consisting of optionally substituted arylalkyl, furoyl, pyridinyl, and halophenyloxy; the pyridinyl optionally substituted with 0, 1, 2 or 3 substituents independently selected from alkenyl, alkenylthio, alkenyloxy, alkoxy, alkoxyalkoxy, alkoxyalkoxyalkyl, alkoxyalkoxyalkyl, alkoxyalkyl, alkoxycarbonyl, alkoxycarbonylalkoxy, alkoxycarbonylalkyl, alkoxysulfonyl, alkyl, alkylcarbonyl, alkylcarbonylalkoxy, alkyl carbonyl alkyl, alkyl carbonylalkylthio, alkylcarbonyloxy, alkylcarbonylthio, alkylsulfinyl, alkylsulfonylalkyl, alkyl sulfonyl, alkylsulfonylalkyl, alkylthio, alkylthioalkyl, alkylthioalkoxy, alkynyl, alkynyloxy, alkynylthio, aryl, arylcarbonyl, aryloxy, arylsulfonyl, carboxy, carboxyalkoxy, carboxyalkyl, cyanoalkoxy, cyanoalkyl, cyanoalkylthio, ethylenedioxy, formyl, formylalkoxy, formylalkyl, haloalkenyl, haloalkenyloxy, haloalkoxy, haloalkyl, haloalkynyl, haloalkynyloxy, halogen, heterocycle, heterocyclecarbonyl, heterocycleoxy, heterocyclesulfonyl, hydroxy, hydroxyalkoxy, hydroxyalkyl, mercapto, mercaptoalkoxy, mercaptoalkyl, methylenedioxy, oxo, nitro, $R_fR_gN-$, $R_fR_gNalkyl$, $R_fR_gNcarbonyl$ and $R_fR_gNsulfonyl$, wherein $R_f$ and $R_g$ are members independently selected from the group consisting of hydrogen, alkyl, alkoxyalkyl, alkylcarbonyl, alkylsulfonyl, alkoxycarbonyl, cycloalkyl, cycloalkylalkyl, cycloalkylcarbonyl and cycloalkylsulfonyl, and wherein substituent aryl, the aryl of arylcarbonyl, the aryl of aryloxy, the aryl of arylsulfonyl, the substituent heterocycle, the heterocycle of heterocyclecarbonyl, the heterocycle of heterocycleoxy, the heterocycle of heterocyclesulfonyl may be optionally substituted with 0, 1, 2 or 3 substituents independently selected from the group consisting of alkenyl, alkenylthio, alkenyloxy, alkoxy, alkoxyalkoxy, alkoxyalkoxyalkoxy, alkoxyalkoxyalkyl, alkoxyalkyl, alkoxycarbonyl, alkoxycarbonylalkoxy, alkoxycarbonylalkyl, alkoxysulfonyl, alkyl, alkylcarbonyl, alkylcarbonylalkoxy, alkylcarbonylalkyl, alkylcarbonylalkylthio, alkylcarbonyloxy, alkylcarbonylthio, alkylsulfinyl, alkylsulfonylalkyl, alkyl sulfonyl, alkylsulfonylalkyl, alkylthio, alkylthioalkyl, alkylthioalkoxy, alkynyl, alkynyloxy, alkynylthio, carboxy, carboxyalkoxy, carboxyalkyl, cyano, cyanoalkoxy, cyanoalkyl, cyanoalkylthio, ethylenedioxy, formyl, formylalkoxy, formylalkyl, haloalkenyl, haloalkenyloxy, haloalkoxy, haloalkyl, haloalkynyl, haloalkynyloxy, halogen, hydroxy, hydroxyalkoxy, hydroxyalkyl, mercapto, mercaptoalkoxy, mercaptoalkyl, methyl enedioxy, oxo, nitro, $R_fR_gN-R_fR_gNalkyl$, $R_fR_gNcarbonyl$ and $R_fR_gN-sulfonyl$ $R^3$ and $R^4$ are each independently hydrogen, alkyl, carboxyalkyl, carboxycycloalkyl, cycloalkyl, haloalkyl, aryl, or heterocycle, or $R^3$ and $R^4$ together with the atom to which they are attached form a ring selected from the group consisting of cycloalkyl and non-aromatic heterocycle;

$R^5$ is hydrogen, alkyl, carboxyalkyl, carboxycycloalkyl, cycloalkyl, aryl, arylalkyl, aryloxyalkyl, heterocycle, heterocyclealkyl, or heterocycleoxyalkyl;

$R^6$ is selected from the group consisting of hydrogen, alkyl, or carboxy;

$R^7$ is selected from the group consisting of hydrogen, alkyl, carboxyalkyl, cycloalkyl, carboxycycloalkyl, aryl, arylalkyl, aryloxyalkyl, aryloxy, hydroxy, alkoxy, cycloalkyloxy, heterocycleoxy, heterocycle, heterocyclealkyl, and heterocycleoxyalkyl;

$R^8$ and $R^9$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or $R^8$ and $R^9$ together with the atom to which they are attached form a ring selected from the group consisting of cycloalkyl and non-aromatic heterocycle;

$R^1$ is selected from the group consisting of hydrogen, alkyl, carboxy, carboxyalkyl, cycloalkyl, carboxycycloalkyl, aryl, aryloxy, arylalkyl, aryloxyalkyl, hydroxy, alkoxy, cycloalkyloxy, heterocycleoxy, heterocycle, heterocyclealkyl, heterocycleoxyalkyl, and $-N(R^{27}R^{28})$;

$R^{11}$ and $R^{12}$ are each independently selected from the group consisting of hydrogen, alkyl, carboxy, carboxyalkyl, cycloalkyl, carboxycycloalkyl, aryl, arylalkyl, aryloxyalkyl, heterocycle, heterocyclealkyl, and heterocycleoxyalkyl, or $R^{11}$ and $R^{12}$ together with the atom to which they are attached form a ring selected from the group consisting of cycloalkyl and non-aromatic heterocycle;

$R^{13}$ is selected from the group consisting of hydrogen, alkyl, carboxy, carboxyalkyl, cycloalkyl, carboxycycloalkyl, aryl, arylalkyl, aryloxy, aryloxyalkyl, hydroxy, alkoxy, cycloalkyloxy, heterocycleoxy, heterocycle, heterocyclealkyl, heterocycleoxyalkyl, and $-N(R^{29}R^{30})$;

$R^{14}$ is selected from the group consisting of hydrogen, alkyl, carboxyalkyl, cycloalkyl, carboxycycloalkyl, aryl, arylalkyl, aryloxyalkyl, haloalkyl, heterocycle, heterocyclealkyl, and heterocycleoxyalkyl;

$R^{15}$ and $R^{16}$ are each independently selected from the group consisting of hydrogen, alkyl, carboxyalkyl, cycloalkyl, carboxycycloalkyl, aryl, arylalkyl, aryloxyalkyl, heterocycle, heterocyclealkyl, heterocycleoxyalkyl, alkylsulfonyl, cycloalkylsulfonyl, arylsulfonyl, and heterocyclesulfonyl, or $R^{15}$ and $R_{16}$ together with the atom to which they are attached form a heterocycle;

$R^{17}$ is selected from the group consisting of hydrogen, alkyl, carboxyalkyl, cycloalkyl, carboxycycloalkyl, aryl, arylalkyl, aryloxyalkyl, heterocycle, heterocyclealkyl, and heterocycleoxyalkyl;

$R^{18}$ and $R^{19}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{18}$ and $R^{19}$ together with the atom to which they are attached form a non-aromatic heterocycle;

$R^{20}$, $R^{21}$ and $R^{22}$ are each independently selected from the group consisting of hydrogen, alkyl, carboxyalkyl, carboxycycloalkyl, cycloalkyl, haloalkyl, aryl, and heterocycle;

$R^{23}$ and $R^{24}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, cycloalkyl, aryl, and heterocycle;

$R^{25}$ and $R^{26}$ are each independently selected from the group consisting of hydrogen, alkyl, alkylcarbonyl, alkylsulfonyl, carboxyalkyl, carboxycycloalkyl, cycloalkylcarbonyl, cycloalkylsulfonyl, arylcarbonyl, arylsulfonyl, heterocyclecarbonyl, heterocyclesulfonyl, hydroxy, alkoxy, cycloalkyloxy, aryloxy, heterocycleoxy, cycloalkyl, aryl, and heterocycle, or $R^{25}$ and $R^{26}$ together with the atom to which they are attached form a heterocycle;

$R^{27}$ and $R^{28}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{27}$ and $R^{28}$ together with the atom to which they are attached form a non-aromatic heterocycle; and $R^{29}$ and $R^{30}$ are each independently selected from the group consisting of hydrogen, alkyl, carboxy, carboxyalkyl, cycloalkyl, cycloalkyloxy, carboxycycloalkyl, aryl, arylalkyl, aryloxy, aryloxyalkyl, heterocycle, heterocyclealkyl, heterocycleoxyalkyl, heterocycleoxy, hydroxy, alkoxy, alkylsulfonyl, cycloalkylsulfonyl, arylsulfonyl, and heterocyclesulfonyl, or $R^{29}$ and $R^{30}$ together with the atom to which they are attached form a non-aromatic heterocycle;

or a therapeutically acceptable salt thereof.

10. The compound according to claim that is

N-[(Z)-5-hydroxy-2-adamantyl]-2-{4-[5-(trifluoromethyl)pyridin-2-yl]piperazin-1-yl}acetamide;

N-[(E)-5-hydroxy-2-adamantyl]-2-{4-[5-(trifluoromethyl)pyridin-2-yl]piperazin-1-yl}acetamide;

(2S)-N-[(E)-5-hydroxy-2-adamantyl]-2-{4-[5-(trifluoromethyl)pyridin-2-yl]piperazin-1-yl}propanamide;

(2R)-N-[(E)-5-hydroxy-2-adamantyl]-2-{4-[5-(trifluoromethyl)pyridin-2-yl]piperazin-1-yl}propanamide;

N-[(E)-5-fluoro-2-adamantyl]-2-{4-[5-(trifluoromethyl)pyridin-2-yl]piperazin-1-yl}acetamide;

N-[(Z)-5-fluoro-2-adamantyl]-2-{4-[5-(trifluoromethyl)pyridin-2-yl]piperazin-1-yl}acetamide;

N-[(E)-5-hydroxy-2-adamantyl]-2-[4-(5-methylpyridin-2-yl)piperazin-1-yl]propanamide;

N-[(E)-5-hydroxy-2-adamantyl]-2-methyl-2-{4-[5-(trifluoromethyl)pyridin-2-yl]piperazin-1-yl }propanamide;

N-[(E)-5-hydroxy-2-adamantyl]-2-(4-pyridin-2-ylpiperazin-1-yl)propanamide;

2-[4-(4-fluorophenyl)piperazin-1-yl]-N-[(E)-5-hydroxy-2-adamantyl]propanamide;

N-[(E)-5-hydroxy-2-adamantyl]-2-[4-(4-methoxyphenyl)piperazin-1-yl]propanamide;

2-[4-(2-furoyl)piperazin-1-yl]-N-[(E)-5-hydroxy-2-adamantyl]propanamide;

N-[(E)-5-hydroxy-2-adamantyl]-2-{4-[4-(trifluoromethyl)phenyl]piperazin-1-yl}propanamide;

2-[4-(6-chloropyridin-3-yl)piperazin-1-yl]-N-[(E)-5-hydroxy-2-adamantyl]propanamide;

2-(4-benzylpiperidin-1-yl)-N-[(E)-5-hydroxy-2-adamantyl]propanamide;

2-[4-(2-fluorophenoxy)piperidin-1-yl]-N-[(E)-5-hydroxy-2-adamantyl]propanamide; or 2-[3-(2-fluorophenoxy)piperidin-1-yl]-N-[(E)-5-hydroxy-2-adamantyl]propanamide;

or a therapeutically acceptable salt thereof.

11. A pharmaceutical composition comprising a therapeutically effective amount of the compound according to claim 9 in combination with a pharmaceutically suitable carrier.

12. A method of inhibiting 11-beta-hydroxysteroid dehydrogenase Type 1 enzyme, comprising administering to a mammal, a therapeutically effective amount of a compound of formula I of claim 9 for treating a disorder selected from the group consisting of non insulin dependent type 2 diabetes, obesity, hypertension, and cognitive impairment associated with aging.

13. A compound that is 2-[4-(5-cyanopyridin-2-yl)piperazin-1-yl]-N-[(E)-5-hydroxy-2-adamantyl]propanamide, or a therapeutically acceptable salt thereof.

* * * * *